US012637478B2

(12) United States Patent
Hwang et al.

(10) Patent No.: US 12,637,478 B2
(45) **Date of Patent: *May 26, 2026**

(54) COMPOUND, PREPARATION METHOD THEREOF, AND ANTIBIOTIC COMPOSITION COMPRISING SAME

(71) Applicant: A&J Science Co., Ltd., Daegu (KR)

(72) Inventors: Hee-Jong Hwang, Daegu (KR); Young-Jin Son, Daegu (KR); Dahyun Kim, Daegu (KR); Jusuk Lee, Daegu (KR); Marco Ciufolini, Vancouver (CA)

(73) Assignee: A&J Science Co., Ltd. (KR)

( * ) Notice: Subject to any disclaimer, the term of this patent is extended or adjusted under 35 U.S.C. 154(b) by 374 days.

This patent is subject to a terminal disclaimer.

(21) Appl. No.: 18/037,102

(22) PCT Filed: Nov. 18, 2021

(86) PCT No.: PCT/KR2021/016975

§ 371 (c)(1),
(2) Date: May 16, 2023

(87) PCT Pub. No.: WO2022/108354

PCT Pub. Date: May 27, 2022

(65) Prior Publication Data

US 2023/0416274 A1 Dec. 28, 2023

(30) Foreign Application Priority Data

Nov. 19, 2020 (KR) ........................ 10-2020-0155605
Nov. 17, 2021 (KR) ........................ 10-2021-0158467

(51) Int. Cl.
*C07D 513/22* (2006.01)
*A61P 31/04* (2006.01)

(52) U.S. Cl.
CPC ............ *C07D 513/22* (2013.01); *A61P 31/04* (2018.01)

(58) Field of Classification Search
CPC ....... A61P 31/04; C07D 513/22; C07F 5/025; C07F 5/027; C07K 5/0821; C07K 7/56; A61K 31/4353; A61K 31/496; A61K 31/5377
See application file for complete search history.

(56) References Cited

FOREIGN PATENT DOCUMENTS

| | | | |
|---|---|---|---|
| EP | 1369425 | A1 | 12/2003 |
| JP | 2008115165 | A | 5/2008 |
| KR | 20040000404 | A | 1/2004 |
| KR | 100872059 | B1 | 12/2008 |
| RU | 2016150134 | A | 7/2018 |
| WO | 2015063711 | A1 | 5/2015 |

OTHER PUBLICATIONS

Patani et al (Chem. Rev. 1996, 96, 3147-3176) (Year: 1996).*
Talele et al (J. Med. Chem. 2016, 59, 8712-8756) (Year: 2016).*
Acker et al (J Am Chem Soc. Dec. 9, 2009; 131(48): 17563-17565) (Year: 2009).*
Korean Intellectual Property Office, Daejeon, Korea, International Search Report of International Application No. PCT/KR2021/016975, Mailed Feb. 28, 2022, 2 pages.
Marco A. Ciufolini et al., "Micrococcin P1: Structure, biology and systhesis," Natural Product Reports, 2010, vol. 27, No. 3, 13 pages.
Marco A. Ciufolini et al., "Systhesis of the Bycroft-Gowland Structure of Micrococcin P1," Organic Letters, 1999, vol. 1, No. 11, 4 pages.
David Lefranc et al., "Total Systhesis and Stereochemical Assignment of Micrococcin P1," Angewandte Chemie Int. Ed. 2009, vol. 48, 4 pages.
M. John Rogers et al., "The Antibiotic Micrococcin Is A Potent Inhibitor of Growth And Protein Synthesis In The Malaria Parasite," Antimicrobial Agents and Chemotherapy, Mar. 1998, American Society for Microbiology, 2 pages.

* cited by examiner

*Primary Examiner* — Jean P Cornet
(74) *Attorney, Agent, or Firm* — Dickinson Wright PLLC

(57) ABSTRACT

The present invention provides a novel compound, a solvate thereof, a hydrate thereof, a prodrug thereof, an isomer thereof, or a pharmaceutically acceptable salt thereof, a preparation method thereof, and an antibiotic composition comprising the same. The novel compound of the present invention having excellent antimicrobial activity is very useful for preventing and treating a bacterial infection.

16 Claims, No Drawings

COMPOUND, PREPARATION METHOD THEREOF, AND ANTIBIOTIC COMPOSITION COMPRISING SAME

CROSS REFERENCE TO RELATED APPLICATIONS

This application is a 35 U.S.C. § 371 national phase application of International Application No.: PCT/KR2021/016975, filed Nov. 18, 2021, which claims the benefit of priority under 35 U.S.C. § 119 to Korean Patent Application No.: 10-2020-0155605, filed Nov. 19, 2020 and Korean Patent Application No.: 10-2021-0158467, filed Nov. 17, 2021, the contents of which are incorporated herein by reference in their entirety.

TECHNICAL FIELD

The present invention relates to a novel compound, a method for preparing the same, and an antibiotic composition containing the same.

BACKGROUND ART

Antibiotics are used for treatment of bacterial infections, and various types of antibiotics such as aminoglycoside, glycopeptide, macrolide, and quinoline antibiotics have been developed.

Most of the antibiotics developed previously showed antibacterial performance as an action of killing bacteria.

However, in controlling bacteria that cause the onset of diseases, it is significantly important not only to kill bacteria but also to prevent propagation of bacteria in advance by interfering with communication between bacteria. A typical function achieved by bacteria through communication is a biofilm, and the biofilm causes numerous diseases while remaining in human organs. Examples of the disease or disease sites include dental caries, gingivitis, periodontitis, otitis media, voice prostheses, hydrocephalus hunts, cystic fibrosis, valvular endocarditis, prosthetic heart valves, central venous catheters, prosthetic hip joints, prosthetic knee joints, chronic bacterial prostatitis, intrauterine devices, urinary catheters, and the like.

Therefore, studies on a multi-functional antibiotic that not only kills bacteria, but also inhibits functions such as biofilm formation of bacteria in advance by interfering with communication between bacteria have been also conducted.

Meanwhile, the mechanisms by which the antibiotic acts on bacteria may be largely divided into mechanisms that interfere with cell wall formation, protein synthesis, bacterial DNA and RNA synthesis, and production of mycolic acid and folic acid.

The existing developed antibiotics have chemical structural characteristics according to the mechanisms of action as described above. Representative chemical structures may be divided into penicillins (beta-lactams), cephalosporins, aminoglycosides, macrolides, sulfonamides, quinolones, tetracyclines, polypeptides, and the like.

However, although antibiotics play an important role in treating bacterial infections and diseases, antibiotic-resistant bacteria have emerged due to overuse of antibiotics and repeated use of the same antibiotics.

For example, beta-lactam antibiotics used for infection with Gram-negative bacteria are the second most widely used antibiotics after quinoline antibiotics. However, bacteria develop resistance to antibiotics by producing beta-lactamase, which is an enzyme that neutralizes the beta-lactam antibiotics.

As such, the emergence of multidrug-resistant bacteria, that is, superbacteria, which are difficult to treat with conventional antibiotics, has caused many limitations in the treatment of bacterial infections.

Therefore, in order to treat infections with newly emerging antibiotic-resistant bacteria, development of a novel antibiotic having a chemical structure completely different from that of the conventional antibiotic has been urgently needed.

DISCLOSURE

Technical Problem

The present invention provides a novel compound, or a solvate, hydrate, prodrug, isomer, or pharmaceutically acceptable salt thereof.

Further, the present invention provides a method for preparing the novel compound of the present invention.

Further, the present invention provides an antibiotic composition containing the novel compound of the present invention, or the solvate, hydrate, prodrug, isomer, or pharmaceutically acceptable salt thereof.

Technical Solution

The present invention provides a novel compound that may be effectively used as an antibiotic, or a solvate, hydrate, prodrug, isomer, or pharmaceutically acceptable salt thereof, and the novel compound of the present invention is represented by the following Chemical Formula 1.

[Chemical Formula 1]

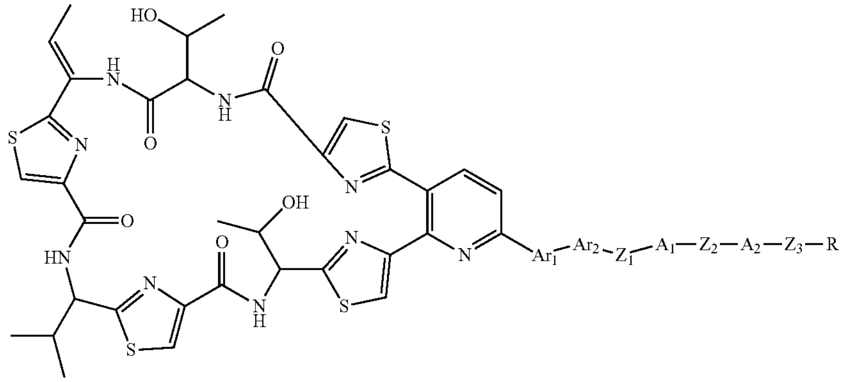

(In Chemical Formula 1, $Ar_1$ and $Ar_2$ are each independently a single bond, substituted or unsubstituted $C_6$-$C_{20}$ arylene, or substituted or unsubstituted $C_3$-$C_{20}$ heteroarylene;

$Z_1$ to $Z_3$ are each independently a single bond, —$CONR_1$—, —$NR_2CO$—, —COO—, —OCO—, —$CR_3R_4$—, —$NR_5COO$—, —$NR_6$—, —S—, —O—, —$SO_2$—, or —$OCONR_7$—;

$R_1$ to $R_7$ are each independently hydrogen, hydroxy, C1-C10 alkyl, carboxy C1-C10 alkyl, or C1-C10 alkoxycarbonyl C1-C10 alkyl;

$A_1$ is

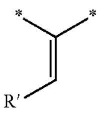 or 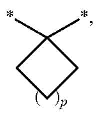,

R' is hydrogen, C1-C10 alkyl, C2-C10 alkenyl, or C1-C10 alkoxy C1-C10 alkyl, and p is an integer of 0 to 4;

$A_2$ is a single bond, C1-C10 alkylene, C3-C10 cycloalkylene, C3-C10 heterocycloalkylene, C6-C20 arylene, or C6-C20 heteroarylene; and R is hydrogen, halogen, amino, hydroxy, —$B(OH)_2$, substituted or unsubstituted halo C1-C10 alkyl, substituted or unsubstituted C1-C10 alkyl, substituted or unsubstituted C2-C10 alkenyl, substituted or unsubstituted C3-C10 cycloalkyl, substituted or unsubstituted C3-C10 heterocycloalkyl, substituted or unsubstituted C6-C20 aryl, or substituted or unsubstituted C3-C20 heteroaryl.)

Further, the present invention provides an antibiotic composition containing, as an active ingredient, the compound of the present invention, or the hydrate, solvate, isomer, prodrug, or pharmaceutically acceptable salt thereof.

Advantageous Effects

The novel compound of the present invention is a compound having a chemical structure different from that of the conventional antibiotic and has an improved effect of treating and preventing various bacterial infections.

Therefore, the antibiotic composition containing the novel compound of the present invention, or the solvate, hydrate, prodrug, isomer, or pharmaceutically acceptable salt thereof may be used for effective treatment and prevention of bacterial infections.

BEST MODE

Hereinafter, a novel compound of the present invention, or a solvate, hydrate, prodrug, isomer, or pharmaceutically acceptable salt thereof will be described in detail. However, unless otherwise defined, all the technical terms and scientific terms used herein have the same meanings as commonly understood by those skilled in the art to which the present invention pertains, and a description for the known function and configuration unnecessarily obscuring the gist of the present disclosure will be omitted in the following description.

The following terms used in the present specification are defined as follows, but these terms are merely illustrative and are not intended to limit the present invention, application, or use.

The terms "substituent", "radical", "group", "moiety", and "fragment" used in the present specification may be used interchangeably.

The term "protecting group" used in the present specification includes, but is not limited to, an "amino protecting group" or a "hydroxyl protecting group". The "amino protecting group" refers to a protecting group suitable for preventing a side reaction at the amino nitrogen position. Representative amino protecting groups include, but are not limited to, a formyl group; an alkanoyl group, for example, an acyl group such as an acetyl group, a trichloroacetyl group, or a trifluoroacetyl group; an alkoxycarbonyl group such as a tert-butoxycarbonyl group (Boc); an arylmethoxycarbonyl group such as a benzyloxycarbonyl group (Cbz) or a 9-fluorenylmethoxycarbonyl group (Fmoc); an arylmethyl group such as a benzyl group (Bn), a triphenylmethyl group (Tr), or a 1,1-bis-(4'-methoxyphenyl)methyl group; a silyl group such as a trimethylsilyl group (TMS) or a tert-butyldimethylsilyl group (TBS), and the like. The "hydroxyl protecting group" refers to a protecting group suitable for suppressing a side reaction of a hydroxyl group. Representative hydroxyl protecting groups include, but are not limited to, an alkyl group such as a methyl group, an ethyl group, or a tert-butyl group; an acyl group such as an alkanoyl group (for example, an acetyl group); an arylmethyl group such as a benzyl group (Bn), a p-methoxybenzyl group (PMB), a 9-fluorenylmethyl group (Fm), or a diphenylmethyl group (DPM); a silyl group such as a trimethylsilyl group (TMS) or a tert-butyldimethylsilyl group (TBS), and the like.

"$C_A$-$C_B$" used in the present specification means that "the number of carbon atoms is A or more and B or less". That is, a description of "C1-C10" means that the number of carbon atoms is 1 to 10. For example, C1-C10 alkyl refers to an alkyl having 1 to 10 carbon atoms.

The term "alkyl" used in the present specification refers to a saturated, linear or branched, non-cyclic hydrocarbon having 1 to 20 carbon atoms, preferably 1 to 15 carbon atoms, more preferably 1 to 10 carbon atoms, and still more preferably 1 to 6 carbon atoms (when the number of carbon atoms is not particularly limited). "Lower alkyl" refers to a linear or branched alkyl having 1 to 4 carbon atoms or 1 to 6 carbon atoms. Representative saturated linear alkyl includes methyl, ethyl, n-propyl, n-butyl, n-pentyl, n-hexyl, n-heptyl, n-octyl, n-nonyl, and n-decyl; while representative saturated branched alkyl includes isopropyl, sec-butyl, isobutyl, tert-butyl, isopentyl, 2-methylhexyl, 3-methylbutyl, 2-methylpentyl, 3-methylpentyl, 4-methylpentyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, and 3,3-diethylhexyl.

The term "alkenyl" used in the present specification refers to a saturated, linear or branched, non-cyclic hydrocarbon having 2 to 20 carbon atoms, preferably 2 to 15 carbon atoms, more preferably 2 to 10 carbon atoms, and still more preferably 2 to 6 carbon atoms, and at least one carbon-carbon double bond. Representative linear and branched (C2-C10) alkenyls include vinyl, allyl, 1-butenyl, 2-butenyl, isobutenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, and 3-decenyl. These alkenyl groups may be optionally substituted.

The term "halogen" or "halo" used in the present specification refers to fluorine, chlorine, bromine, or iodine.

The term "haloalkyl", "haloalkoxy", "haloalkenyl", and "haloalkynyl" used in the present specification refer to alkyl, alkoxy, alkenyl, and alkynyl groups, respectively, in which one or more hydrogen atoms are substituted with halogen atoms. For example, haloalkyl includes $—CF_3$, $—CHF_2$, $—CH_2F$, $—CBr_3$, $—CHBr_2$, $—CH_2Br$, $—CCl_3$, $—CHCl_2$, $—CH_2Cl$, $—Cl_3$, $—CHI_2$, $—CH_2I$, $—CH_2—CF_3$, $—CH_2—CHF_2$, $—CH_2—CH_2F$, $—CH_2—CBr_3$, $—CH_2—CHBr_2$, $—CH_2—CH_2Br$, $—CH_2—CCl_3$, $—CH_2—CHCl_2$, $—CH_2—CH_2Cl$, $—CH_2—Cl_3$, $—CH_2—CHI_2$, $—CH_2—CH_2I$, and the like. Here, alkyl and halogen are as defined above.

The term "alkoxy" used in the present specification refers to —O-(alkyl) including $—OCH_3$, $—OCH_2CH_3$, $—O(CH_2)_2CH_3$, $—O(CH_2)_3CH_3$, $—O(CH_2)_4CH_3$, $—O(CH_2)$ $SCH_3$, and the like, where alkyl is as defined above.

The term "lower alkoxy" used in the present specification refers to —O-(lower alkyl), where lower alkyl is as defined above.

The term "aryl" used in the present specification refers to a carbocyclic aromatic group containing 5 to 10 ring atoms. Representative examples thereof include, but are not limited to, phenyl, tolyl, xylyl, naphthyl, tetrahydronaphthyl, anthracenyl, fluorenyl, indenyl, azulenyl, and the like. The carbocyclic aromatic group may be optionally substituted.

The term "cycloalkyl" used in the present specification refers to a monocyclic or polycyclic saturated ring having carbon and hydrogen atoms and no carbon-carbon multiple bonds. Examples of a cycloalkyl group include, but are not limited to, (C3-C10) cycloalkyl (for example, cyclopropyl, cyclobutyl, cyclopentyl, cyclohexyl, and cycloheptyl). The cycloalkyl group may be optionally substituted. In an embodiment, the cycloalkyl group is a monocyclic or bicyclic ring.

The term "heterocycloalkyl" used in the present specification refers to a stable 3- to 18-membered saturated or partially unsaturated radical which consists of 2 to 20 carbon atoms, preferably 2 to 15 carbon atoms, more preferably 2 to 10 carbon atoms, and still more preferably 2 to 6 carbon atoms, and 1 to 6 heteroatoms, for example, 1 to 5 heteroatoms, 1 to 4 heteroatoms, 1 to 3 heteroatoms, or 1 or 2 heteroatoms selected from the group consisting of nitrogen, oxygen, and sulfur. Exemplary heterocycloalkyl includes, without limitation, a stable 3- to 15-membered saturated or partially unsaturated radical, a stable 3- to 12-membered saturated or partially unsaturated radical, a stable 3- to 9-membered saturated or partially unsaturated radical, a stable 8-membered saturated or partially unsaturated radical, a stable 7-membered saturated or partially unsaturated radical, a stable 6-membered saturated or partially unsaturated radical, or a stable 5-membered saturated or partially unsaturated radical. Heterocycloalkyl includes all forms of saturated or unsaturated monocycle, polycycle, or spirocycle, and may be bonded through a heteroatom or a carbon atom. Examples of the heterocycloalkyl radical include monovalent radicals of non-aromatic heterocycles such as oxetane, aziridine, pyrrolidine, azetidine, piperidine, tetrahydropyridine, piperazine, morpholine, thiomorpholine, 1,3-dihydrobenzo[c][1,2]oxaborole, imidazolidine-2,4-dione, thiazolidine-2,4-dione, pyrimidine-2,4(1H,3H)-dione, 3-azabicyclo[3.1.0]hexane, octahydropyrrolo[3,4-c]pyrrole, 2,7-diazaspiro[4.4]nonane, and 2-azaspiro[4.4]nonane.

The term "mono-alkylamino" used in the present specification refers to —NH(alkyl) including $—NHCH_3$, $—NHCH_2CH_3$, $—NH(CH_2)_2CH_3$, $—NH(CH_2)_3CH_3$, $—NH(CH_2)_4CH_3$, $—NH(CH_2)$ $SCH_3$, and the like, where alkyl is as defined above.

The term "di-alkylamino" used in the present specification refers to —N(alkyl) (alkyl) including $—N(CH_3)_2$, $—N(CH_2CH_3)_2$, $—N((CH_2)_2CH_3)_2$, $—N(CH_3)(CH_2CH_3)$, and the like, where each alkyl is independently alkyl as defined above.

The term "alkylamino" used in the present specification is a concept that includes mono-alkylamino, di-alkylamino, and tri-alkylamino as defined above.

The terms "carboxylic acid", "carboxyl", and "carboxy" used in the present specification refer to —COOH.

The term "carboxyalkyl" refers to alkyl, in which one or more hydrogen atoms are substituted with —COOH. For example, carboxyalkyl includes $—CH_2COOH$, $—CH_2CH_2COOH$, $—(CH_2)_2CH_2COOH$, $—(CH_2)_3CH_2COOH$, $—(CH_2)_4CH_2COOH$, $—(CH_2)_5CH_2COOH$, $—CH(COOH)—CH_3$, $—CH_2CH(COOH)CH_3$, and the like. Here, alkyl is as defined above.

The term "aminoalkyl" used in the present specification refers to -(alkyl)-$NH_2$ including $—CH_2—NH_2$, $—(CH_2)_2—NH_2$, $—(CH_2)_3—NH_2$, $—(CH_2)_4—NH_2$, $—(CH_2)_5—NH_2$, and the like, where alkyl is as defined above.

The term "mono-alkylaminoalkyl" used in the present specification refers to -(alkyl)-NH(alkyl) including $—CH_2—NH—CH_3$, $—CH_2—NHCH_2CH_3$, $—CH_2—NH(CH_2)_2CH_3$, $—CH_2—NH(CH_2)_3CH_3$, $—CH_2—NH(CH_2)_4CH_3$, $—CH_2—NH(CH_2)_5CH_3$, $—(CH_2)_2—NH—CH_3$, and the like, where each alkyl is independently alkyl as defined above.

"Heteroaryl" used in the present specification refers to a 5- to 10-membered aromatic heterocyclic ring containing at least one heteroatom selected from the group consisting of nitrogen, oxygen, and sulfur, including mono- and bicyclic ring systems, and having at least one carbon atom. Representative heteroaryl is triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, oxetanyl, azepinyl, piperazinyl, morpholinyl, dioxanyl, thietanyl, or oxazolyl. A heteroaryl group may be monocyclic or bicyclic. Heteroaryl may be used interchangeably with the term "heteroaryl ring", "heteroaryl group", or "heteroaromatic", and all of these terms may include optionally substituted rings.

"Heterocycle" used in the present specification refers to a saturated or unsaturated 5- to 7-membered monocyclic, 7- to 10-membered bicyclic, or heterocyclic ring containing 1 to 4 heteroatoms independently selected from nitrogen, oxygen, and sulfur, in which the nitrogen and sulfur heteroatoms may be optionally oxidized, the nitrogen heteroatom may be optionally quaternized, and a bicyclic ring in which a part of the heterocycle is fused to a benzene ring is included. The heterocycle may be attached by heteroatoms or carbon atoms. The heterocycle includes the heteroaryl as defined above. Representative heterocycle includes morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, and tetrahydrothiopyranyl. "Heterocycle fused to phenyl" refers to heterocycle attached to two adjacent carbon atoms of a phenyl ring, where heterocycle is as defined above.

The term "hydroxyalkyl" used in the present specification refers to alkyl, in which one or more hydrogen atoms are substituted with hydroxy. For example, hydroxyalkyl includes $-CH_2OH$, $-CH_2CH_2OH$, $-(CH_2)_2CH_2OH$, $-(CH_2)_3CH_2OH$, $-(CH_2)_4CH_2OH$, $-(CH_2)_5CH_2OH$, $-CH(OH)-CH_3$, $-CH_2CH(OH)CH_3$, and the like. Here, alkyl is as defined above.

The term "alkylsulfonyl" used in the present specification refers to $-SO_2$-(alkyl) including $-SO_2-CH_3$, $-SO_2-CH_2CH_3$, $-SO_2-(CH_2)_2CH_3$, $-SO_2-(CH_2)_3CH_3$, $-SO_2-(CH_2)_4CH_3$, and $-SO_2-(CH_2)_5CH_3$, where alkyl is as defined above.

The term "aminosulfonyl" used in the present specification refers to $-SO_2-NH_2$.

The term "substituted" used in the present specification means that a hydrogen atom of a moiety (for example, alkyl, aryl, heteroaryl, heterocycle, or cycloalkyl) to be substituted is substituted with a substituent. In an embodiment, each carbon atom of a group to be substituted is substituted with no more than two substituents. In another embodiment, each carbon atom of the group to be substituted is substituted with no more than one substituent. In the case of a keto substituent, two hydrogen atoms are substituted with oxygen attached to carbon by a double bond. Unless otherwise specified with respect to the substituent, as an optionally substituted substituent of the present invention, halogen, hydroxyl, (lower) alkyl, haloalkyl, mono- or di-alkylamino, aryl, heterocycle, $-NO_2$, $-NR_{a1}R_{b1}$, $-NR_{a1}C(=O)R_{b1}$, $-NR_{a1}C(=O)NR_{a1}R_{b1}$, $-NR_{a1}C(=O)OR_{b1}$, $-NR_{a1}SO_2R_{b1}$, $-OR_{a1}$, $-CN$, $-C(=O)R_{a1}$, $-C(=O)OR_{a1}$, $-C(=O)NR_{a1}R_{b1}$, $-OC(=O)R_{a1}$, $-OC(=O)OR_{a1}$, $-OC(=O)NR_{a1}R_{b1}$, $-NR_{a1}SO_2R_{b1}$, $-PO_3R_{a1}$, $-PO(OR_{a1})(OR_{b1})$, $-SO_2R_{a1}$, $-S(O)R_{a1}$, $-SO(NR_{a1})R_{b1}$ (for example, sulfoximine), $-S(NR_{a1})R_{b1}$ (for example, sulfilimine), and $-SR_{a1}$ may be used, where $R_{a1}$ and $R_{b1}$ may be the same as or different from each other and are each independently hydrogen, halogen, amino, alkyl, alkoxyalkyl, haloalkyl, aryl, or heterocycle, or $R_{a1}$ and $R_{b1}$ may be in the form of heterocycle together with an attached nitrogen atom. Here, $R_{a1}$ and $R_{b1}$ may be plural depending on the bonded atoms, the alkyl may be C1-C20 alkyl, the aryl may be C6-C20, and the heterocycle may be C3-C20.

Preferably, the substituted substituent of the present invention may be one or more selected from the group consisting of halogen, amino, nitro, hydroxy, a carboxylic acid group, $-B(OH)_2$, C1-C10 alkylcarbonyl, C1-C10 alkoxycarbonyl, C2-C10 alkenyl, C1-C10 alkyl, halo C1-C10 alkyl, C3-C10 heterocyclocarbonyl, allylamino, C1-C10 alkylsulfonyl, aminosulfonyl, amino C1-C10 alkyl, hydroxy C1-C10 alkyl, dihydroxy C1-C10 alkyl, cyano C1-C10 alkyl, C1-C10 alkylamino, di C1-C10 alkylamino, C6-C20 arylamino, di C6-C20 arylamino, C3-C20 heteroaryl, halo C6-C20 aryl, halo C1-C10 alkyl C6-C20 aryl, C6-C20 aryl, C3-C10 cycloalkyl, C3-C10 cycloalkylcarbonyl, C1-C10 alkoxycarbonyl C1-C10 alkyl, and carboxy C1-C10 alkyl.

A "pharmaceutically acceptable salt" used in the present specification includes salts of active compounds prepared with relatively non-toxic acids and bases depending on particular substituents found in the compounds described herein. When the compounds of the present invention have a relatively acidic functionality, base addition salts may be obtained by bringing the neutral forms of the compounds into contact with a sufficient amount of a desired base and a pure or suitable inert solvent. Examples of the pharmaceutically acceptable base addition salts include sodium, potassium, calcium, ammonium, organic amino, or magnesium salts, or similar salts. When the compounds of the present invention have a relatively basic functionality, acid addition salts may be obtained by bringing the neutral forms of the compounds into contact with a sufficient amount of a desired acid and a pure or suitable inert solvent. Examples of the pharmaceutically acceptable acid addition salts include salts derived from relatively non-toxic organic acids including acetic acid, propionic acid, isobutylic acid, oxalic acid, maleic acid, malonic acid, benzoic acid, succinic acid, suberic acid, fumaric acid, mandelic acid, phthalic acid, benzenesulfonic acid, p-tolylsulfonic acid, citric acid, tartaric acid, methanesulfonic acid, and analogs thereof, and also include hydrogen chloride, hydrogen bromide, nitric acid, carbonic acid, monohydrogen carbonate, phosphoric acid, monohydrogen phosphate, dihydrogen phosphate, sulfuric acid, monohydrogen sulfate, hydrogen iodide, or phosphorous acid, and an analog thereof. In addition, the pharmaceutically acceptable acid addition salts include salts of amino acids such as arginate and an analog thereof and analogs of organic acids such as glucuronic or galacturonic acid and an analog thereof (for example, Berge et al. (1977) J. Pharm. Sci. 66: 1-19). Some specific compounds of the present invention have both basic and acidic functionalities to convert the compounds into base or acid addition salts. Other examples of the salts are disclosed in documents known in the art to which the present invention pertains, for example, Remington's Pharmaceutical Sciences, $18^{th}$ eds., Mack Publishing, Easton PA (1990) or Remington: The Science and Practice of Pharmacy, $19^{th}$ eds., Mack Publishing, Easton PA (1995).

As used in the present specification, the terms "individual" and "subject" are animals (for example, cows, horses, sheep, pigs, chickens, turkeys, quails, cats, dogs, mice, rats, rabbits, or guinea pigs), preferably mammals (for example, monkeys and humans) such as non-primates and primates, and most preferably humans.

An "effective dose" used in the present specification refers to the amount of the compound of the present invention sufficient to provide a therapeutic benefit in the treatment or management of bacterial infections. The "effective dose" also refers to the amount of the compound of the present invention sufficient to cause killing or inhibiting of bacteria. The "effective dose" also refers to the amount of the compound sufficient to treat and prevent bacterial infections either in vitro or in vivo. The "effective dose" may be easily determined by those skilled in the art depending on elements including gender, age, weight, and health condition of a patient, the type and severity of bacterial infection, drug activity, drug sensitivity, an administration method, an administration time, an administration route, an excretion rate, a treatment period, and drugs used in combination or at the same time, and other elements which are well known in the medical field.

"Prevention" used in the present specification includes prevention of recurrence, extension, or onset of a bacterial infection in a patient.

"Treatment" used in the present specification includes bacterial killing and inhibition.

The term "compound of the present invention" used in the present specification includes not only a compound of Chemical Formula 1, but also a solvate, hydrate, or prodrug thereof. In addition, the term "compound of the present invention" also includes a pharmaceutically acceptable salt of the compound of the present invention when a pharmaceutically acceptable salt thereof is not mentioned. In an embodiment, the compounds of the present invention may exist as stereomerically pure compounds (for example, compounds substantially free of other stereoisomers (for example, 85% ee or greater, 90% ee or greater, 95% ee or greater, 97% ee or greater, or 99% ee or greater)). That is, when the compounds according to the present invention or salts thereof are tautomeric isomers and/or stereoisomers (for example, geometrical isomers and conformational isomers), each of isolated isomers and mixtures thereof is also included in the scope of the compounds of the present invention. When the compounds of the present invention or salts thereof have an asymmetric carbon in their structures, optically active compounds and racemic mixtures thereof are also included in the scope of the compounds of the present invention. For example, when the compounds of the present invention have a sulfoxide (SOR) structure, these compounds may have chirality. The compounds of the present invention include isomeric R and S forms, and mixtures of the R and S forms are also included in the scope of the compounds of the present invention.

In addition, the compounds of the present invention may exist in either a Keto form or an Enol form, and both of these forms are included in the scope of the compounds of the present invention.

The term "solvate" used in the present specification refers to a compound of the present invention containing a stoichiometric or non-stoichiometric amount of a solvent bound by non-covalent intermolecular forces, or a pharmaceutically acceptable salt thereof. Preferred solvents are volatile and non-toxic, and may be administered to humans in trace amounts.

The term "hydrate" used in the present specification refers to a compound of the present invention containing a stoichiometric or non-stoichiometric amount of water bound by non-covalent intermolecular forces, or a pharmaceutically acceptable salt thereof.

A prodrug may be used for modifying or improving a physical and/or pharmacokinetic profile of a parent compound, and may be formed when the parent compound contains an appropriate group or substituent which may be derived to form a prodrug. When a certain compound (prodrug) is decomposed in the body to produce the compound of the present invention or a salt thereof, the compound is also included in the scope of the present invention. Unless otherwise used and indicated in the present specification, the term "prodrug" refers to the compound of the present invention that may hydrolyze, oxidize, and otherwise react under biological conditions (in vitro or in vivo) for supplying an active compound, in particular, the compound of the present invention. Examples of the prodrug include compounds that biohydrolyze to produce the compound of the present invention, including biohydrolyzable moieties such as biohydrolyzable amides, biohydrolyzable esters, biohydrolyzable carbamates, biohydrolyzable carbonates, biohydrolyzable ureides, and biohydrolyzable phosphate analogs, but are not limited to these specific embodiments. Preferably, a prodrug of a compound having a carboxyl functional group is a lower alkyl ester of a carboxylic acid. A carboxylic ester is usually formed by esterifying a part of a carboxylic acid present in a molecule. The prodrug may be easily prepared using a known method such as those described in Burger's Medicinal Chemistry and Drug Discovery $6^{th}$ ed. (Donald J. Abrahamed, 2001, Wiley) and Design and Application of Prodrugs (H. Bundgaard ed., 1985, Harwood Academic Publishers Gmfh).

The term "purified" used in the present specification indicates that, when a substance is isolated, the isolate is at least 90% pure, at least 95% pure in an embodiment, at least 99% pure in another embodiment, and at least 99.9% pure in still another embodiment.

The term "hydrido" used in the present specification refers to a single —H atom (H), and is used interchangeably with the symbol "H" or the term "hydrogen".

When a substituent is described as "substitution or substituted", the substituent may be (1) unsubstituted or (2) substituted with one or more of the defined substituents. When the substitutable position is unsubstituted, the default substituent is a hydrido radical.

The singular forms "a" and "an" used in the present specification may include plural forms unless the context clearly dictates otherwise.

The term "pharmaceutically acceptable" used in the present specification means that it is suitable for use as a pharmaceutical formulation, generally considered to be safe for such use, and officially approved by a regulatory agency of a national or state government for such use, or being listed in the Korean Pharmacopoeia or the U.S. Pharmacopoeia.

The present invention provides a novel compound that may have an excellent effect as an antibiotic, or a solvate, hydrate, prodrug, isomer, or pharmaceutically acceptable salt thereof, and the novel compound of the present invention is represented by the following Chemical Formula 1.

[Chemical Formula 1]

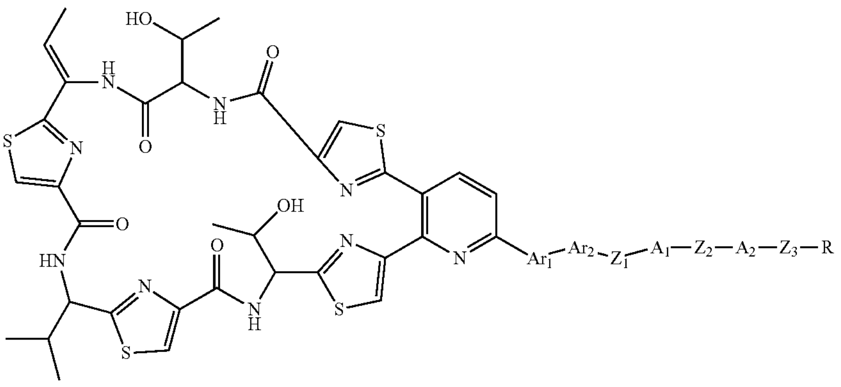

(In Chemical Formula 1, $Ar_1$ and $Ar_2$ are each independently a single bond, substituted or unsubstituted C6-C20 arylene, or substituted or unsubstituted C3-C20 heteroarylene;

$Z_1$ to $Z_3$ are each independently a single bond, —$CONR_1$—, —$NR_2CO$—, —COO—, —OCO—, —$CR_3R_4$—, —$NR_5COO$—, —$NR_6$—, —S—, —O—, —$SO_2$—, or —$OCONR_7$—;

$R_1$ to $R_7$ are each independently hydrogen, hydroxy, C1-C10 alkyl, carboxy C1-C10 alkyl, or C1-C10 alkoxycarbonyl C1-C10 alkyl;

$A_1$ is

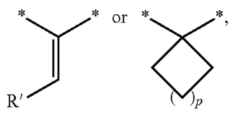

R' is hydrogen, C1-C10 alkyl, C2-C10 alkenyl, or C1-C10 alkoxy C1-C10 alkyl, and p is an integer of 0 to 4;

C1-C10 alkyl, C3-C10 heterocyclocarbonyl, allylamino, C1-C10 alkylsulfonyl, aminosulfonyl, amino C1-C10 alkyl, hydroxy C1-C10 alkyl, dihydroxy C1-C10 alkyl, cyano C1-C10 alkyl, C1-C10 alkylamino, di C1-C10 alkylamino, C6-C20 arylamino, di C6-C20 arylamino, C3-C20 heteroaryl, halo C6-C20 aryl, halo C1-C10 alkyl C6-C20 aryl, C6-C20 aryl, C3-C10 cycloalkyl, C3-C10 cycloalkylcarbonyl, C1-C10 alkoxycarbonyl C1-C10 alkyl, and carboxy C1-C10 alkyl.

More preferably, in Chemical Formula 1 according to an embodiment of the present invention, $Ar_1$ may be C3-C20 heteroarylene; $Ar_2$ may be a single bond, C6-C20 arylene, or C3-C20 heteroarylene; $Z_1$ may be a single bond or —$CONR_1$—; $Z_2$ may be a single bond, —$CONR_1$—, —$NR_2CO$—, or —COO—; $Z_3$ may be a single bond, —$CONR_1$—, —$NR_2CO$—, —$NR_5COO$—, —$NR_6$—, —S—, or —$OCONR_7$—; and $R_1$, $R_2$, and $R_5$ to $R_7$ may be each independently hydrogen, hydroxy, C1-C10 alkyl, C1-C10 alkoxycarbonyl C1-C10 alkyl, or carboxy C1-C10 alkyl.

The compound of Chemical Formula 1 according to an embodiment of the present invention may be represented by the following Chemical Formula 2.

[Chemical Formula 2]

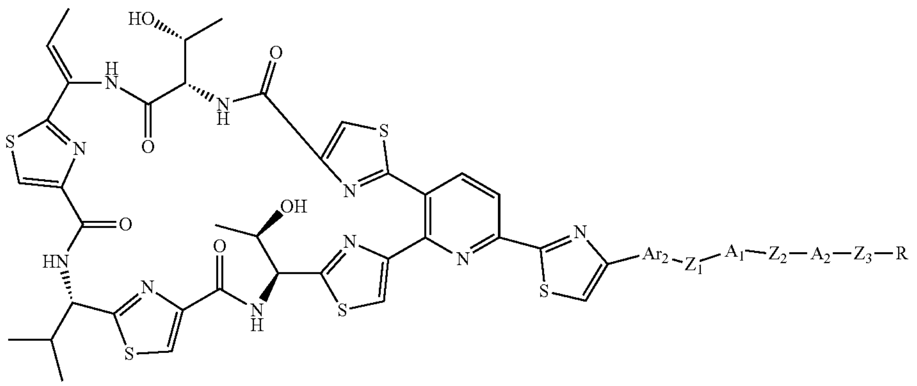

$A_2$ is a single bond, C1-C10 alkylene, C3-C10 cycloalkylene, C3-C10 heterocycloalkylene, C6-C20 arylene, or C6-C20 heteroarylene; and R is hydrogen, halogen, amino, hydroxy, —$B(OH)_2$, substituted or unsubstituted halo C1-C10 alkyl, substituted or unsubstituted C1-C10 alkyl, substituted or unsubstituted C2-C10 alkenyl, substituted or unsubstituted C3-C10 cycloalkyl, substituted or unsubstituted C3-C10 heterocycloalkyl, substituted or unsubstituted C6-C20 aryl, or substituted or unsubstituted C3-C20 heteroaryl.)

The novel compound of the present invention has a chemical structure completely different from that of the conventional antibiotic and has a significantly excellent effect.

Furthermore, the novel compound of the present invention is effective in killing and inhibiting various bacteria.

Preferably, in Chemical Formula 1 according to an embodiment of the present invention, the arylene or heteroarylene of $Ar_1$ and $Ar_2$ and the haloalkyl, alkyl, alkenyl, cycloalkyl, heterocycloalkyl, aryl, or heteroaryl of R may be further substituted with one or more selected from the group consisting of halogen, amino, nitro, hydroxy, a carboxylic acid group, —$B(OH)_2$, C1-C10 alkylcarbonyl, C1-C10 alkoxycarbonyl, C2-C10 alkenyl, C1-C10 alkyl, halo (In Chemical Formula 2, $Ar_2$ is a single bond, substituted or unsubstituted C6-C20 arylene, or substituted or unsubstituted C3-C20 heteroarylene;

$Z_1$ to $Z_3$ are each independently a single bond, —$CONR_1$—, —$NR_2CO$—, —COO—, —OCO—, —$CR_3R_4$—, —$NR_5COO$—, —$NR_6$—, —S—, —O—, —$SO_2$—, or —$OCONR_7$—;

$R_1$ to $R_7$ are each independently hydrogen, hydroxy, C1-C10 alkyl, carboxy C1-C10 alkyl, or C1-C10 alkoxycarbonyl C1-C10 alkyl;

$A_1$ is

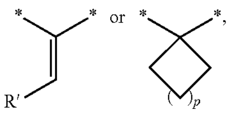

R' is hydrogen, C1-C10 alkyl, C2-C10 alkenyl, or C1-C10 alkoxy C1-C10 alkyl, and p is an integer of 0 to 4;

$A_2$ is a single bond, C1-C10 alkylene, C3-C10 cycloalkylene, C3-C10 heterocycloalkylene, C6-C20 arylene, or C6-C20 heteroarylene; and R is hydrogen, halogen, amino, hydroxy, —B(OH)$_2$, substituted or unsubstituted halo C1-C10 alkyl, substituted or unsubstituted C1-C10 alkyl, substituted or unsubstituted C2-C10 alkenyl, substituted or unsubstituted C3-C10 cycloalkyl, substituted or unsubstituted C3-C10 heterocycloalkyl, substituted or unsubstituted C6-C20 aryl, or substituted or unsubstituted C3-C20 heteroaryl.)

Preferably, in Chemical Formula 2 according to an embodiment of the present invention, Ar$_2$ may be a single bond, C6-C20 arylene, or C3-C20 heteroarylene; Z$_1$ may be a single bond or —CONR$_1$—; Z$_2$ may be a single bond, —CONR$_1$—, —NR$_2$CO—, or —COO—; Z$_3$ may be a single bond, —CONR$_1$—, —NR$_2$CO—, —NR$_5$COO—, —NR$_6$—, —S—, or —OCONR$_7$—; R$_1$, R$_2$, and R$_5$ to R$_7$ may be each independently hydrogen, hydroxy, C1-C10 alkyl, C1-C10 alkoxycarbonyl C1-C10 alkyl, or carboxy C1-C10 alkyl; A$_1$ may be

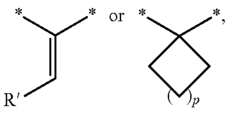

R' may be hydrogen or C1-C10 alkyl, and p may be an integer of 0 to 2; A$_2$ may be a single bond, C1-C10 alkylene, or C3-C10 heterocycloalkylene; R may be hydrogen, halogen, amino, hydroxy, —B(OH)$_2$, C1-C10 alkyl, C2-C10 alkenyl, C3-C10 cycloalkyl, C3-C10 heterocycloalkyl, C6-C20 aryl, or C3-C20 heteroaryl; and the arylene or heteroarylene of Ar$_2$ and the alkyl, alkenyl, cycloalkyl, heterocycloalkyl, aryl, or heteroaryl of R may be further substituted with one or more selected from the group consisting of halogen, amino, nitro, hydroxy, a carboxylic acid group, —B(OH)$_2$, C1-C10 alkylcarbonyl, C1-C10 alkoxycarbonyl, C2-C10 alkenyl, C1-C10 alkyl, halo C1-C10 alkyl, C3-C10 heterocyclocarbonyl, allylamino, C1-C10 alkylsulfonyl, aminosulfonyl, amino C1-C10 alkyl, hydroxy C1-C10 alkyl, dihydroxy C1-C10 alkyl, cyano C1-C10 alkyl, C1-C10 alkylamino, di C1-C10 alkylamino, C6-C20 arylamino, di C6-C20 arylamino, C3-C20 heteroaryl, halo C6-C20 aryl, halo C1-C10 alkyl C6-C20 aryl, C6-C20 aryl, C3-C10 cycloalkyl, C3-C10 cycloalkylcarbonyl, C1-C10 alkoxycarbonyl C1-C10 alkyl, and carboxy C1-C10 alkyl.

In terms of having a more excellent effect as an antibiotic, preferably, Chemical Formula 1 according to an embodiment of the present invention may be represented by the following Chemical Formula 3.

[Chemical Formula 3]

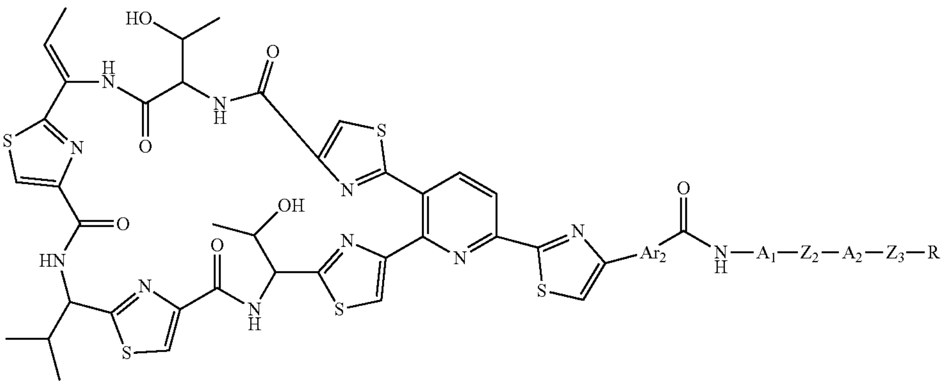

(In Chemical Formula 3,

Ar$_2$ is substituted or unsubstituted C6-C20 arylene or substituted or unsubstituted C3-C20 heteroarylene;

Z$_2$ is a single bond, —CONR$_1$—, —NR$_2$CO—, or —COO—;

Z$_3$ is a single bond, —CONR$_1$—, —NR$_2$CO—, —NR$_5$COO—, —NR$_6$—, —S—, or —OCONR$_7$—;

R$_1$, R$_2$, and R$_5$ to R$_7$ are each independently hydrogen, hydroxy, or C1-C10 alkyl;

A$_1$ is

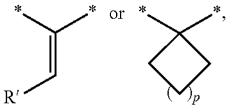

R' is hydrogen or C1-C10 alkyl, and p is an integer of 0 to 2;

A$_2$ is a single bond, C1-C10 alkylene, or C3-C10 heterocycloalkylene; and

R is hydrogen, halogen, amino, hydroxy, —B(OH)$_2$, substituted or unsubstituted C1-C10 alkyl, substituted or unsubstituted C2-C10 alkenyl, substituted or unsubstituted C3-C10 cycloalkyl, substituted or unsubstituted C3-C10 heterocycloalkyl, substituted or unsubstituted C6-C20 aryl, or substituted or unsubstituted C3-C20 heteroaryl.)

Preferably, in Chemical Formula 3 according to an embodiment of the present invention, Ar$_2$ may be C6-C20 arylene or C3-C20 heteroarylene; Z$_2$ may be a single bond, —CONR$_1$—, —NR$_2$CO—, or —COO—; Z$_3$ may be a single bond, —CONR$_1$—, —NR$_2$CO—, —NR$_5$COO—, —NR$_6$—, —S—, or —OCONR$_7$—; R$_1$, R$_2$, and R$_5$ to R$_7$ may be each independently hydrogen, hydroxy, or C1-C10 alkyl; A$_1$ may be

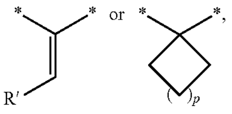

R' may be hydrogen or C1-C10 alkyl, and p may be an integer of 0 to 2; $A_2$ may be a single bond, C1-C10 alkylene, or C3-C10 heterocycloalkylene; R may be hydrogen, halogen, amino, hydroxy, —$B(OH)_2$, C1-C10 alkyl, C2-C10 alkenyl, C3-C10 cycloalkyl, C3-C10 heterocycloalkyl, C6-C20 aryl, or C3-C20 heteroaryl; and the arylene and heteroarylene of $Ar_2$ and the alkyl, alkenyl, cycloalkyl, heterocycloalkyl, aryl, and heteroaryl of R may be further substituted with one or more selected from the group consisting of halogen, amino, nitro, hydroxy, a carboxylic acid group, —$B(OH)_2$, C1-C10 alkylcarbonyl, C1-C10 alkoxycarbonyl, C2-C10 alkenyl, C1-C10 alkyl, halo C1-C10 alkyl, C3-C10 heterocyclocarbonyl, allylamino, C1-C10 alkylsulfonyl, aminosulfonyl, amino C1-C10 Alkyl, hydroxy C1-C10 alkyl, dihydroxy C1-C10 alkyl, cyano C1-C10 alkyl, C1-C10 alkylamino, di C1-C10 alkylamino, C6-C20 arylamino, di C6-C20 arylamino, C3-C20 heteroaryl, halo C6-C20 aryl, halo C1-C10 alkyl C6-C20 aryl, C6-C20 aryl, C3-C10 cycloalkyl, C3-C10 cycloalkylcarbonyl, C1-C10 alkoxycarbonyl C1-C10 alkyl, and carboxy C1-C10 alkyl, and more preferably, in Chemical Formula 3, $Ar_2$ may be selected from the following structures.

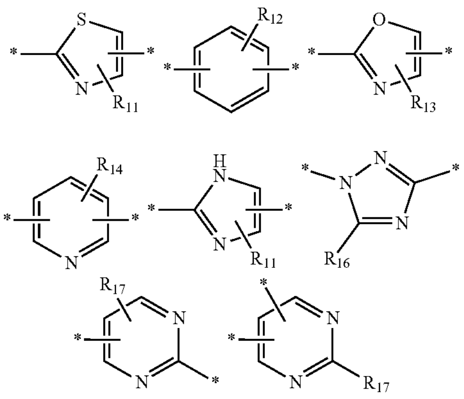

(In the structural formulas, $R_{11}$ to $R_{17}$ are each independently hydrogen, halogen, or C1-C10 alkyl.)

More preferably, in Chemical Formula 3 according to an embodiment of the present invention, $Ar_2$ is selected from the following structures:

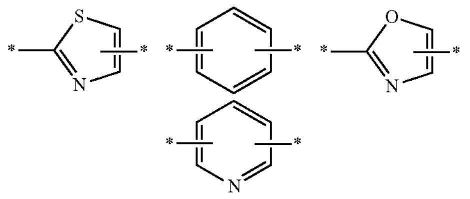

$Z_2$ may be a single bond, —$CONR_1$—, —$NR_2CO$—, or —COO—;

$Z_3$ may be a single bond, —$NR_2CO$—, —$NR_5COO$—, —$NR_6$—, or —S—;

$R_1$, $R_2$, $R_5$, and $R_6$ may be each independently hydrogen, hydroxy, or C1-C10 alkyl;

$A_1$ may be

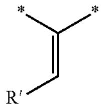 or 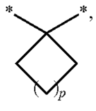,

R' may be C1-C10 alkyl, and p may be an integer of 0 to 2;

$A_2$ may be a single bond or C1-C10 alkylene;

R may be hydrogen, halogen, amino, hydroxy, —$B(OH)_2$, C1-C10 alkyl, C2-C10 alkenyl, C3-C10 cycloalkyl, C3-C10 heterocycloalkyl, C6-C20 aryl, or C3-C20 heteroaryl; and the alkyl, alkenyl, cycloalkyl, heterocycloalkyl, aryl, or heteroaryl of R may be further substituted with one or more selected from the group consisting of halogen, amino, nitro, hydroxy, a carboxylic acid group, —$B(OH)_2$, C1-C10 alkylcarbonyl, C1-C10 alkoxycarbonyl, C2-C10 alkenyl, C1-C10 alkyl, halo C1-C10 alkyl, C3-C10 heterocyclocarbonyl, allylamino, C1-C10 alkylsulfonyl, aminosulfonyl, amino C1—C10 alkyl, hydroxy C1-C10 alkyl, dihydroxy C1-C10 alkyl, cyano C1-C10 alkyl, C1-C10 alkylamino, di C1-C10 alkylamino, C6-C20 arylamino, di C6-C20 arylamino, C3-C20 heteroaryl, halo C6-C20 aryl, halo C1-C10 alkyl C6-C20 aryl, C6-C20 aryl, C3-C10 cycloalkyl, C3-C10 cycloalkylcarbonyl, C1-C10 alkoxycarbonyl C1-C10 alkyl, and carboxy C1-C10 alkyl.

Preferably, Chemical Formula 3 according to an embodiment of the present invention may be represented by the following Chemical Formula 4-1 or 4-2.

[Chemiical Formula 4-1]

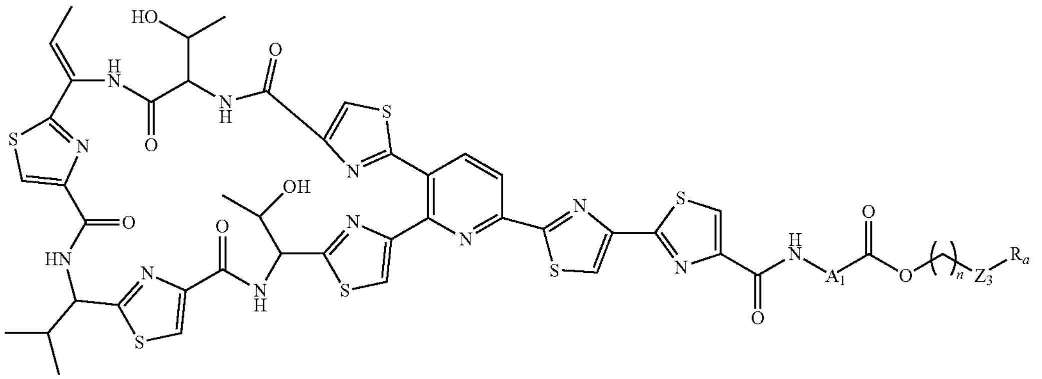

-continued

[Chemical Formula 4-2]

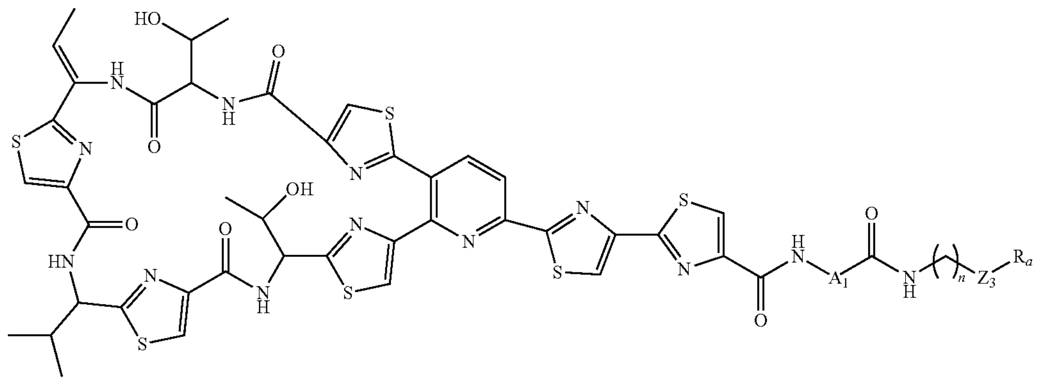

(In Chemical Formulas 4-1 and 4-2, $A_1$ is

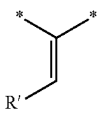
or
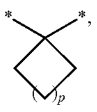
,

R' is C1-C10 alkyl, and p is an integer of 0 to 2;

n is an integer of 0 to 5;

$Z_3$ is a single bond or —$NR_6$—, and $R_6$ is hydrogen or C1-C10 alkyl;

$R_a$ is hydrogen, amino, or —$B(OH)_2$, or is any one selected from the following structures;

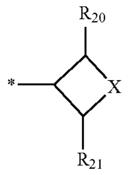
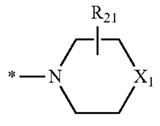
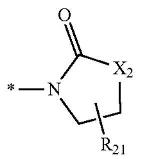
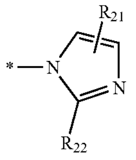
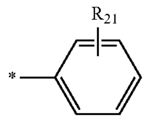
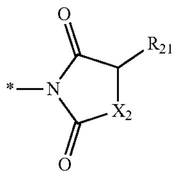
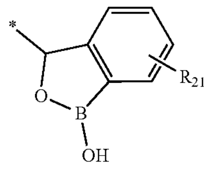
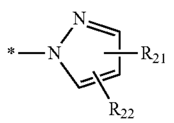
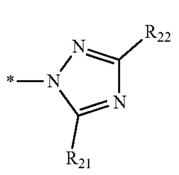
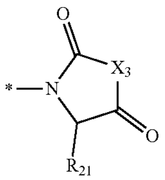

-continued

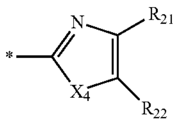
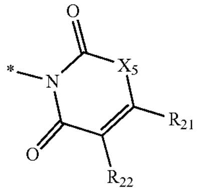

X is O or S;

$X_1$ is $NR_{31}$, O, S, or $SO_2$;

$X_2$ to $X_5$ are each independently $NR_{32}$, O, or S; and $R_{21}$ to $R_{22}$, $R_{31}$, and $R_{32}$ are each independently hydrogen, halogen, nitro, C1-C10 alkylcarbonyl, C1-C10 alkoxycarbonyl, C1-C10 alkyl, C1-C10 alkylsulfonyl, aminosulfonyl, hydroxy C1-C10 alkyl, dihydroxy C1-C10 alkyl, cyano C1-C10 alkyl, C3-C10 cycloalkyl, C1-C10 alkoxycarbonyl C1-C10 alkyl, or carboxy C1-C10 alkyl.)

More preferably, in an embodiment of the present invention, $R_a$ may be hydrogen, amino, or —$B(OH)_2$, or may be any one selected from the following structures:

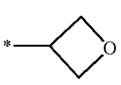
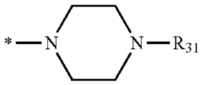
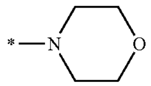
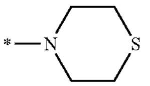
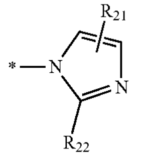
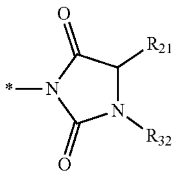
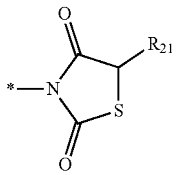
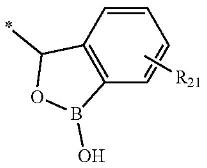
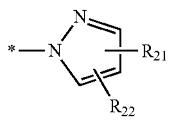

-continued

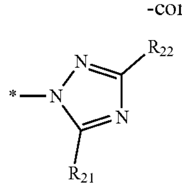

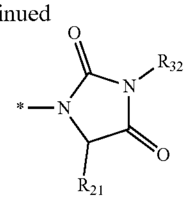

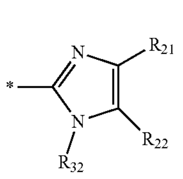

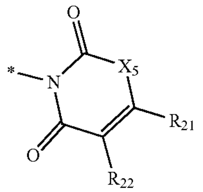

(in the structural formulas, $R_{21}$ and $R_{22}$ are each independently hydrogen, halogen, nitro, C1-C10 alkylcarbonyl, C1-C10 alkoxycarbonyl, C1-C10 alkyl, C1-C10 alkylsulfonyl, aminosulfonyl, hydroxy C1-C10 alkyl, dihydroxy C1-C10 alkyl, cyano C1-C10 alkyl, C3-C10 cycloalkyl, C1-C10 alkoxycarbonyl C1-C10 alkyl, or carboxy C1-C10 alkyl; and $R_{31}$ and $R_{32}$ are each independently hydrogen, C1-C10 alkylcarbonyl, C1-C10 alkoxycarbonyl, C1-C10 alkyl, C1-C10 alkylsulfonyl, aminosulfonyl, hydroxy C1-C10 alkyl, dihydroxy C1-C10 alkyl, cyano C1-C10 alkyl, C3-C10 cycloalkyl, C1-C10 alkoxycarbonyl C1-C10 alkyl, or carboxy C1-C10 alkyl).

More preferably, $R_{21}$ and $R_{22}$ may be each independently hydrogen, halogen, nitro, C1-C10 alkyl, or C3-C10 cycloalkyl; and $R_{31}$ and $R_{32}$ may be each independently hydrogen, C1-C10 alkyl, C1-C10 alkylsulfonyl, aminosulfonyl, hydroxy C1-C10 alkyl, dihydroxy C1-C10 alkyl, cyano C1-C10 alkyl, C3-C10 cycloalkyl, C1-C10 alkoxycarbonyl C1-C10 alkyl, or carboxy C1-C10 alkyl.

In Chemical Formula 4-1 according to an embodiment of the present invention, $Z_3$ may be a single bond.

In Chemical Formula 4-1 according to an embodiment of the present invention, $Z_3$ may be a single bond; and $R_a$ may be hydrogen, amino, or —$B(OH)_2$.

In Chemical Formula 4-2 according to an embodiment of the present invention, $Z_3$ may be a single bond or —NH—.

In Chemical Formula 4-2 according to an embodiment of the present invention, $Z_3$ may be —NH—; $R_a$ may be

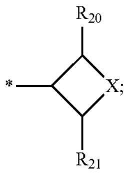

X may be O or S; and $R_{20}$ and $R_{21}$ may be each independently hydrogen, halogen, nitro, C1-C10 alkylcarbonyl, C1-C10 alkoxycarbonyl, C1-C10 alkyl, C1-C10 alkylsulfonyl, aminosulfonyl, hydroxy C1-C10 alkyl, dihydroxy C1-C10 alkyl, cyano C1-C10 alkyl, C3-C10 cycloalkyl, C1-C10 alkoxycarbonyl C1-C10 alkyl, or carboxy C1-C10 alkyl.

In Chemical Formula 4-2 according to an embodiment of the present invention, $Z_3$ may be a single bond; and $R_a$ may be hydrogen, amino, or —$B(OH)_2$, or may be any one selected from the following structures.

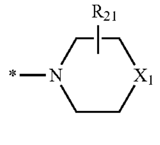

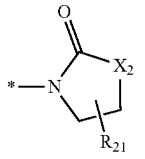

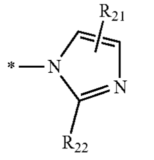

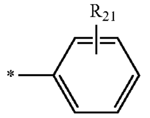

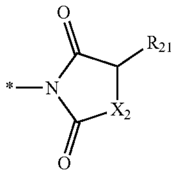

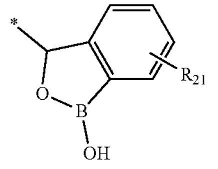

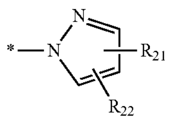

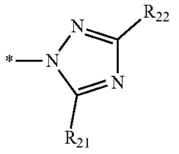

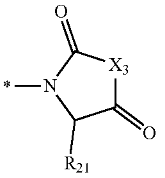

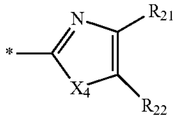

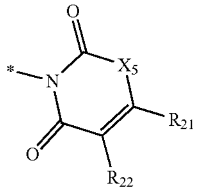

(In the structural formulas, $X_1$ is $NR_{31}$, O, S, or $SO_2$;

$X_2$ to $X_5$ are each independently $NR_{32}$, O, or S; and $R_{21}$, $R_{22}$, $R_{31}$, and $R_{32}$ are each independently hydrogen, halogen, nitro, C1-C10 alkylcarbonyl, C1-C10 alkoxycarbonyl, C1-C10 alkyl, C1-C10 alkylsulfonyl, aminosulfonyl, hydroxy C1-C10 alkyl, dihydroxy C1-C10 alkyl, alkyl, cyano C1-C10 alkyl, C3-C10 cycloalkyl, C1-C10 alkoxycarbonyl C1-C10 alkyl, or carboxy C1-C10 alkyl.)

Chemical Formula 1 according to an embodiment of the present invention may be any one of compounds represented by the following Chemical Formulas 5 to 12.

[Chemical Formula 5]
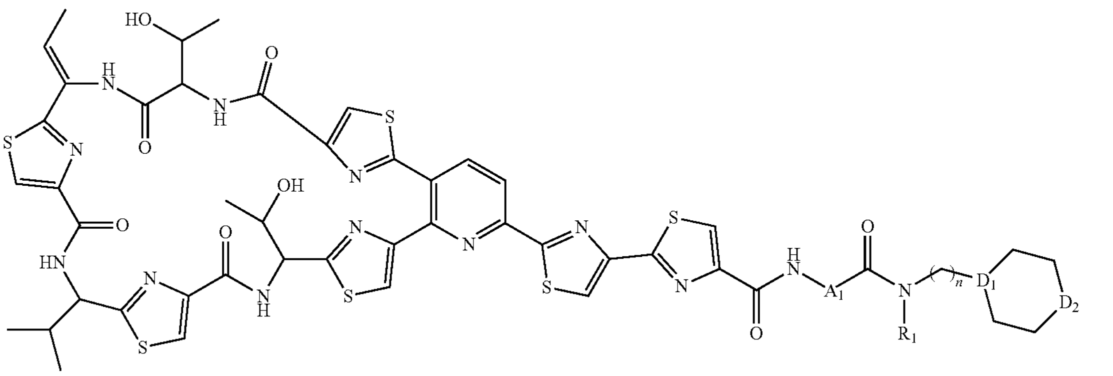
[Chemical Formula 6]
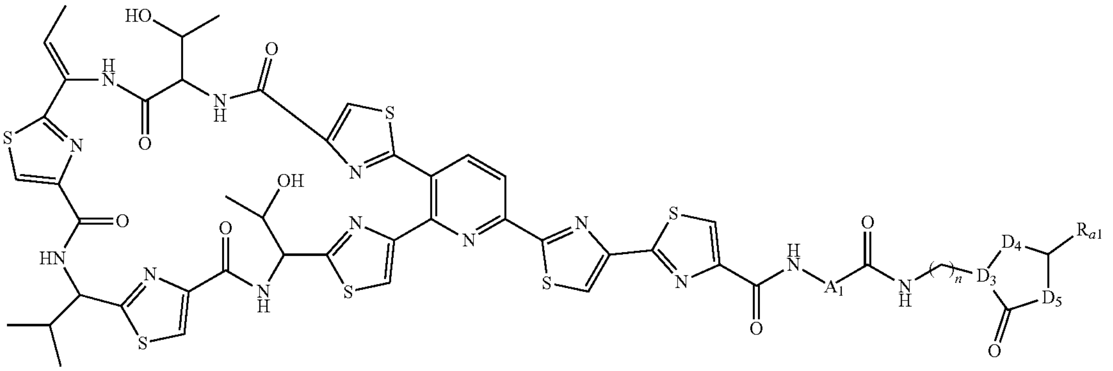
[Chemical Formula 7]
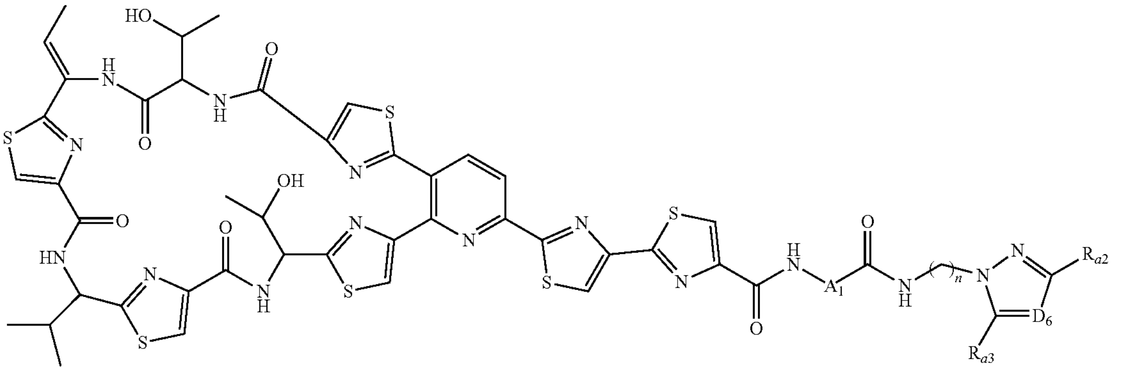
[Chemical Formula 8]
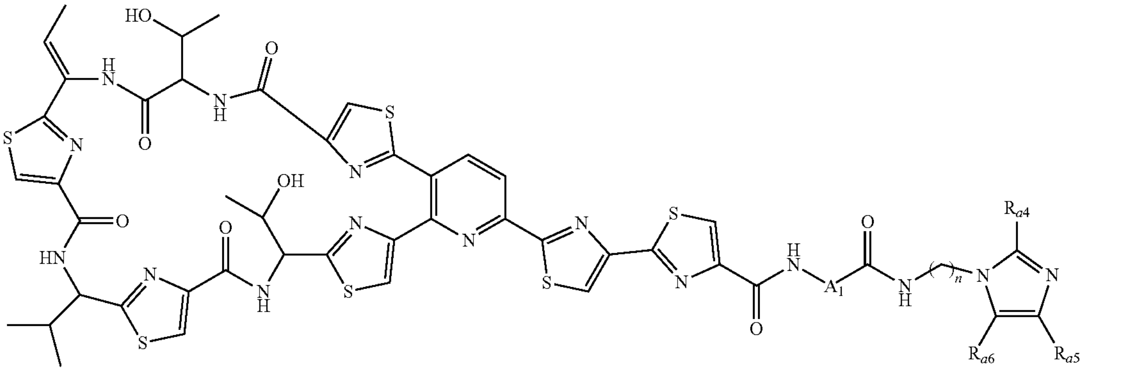

-continued
[Chemical Formula 9]
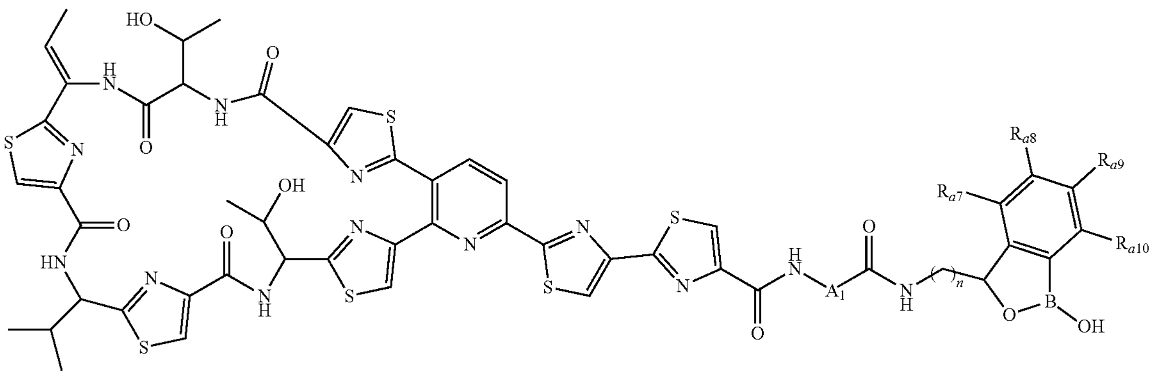
[Chemical Formula 10]
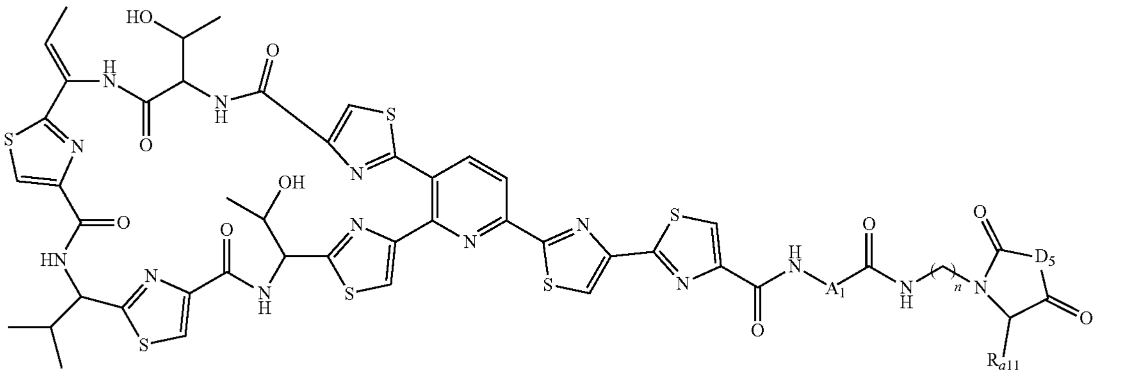
[Chemical Formula 11]
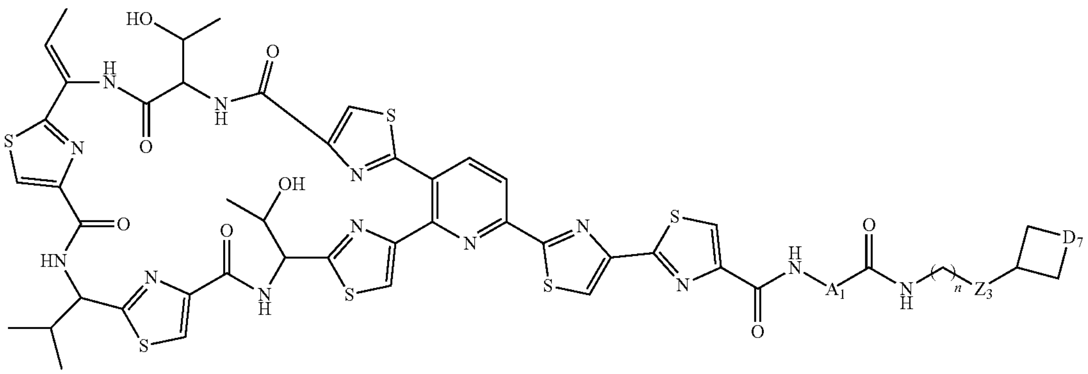
[Chemical Formula 12]
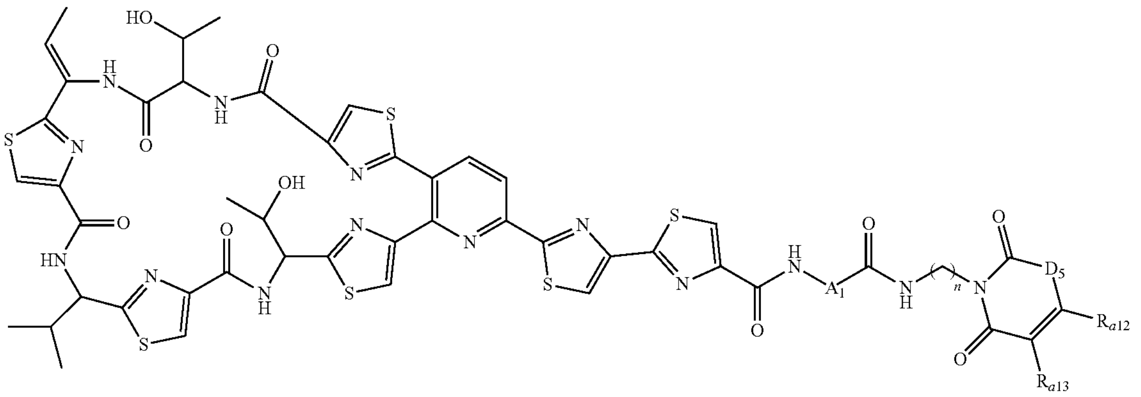

(In Chemical Formulas 5 to 12, $A_1$ is

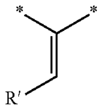

or

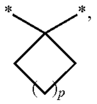

R' is C1-C10 alkyl, and p is an integer of 0 to 2;

$D_1$ is CH or N;

$D_2$ is O, S, $SO_2$, $C(R_{b1})(R_{b2})$, or $NR_{c1}$;

$D_3$ is CH or N;

$D_4$ is CO, NH, or CH;

$D_5$ is O, S, or $NR_{c2}$;

$D_6$ is $CR_{b3}$ or N;

$D_7$ is O or S;

$R_1$ is hydrogen or C1-C10 alkyl;

$Z_3$ is a single bond or —$NR_6$—, and $R_6$ is hydrogen or C1-C10 alkyl;

$R_{a1}$ to $R_{a13}$, $R_{b1}$ to $R_{b3}$, $R_{c1}$, and $R_{c2}$ are each independently hydrogen, halogen, amino, nitro, hydroxy, a carboxylic acid group, —$B(OH)_2$, C1-C10 alkylcarbonyl, C1-C10 alkoxycarbonyl, C2-C10 alkenyl, C1-C10 alkyl, halo C1-C10 alkyl, C3-C10 heterocyclocarbonyl, allylamino, C1-C10 alkylsulfonyl, aminosulfonyl, amino C1-C10 alkyl, hydroxy C1-C10 alkyl, dihydroxy C1-C10 alkyl, cyano C1-C10 alkyl, C1-C10 alkylamino, di C1-C10 alkylamino, C6-C20 arylamino, di C6-C20 arylamino, C3-C20 heteroaryl, halo C6-C20 aryl, halo C1-C10 alkyl C6-C20 aryl, C6-C20 aryl, C3-C10 cycloalkyl, C3-C10 cycloalkylcarbonyl, C1-C10 alkoxycarbonyl C1-C10 alkyl, or carboxy C1-C10 alkyl; and n is an integer of 0 to 5.)

More preferably, in Chemical Formulas 5 to 12 according to an embodiment of the present invention, $A_1$ may be

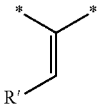

or

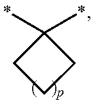

R' may be C1-C10 alkyl, and p may be an integer of 0 or 1; $D_1$ may be N; $D_2$ may be O, S, or $NR_{c1}$; $D_3$ may be N; $D_4$ may be CO, NH, or CH; $D_5$ may be O, S, or $NR_{c2}$; $D_6$ may be $CR_{b3}$ or N; $R_1$ may be hydrogen; $Z_3$ may be a single bond or —NH—; $R_{a1}$ to $R_{a13}$ and $R_{b3}$ may be each independently hydrogen, halogen, nitro, C1-C10 alkylcarbonyl, C1-C10 alkoxycarbonyl, C1-C10 alkyl, C1-C10 alkylsulfonyl, aminosulfonyl, hydroxy C1-C10 alkyl, dihydroxy C1-C10 alkyl, cyano C1-C10 alkyl, C3-C10 cycloalkyl, C1-C10 alkoxycarbonyl C1-C10 alkyl, or carboxy C1-C10 alkyl; $R_{c1}$ and $R_{c2}$ may be each independently hydrogen, C1-C10 alkylcarbonyl, C1-C10 alkoxycarbonyl, C1-C10 alkyl, C1-C10 alkylsulfonyl, aminosulfonyl, hydroxy C1-C10 alkyl, dihydroxy C1-C10 alkyl, cyano C1-C10 alkyl, C3-C10 cycloalkyl, C1-C10 alkoxycarbonyl C1-C10 alkyl, or carboxy C1-C10 alkyl; and n may be an integer of 0 to 5.

Still more preferably, in Chemical Formulas 5 to 12 according to an embodiment of the present invention, $R_{a1}$ to $R_{a13}$ and $R_{b3}$ may be each independently hydrogen, halogen, nitro, C1-C10 alkyl, or C3-C10 cycloalkyl; $R_{c1}$ and $R_{c2}$ may be each independently hydrogen, C1-C10 alkyl, C1-C10 alkylsulfonyl, aminosulfonyl, hydroxy C1-C10 alkyl, dihydroxy C1-C10 alkyl, cyano C1-C10 alkyl, C3-C10 cycloalkyl, C1-C10 alkoxycarbonyl C1-C10 alkyl, or carboxy C1-C10 alkyl; and n may be an integer of 0 to 3.

Preferably, Chemical Formula 1 according to an embodiment of the present invention may be represented by the following Chemical Formula 13-1 or 13-2.

[Chemical Formula 13-1]

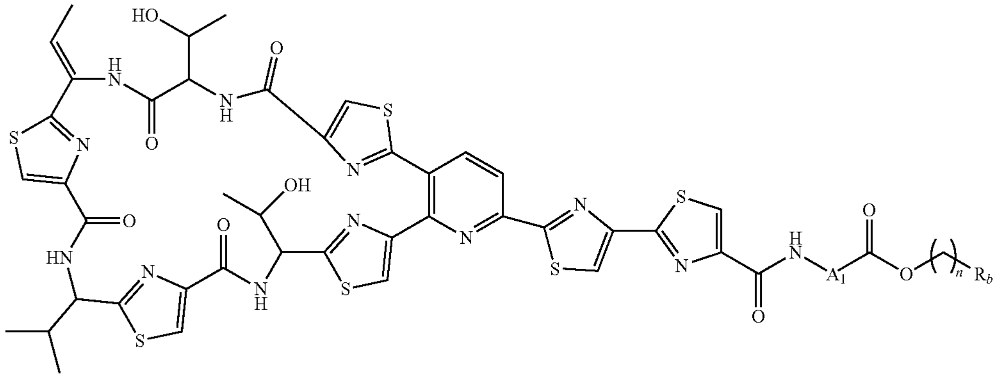

-continued

[Chemical Formula 13-2]

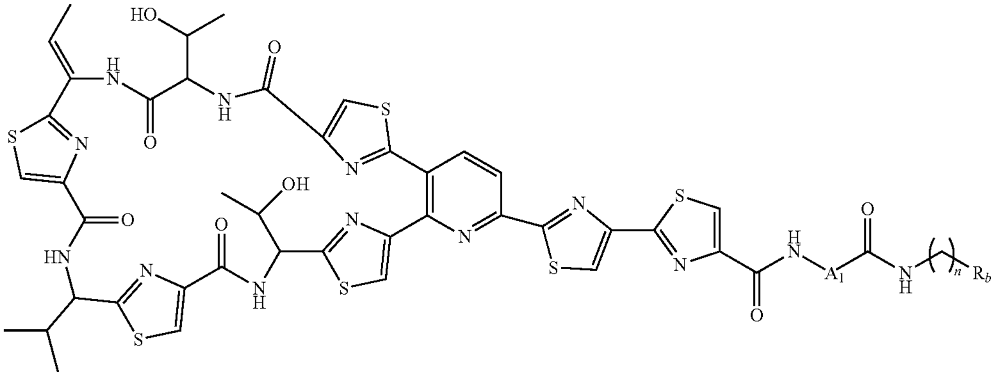

(In Chemical Formulas 13-1 and 13-2, $R_b$ is hydrogen, amino, or $—B(OH)_2$;

$A_1$ is

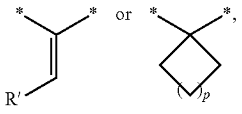

R' is C1-C10 alkyl, and p is an integer of 0 to 2; and n is an integer of 0 to 10.)

More preferably, in Chemical Formula 13-1 according to an embodiment of the present invention, $R_b$ may be hydrogen; $A_1$ may be

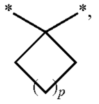

and p may be an integer of 0 or 1; and n may be an integer of 0.

More preferably, in Chemical Formula 13-2 according to an embodiment of the present invention, $A_1$ may be

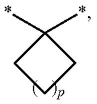

and p may be an integer of 0 or 1; and n may be an integer of 1 to 6.

Still more preferably, in Chemical Formula 13-2 according to an embodiment of the present invention, $R_b$ may be amino or $—B(OH)_2$; $A_1$ may be

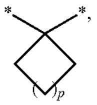

and p may be an integer of 0 or 1; and n may be an integer of 1 to 6.

The novel compound of the present invention may be selected from, but are not limited to, the following compounds.

1

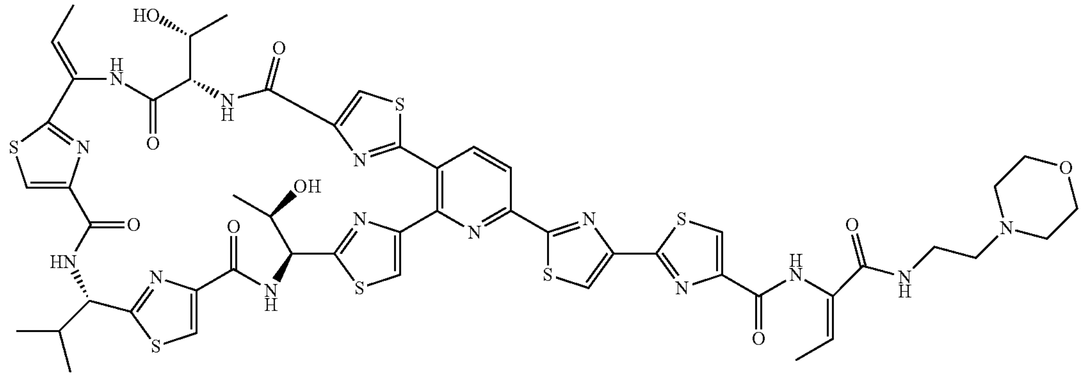

-continued
2
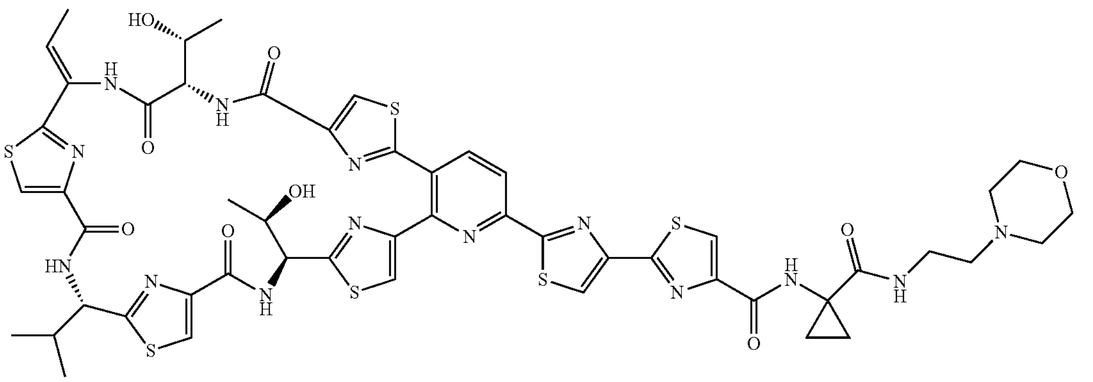
3
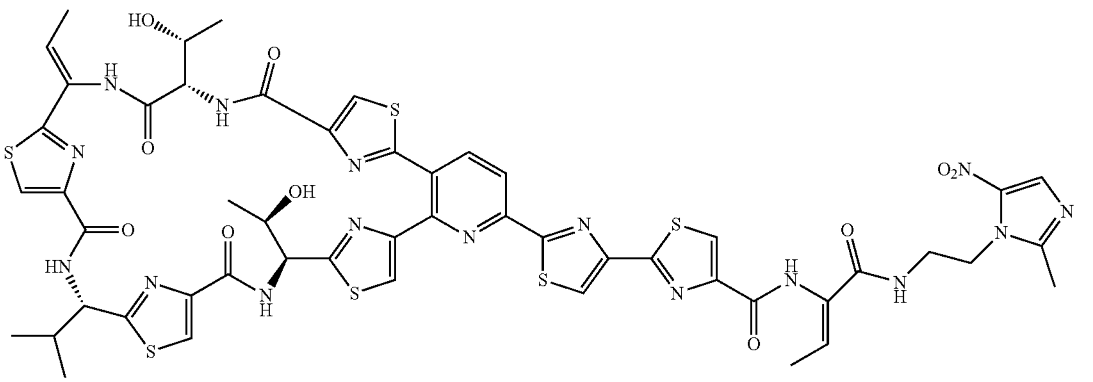
4
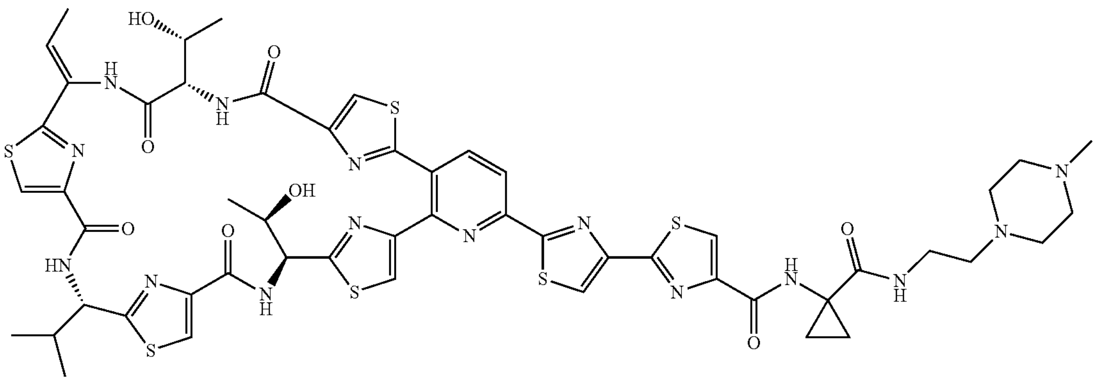
5
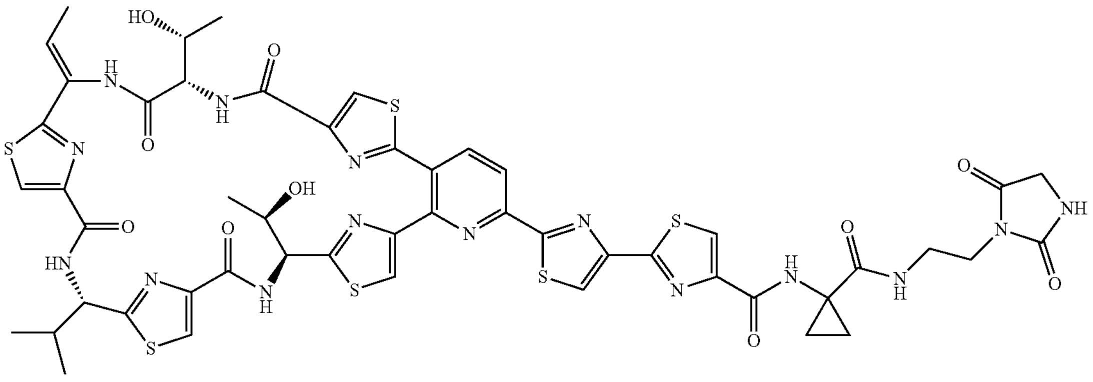

-continued
6
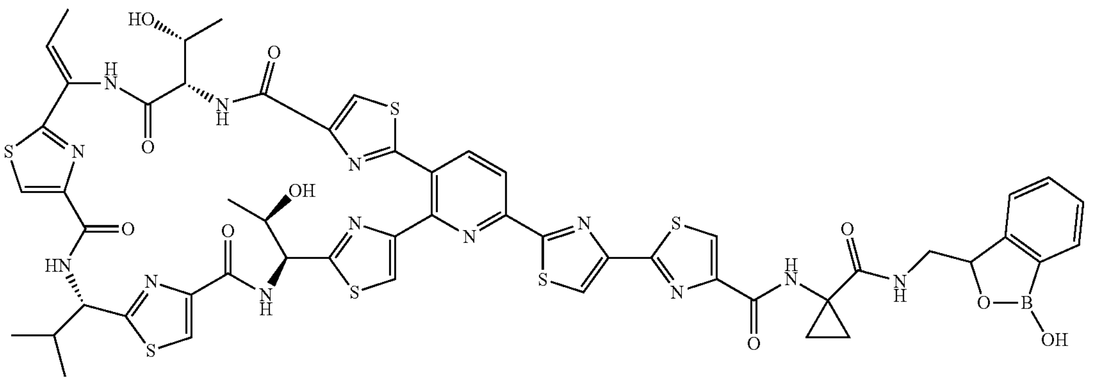
7
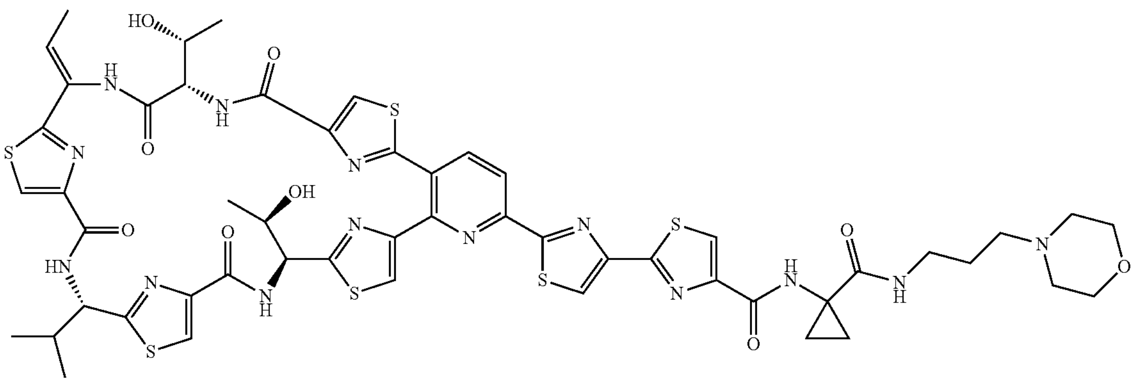
8
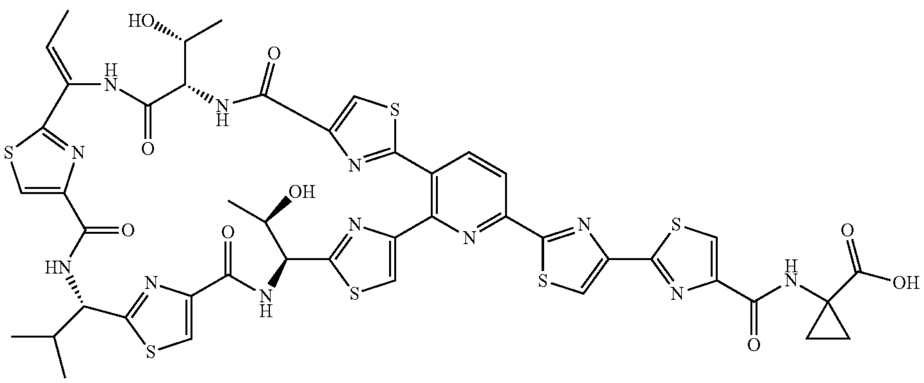
9
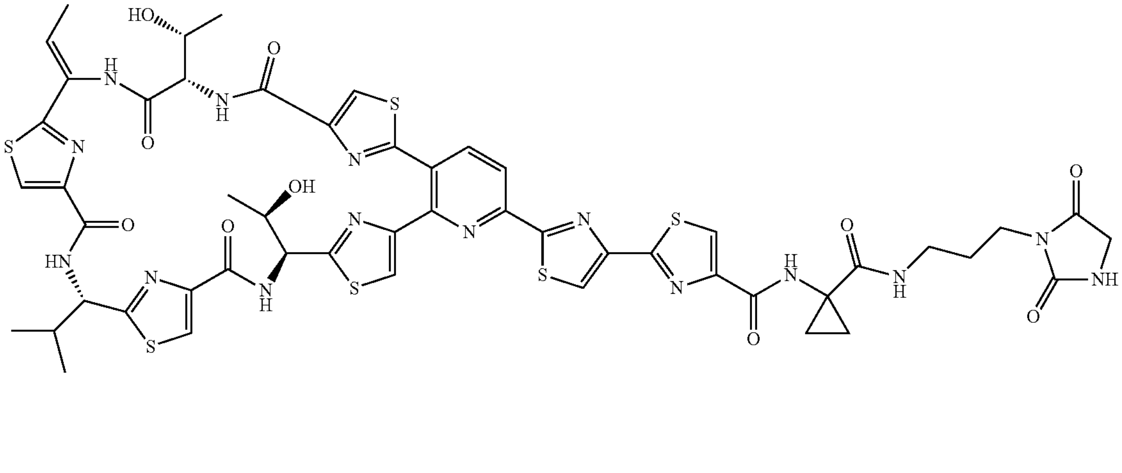

-continued
10
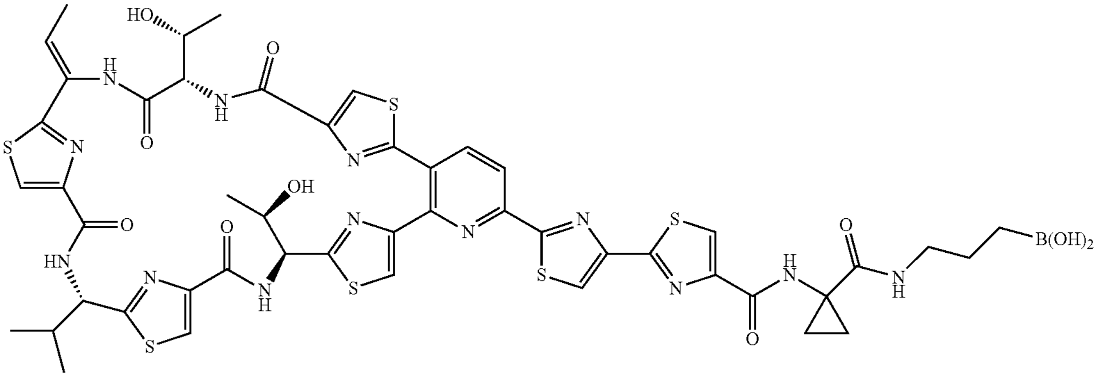
11
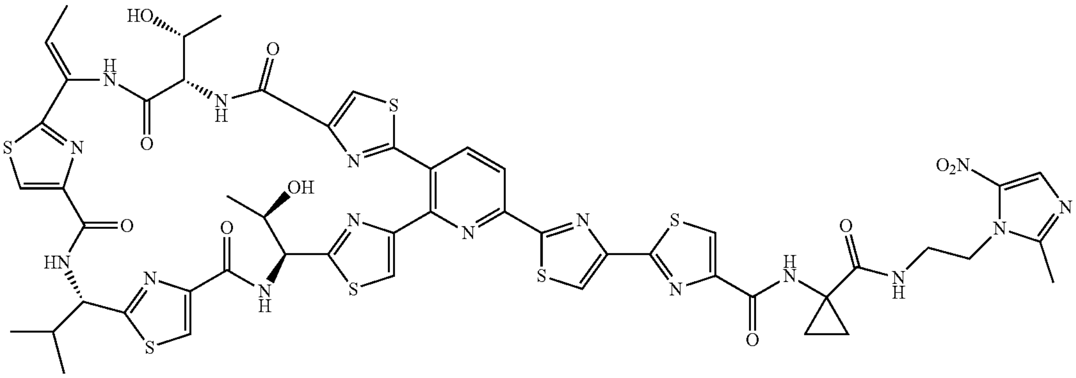
12
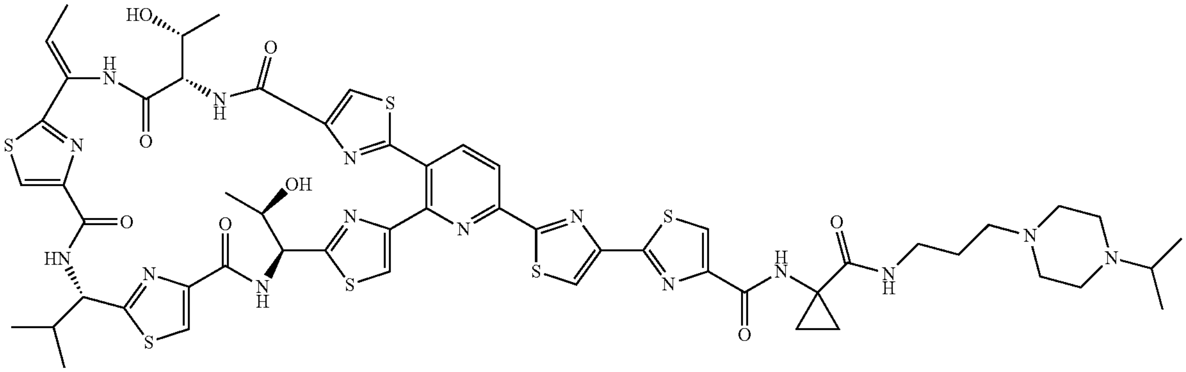
13
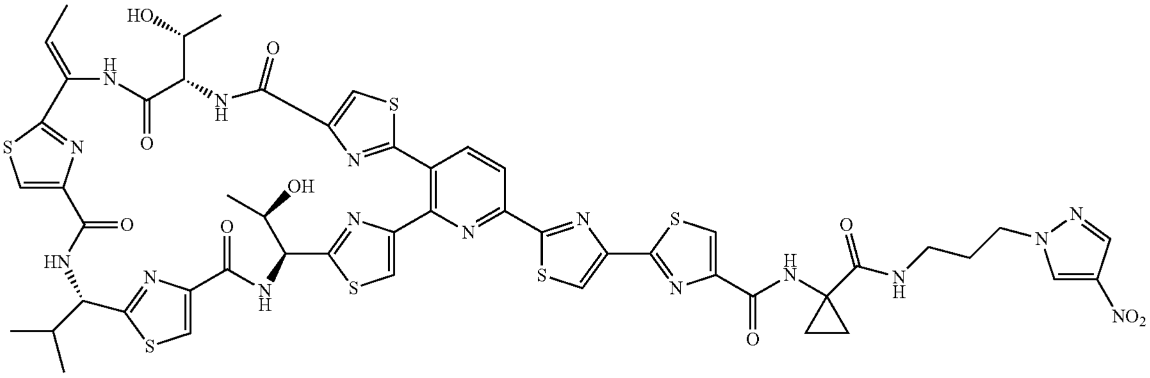

-continued
14
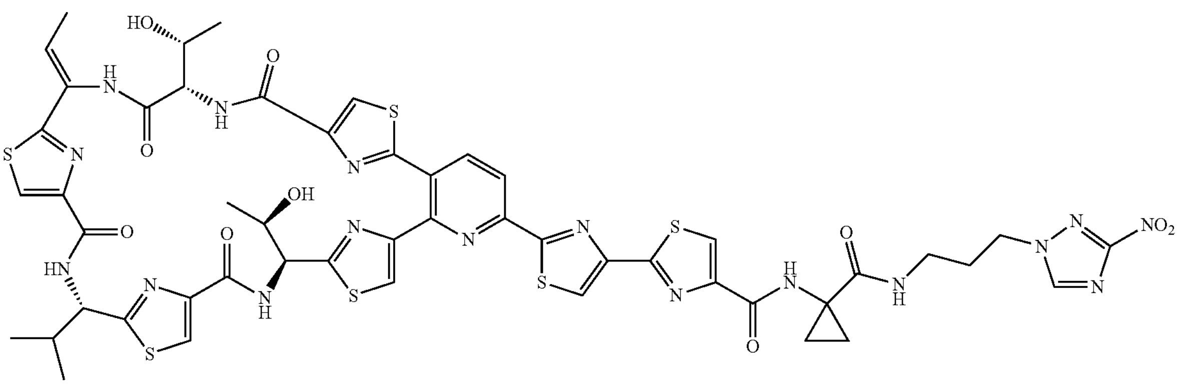
15
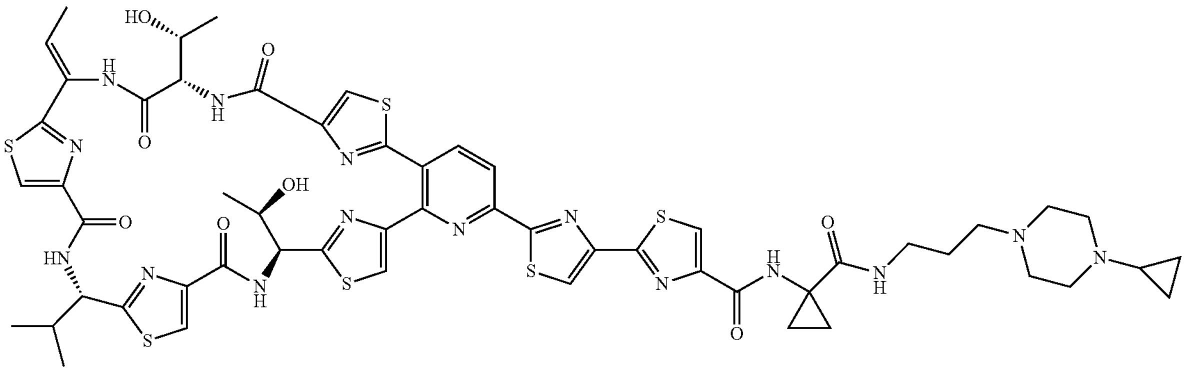
16
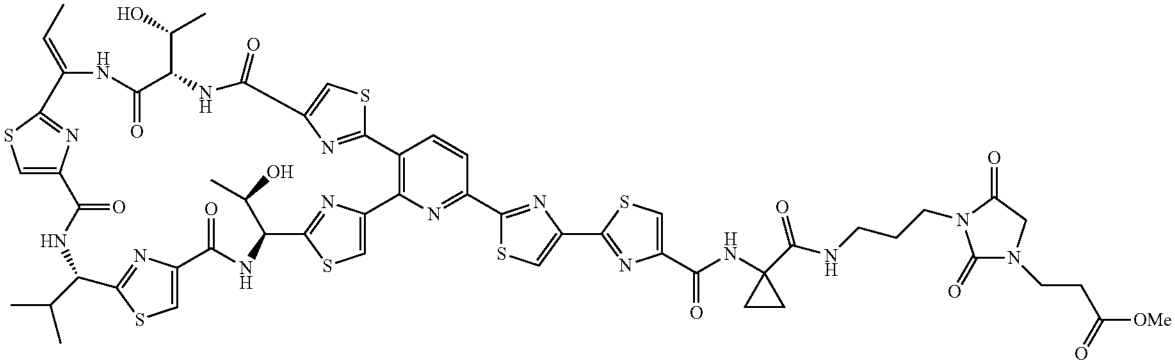
17
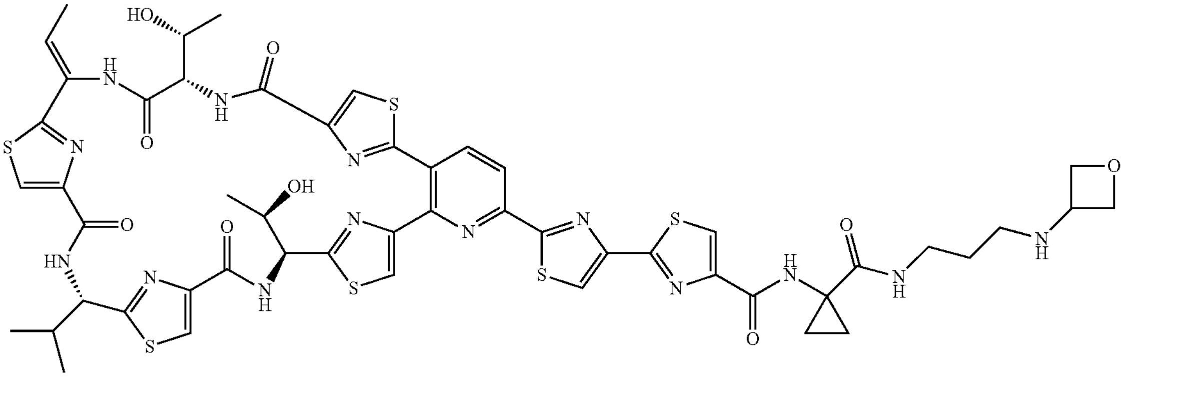

-continued
18
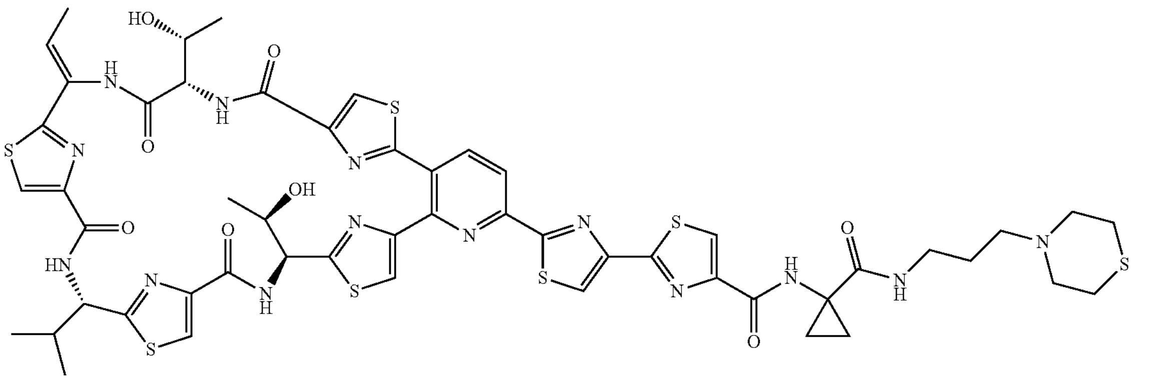
19
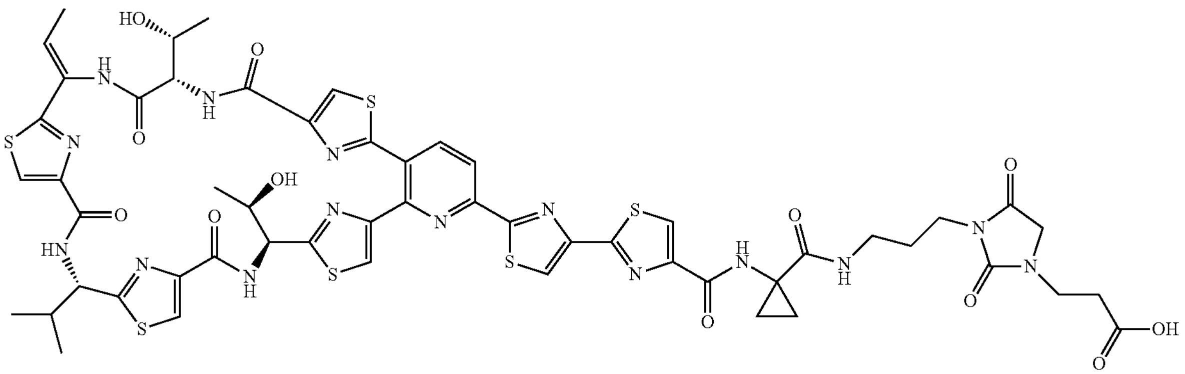
20
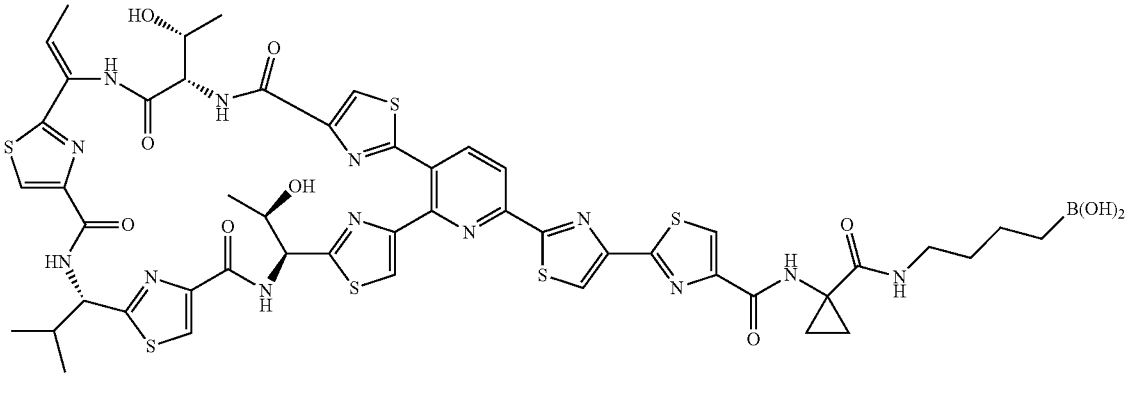
21
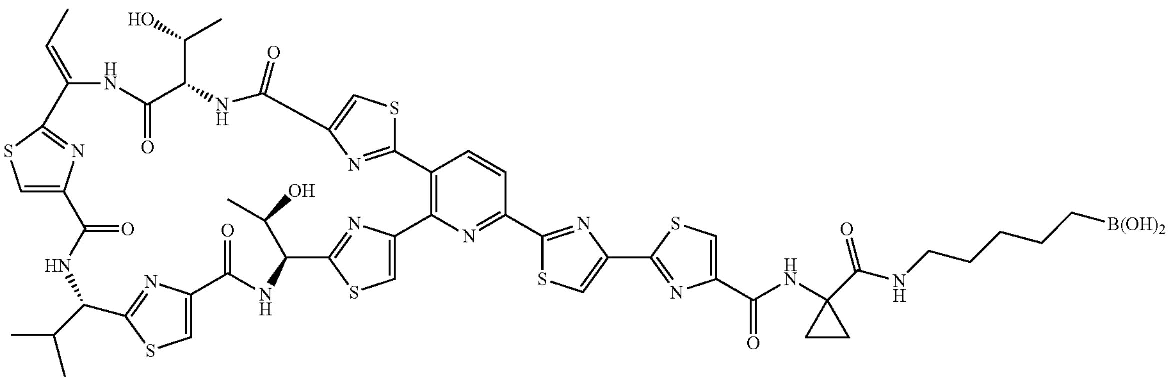

-continued
22
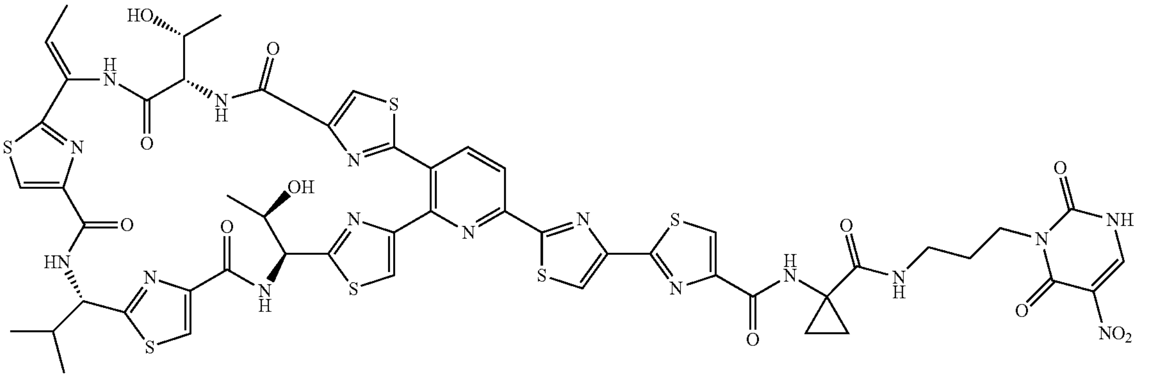
23
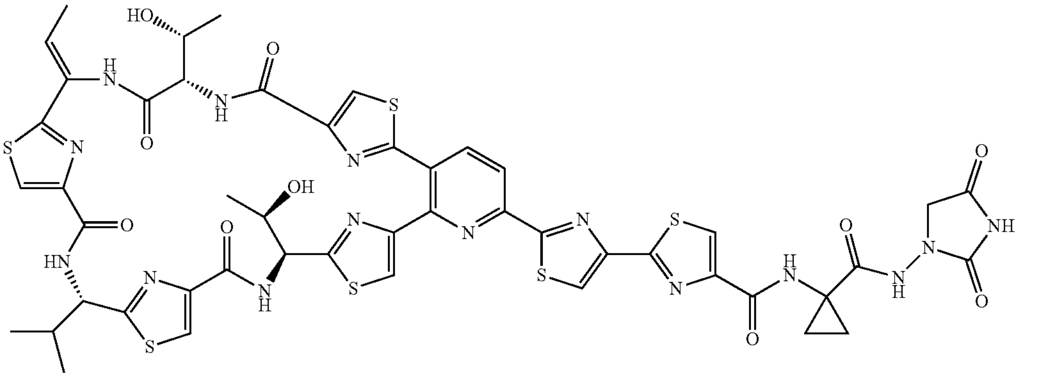
24
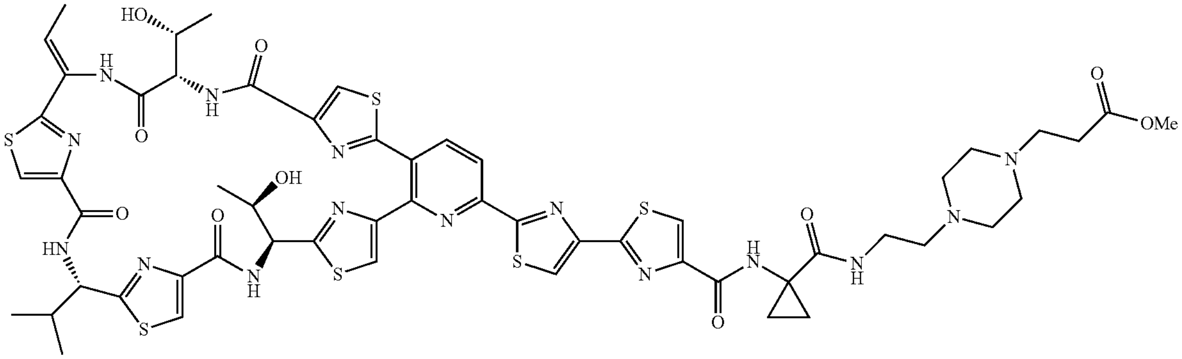
25
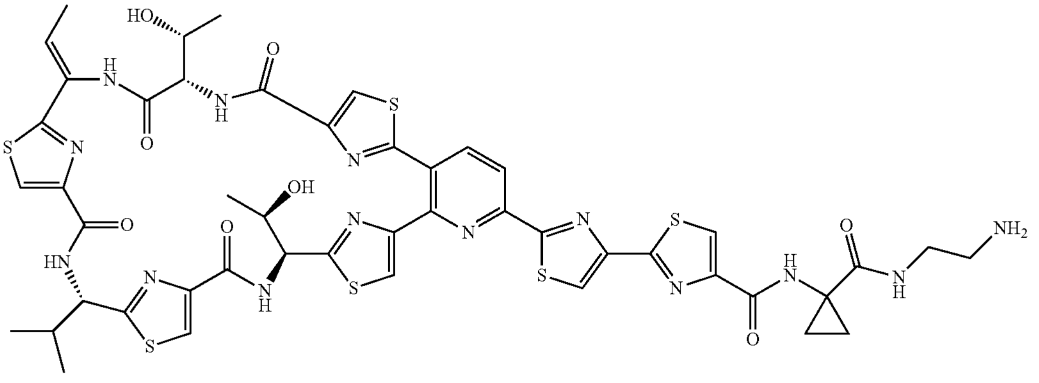

-continued
26
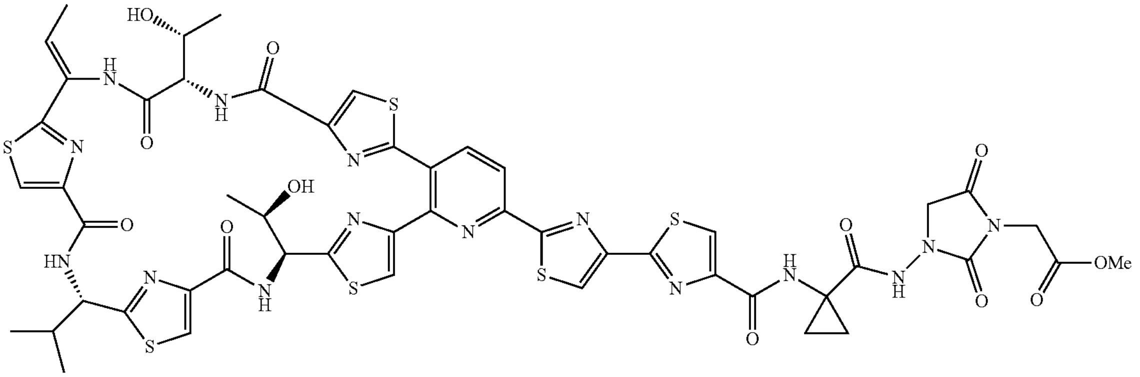
27
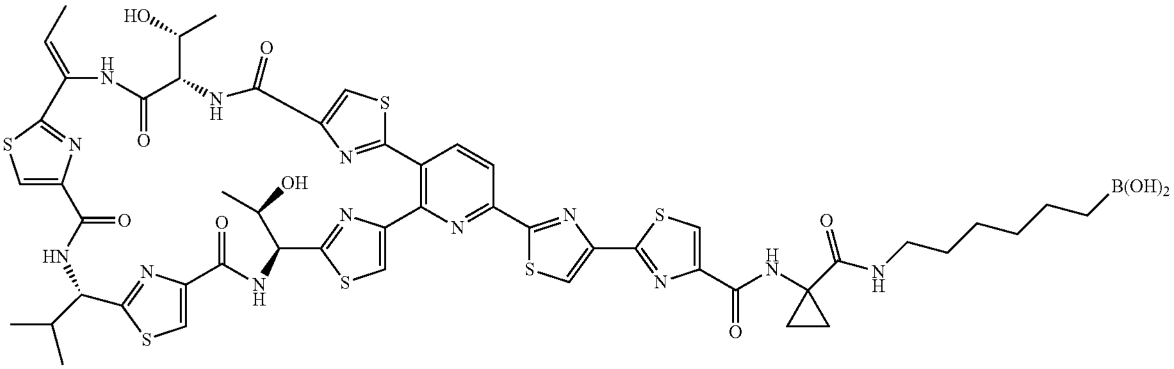
28
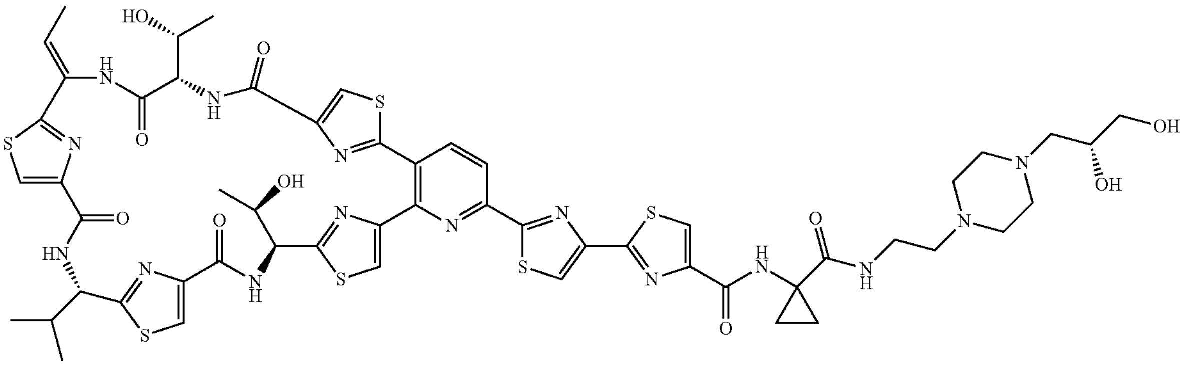
29
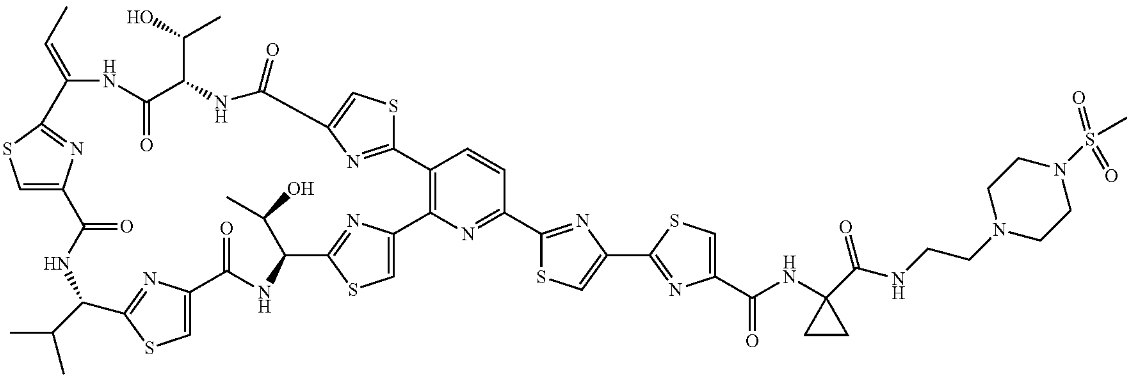

-continued
30
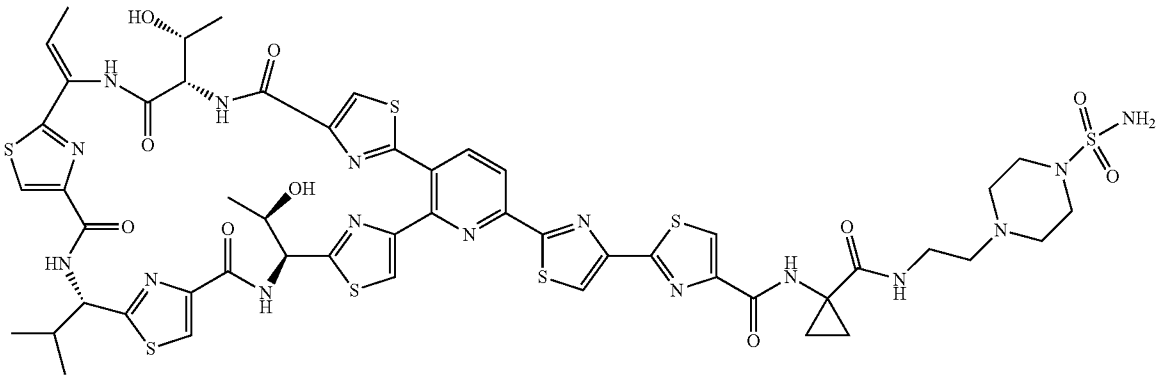
31
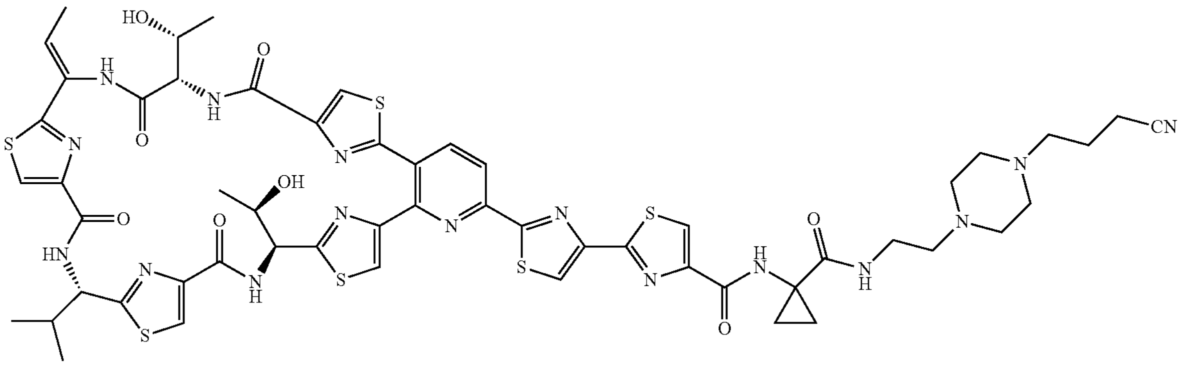
32
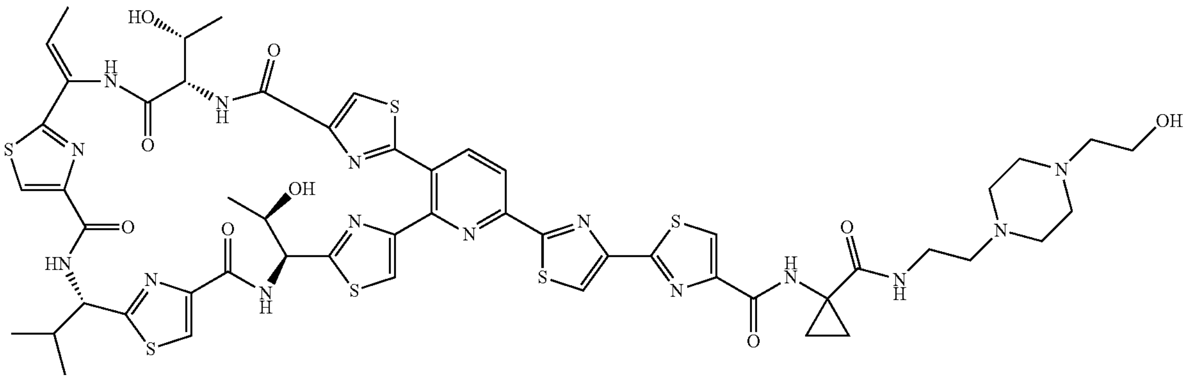
33
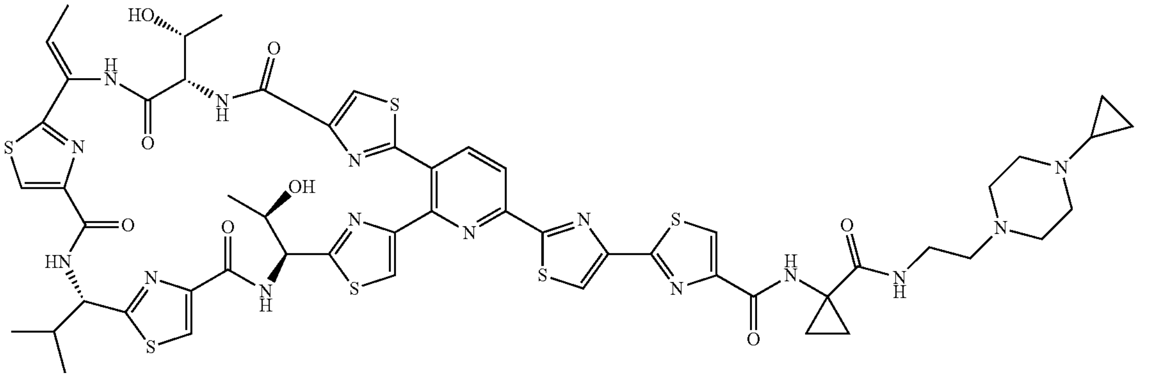

-continued
34
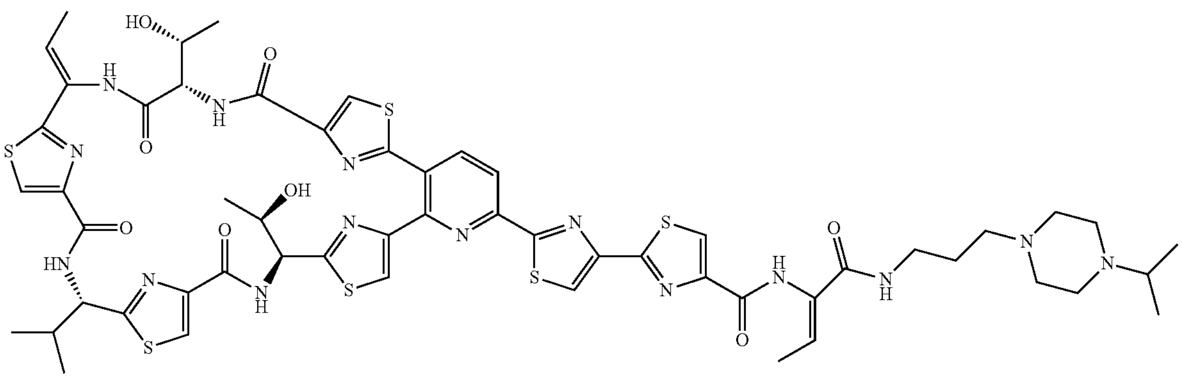
35
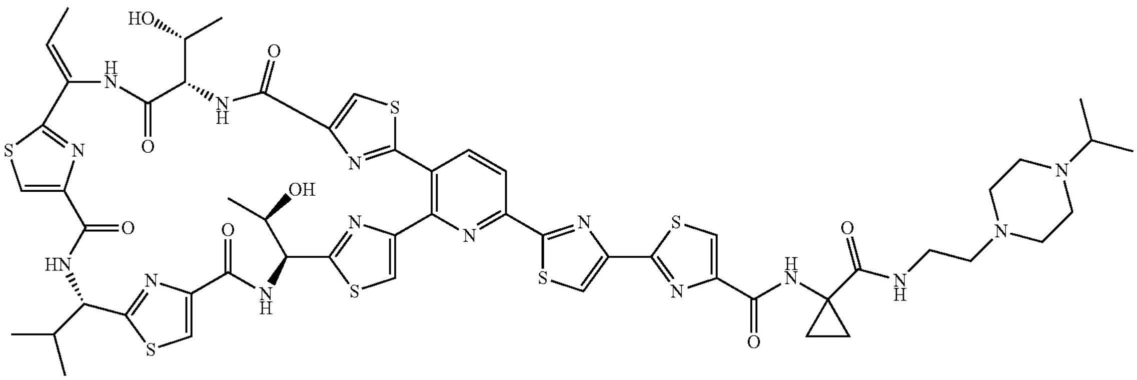
36
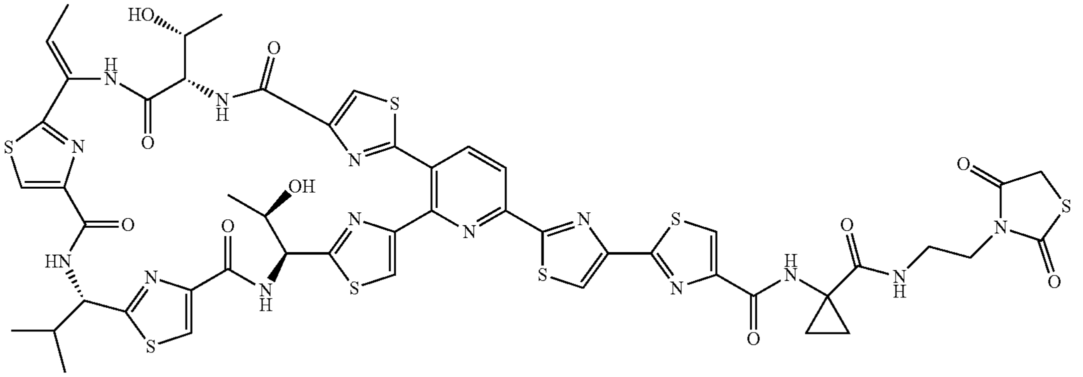
37
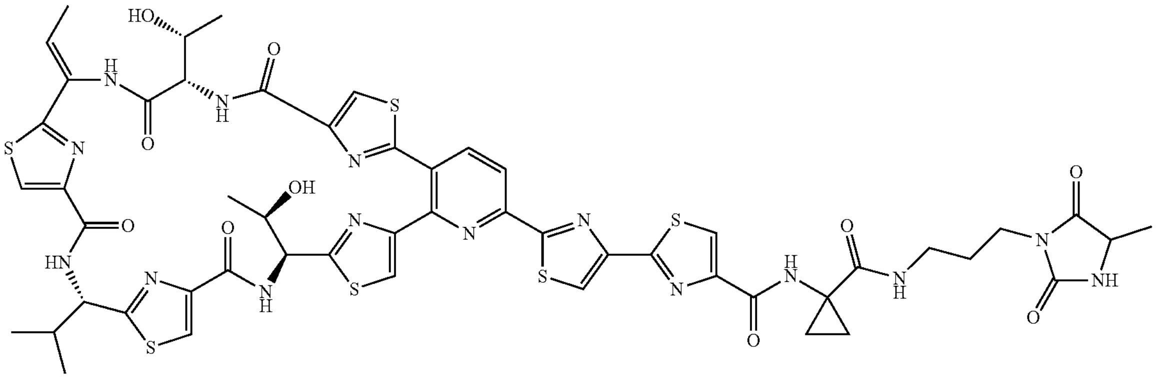

-continued
38
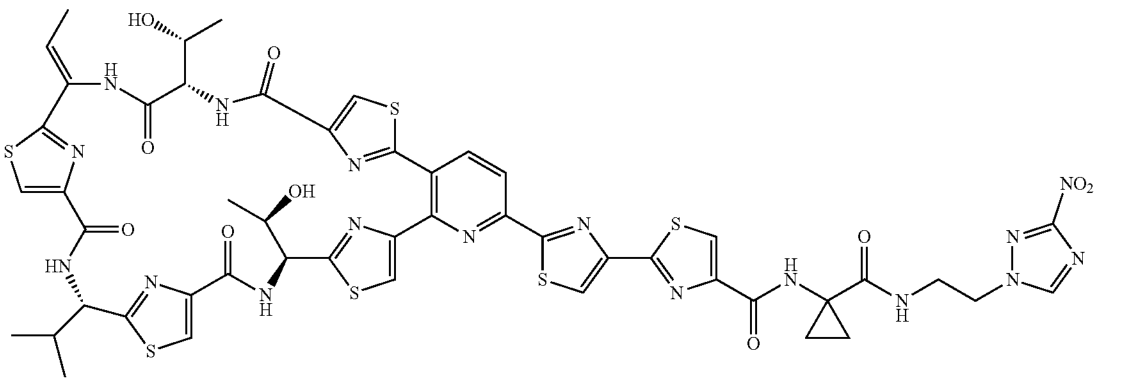
39
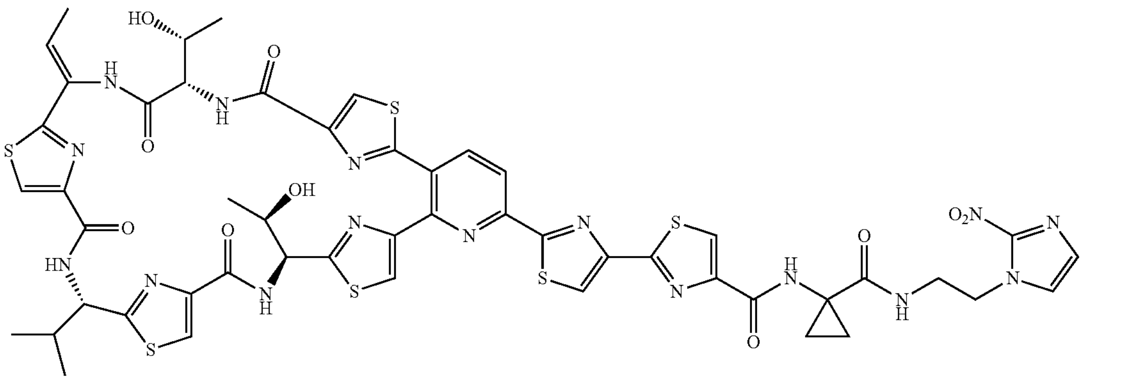
40
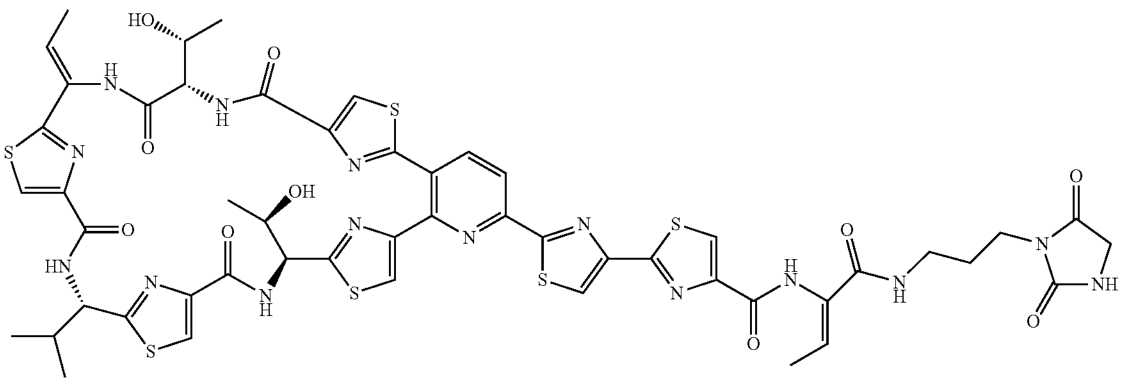
41
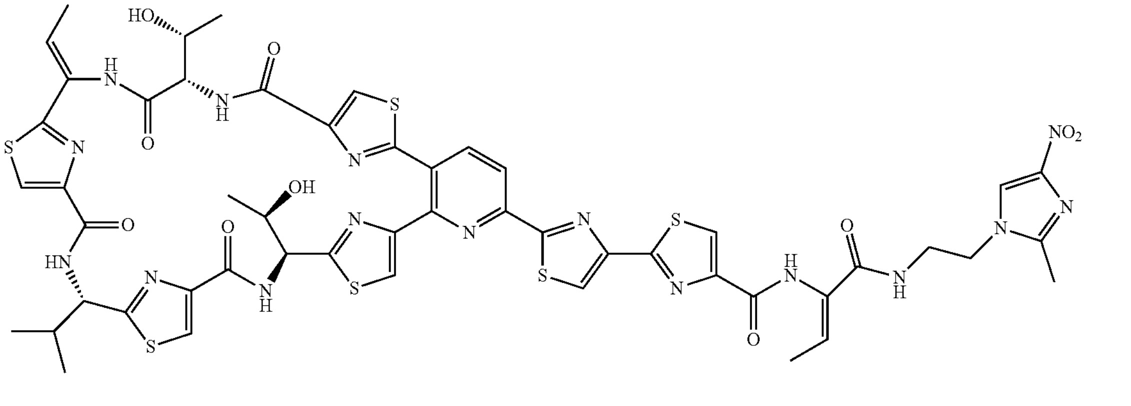

-continued
42
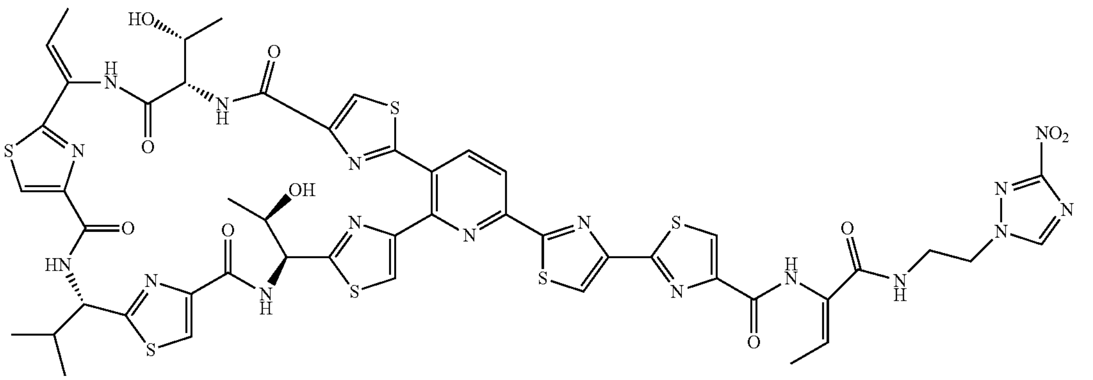
43
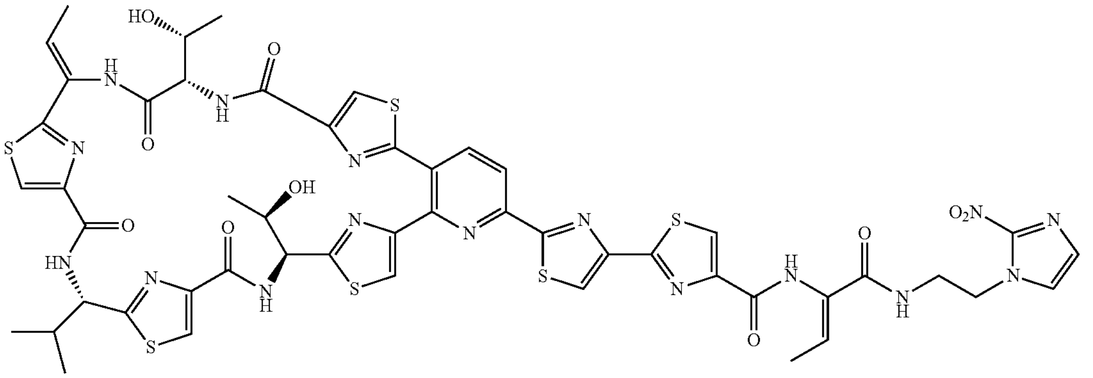
44
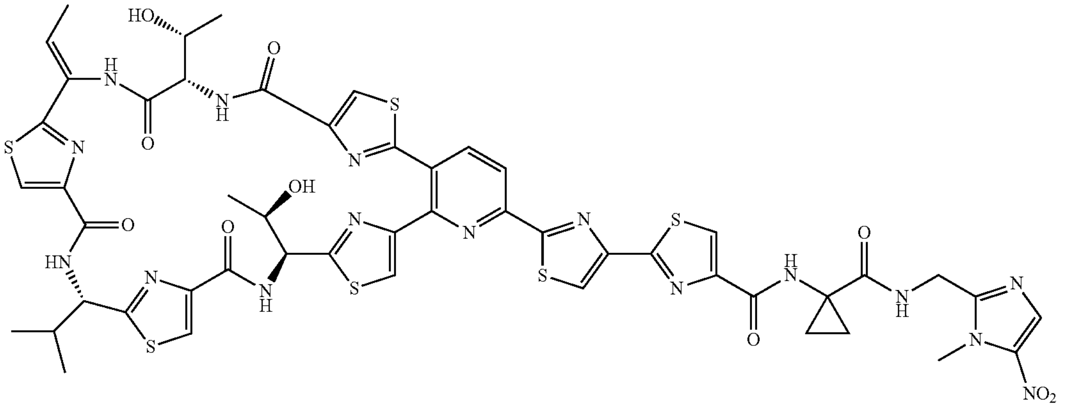
45
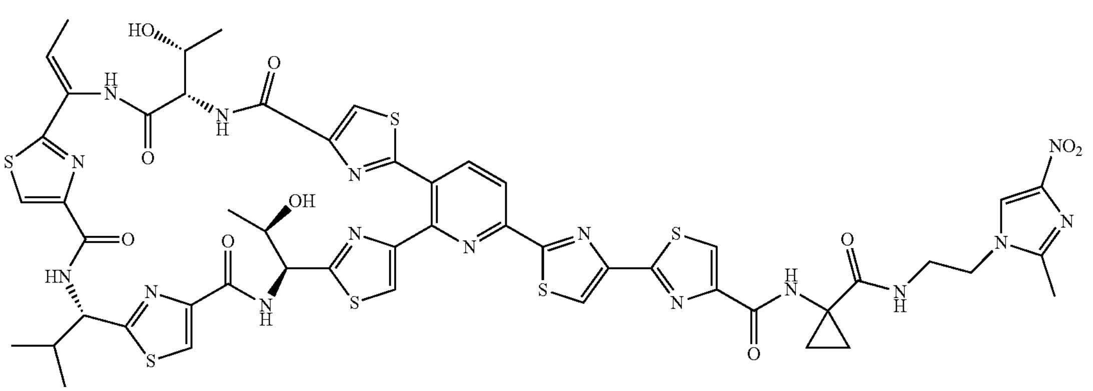

-continued

46

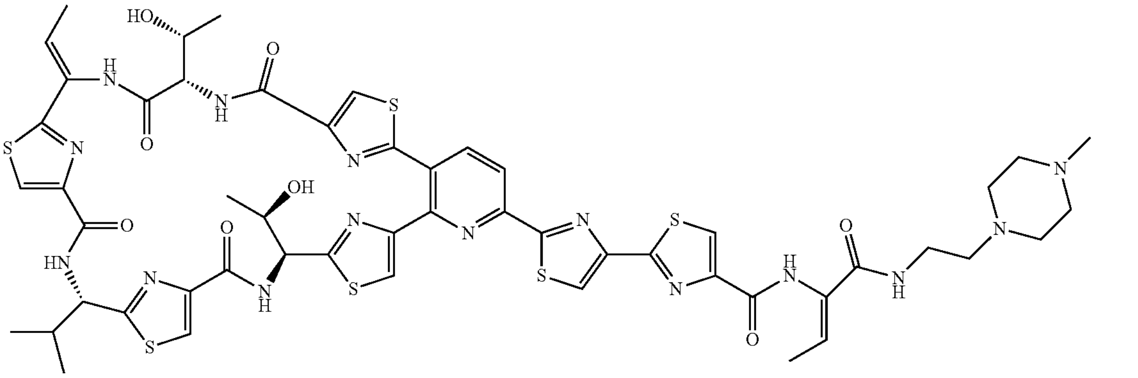

47

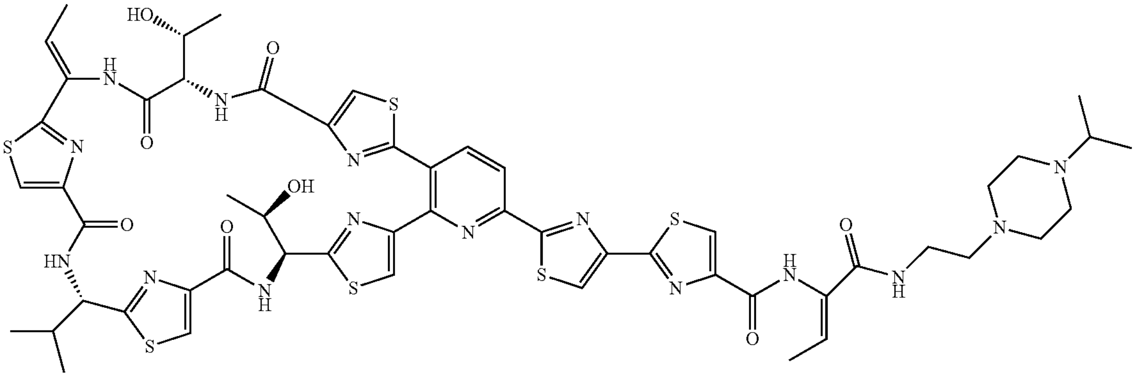

48

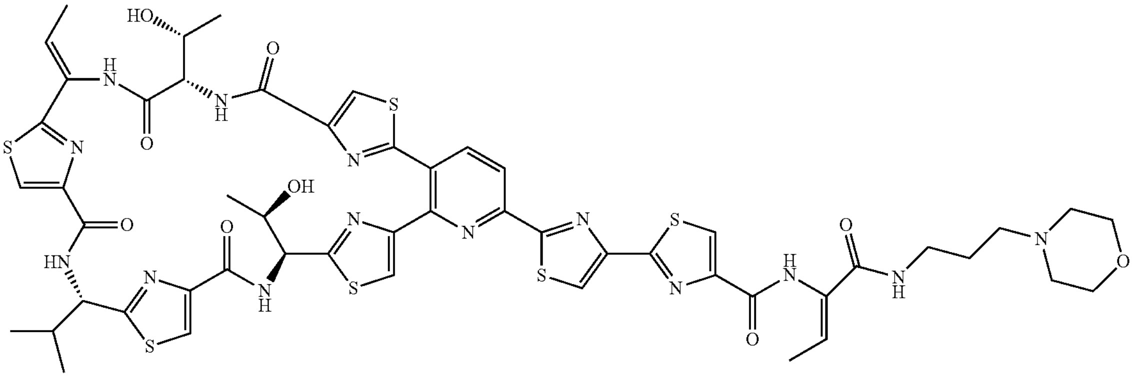

In addition, the present invention provides a method for preparing the compound represented by Chemical Formula 1 of the present invention, and the method for preparing the compound of the present invention includes:

preparing a compound of the following Chemical Formula 22 by reacting a compound of the following Chemical Formula 21 with a boronic acid precursor; and preparing a compound of the following Chemical Formula 1 by reacting the compound of Chemical Formula 22 with a compound of the following Chemical Formula 23.

[Chemical Formula 1]

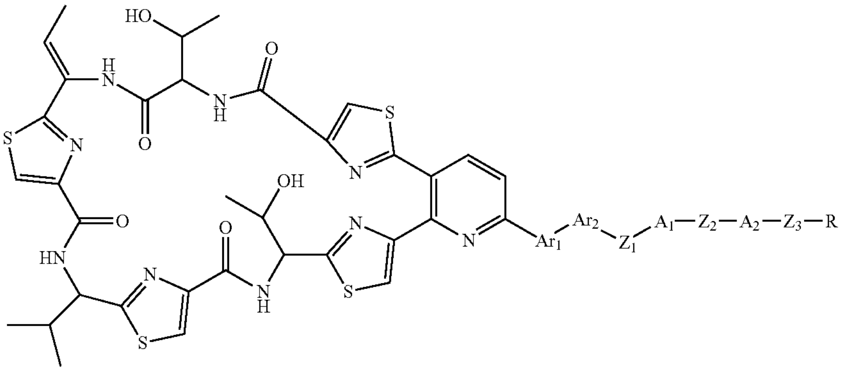

[Chemical Formula 21]

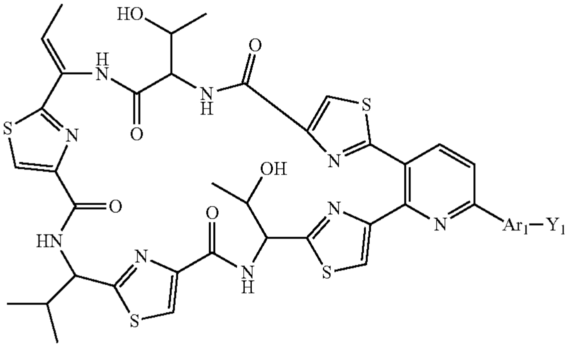

[Chemical Formula 22]

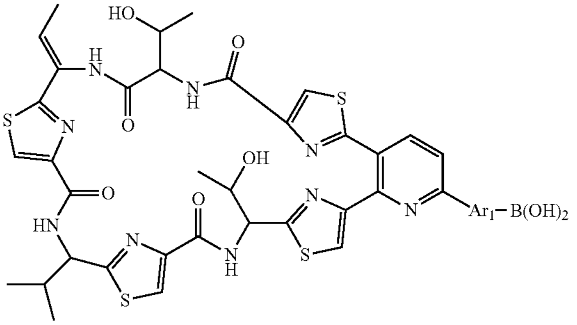

[Chemical Formula 23]

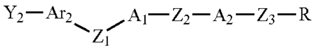

(In Chemical Formula 1 and Chemical Formulas 21 to 23, $Ar_1$ and $Ar_2$ are each independently a single bond, substituted or unsubstituted C6-C20 arylene, or substituted or unsubstituted C3-C20 heteroarylene;

$Z_1$ to $Z_3$ are each independently a single bond, —$CONR_1$—, —$NR_2CO$—, —COO—, —OCO—, —$CR_3R_4$—, —$NR_5COO$—, —$NR_6$—, —S—, —O—, —$SO_2$—, or —$OCONR_7$—;

$R_1$ to $R_7$ are each independently hydrogen, hydroxy, C1-C10 alkyl, carboxy C1-C10 alkyl, or C1-C10 alkoxycarbonyl C1-C10 alkyl;

$A_1$ is

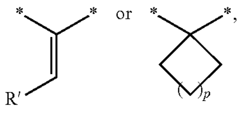

R' is hydrogen, C1-C10 alkyl, C2-C10 alkenyl, or C1-C10 alkoxy C1-C10 alkyl, and p is an integer of 0 to 4;

$A_2$ is a single bond, C1-C10 alkylene, C3-C10 cycloalkylene, C3-C10 heterocycloalkylene, C6-C20 arylene, or C6-C20 heteroarylene;

R is hydrogen, halogen, amino, hydroxy, —$B(OH)_2$, substituted or unsubstituted halo C1-C10 alkyl, substituted or unsubstituted C1-C10 alkyl, substituted or unsubstituted C2-C10 alkenyl, substituted or unsubstituted C3-C10 cycloalkyl, substituted or unsubstituted C3-C10 heterocycloalkyl, substituted or unsubstituted C6-C20 aryl, or substituted or unsubstituted C3-C20 heteroaryl; and $Y_1$ and $Y_2$ are each independently halogen.)

In the method for preparing the compound of Chemical Formula 1 according to an embodiment of the present invention, the compound of Chemical Formula 21, which is a compound into which a halogen functional group is introduced, is used, such that the compound of Chemical Formula 1 may be easily prepared through an aryl-aryl coupling reaction by easily substituting a halogen group of the compound of Chemical Formula 21 with a boronic acid functional group.

As the aryl-aryl coupling, for example, Yamamoto coupling, Suzuki coupling, Stille coupling, Sonogashira coupling, Heck coupling, or Buchwald coupling may be preferable, and the Suzuki coupling reaction is particularly preferable.

As the boronic acid precursor according to an embodiment of the present invention, any organic boronic acid compound may be used as long as it is a compound capable of introducing a boronic acid or a boronic acid derivative group by reacting with the compound of Chemical Formula 21 in the presence of a catalyst, and examples of the boronic acid precursor include bis(pinacolato)diboron and —$B(OH)_2$.

Preferably, the aryl-aryl coupling of the present invention may be performed in the presence of a transition metal catalyst, and in the Suzuki coupling reaction, a Pd(0) complex or a Pd(II) salt may be used, and a preferred Pd(0) complex may contain one or more phosphine ligands such as $Pd(Ph_3P)_4$. Another preferred phosphine ligand may be tris(ortho-tolyl)phosphine ($Pd(o\text{-}Tol)_4$).

A preferred Pd(II) salt contains palladium acetate, that is, $Pd(OAc)_2$. The Suzuki coupling may be performed in the presence of a base, for example, sodium carbonate, potassium phosphate, or an organic base such as tetraethylammonium carbonate, and in Yamamoto coupling, a Ni(0) complex, for example, bis(1,5-cycloctadienyl)nickel(0) may be used.

Preferably, Chemical Formula 21 according to an embodiment of the present invention may be prepared by preparing a compound of the following Chemical Formula 26 by reacting a compound of the following Chemical Formula 24 with a compound of the following Chemical Formula 25; and preparing the compound of Chemical Formula 21 by deprotecting the compound of Chemical Formula 26.

[Chemical Formula 24]

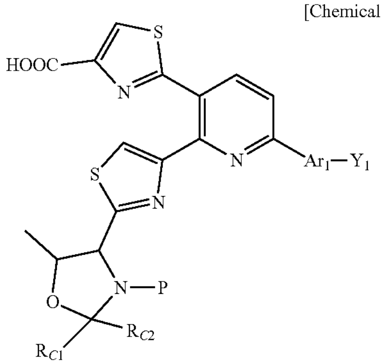

[Chemical Formula 25]

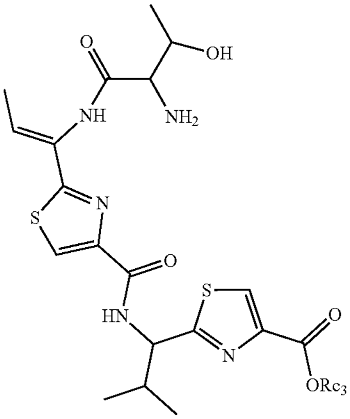

[Chemical Formula 26]

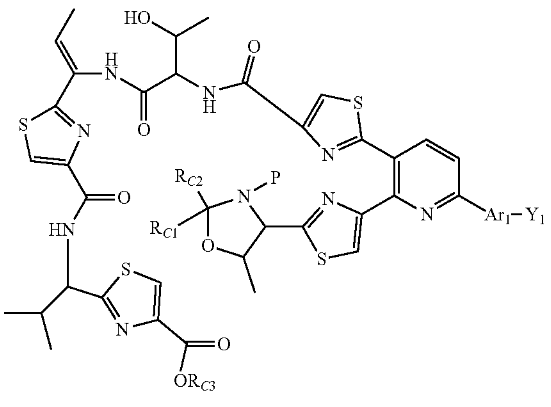

(In Chemical Formulas 24 to 26, $Ar_1$ and $Y_1$ are as defined in Chemical Formulas 1, 21, and 22;

$R_{C1}$ to $R_{C3}$ are each independently C1-C10 alkyl; and

P is a protecting group.)

The deprotection according to an embodiment of the present invention is to remove a protecting group, the protecting group may be any protecting group that may be used by those skilled in the art of the present invention, and the protecting group of the present invention is a hydroxy protecting group or an amine protecting group.

A reaction time in the preparation method according to an embodiment of the present invention may vary depending on the reactant, the type of solvent, and the amount of solvent, and the reaction is completed after confirming that the starting material is completely consumed through, for example, TLC or the like. When the reaction is completed, the solvent may be distilled off under reduced pressure, and then the target product may be separated and purified through a conventional method such as column chromatography, and the like.

In addition, the present invention provides an antibiotic composition containing, as an active ingredient, the compound of the present invention, or the hydrate, solvate, isomer, prodrug, or pharmaceutically acceptable salt thereof.

The compound of the present invention or the antibiotic composition of the present invention may be administered to a subject before or after the onset of a bacterial infection. In addition, several divided doses, as well as staggered doses, may be administered daily or sequentially, or the dose may be continuously infused or may be bolus-infused. Furthermore, the dose of the compound(s) of the present invention or the antibiotic composition containing the same may be proportionally increased or decreased as indicated by the requirements of the therapeutic or prophylactic situation.

In addition, the compound of the present invention or the antibiotic composition of the present invention may be used in a pharmaceutical formulation for treating diseases caused by bacterial infections, and the antibiotic composition of the present invention includes a formulation suitable for administration to mammals (for example, humans).

The antibiotic composition according to an embodiment of the present invention essentially contains, as an active ingredient, the compound of the present invention, or the hydrate, solvate, isomer, prodrug, or pharmaceutically acceptable salt thereof, such that the antibiotic composition has high antibacterial activity.

The novel compound of the present invention contained in the antibiotic composition according to an embodiment of the present invention may be contained in an amount of, preferably 0.001 to 10 wt %, more preferably 0.005 to 10 wt %, and still more preferably 0.1 to 5 wt %, with respect to the total weight of the antibiotic composition.

The antibiotic composition according to an embodiment of the present invention may be used for treatment and prevention of bacterial infections.

The bacterial infections according to an embodiment of the present invention may be associated with *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella enterica, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mira-*

*bilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis*, Kingella, Moraxella, Gardnerella vaginalis, Bacteroides fragilis, Bacteroides distasonis, Bacteroides 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium-intracellulare* complex, *Mycobacterium avium, Mycobacterium intracellulare, Mycobacterium abscessus, Mycobacterium leprae, Mycobacterium bolletii, Mycobacterium kansasii, Mycobacterium xenopi, Mycobacterium malmoennse, Mycobacterium scrofulaceum, Mycobacterium marinum, Mycobacterium fortuitum, Mycobacterium chelonae, Mycobacterium ulcerans, Mycobacterium haemophilum, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus*, or may be associated with *Plasmodium falciparum, Plasmodium vivax, Plasmodium malariae, Plasmodium Ovale, Plasmodium knowlesi*, and COVID-19, may be preferably associated with *Clostridioides difficile, Mycobacterium tuberculosis, Mycobacterium avium-intracellulare* complex, *Mycobacterium avium, Mycobacterium intracellulare, Mycobacterium kansasii, Mycobacterium abscessus, Enterococcus faecalis, Enterococcus faecium*, or *Staphylococcus aureus*, and may be more preferably associated with *Clostridioides difficile, Mycobacterium Tuberculosis, Mycobacterium avium-intracellulare* complex, *Mycobacterium abscessus, Mycobacterium avium, Mycobacterium intracellulare*, or *Staphylococcus aureus*.

Preferably, the antibiotic composition according to an embodiment of the present invention may further contain a pharmaceutically acceptable carrier.

The pharmaceutically acceptable carrier according to an embodiment of the present invention is a material recognized by those skilled in the art, and contains a pharmaceutically acceptable material, composition, or vehicle suitable for administration to a mammal.

The carrier includes a liquid or solid filler, diluent, excipient, solvent, or encapsulating material involved in carrying or transporting the subject agent from one organ, or portion of the body, to another organ, or portion of the body. Each carrier should be acceptable in the sense of being compatible with the other ingredients of the formulation and should not be injurious to the patient. Some examples of the material which may serve as the pharmaceutically acceptable carrier include: sugars such as lactose, glucose, and sucrose; starches such as corn starch and potato starch; celluloses and derivatives thereof, such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such as propylene glycol; polyols such as glycerin, sorbitol, mannitol, and polyethylene glycol; esters such as ethyl oleate and ethyl laurate; agar; buffers such as magnesium hydroxide and aluminum hydroxide; alginic acid; pyrogen-free water; isotonic saline; Ringer's solution; ethyl alcohol; phosphate buffer solutions; and other commercially available non-toxic materials employed in pharmaceutical formulations.

In addition, the antibiotic composition of the present invention may contain a wetting agent, an emulsifier and a lubricant (for example, sodium lauryl sulfate and magnesium stearate) as well as a coloring agent, a release agent, a coating agent, a sweetening agent, a flavor agent and a perfuming agent, a preservative, and an antioxidant.

Examples of a pharmaceutically acceptable antioxidant include: water-soluble antioxidants such as ascorbic acid, cysteine hydrochloride, sodium bisulfate, sodium metabisulfite, and sodium sulfite; oil-soluble antioxidants such as ascorbyl palmitate, butylated hydroxyanisole (BHA), butylated hydroxytoluene (BHT), lecithin, propyl gallate, and α-tocopherol; and metal chelating agents such as citric acid, ethylenediamine tetraacetic acid (EDTA), sorbitol, tartaric acid, and phosphoric acid.

The antibiotic composition of the present invention includes antibiotic compositions suitable for oral, nasal, topical, buccal, sublingual, rectal, vaginal, and/or parenteral administration, may be conveniently provided as a unit dosage form, and may be prepared by any method well known in the art of pharmacy. The amount of active ingredient that may be combined with a carrier material to produce a single dosage form generally corresponds to the amount of compound that produces a therapeutic effect.

A method for preparing the antibiotic composition (or formulation) according to an embodiment of the present invention includes combining the compound of the present invention with a carrier and one or more optional accessory ingredients. In general, the formulation is prepared by uniformly and intimately combining the compound of the present invention with a liquid carrier, a finely divided solid carrier, or both of them, and then, if necessary, shaping a product.

The formulation of the present invention suitable for oral administration may be in the form of a capsule, a cachet, a pill, a tablet, a lozenge (using a flavored base, usually sucrose and acacia or tragacanth), a powder, a granule, or may be a solution or a suspension in an aqueous or non-aqueous liquid, an oil-in-water or water-in-oil liquid emulsion, an elixir or a syrup, a pastille (using an inert base such as gelatin and glycerin, or sucrose and acacia), and/or a mouthwash, each containing a predetermined amount of the compound of the present invention as an active ingredient. The compound of the present invention may also be administered as a bolus, electuary, or paste.

In a solid dosage form of the present invention for oral administration (a capsule, a tablet, a pill, a dragee, a powder, a granule, or the like), the active ingredient is mixed with one or more pharmaceutically acceptable carriers such as sodium citrate and dicalcium phosphate, and/or any one of a filler or extender, such as starch, lactose, sucrose, glucose, mannitol, and/or silicic acid; a binder such as carboxymethyl cellulose, alginate, gelatin, polyvinyl pyrrolidone, sucrose, and/or acacia; a humectant such as glycerol; a disintegrant such as agar-agar, calcium carbonate, potato or tapioca starch, alginic acid, a certain silicate, or sodium carbonate; a solution retarding agent such as paraffin; an absorption accelerator such as a quaternary ammonium compound; a wetting agent such as cetyl alcohol or glycerol monostearate; an absorbent such as kaolin or bentonite clay; a lubricant such as a talc, calcium stearate, magnesium stearate, a solid polyethylene glycol, sodium lauryl sulfate, or a mixture thereof; and a coloring agent.

In the case of the capsule, tablet, and pill, the antibiotic composition may also contain a buffer. Solid compositions of a similar type may also be used as fillers in soft and hard-filled gelatin capsules using lactose or milk sugar as well as excipients such as high molecular weight polyethylene glycols.

Tablets may be prepared by compression or molding with one or more optional accessory ingredients. Compressed tablets may be prepared using a binder (for example, gelatin or hydroxypropylmethyl cellulose), a lubricant, an inert diluent, a preservative, a disintegrant (for example, sodium starch glycolate or cross-linked sodium carboxymethyl cellulose), a surfactant, or a dispersing agent. Molded tablets may be prepared by molding a mixture of the powdered compound moistened with an inert liquid diluent in a suitable machine.

The tablets, and other solid dosage forms of the antibiotic composition of the present invention, such as a dragee, a capsule, a pill, and a granule, may optionally be scored or prepared to have coatings and shells such as enteric coatings and other coatings well known in the pharmaceutical formulation art. These formulations may also be formulated so as to provide slow or controlled release of the active ingredients therein using, for example, hydroxypropylmethyl cellulose at various ratios, such that it is possible to provide a desired release profile, other polymer matrices, liposomes and/or microspheres. These formulations may be sterilized by, for example, filtration through a bacteria-retaining filter, or by incorporating a sterilizing agent in the form of a sterile solid composition that may be dissolved in sterile water, or some other sterile injectable media immediately before use.

The antibiotic composition of the present invention may also optionally contain an opacifying agent, and may be a composition that releases the active ingredient(s) only, or preferentially, at a certain site of the gastrointestinal tract, optionally, in a delayed manner. Examples of an embedding composition which may be used include polymeric materials and waxes. The active ingredient may also be present in a micro-encapsulated form, when appropriate, with one or more of the excipients described above.

Liquid dosage forms for oral administration of the compound or the antibiotic composition of the present invention include pharmaceutically acceptable emulsions, microemulsions, solutions, suspensions, syrups, and elixirs. In addition to the active ingredient, the liquid dosage form may contain an inert diluent commonly used in the art such as water or another solvent, a solubilizing agent and an emulsifier such as ethyl alcohol, isopropyl alcohol, ethyl carbonate, ethyl acetate, benzyl alcohol, benzyl benzoate, propylene glycol, 1,3-butylene glycol, oil (in particular, cottonseed oil, peanut oil, corn oil, germ oil, olive oil, castor oil, or sesame oil), glycerol, tetrahydrofurfuryl alcohol, polyethylene glycol, and a fatty acid ester of sorbitan, and a mixture thereof.

When the antibiotic composition of the present invention is an oral composition, in addition to the inert diluent, the antibiotic composition may also contain an adjuvant such as a wetting agent, an emulsifier and a suspending agent, a sweetening agent, a flavor agent, a coloring agent, a perfuming agent, and a preservative. The suspension may contain, in addition to the compound of the present invention, for example, a suspending agent such as ethoxylated isostearyl alcohol, polyoxyethylene sorbitol and sorbitan esters, microcrystalline cellulose, aluminum metahydroxide, bentonite, agar-agar and tragacanth, and a mixture thereof.

The antibiotic composition (formulation) of the present invention for rectal or vaginal administration may be provided as a suppository, and the suppository may be prepared by mixing one or more compounds of the present invention with one or more suitable nonirritating excipients or carriers containing, for example, cocoa butter, polyethylene glycol, a suppository wax, or a salicylate. The suppository is a solid at room temperature, but is a liquid at body temperature, and therefore, the suppository will melt in the rectum or vaginal cavity and release the active compound.

The antibiotic composition (formulation) of the present invention suitable for vaginal administration also includes a pessary, a tampon, a cream, a gel, a paste, foams, or a spray formulation containing the carriers known in the art to be appropriate.

Dosage forms for topical or transdermal administration of the compound or the antibiotic composition of the present invention include a powder, a spray, an ointment, a paste, a cream, a lotion, a gel, a solution, a patch, and an inhalant. The active compound may be mixed under sterile conditions with a pharmaceutically acceptable carrier, and any preservative, buffer, or propellant that may be required.

The ointment, paste, cream, and gel may contain, in addition to the compound of the present invention, an excipient such as animal and vegetable fat, oil, wax, paraffin, starch, tragacanth, a cellulose derivative, polyethylene glycol, silicone, bentonite, silicic acid, talc, and zinc oxide, or a mixture thereof.

The powder and spray may contain, in addition to the compound of the present invention, an excipient such as lactose, talc, silicic acid, aluminum hydroxide, calcium silicate, and a polyamide powder, or a mixture of these materials. The spray may additionally contain a general propellant such as chlorofluorohydrocarbon and volatile unsubstituted hydrocarbons such as butane and propane.

A transdermal patch has an additional advantage of providing a controlled delivery of the compound of the present invention to the body. Such dosage form may be prepared by dissolving or dispersing the compound of the present invention in a proper medium.

An absorption enhancer may also be used to increase the flux of the compound of the present invention through the skin. Such a flux rate may be controlled by providing a rate controlling membrane or dispersing the active compound in a polymer matrix or gel.

An ophthalmic formulation, an eye ointment, a powder, a solution, and the like are also included in the scope of the present invention.

The antibiotic composition of the present invention suitable for parenteral administration contains one or more compounds of the present invention in combination with one or more pharmaceutically acceptable sterile isotonic aqueous or non-aqueous solutions, a dispersion, a suspension or an emulsion, or a sterile powder which may be reconstituted into a sterile injectable solution or dispersion immediately before use, and may contain an antioxidant, a buffer, a bacteriostatic agent, a solute that renders the formulation isotonic with the blood of the intended recipient or a suspending agent or a thickener.

Examples of a suitable aqueous and non-aqueous carrier that may be used in the antibiotic composition of the present invention include water, ethanol, polyols (such as glycerol, propylene glycol, polyethylene glycol, and the like), and a suitable mixture thereof, a vegetable oil (such as olive oil), and injectable organic esters (such as ethyl oleate). A suitable fluidity may be maintained, for example, by use of a coating material such as lecithin, maintenance of a required particle size in the case of a dispersion, and by use of a surfactant. Furthermore, the antibiotic composition of the present invention may also contain an adjuvant such as a preservative, a wetting agent, an emulsifier, or a dispersing agent. The antibiotic composition of the present invention contains various antibacterial agents and antifungal agents, for example, paraben, chlorobutanol, phenol sorbic acid, and the like, such that the activity of microorganisms may be prevented. In addition, it is preferable that an isotonic agent such as a sugar or sodium chloride is contained in the composition.

In addition, the absorption of the injectable antibiotic composition (formulation) of the present invention may be prolonged by containing an agent that delays absorption, such as aluminum monostearate or gelatin.

The formulation containing the compound and the antibiotic composition of the present invention may be provided orally, parenterally, topically, or rectally. This formulation is provided in a form suitable for each route of administration. For example, these formulations are administered in tablets or capsule form by injection and inhalation, eye drops, an ointment, a suppository, and the like, and administration by injection, infusion, or inhalation; topical administration by a lotion or an ointment; and rectal administration by a suppository. Preferably, the formulation may be administered by oral administration and/or IV administration.

The antibiotic composition of the present invention may be administered by various methods accepted in the art, and for example, the antibiotic composition may be administered by parenteral administration which means administration other than enteral and topical administration, usually, injection, or may be administered parenterally. That is, the parenteral administration includes, but is not limited to, intravenous, intramuscular, intraarterial, intradural, intracapsular, intraorbital, intracardiac, intradermal, intraperitoneal, transtracheal, subcutaneous, subepidermal, intra-articular, subcapsular, subarachnoid, intraspinal, and intrasternal injection and infusion. Similarly, the number of administrations and the dosage may be at various levels accepted in the art.

In addition, the antibiotic composition (formulation) of the present invention may be used in combination with another agent, for example, an additional antibacterial agent, which is the compound of the present invention or is not the compound of the present invention, for the treatment of a bacterial infection in a subject.

The antibacterial agent includes an antibiotic, a biocide, an antimicrobial agent, and a bacteriostatic agent, and any known types of antibiotic, biocide, antimicrobial agent, and bacteriostatic agent may be used.

In addition, the compound and the antibiotic composition of the present invention may be formulated for administration separately from each other with any additional agents, and may be formulated together for administration at one time. For example, the compound and the antibiotic composition of the present invention may be formulated into one dosage form, and then may be formulated together with additional agents into another dosage form. Any individual dosage forms may be administered simultaneously or at different times.

Alternatively, the antibiotic composition of the present invention may include additional agents described in the present invention, and each component may be provided as a separate composition, a composite composition, or a single composition.

Hereinafter, specific Examples of the novel compound of the present invention will be described, but the present invention is not limited to these specific Examples.

[Preparation Example 1] Preparation of Compound XI

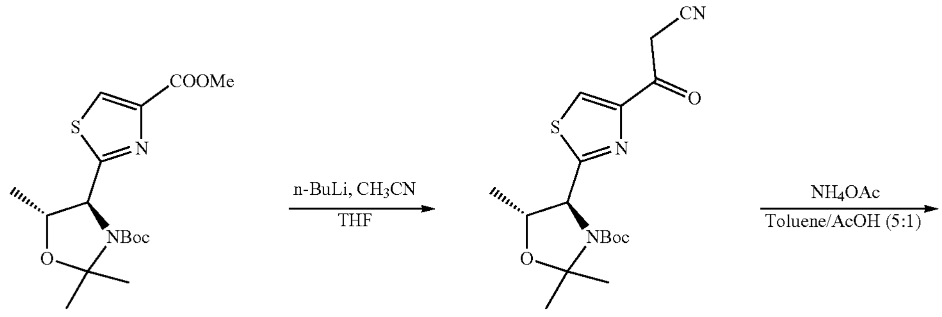

I

II

-continued
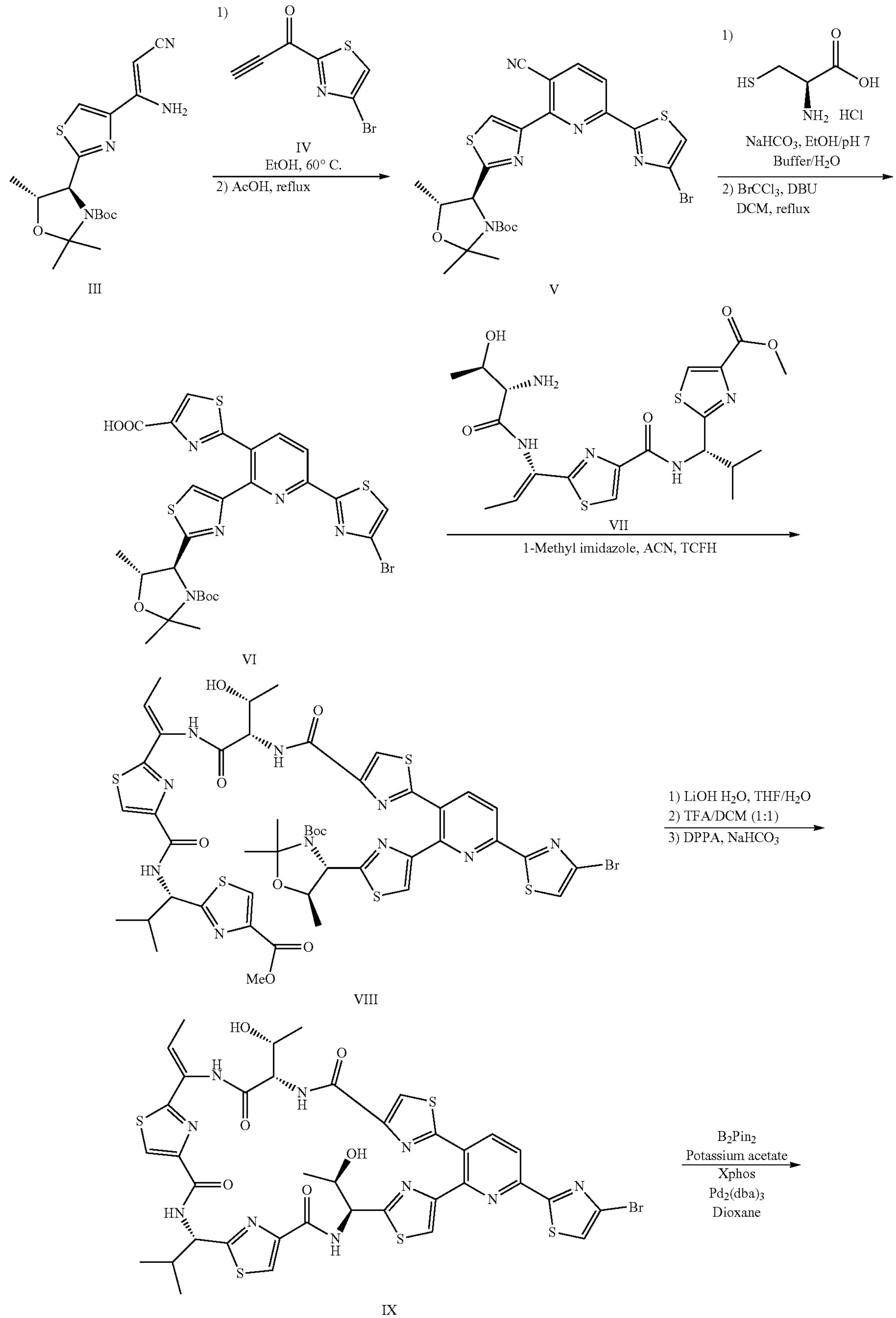

-continued

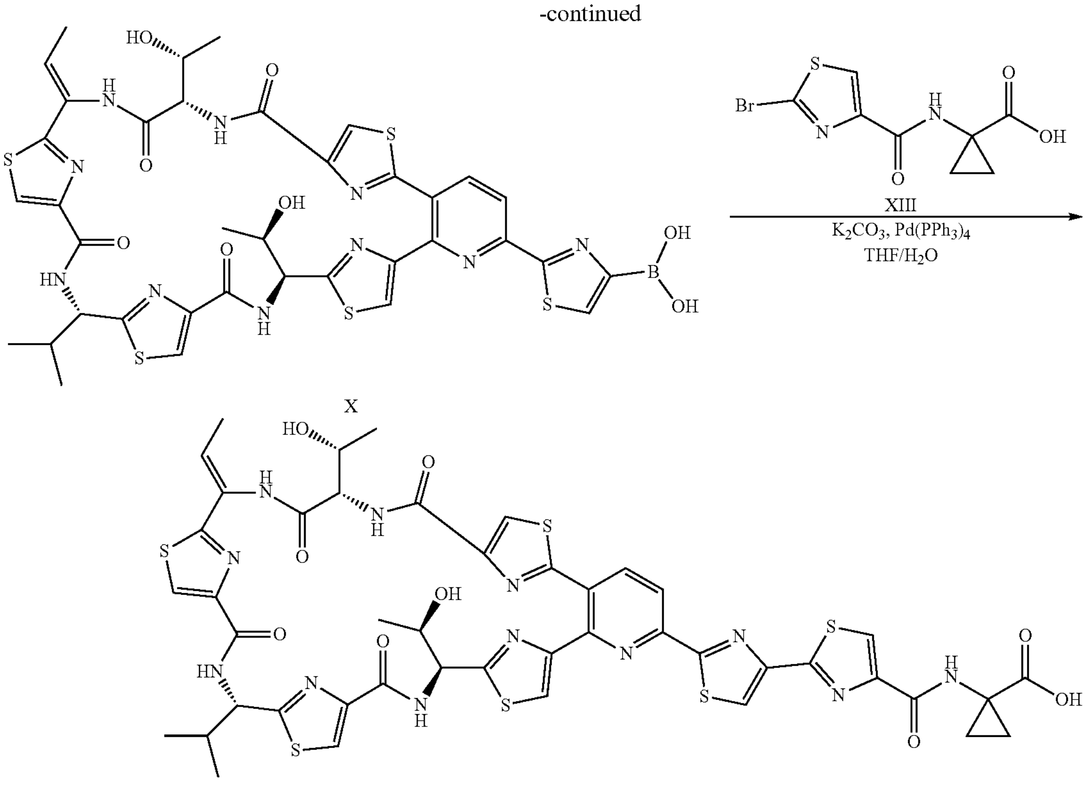

X

XI

Preparation of Compound II

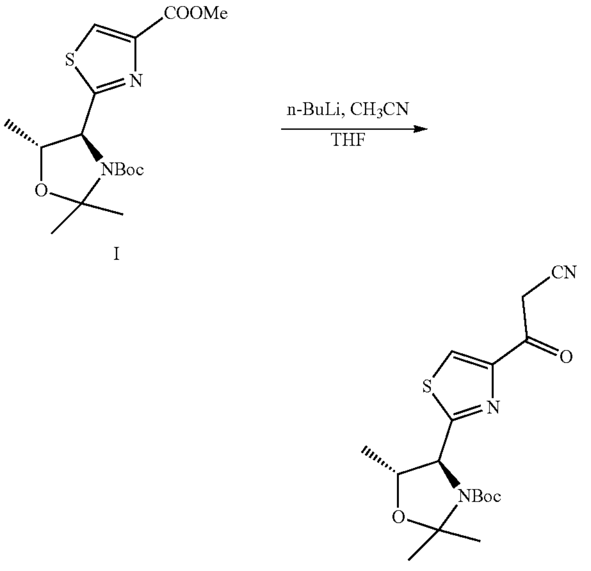

I

II

A solution of n-BuLi (2.5 M in hexanes, 16 mL, 38.3 mmol) was slowly added dropwise to a solution of acetonitrile (1.8 mL, 34.8 mmol) in tetrahydrofuran (100 mL) at −78° C., the mixture was stirred at −78° C. for 15 minutes, and then a solution of Compound I (6.22 g, 17.4 mmol) in tetrahydrofuran (25 mL) was slowly added dropwise at the same temperature. The temperature was slowly raised to room temperature, and then 1 M hydrochloric acid was added to quench the reaction. The mixture was diluted with ethyl acetate, and acidified with hydrochloric acid to pH 3. The organic solvent was extracted, dried over anhydrous sodium sulfate, concentrated under reduced pressure, and then purified by column chromatography (eluent: 30 to 50% ethyl acetate/hexane) to obtain Compound II (4.46 g, 70%) as a brown solid.

$^1H$ NMR (400 MHz, $CDCl_3$) δ 8.29 (s, 1H), 4.71 (d, J=17.7 Hz, 1H), 4.32-4.09 (m, 3H), 1.70 (broad peak, 6H), 1.54-1.38 (t, J=8.4 Hz, 7H), 1.31-1.06 (m, 5H).

Preparation of Compound III

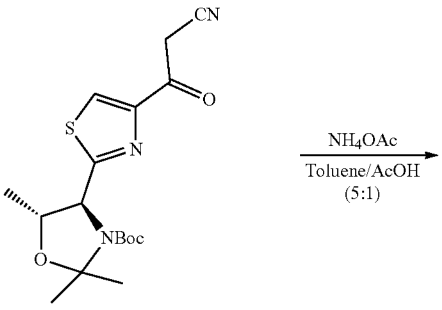

II

-continued

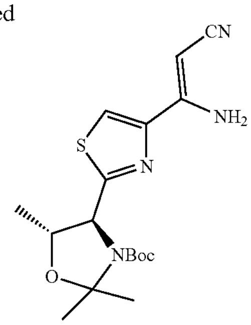

III

Compound II (4.46 g, 12.2 mmol) was dissolved in a mixture of toluene (100 mL) and acetic acid (20 mL), and then ammonium acetate (9.4 g, 122 mmol) was added dropwise. The mixture was stirred at 120° C. for 90 minutes, and then slowly cooled to room temperature. The mixture was diluted with ethyl acetate and then washed with a supersaturated sodium bicarbonate solution and water. The organic solvent was extracted, dried over anhydrous sodium sulfate, and then concentrated under reduced pressure to obtain Compound III (4.24 g, 95%) as a yellow oil.

$^1$H NMR (400 MHz, $CDCl_3$) δ 7.60 (s, 1H), 5.59-5.51 (m, 2H), 4.81-4.50 (m, 2H), 4.21-4.10 (m, 1H), 1.67 (s, 6H), 1.40 (t, J=13.7 Hz, 6H), 1.27-0.96 (m, 6H).

Preparation of Compound IV

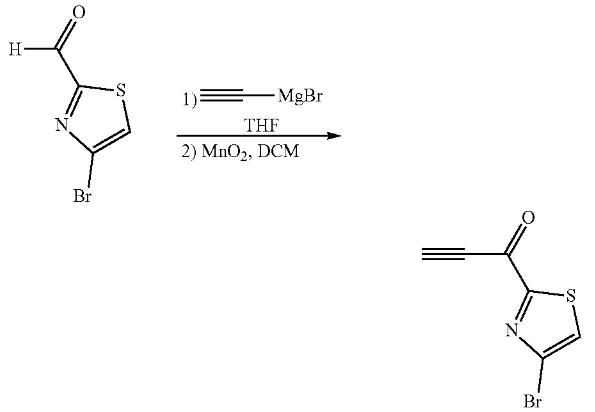

IV

Methyl 2-formyl-[2,4-bithiazole]-4-carboxylate (768 mg, 4 mmol) was dissolved in tetrahydrofuran (10 mL), and then an ethynylmagnesium bromide solution (0.5 M in THF, 16 mL, 8 mmol) was slowly added dropwise at 0° C. The mixture was stirred at room temperature for 30 minutes, and a supersaturated ammonium chloride solution was added to quench the reaction. The mixture was extracted with ethyl acetate, dried over anhydrous sodium sulfate, and then concentrated under reduced pressure. The resulting residue was purified by column chromatography (eluent: 30% ethyl acetate/70% hexane) to obtain a white solid compound. The obtained compound (632 mg, 2.9 mmol) was dissolved in dichloromethane (30 mL), manganese dioxide (2.52 g, 29 mmol) was added, and then the mixture was stirred at room temperature for 12 hours. The manganese residue was removed by celite, the filtrate was extracted with dichloromethane, dried over anhydrous sodium sulfate, and then concentrated under reduced pressure to obtain Compound IV (527 mg, 61%) as a brown solid.

$^1$H NMR (400 MHz, $CDCl_3$) δ 7.69 (s, 1H), 3.67 (s, 1H).

Preparation of Compound V

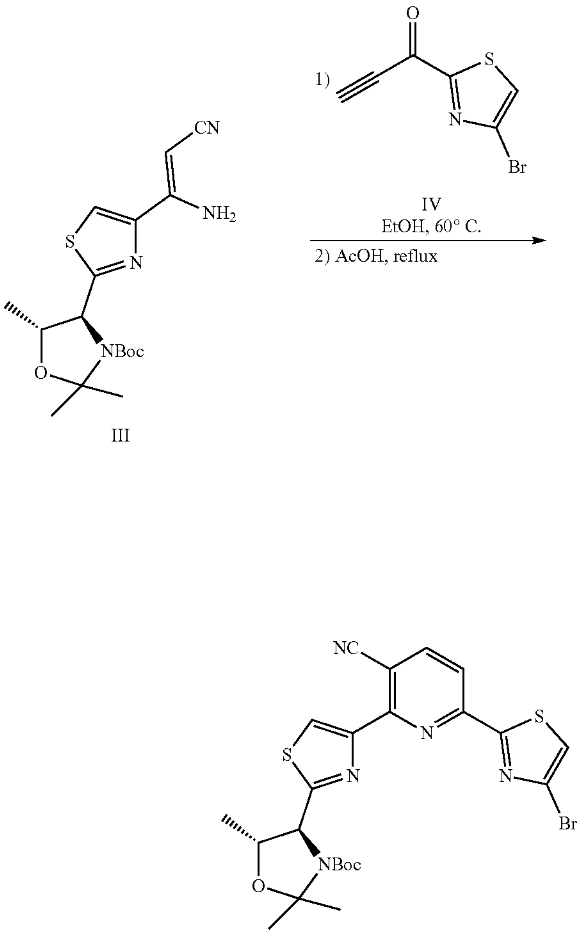

Compound III (4.46 g, 12.2 mmol) was dissolved in ethanol, Compound IV (4.88 g, 22.6 mmol) was added, and then the mixture was stirred at 60° C. for 2 hours. After confirming that the Michael addition reaction occurred by TCL or LC/MS, acetic acid (30% volume, 19 ml) was added and then refluxed at 120° C. for 16 hours. The excess ethanol and acetic acid were removed by concentrating under reduced pressure, and then the resultant residue was diluted with dichloromethane. Sodium bicarbonate was added to quench the reaction, the organic solvent was extracted, dried over anhydrous sodium sulfate, concentrated under reduced pressure, and then purified by column chromatography (eluent: 5 to 15% ethyl acetate/95 to 85% hexane) to obtain Compound V (3.57 g, 50%) as a yellow solid.

$^1$H NMR (400 MHz, $CDCl_3$) δ 8.27 (s, 1H), 8.19 (s, 2H), 7.48 (s, 1H), 4.85 (d, J=7.3 Hz, 1H), 4.58-4.23 (broad peak, 1H), 1.83-1.67 (broad peak, 6H), 1.57-1.45 (m, 6H), 1.33-1.20 (m, 6H).

Preparation of Compound VI

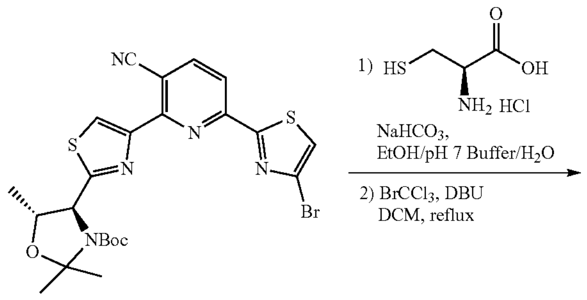

V

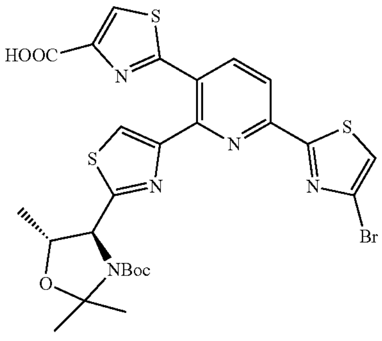

VI

Compound V (1.42 g, 2.53 mmol) was dissolved in a mixed solution of ethanol (27 mL), a sodium phosphate buffer solution (pH 7, 9 mL), and water (4.5 mL), L-cysteine (4.34 g, 25.3 mmol) was added dropwise, sodium bicarbonate (850 mg, 10.12 mmol) was added, and the mixture was stirred at 100° C. for 24 hours. After confirming that the reaction was completed, concentration under reduced pressure was performed to remove ethanol, and the resultant residue was diluted with ethyl acetate. The mixture was washed with 1 M hydrochloric acid to remove an excessive amount of cysteine, dried over anhydrous sodium sulfate, extracted, and then concentrated under reduced pressure to obtain thiazoline as a brown oil.

The thiazoline (1.68 g, 2.53 mmol) as a brown oil was dissolved in dichloromethane (30 mL), bromotrichloromethane (0.8 mL, 8.07 mmol) was added, and then 1,8-diazabicyclo[5.4.0]undec-7-ene (1.6 mL, 10.76 mmol) was slowly added dropwise. The mixture was stirred at 60° C. for 4 hours, and then 1 M hydrochloric acid was added to quench the reaction. The mixture was extracted with dichloromethane, and then washed with water and brine. The extracted organic solvent was dried over anhydrous sodium sulfate, concentrated under reduced pressure, and purified by column chromatography (eluent: 5 to 15% methanol/dichloromethane) to obtain Compound VI (1.05 g, 62%) as a brown solid.

$^1H$ NMR (400 MHz, $CDCl_3$) δ 8.35-8.05 (m, 3H), 7.89 (bs, 1H), 7.33 (s, 1H), 4.49-4.40 (m, 1H), 4.09-3.97 (m, 1H), 1.71-1.29 (m, 10H), 1.26-1.08 (m, 8H).

Preparation of Compound VIII

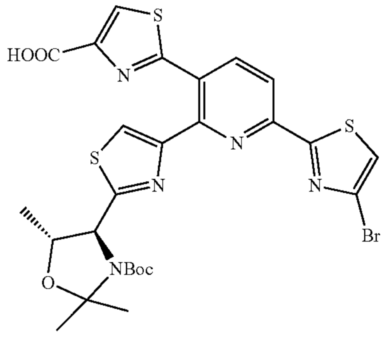

VI

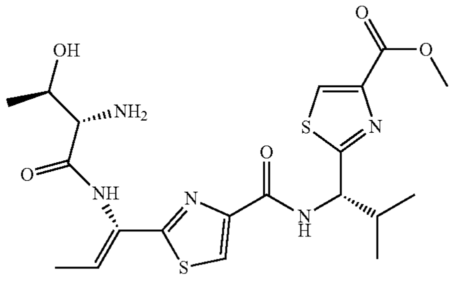

VII

1-Methyl imidazole, ACN, TCFH

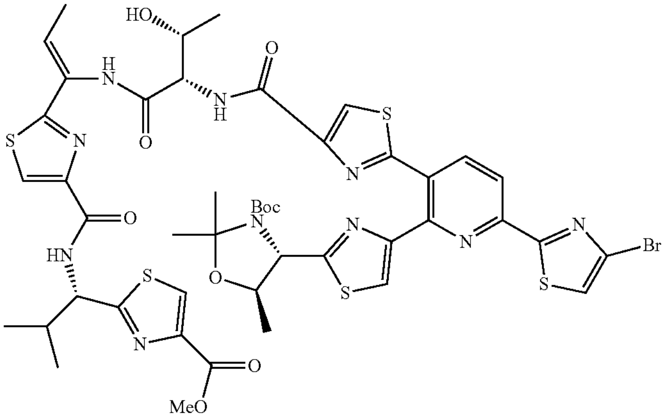

VIII

Compound VI (1.05 g, 1.57 mmol) was dissolved in acetonitrile (8 mL), Compound VII (932 mg, 1.88 mmol), 1-methylimidazole (0.376 mL, 4.71 mmol), and TCFH (0.528 g, 1.88 mmol) were added, and the mixture was stirred at room temperature for 30 minutes. After confirming the completion of the reaction, water was added to quench the reaction, and the organic layer extracted with dichloromethane was dried over anhydrous sodium sulfate. The concentrate obtained by concentration under reduced pressure was purified by column chromatography (eluent: 1.5 to 2.3% methanol/98.5 to 97.7% dichloromethane) to obtain Compound VIII (1.05 g, 60%) as a yellow solid.

$^1$H NMR (400 MHz, $CDCl_3$) δ 8.69 (s, 1H), 8.44 (d, J=9.5 Hz, 1H), 8.35-8.24 (m, 4H), 8.24-8.17 (m, 1H), 8.06 (s, 1H), 7.96 (s, 1H), 7.94-7.87 (m, 1H), 6.45 (dq, J=14.0, 7.1 Hz, 1H), 5.41-5.31 (m, 1H), 4.88 (d, J=5.3 Hz, 1H), 4.78 (s, 1H), 4.68-4.58 (m, 1H), 4.58-4.46 (m, 1H), 4.16-3.98 (m, 1H), 3.86 (s, 3H), 2.49-2.45 (m, 1H), 1.87 (d, J=7.1 Hz, 3H), 1.69-1.48 (m, 6H), 1.45-1.32 (m, 3H), 1.31-1.08 (m, 12H), 0.99 (dd, J=30.6, 6.8 Hz, 6H)

Preparation of Compound IX

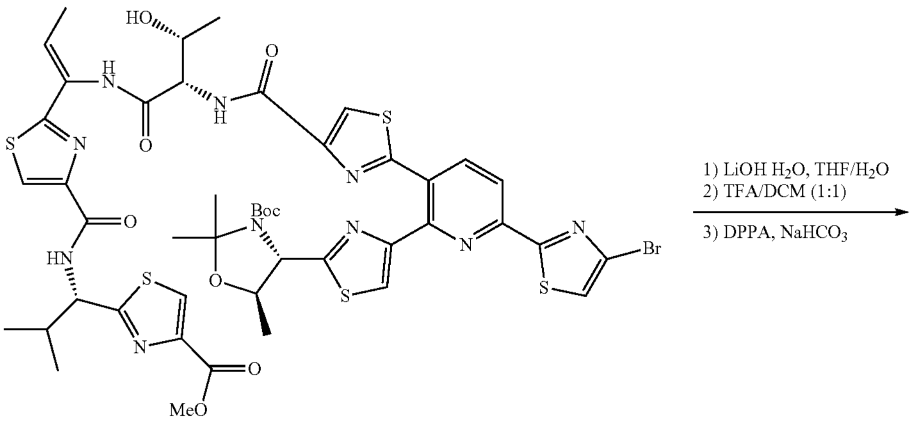

VIII

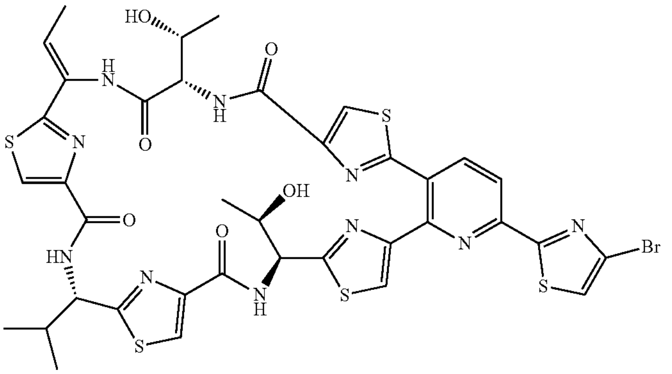

IX

Compound VIII (200 mg, 0.177 mmol) was dissolved in the mixture of tetrahydrofuran (1 mL)/water (1 mL), lithium hydroxide monohydrate (22 mg, 0.53 mmol) was added, and then the mixture was stirred at room temperature for 2 hours. The mixture was diluted with a dichloromethane, washed with a 1 M hydrochloric acid solution, dried over anhydrous sodium sulfate, and then concentrated under reduced pressure to obtain a carboxylic acid. The concentrate was dissolved in the mixture of dichloromethane (1 mL)/trifluoroacetic acid (1 mL), stirred at room temperature for 30 minutes, and then concentrated under reduced pressure to obtain trifluoroacetate. This concentrate was dissolved in DMF (1 mL), diphenylphosphoryl azide (0.065 mL, 0.265 mmol) and sodium bicarbonate (0.178 g, 2.124 mmol) were added, and then stirred at room temperature for 12 hours. After the reaction was completed, a super solvent (4:1=dichloromethane:isopropanol) was added to dilute, and then the organic layer was washed with water three times and then dried over anhydrous sodium sulfate. The residue concentrated under reduced pressure was purified by column chromatography (eluent: 2 to 5% methanol/98 to 95% dichloromethane) to obtain Compound IX (96 mg, 56%) as a yellow solid.

$^1$H NMR (400 MHz, $CDCl_3$) δ 8.77 (s, 1H), 8.39 (d, J=9.6 Hz, 1H), 8.22-8.18 (m, 2H), 8.16-8.09 (m, 3H), 8.01-7.92 (m, 3H), 7.40 (s, 1H), 6.39 (q, J=7.0 Hz, 1H), 5.27-5.18 (m, 2H), 4.92 (d, J=7.8 Hz, 1H), 4.67 (s, 1H), 4.47-4.33 (m, 1H), 2.95 (bs, 1H), 2.48 (dq, J=13.4, 6.6 Hz, 1H), 2.22 (bs, 1H), 1.81 (d, J=7.0 Hz, 3H), 1.57 (d, J=5.2 Hz, 3H), 1.17 (dd, J=20.9, 6.6 Hz, 6H), 0.95 (d, J=6.6 Hz, 3H).

Preparation of Compound X

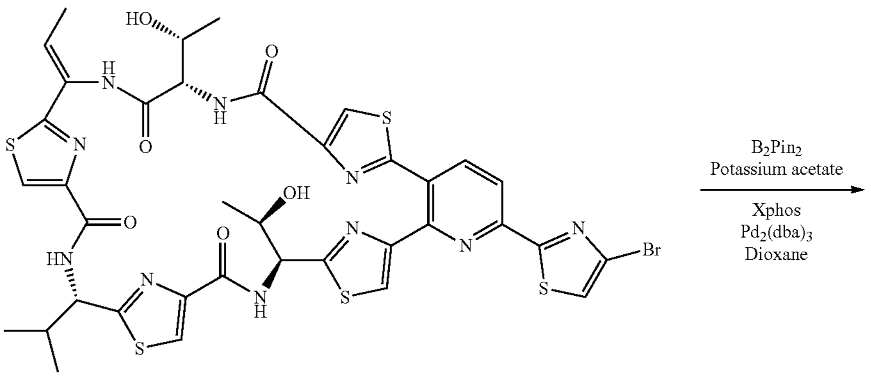

IX

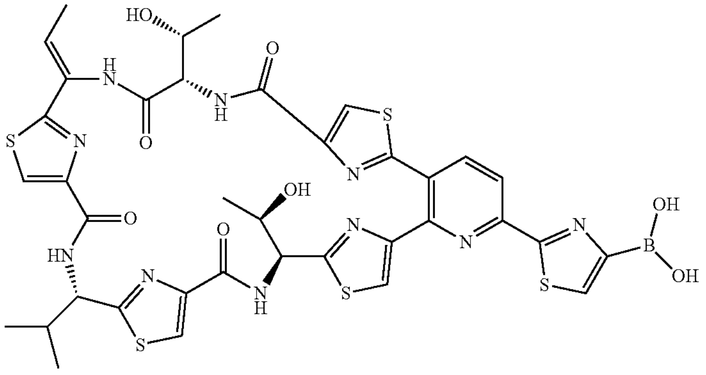

X

Compound IX (41 mg, 0.043 mmol) was dissolved in 1,4-dioxane (0.6 mL), and then bis(pinacolato)diboron (14.2 mg, 0.056 mmol), potassium acetate (6.7 mg, 0.065 mmol), and Xphos (3.1 mg, 15 mol %) were added. After completion of the addition, nitrogen was added for 1 minute, and then tris(dibenzylideneacetone)dipalladium(0) (4 mg, 10 mol %) was added. The mixture was stirred at 85° C. for 3 hours, diluted with dichloromethane, and then the organic solvent was extracted. The extracted organic solvent was washed with water, dried over anhydrous sodium sulfate and concentrated under reduced pressure, thereby obtaining Compound X (18 mg, 47%) as a solid.

$^1$H NMR (400 MHz, MeOD) δ 8.40-8.21 (m, 4H), 8.13 (s, 1H), 7.93 (s, 1H), 7.76 (s, 1H), 6.61 (q, J=6.9 Hz, 1H), 5.23 (dd, J=13.3, 5.7 Hz, 2H), 4.75 (d, J=3.1 Hz, 1H), 4.62-4.50 (m, 1H), 4.30 (dd, J=6.3, 2.9 Hz, 1H), 2.64 (td, J=13.4, 6.7 Hz, 1H), 1.85 (d, J=7.0 Hz, 3H), 1.53 (d, J=6.4 Hz, 3H), 1.31 (d, J=3.9 Hz, 2H), 1.19 (d, J=6.3 Hz, 3H), 1.13 (d, J=6.7 Hz, 3H), 0.99 (d, J=6.7 Hz, 3H).

Preparation of Compound XI

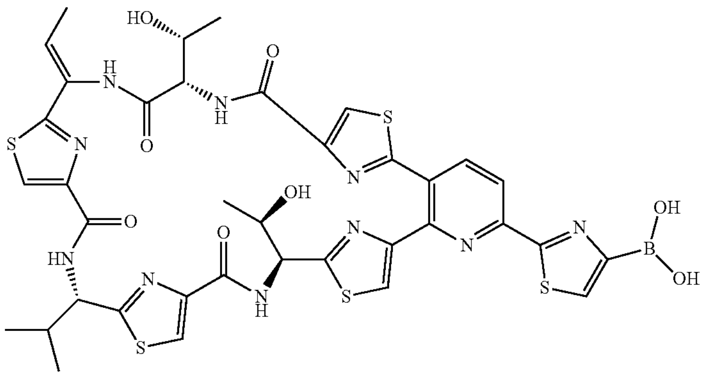

X

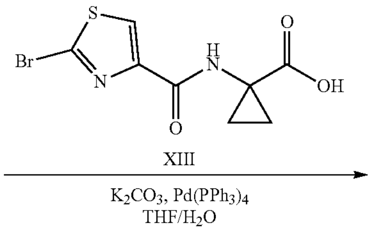

-continued

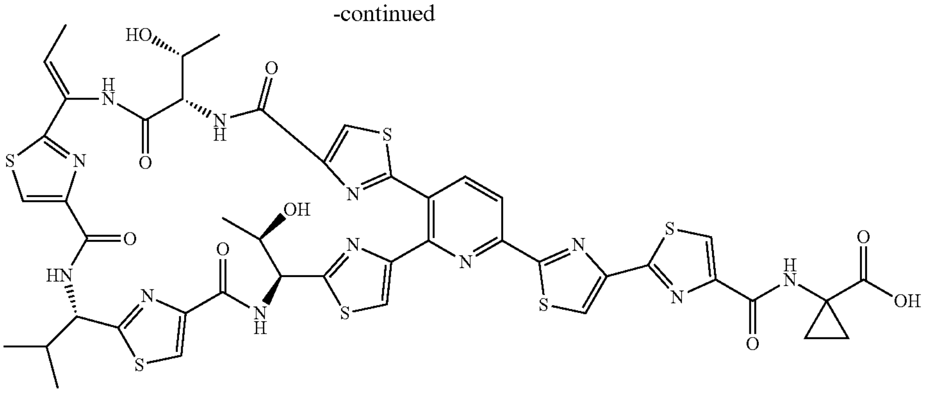

XI

Compound X (276 mg, 0.3 mmol) was dissolved in a mixture of tetrahydrofuran (6 mL) and water (1.5 mL). Compound XIII (131 mg, 0.45 mmol) was added, and then nitrogen was supplied for 3 minutes. Thereafter, potassium carbonate (124 mg, 0.9 mmol) and tetrakis(triphenylphosphine)palladium (10 mol %, 35 mg) were added, and nitrogen was added again for 1 minute. The mixture was stirred at 38° C. for 3 hours, and then concentrated under reduced pressure. The resulting residue was purified by column chromatography (eluent: 0 to 25% methanol/100 to 75% dichloromethane) to obtain Compound XI (179 mg, 55%) as a white solid.

$^1$H NMR (400 MHz, MeOD) δ 8.49-8.38 (m, 5H), 8.34-8.22 (m, 5H), 8.14 (s, 1H), 7.95 (s, 1H), 6.65-6.62 (m, 1H), 5.31-5.12 (m, 2H), 4.81-4.75 (m, 1H), 4.62-4.56 (m, 1H), 4.38-4.25 (m, 1H), 2.72-2.61 (m, 1H), 1.86 (d, J=7.0 Hz, 3H), 1.68-1.59 (m, 2H) 1.53 (d, J=6.4 Hz, 3H), 1.25-1.02 (m, 8H), 1.00 (d, J=6.6 Hz, 3H)

[Preparation Example 2] Preparation of Compound XVII

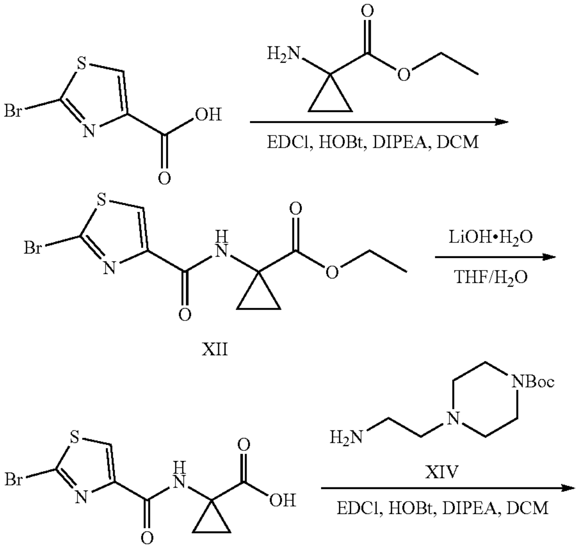

XII

XIII

-continued

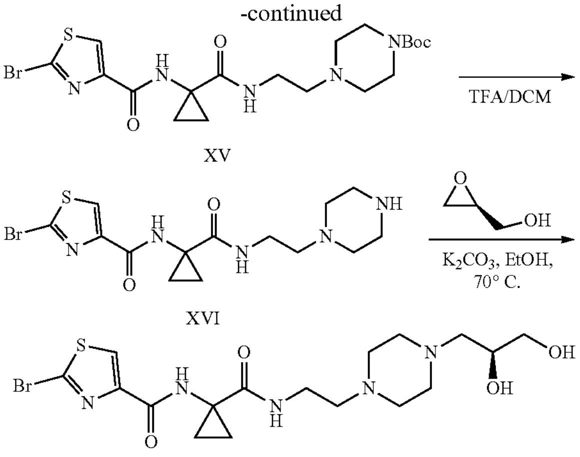

XV

XVI

XVII

Preparation of Compound XII

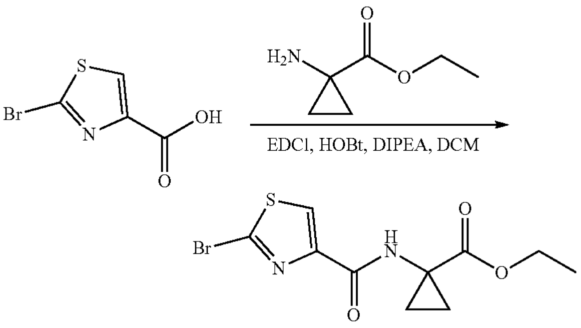

XII

2-Bromo-thiazole-4-carboxylic acid (832 mg, 4 mmol) was dissolved in dichloromethane (20 mL), and then ethyl 1-aminocyclopropanecarboxylate (726 mg, 4.4 mmol) and N,N-diisopropylethylamine (1.74 mL, 10 mmol) were added dropwise. Thereafter, 1-ethyl-3-(3-dimethylaminopropyl) carbodiimide (840 mg, 4.4 mmol) and hydroxybenzotriazole (594 mg, 4.4 mmol) were added, and the mixture was stirred at room temperature for 12 hours. The reaction was quenched with water, and the organic solvent was extracted with dichloromethane. The extracted organic solvent was dried over anhydrous sodium sulfate and concentrated under reduced pressure. The resulting residue was purified by column chromatography (eluent: 20 to 50% ethyl acetate/80 to 50% hexane) to obtain Compound XII (1.04 g, 82%) in the form of an oil.

$^1$H NMR (400 MHz, $CDCl_3$) δ 8.10 (s, 1H), 7.68 (s, 1H), 4.17 (q, J=7.1 Hz, 2H), 1.67 (q, J=4.8 Hz, 2H), 1.32-1.21 (m, 5H).

Preparation of Compound XIII

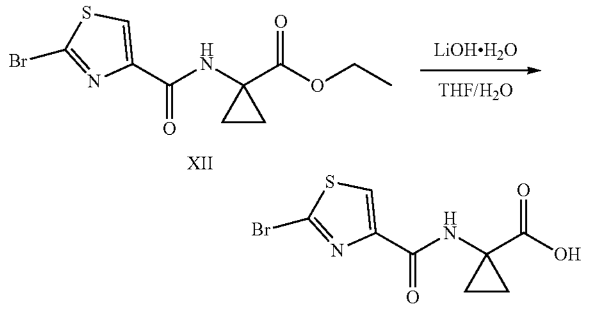

XII

XIII

Compound XII (1.048 g, 3.26 mmol) was dissolved in a mixture of tetrahydrofuran/water (1:1, 30 mL), lithium hydroxide monohydrate (342 mg, 8.15 mmol) was added, and then the mixture was stirred for 2 hours. The reaction was quenched using 1 M hydrochloric acid at 0° C., and then the mixture was extracted with ethyl acetate. The extracted organic solvent was dried over anhydrous sodium sulfate and concentrated under reduced pressure to obtain Compound XIII (940 mg, 98%) in the form of an oil.

$^1$H NMR (400 MHz, $CDCl_3$) δ 8.13 (s, 1H), 7.71 (s, 1H), 1.79-1.71 (m, 2H), 1.41-1.33 (m, 2H).

Preparation of Compound XV

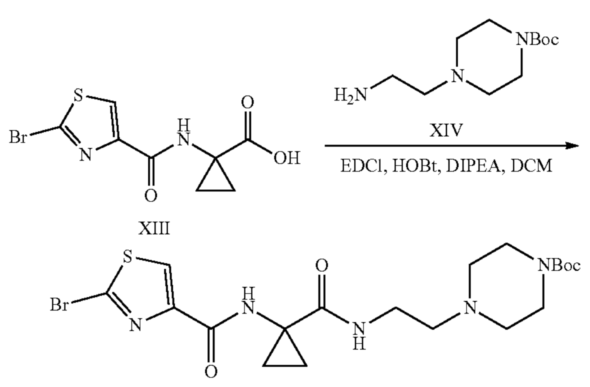

XIII

XV

Compound XIII (231 mg, 0.8 mmol) was dissolved in dimethylformamide (4 mL), Compound XIV (209 mg, 0.909 mmol) and N,N-diisopropylethylamine (0.56 ml, 3.2 mmol) were added dropwise. Thereafter, 1-ethyl-3-(3-dimethylaminopropyl)carbodiimide (174 mg, 0.91 mmol) and hydroxybenzotriazole (123 mg, 0.91 mmol) were added, and the mixture was stirred at room temperature for 12 hours. The residue obtained by concentration under reduced pressure was purified by column chromatography (eluent: 3 to 5% methanol/97 to 95% dichloromethane) to obtain Compound XV (337 mg, 84%) as a white solid.

$^1$H NMR (400 MHz, $CDCl_3$) δ 8.12 (s, 1H), 7.70 (s, 1H), 7.06 (s, 1H), 3.35 (dd, J=11.1, 5.3 Hz, 2H), 3.26-3.17 (m, 4H), 2.49 (t, J=5.9 Hz, 2H), 2.41-2.28 (m, 4H), 1.71-1.65 (m, 2H), 1.47 (d, J=1.1 Hz, 9H), 1.16 (q, J=4.6 Hz, 2H).

Preparation of Compound XVI

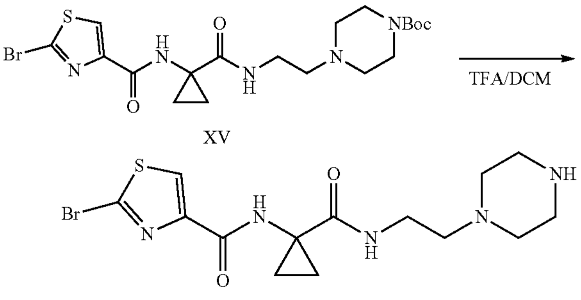

XV

XVI

Compound XV (330 mg, 0.66 mmol) was dissolved in a mixed solution of trifluoroacetic acid (3 mL) and dichloromethane (3 mL), and the mixture was stirred at room temperature for 1 hour. the mixture was concentrated under reduced pressure to obtain Compound XVI (124 mg, 47%) as a white solid.

$^1$H NMR (400 MHz, $CDCl_3$) δ 8.23-8.14 (m, 1H), 8.08 (s, 1H), 8.02 (s, 1H), 3.92-3.64 (m, 10H), 3.48-3.39 (m, 2H), 1.79-1.67 (m, 2H), 1.13-1.04 (m, 2H).

Preparation of Compound XVII

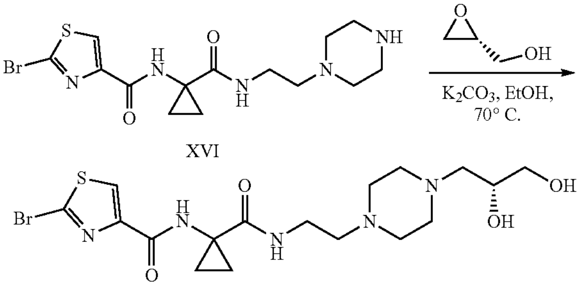

XVI

XVII

Compound XVI (157 mg, 0.391 mmol) was dissolved in ethanol (1 mL), potassium carbonate (27 mg, 0.196 mmol) and R-glycidol (33 uL, 0.469 mmol) were added, the mixture was stirred at 70° C. for 12 hours, and then concentrated under reduced pressure. The concentrate was purified by column chromatography (eluent: 10% methanol/90% dichloromethane) to obtain Compound XVII (37 mg, 21%).

$^1$H NMR (400 MHz, MeOD) δ 8.27 (s, 1H), 3.79 (dq, J=10.5, 5.2 Hz, 1H), 3.58-3.46 (m, 2H), 3.35-3.30 (m, 4H), 2.66-2.43 (m, 8H), 2.45-2.33 (m, 2H), 1.55 (q, J=4.6 Hz, 2H), 1.17 (q, J=4.6 Hz, 2H).

[Example 1] Preparation of Compound 2

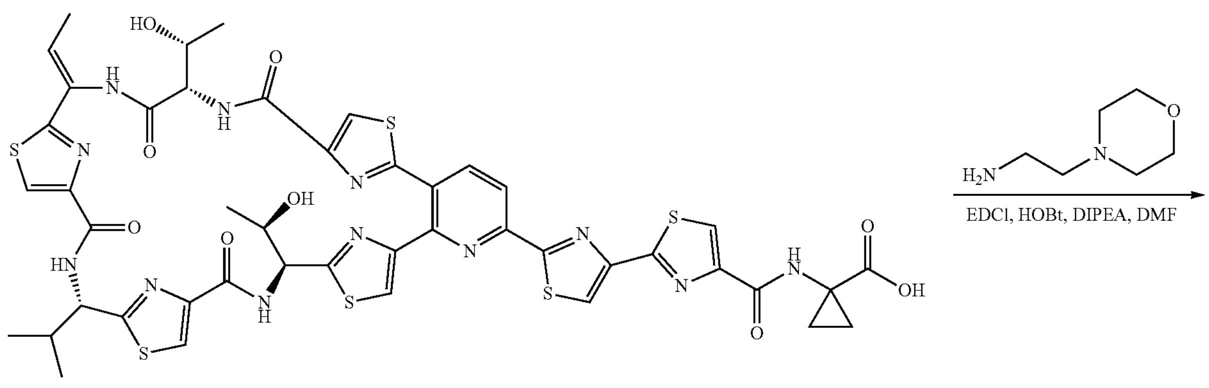

XI

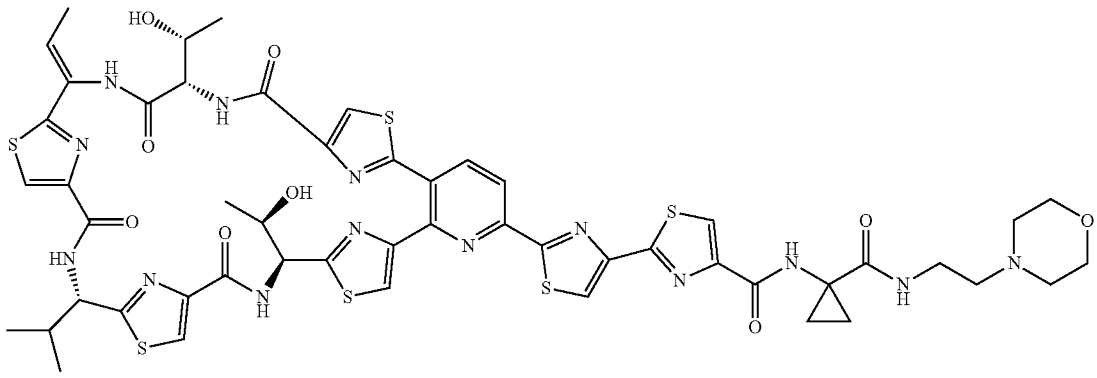

2

Compound XI (11 mg, 0.01 mmol) prepared in Preparation Example 1 was dissolved in DMF (0.1 mL), 1-ethyl-3-(3-dimethylaminopropyl)carbodiimide (3 mg, 0.015 mmol), hydroxybenzotriazole (2 mg, 0.015 mmol), N,N-diisopropylethylamine (3 uL, 0.015 mmol), and 4-(2-aminoethyl)morpholine (0.25 uL, 0.0015 mmol) were added, and the mixture was stirred at room temperature for 12 hours. The residue thus obtained was purified by high-performance liquid chromatography (GX-281 HPLC System, Gilson, USA; column tube 250 mm×21.2 mm on Kinetex 5 μM biphenyl, 100 Å) using (0 to 40% acetonitrile/100 to 60% water) as an eluent, thereby obtaining Compound 2 (1.9 mg, 16%) as a white solid.

$^1$H NMR (400 MHz, MeOD) δ 8.43 (s, 1H), 8.42 (d, J=2.2 Hz, 2H), 8.38 (s, 1H), 8.30 (s, 1H), 8.26 (s, 1H), 8.14 (s, 1H), 7.94 (s, 1H), 6.62 (q, J=6.9 Hz, 1H), 5.25-5.19 (m, 2H), 4.77 (d, J=3.1 Hz, 1H), 4.62-4.52 (m, 1H), 4.36-4.26 (m, 1H), 4.15-4.06 (broad peak, 3H), 3.89-3.71 (broad peak, 3H), 3.69-3.58 (m, 5H), 2.71-2.55 (m, 1H), 1.86 (d, J=7.0 Hz, 3H), 1.71-1.67 (m, 2H), 1.54 (d, J=6.5 Hz, 3H), 1.49-1.31 (m, 2H) 1.20 (d, J=6.3 Hz, 3H), 1.14 (d, J=6.7 Hz, 3H), 1.00 (d, J=6.6 Hz, 3H).

LCMS: 1,199.6 (M+H$^+$) for $C_{51}H_{54}N_{14}O_9S_6$

[Example 2] Preparation of Compound 4

XI

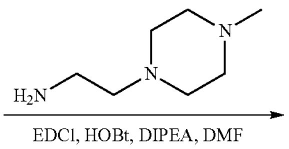

-continued

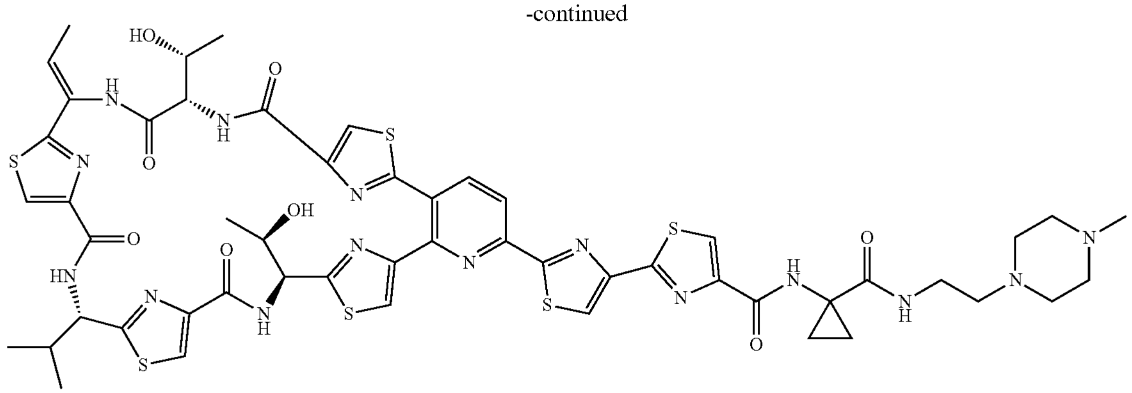

4

Compound 4 (2.4 mg, 20%) was obtained as a white solid from Compound XI in the same manner as that of Example 1.

$^1$H NMR (400 MHz, MeOD) δ 8.44 (s, 1H), 8.40 (d, J=1.8 Hz, 2H), 8.35 (s, 1H), 8.29 (s, 1H), 8.26 (s, 1H), 8.14 (s, 1H), 7.94 (s, 1H), 6.62 (q, J=6.9 Hz, 1H), 5.29-5.18 (m, 2H), 4.78 (d, J=3.1 Hz, 1H), 4.61-4.52 (m, 1H), 4.38-4.29 (m, 1H), 3.45-3.37 (m, 2H), 3.29-3.10 (broad peak, 4H), 2.99-2.82 (broad peak, 2H), 2.81 (s, 3H), 2.67-2.54 (m, 3H), 2.09-1.99 (m, 2H), 1.86 (d, J=7.0 Hz, 3H), 1.62 (dd, J=7.6, 4.4 Hz, 2H), 1.54 (d, J=6.4 Hz, 3H), 1.29-1.23 (m, 2H), 1.20 (d, J=6.3 Hz, 3H), 1.14 (d, J=6.7 Hz, 3H), 1.00 (d, J=6.7 Hz, 3H).

LCMS: 1,212.7 (M+H$^+$) for $C_{52}H_{57}N_{15}O_8S_6$

[Example 3] Preparation of Compound 5

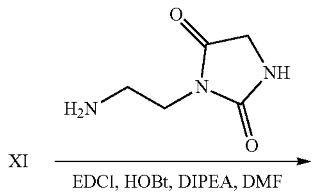

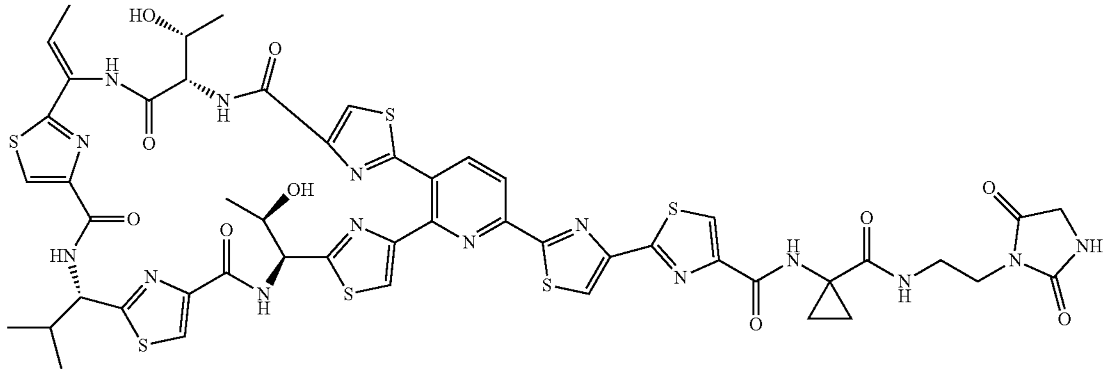

5

Compound 5 (2.8 mg, 23%) was obtained as a white solid from Compound XI in the same manner as that of Example 1.

$^1$H NMR (400 MHz, MeOD) δ 8.43 (d, J=9.5 Hz, 1H), 8.35 (d, J=9.7 Hz, 1H), 8.25-8.08 (m, 6H), 8.05 (s, 1H), 8.00 (s, 1H), 7.81 (s, 2H), 7.55-7.40 (m, 1H), 6.54-6.41 (m, 1H), 5.18-5.07 (m, 2H), 4.73-4.68 (m, 2H), 4.53-4.47 (m, 1H), 4.21-4.15 (m, 1H), 3.82 (s, 2H), 3.59-3.48 (m, 2H), 3.42-3.27 (m, 2H), 2.51-2.48 (m, 1H), 2.05-1.86 (m, 2H), 1.74 (d, J=6.8 Hz, 3H), 1.53-1.38 (m, 5H), 1.03 (dd, J=15.2, 6.4 Hz, 6H), 0.86 (d, J=6.7 Hz, 3H)

LCMS: 1,212.7 (M+H$^+$) for $C_5OH_{49}N_{15}O_1S_6$

[Example 4] Preparation of Compound 6

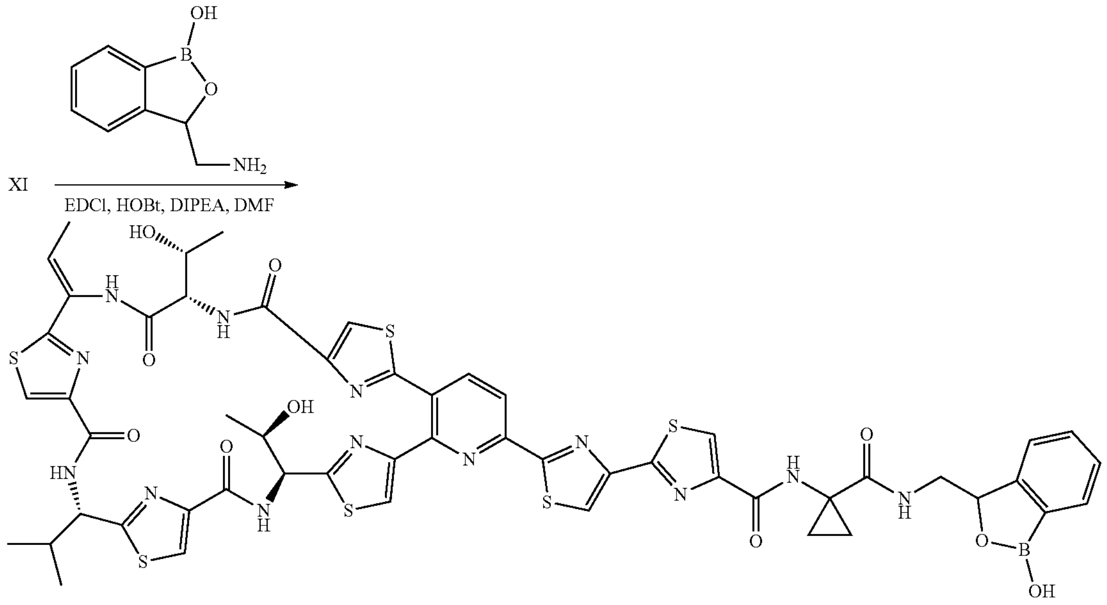

6

Compound 6 (4.2 mg, 34%) was obtained as a white solid from Compound XI in the same manner as that of Example 1.

$^{1}$H NMR (400 MHz, MeOD) δ 8.47-8.34 (m, 3H), 8.32 (s, 1H), 8.27 (d, J=8.9 Hz, 2H), 8.14 (s, 1H), 7.95 (s, 1H), 7.58 (d, J=7.1 Hz, 1H), 7.52-7.39 (m, 2H), 7.34-7.24 (m, 1H), 6.62 (q, J=7.0 Hz, 1H), 5.44-5.07 (m, 4H), 4.61-4.50 (m, 1H), 4.35-4.27 (m, 1H), 4.13-4.01 (m, 1H), 3.99-3.82 (m, 3H), 2.73-2.57 (m, 1H), 1.86 (d, J=7.0 Hz, 3H), 1.68-1.57 (m, 2H), 1.54 (d, J=6.4 Hz, 3H), 1.20 (d, J=6.3 Hz, 3H), 1.13 (d, J=6.7 Hz, 3H), 1.00 (d, J=6.7 Hz, 3H).

LCMS: 1,233.7 (M+H$^+$) for $C_{53}H_{50}BN_{13}O_{10}S_6$

[Example 5] Preparation of Compound 7

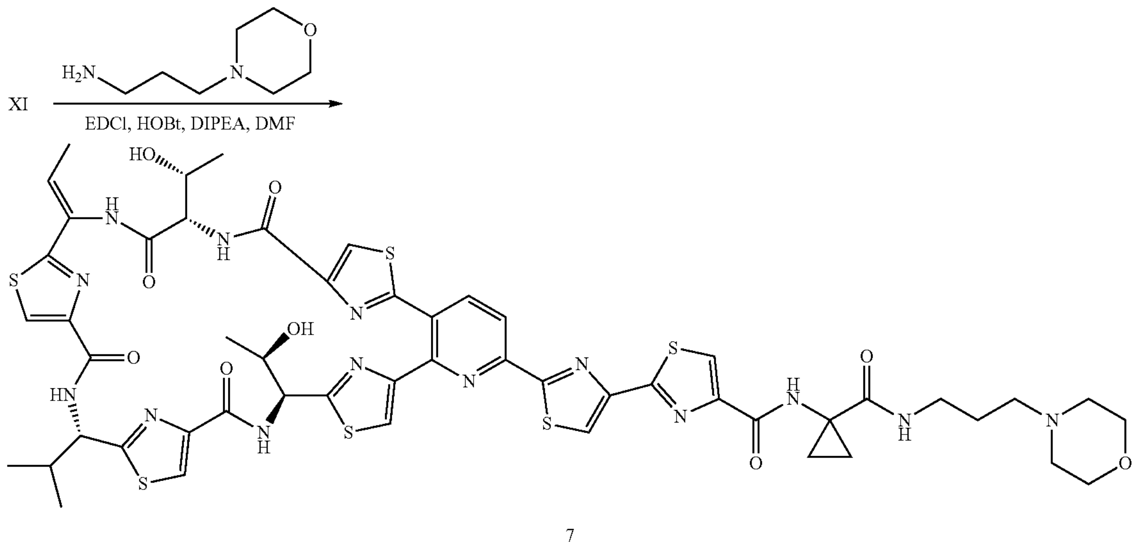

7

Compound 7 (3.1 mg, 26%) was obtained as a white solid from Compound XI in the same manner as that of Example 1.

$^{1}$H NMR (400 MHz, MeOD) δ 9.19 (s, 1H), 8.63-8.43 (m, 2H), 8.38-8.31 (m, 4H), 8.30 (s, 1H), 8.27 (s, 1H), 8.20 (s, 1H), 8.14 (s, 1H), 7.99-7.90 (m, 2H), 6.60 (q, J=6.8 Hz, 1H), 5.29-5.16 (m, 2H), 4.79 (dd, J=7.7, 2.9 Hz, 1H), 4.60 (dd, J=6.3, 2.9 Hz, 1H), 4.29 (dd, J=6.3, 2.7 Hz, 1H), 4.17-4.04 (m, 2H), 3.80 (t, J=12.2 Hz, 2H), 3.53 (d, J=12.5 Hz, 2H), 3.42-3.35 (m, 2H), 3.29-3.10 (m, 6H), 2.61 (dt, J=13.5, 6.7 Hz, 1H), 2.02-1.92 (m, 2H), 1.86 (d, J=6.9 Hz, 3H), 1.75-1.58 (m, 2H), 1.56 (d, J=6.4 Hz, 3H), 1.16 (dd, J=15.0, 6.5 Hz, 6H), 0.98 (d, J=6.6 Hz, 3H).

LCMS: 1,213.8 (M+H$^+$) for $C_{52}H_{56}N_{14}O_9S_6$

[Example 6] Preparation of Compound 9
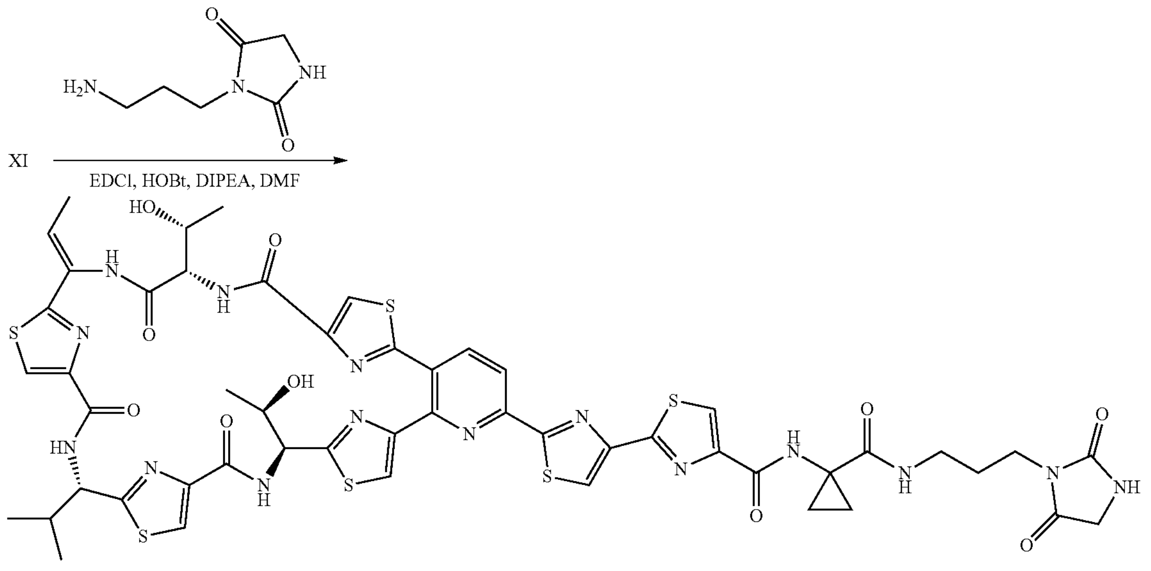
9
Compound 9 (3.7 mg, 30%) was obtained as a white solid from Compound XI in the same manner as that of Example 1.
$^1$H NMR (400 MHz, $CDCl_3$) δ 8.69 (s, 1H), 8.37 (d, J=9.4 Hz, 1H), 8.25 (d, J=8.1 Hz, 1H), 8.18 (d, J=10.6 Hz, 2H), 8.15-8.06 (m, 3H), 7.99-7.89 (m, 4H), 7.39-7.35 (m, 1H), 6.38 (q, J=6.9 Hz, 1H), 5.26-5.13 (m, 2H), 4.87 (d, J=7.8 Hz, 1H), 4.74-4.53 (m, 2H), 4.49-4.29 (m, 1H), 3.89 (s, 2H), 3.59 (t, J=5.9 Hz, 2H), 3.30-3.20 (m, 2H), 2.46 (td, J=13.6, 6.7 Hz, 1H), 1.84-1.75 (m, 5H), 1.68-1.64 (m, 2H), 1.27-1.20 (m, 5H), 1.17 (d, J=6.2 Hz, 3H), 1.12 (d, J=6.6 Hz, 3H), 0.93 (d, J=6.5 Hz, 3H).
LCMS: 1,226.7 ($M+H^+$) for $C_{51}H_{51}N_{15}O_{10}S_6$
[Example 7] Preparation of Compound 10
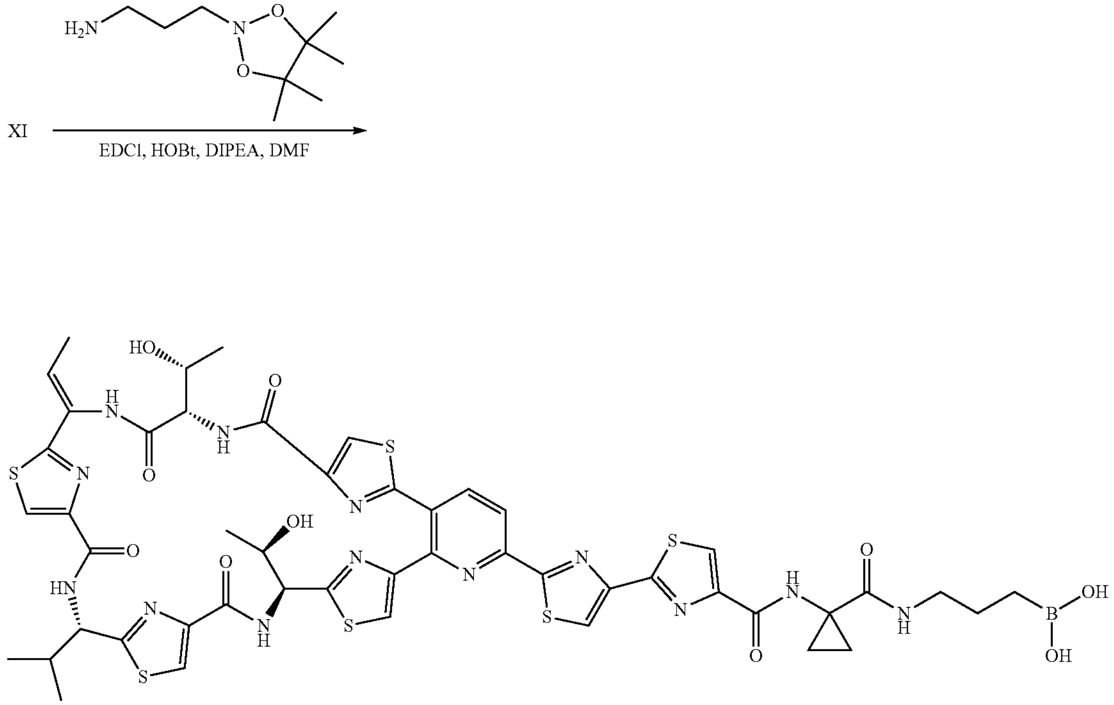
10

Compound 10 (3.2 mg, 28%) was obtained as a white solid from Compound XI in the same manner as that of Example 1.

$^1$H NMR (400 MHz, MeOD) δ 9.04 (s, 1H), 8.66-8.35 (m, 2H), 8.34-8.16 (m, 6H), 8.18-8.03 (m, 2H), 7.97-7.83 (m, 2H), 6.55 (bs, 1H), 5.26-5.13 (m, 2H), 4.79-4.72 (m, 1H), 4.62-4.53 (m, 1H), 4.29-4.19 (m, 1H), 2.57 (bs, 1H), 1.82 (broad peak, 3H), 1.71-1.58 (m, 6H), 1.58-1.47 (m, 6H), 1.11 (dd, J=12.2, 6.4 Hz, 6H), 0.94 (d, J=6.6 Hz, 3H), 0.80-0.69 (m, 2H).

[Example 8] Preparation of Compound 11

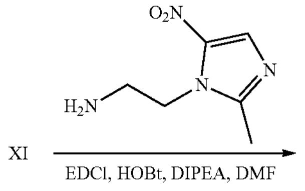

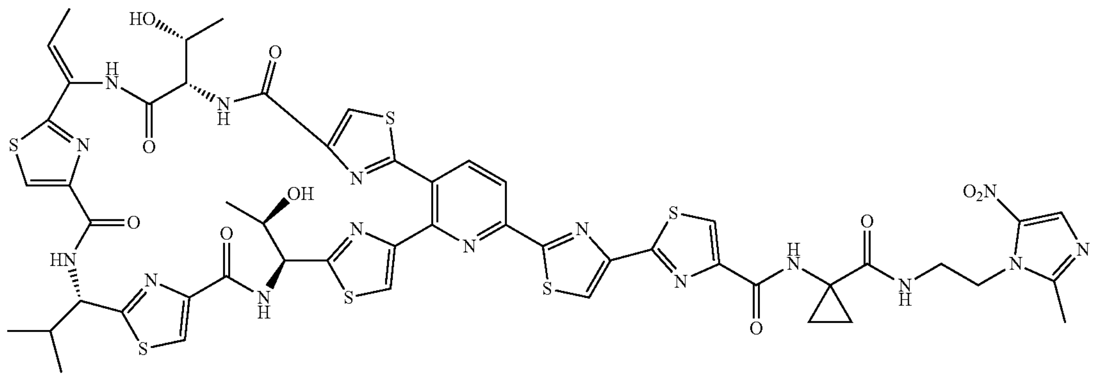

11

Compound 11 (4 mg, 33%) was obtained as a white solid from Compound XI in the same manner as that of Example 1.

$^1$H NMR (400 MHz, MeOD) δ 9.06 (s, 1H), 8.54 (dd, J=24.0, 9.3 Hz, 2H), 8.39-8.23 (m, 6H), 8.14 (s, 2H), 7.98-7.88 (m, 3H), 6.61 (q, J=7.0 Hz, 1H), 5.27-5.19 (m, 2H), 4.83-4.77 (m, 1H), 4.63-4.58 (m, 1H), 4.51 (t, J=5.1 Hz, 2H), 4.33-4.27 (m, 1H), 3.71-3.64 (m, 2H), 2.68-2.54 (m, 4H), 1.86 (d, J=6.9 Hz, 3H), 1.64-1.47 (m, 5H), 1.25-1.21 (m, 2H), 1.16 (dd, J=13.6, 6.5 Hz, 6H), 0.98 (d, J=6.6 Hz, 3H).

LCMS: 1,239.9 (M+H$^+$) for $C_{51}H_{50}N_{16}O_{10}S_6$

[Example 9] Preparation of Compound 12

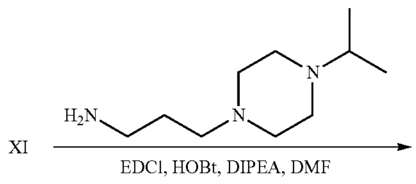

-continued

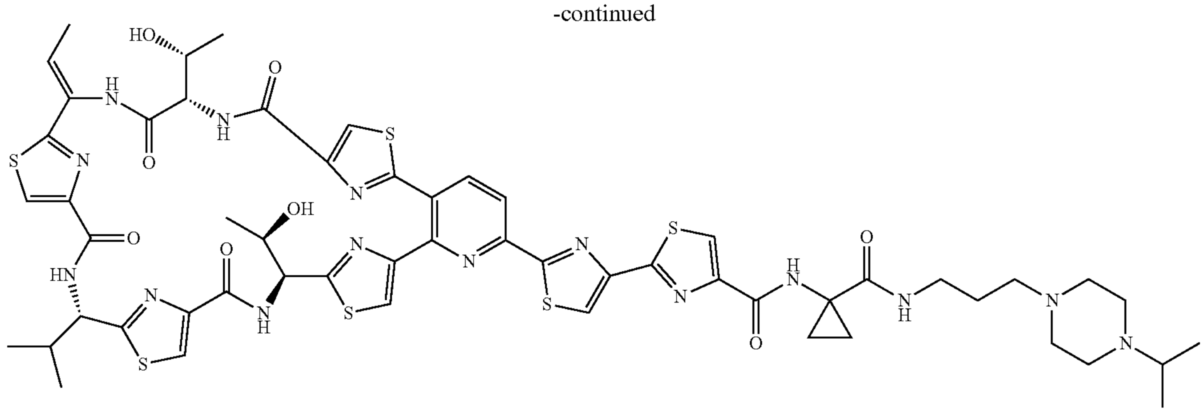

12

Compound 12 (2 mg, 24%) was obtained as a white solid from Compound XI in the same manner as that of Example 1.

$^1$H NMR (400 MHz, MeOD) δ 8.31-8.23 (m, 3H), 8.21 (s, 1H), 8.15 (s, 1H), 8.13 (s, 1H), 8.03 (s, 1H), 7.83 (s, 1H), 6.50 (q, J=6.9 Hz, 1H), 5.14-5.07 (m, 2H), 4.69-4.63 (m, 1H), 4.51-4.43 (m, 1H), 4.23-4.08 (m, 1H), 3.61-3.30 (m, 5H), 3.18-3.09 (m, 6H), 3.02 (t, J=7.2 Hz, 2H), 2.51 (td, J=13.5, 6.7 Hz, 1H), 1.98-1.78 (m, 2H), 1.74 (d, J=7.0 Hz, 3H), 1.61-1.48 (m, 5H), 1.47-1.43 (m, 2H), 1.28 (d, J=6.5 Hz, 6H), 1.05 (dd, J=19.4, 6.5 Hz, 6H), 0.87 (d, J=6.6 Hz, 3H).

LCMS: 1,254.7 (M+H$^+$) for $C_{55}H_{63}N_{15}O_8S_6$

[Example 10] Preparation of Compound 13

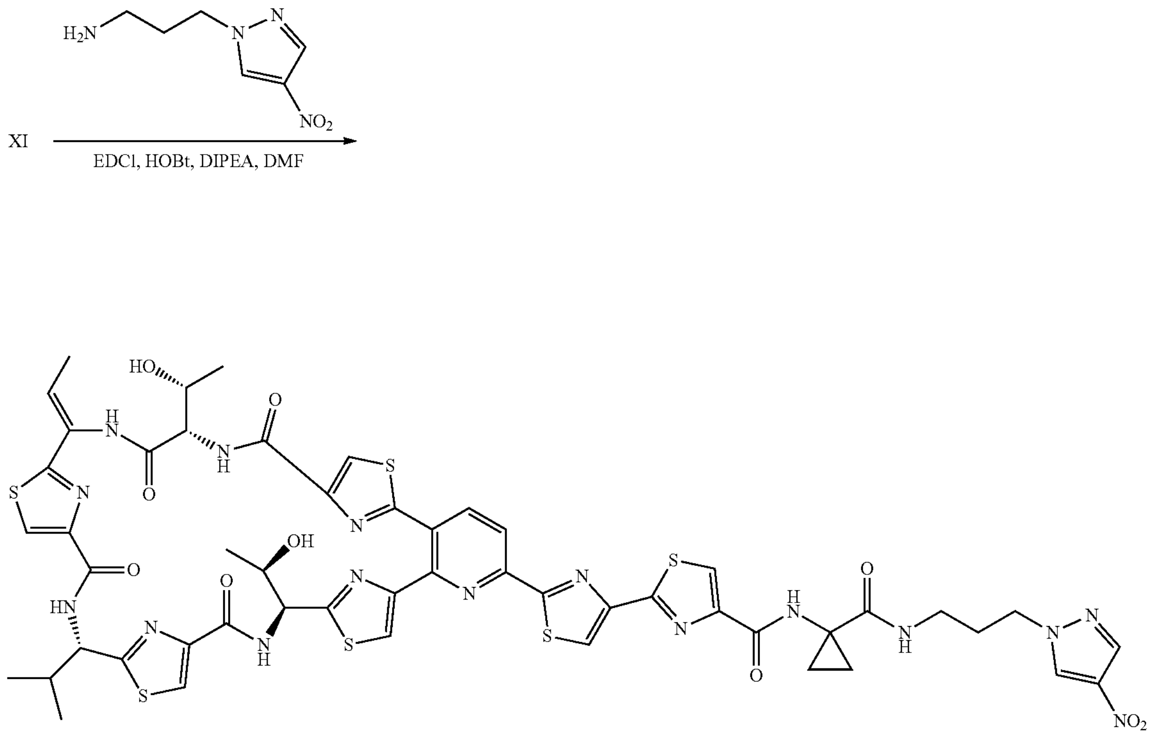

13

Compound 13 (5.1 mg, 42%) was obtained as a white solid from Compound XI in the same manner as that of Example 1.

$^1$H NMR (400 MHz, $CDCl_3$) δ 8.45-8.33 (m, 2H), 8.33-8.21 (m, 2H), 8.19 (s, 2H), 8.14-8.09 (m, 4H), 8.03-7.93 (m, 4H), 7.90 (s, 1H), 6.94 (s, 1H), 6.42 (q, J=7.0 Hz, 1H), 5.28-5.18 (m, 2H), 4.82 (d, J=6.4 Hz, 1H), 4.68-4.58 (m, 1H), 4.37 (q, J=7.2 Hz, 1H), 4.26 (t, J=6.5 Hz, 2H), 3.39-3.23 (m, 2H), 2.44 (td, J=13.5, 6.7 Hz, 1H), 2.21-2.11 (m, 2H), 1.83 (d, J=7.0 Hz, 3H), 1.77-1.68 (m, 2H), 1.53 (d, J=6.4 Hz, 3H), 1.23-1.15 (m, 5H), 1.12 (d, J=6.7 Hz, 3H), 0.95 (d, J=6.6 Hz, 3H)

LCMS: 1,239.8 (M+H$^+$) for $C_{51}H_{50}N_{16}O_{10}S_6$

[Example 11] Preparation of Compound 14

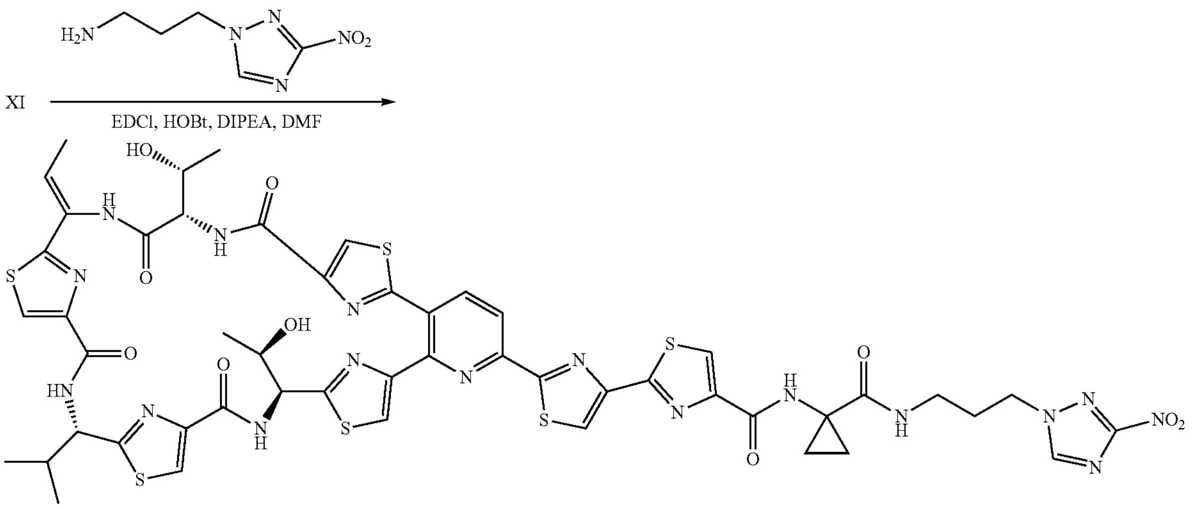

14

Compound 14 (5.3 mg, 43%) was obtained as a white solid from Compound XI in the same manner as that of Example 1.

$^1$H NMR (400 MHz, $CDCl_3$) δ 8.41 (s, 1H), 8.35-8.27 (m, 2H), 8.25-8.19 (m, 2H), 8.14-8.11 (m, 3H), 8.06-8.01 (m, 2H), 7.96-7.89 (m, 2H), 7.89-7.82 (m, 2H), 6.80 (s, 1H), 6.35 (q, J=7.0 Hz, 1H), 5.22-5.13 (m, 2H), 4.75 (d, J=8.2 Hz, 1H), 4.59-4.51 (m, 1H), 4.39-4.27 (m, 3H), 3.37-3.22 (m, 2H), 2.38 (td, J=13.3, 6.4 Hz, 1H), 2.19-2.04 (m, 2H), 1.73-1.62 (m, 2H), 1.47 (d, J=6.4 Hz, 3H), 1.21-1.14 (m, 2H), 1.09 (dd, J=25.3, 6.6 Hz, 6H), 0.89 (d, J=6.6 Hz, 3H).

LCMS: 1,240.6 ($M+H^+$) for $C_{50}H_{49}N_{17}O_{10}S_6$

[Example 12] Preparation of Compound 15

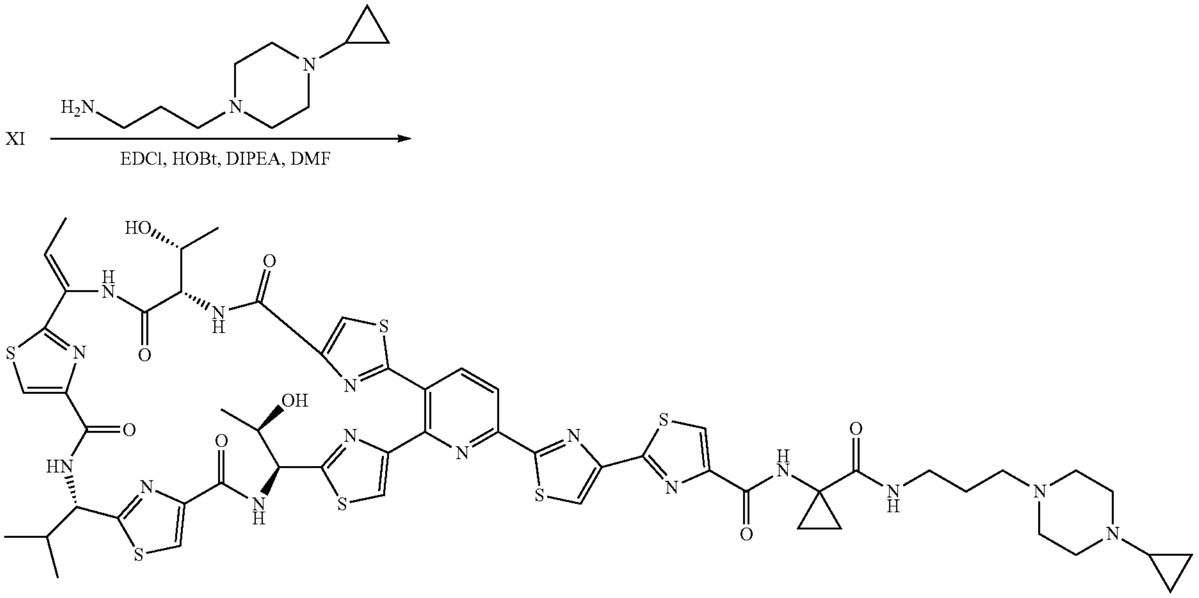

15

Compound 15 (4.2 mg, 34%) was obtained as a white solid from Compound XI in the same manner as that of Example 1.

$^1$H NMR (400 MHz, MeOD) δ 8.55 (dd, J=13.0, 9.7 Hz, 1H), 8.43-8.36 (m, 2H), 8.33 (s, 1H), 8.27 (d, J=2.4 Hz, 1H), 8.14 (s, 1H), 7.97-7.94 (m, 1H), 6.62 (q, J=6.9 Hz, 1H), 5.26-5.18 (m, 2H), 4.80-4.76 (m, 1H), 4.65-4.52 (m, 1H), 4.35-4.28 (m, 1H), 3.15 (t, J=7.4 Hz, 2H), 2.63 (td, J=15.3, 6.7 Hz, 1H), 2.13-1.88 (m, 2H), 1.86 (d, J=7.0 Hz, 3H), 1.68-1.59 (m, 2H), 1.55 (d, J=6.4 Hz, 3H), 1.17 (dd, J=21.7, 6.5 Hz, 6H), 0.99 (d, J=6.6 Hz, 3H), 0.64-0.54 (m, 2H), 0.54-0.43 (m, 2H).

LCMS: 1,252.7 ($M+H^+$) for $C_{55}H_{61}N_{15}O_8S_6$

[Example 13] Preparation of Compound 17

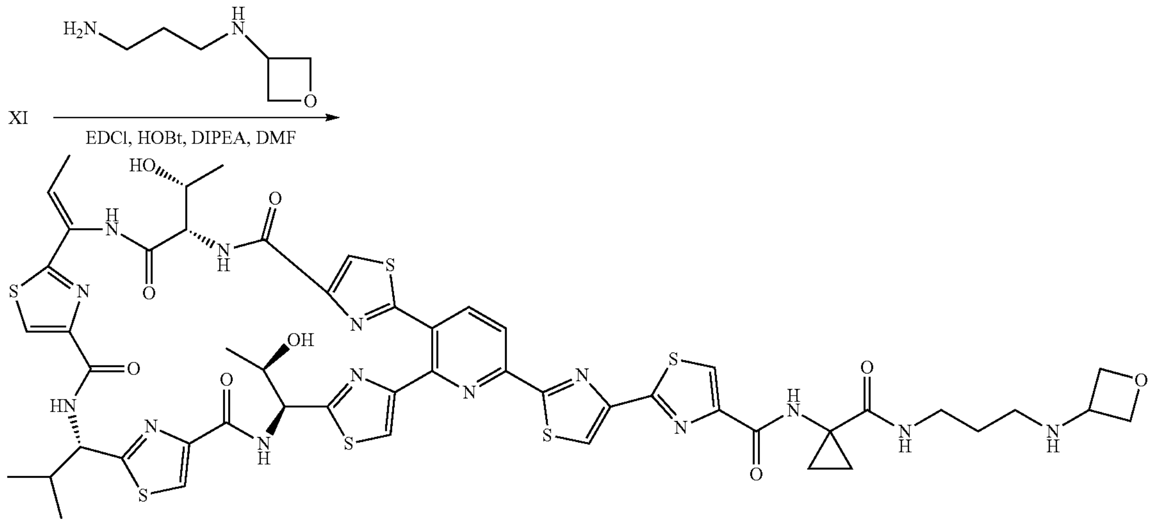

17

Compound 17 (3.2 mg, 27%) was obtained as a white solid from Compound XI in the same manner as that of Example 1.

$^1$H NMR (400 MHz, MeOD) δ 8.42 (dd, J=13.6, 9.7 Hz, 1H), 8.31-8.21 (m, 3H), 8.20 (s, 1H), 8.14 (d, J=3.3 Hz, 2H), 8.02 (s, 1H), 7.83 (s, 1H), 7.61-7.41 (m, 1H), 6.49 (q, J=6.9 Hz, 1H), 5.17-5.09 (m, 2H), 4.83 (t, J=7.5 Hz, 2H), 4.69-4.60 (m, 3H), 4.51-4.43 (m, 1H), 4.35-4.29 (m, 1H), 4.23-4.16 (m, 1H), 3.32-3.24 (m, 2H), 2.90 (t, J=7.1 Hz, 2H), 2.51 (td, J=21.8, 6.7 Hz, 1H), 1.97-1.75 (m, 2H), 1.74 (d, J=7.0 Hz, 3H), 1.56-1.48 (m, 2H), 1.43 (d, J=6.4 Hz, 3H), 1.16 (d, J=3.2 Hz, 2H), 1.05 (dd, J=21.2, 6.5 Hz, 6H), 0.87 (d, J=6.7 Hz, 3H).

LCMS: 1,199.6 (M+H$^+$) for $C_{51}H_{54}N_{14}O_9S_6$

[Example 14] Preparation of Compound 18

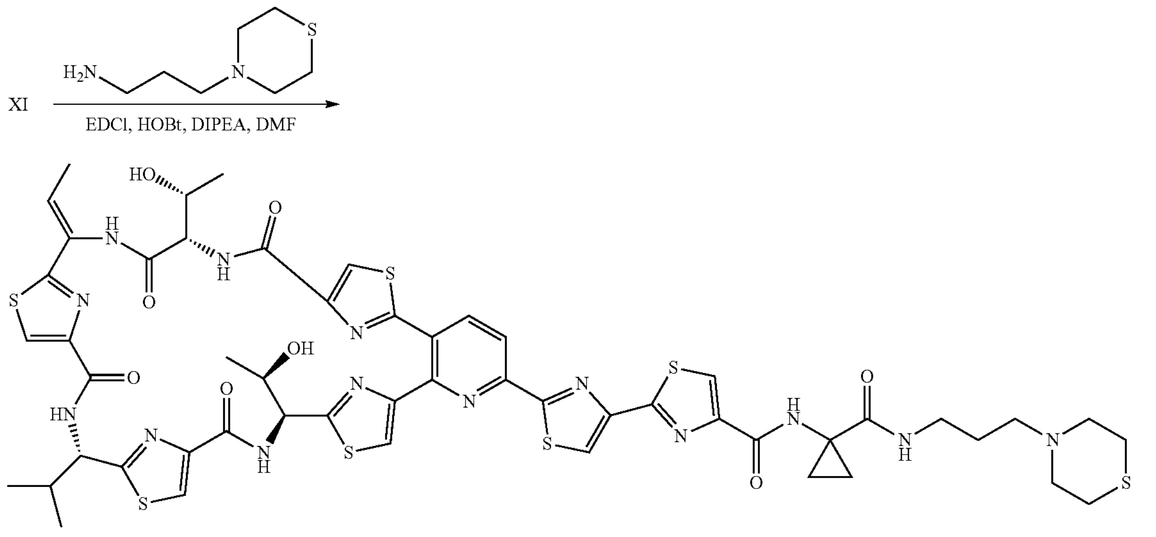

18

Compound 18 (3.4 mg, 28%) was obtained as a white solid from Compound XI in the same manner as that of Example 1.

$^1$H NMR (400 MHz, $CDCl_3$) δ 8.37-8.20 (m, 4H), 8.21-8.06 (m, 2H), 8.06-7.95 (m, 4H), 7.95-7.75 (m, 4H), 6.33 (q, J=7.0 Hz, 1H), 5.24-5.11 (m, 2H), 4.74 (dd, J=8.0, 1.7 Hz, 1H), 4.58-4.52 (m, 1H), 4.34-4.26 (m, 1H), 3.88-3.79 (broad peak, 2H), 3.38-3.21 (m, 4H), 3.13 (t, J=7.0 Hz, 2H), 3.00-2.82 (broad peak, 2H), 2.69-2.61 (broad peak, 2H), 2.38 (td, J=21.8, 6.9 Hz, 1H), 1.76 (d, J=7.0 Hz, 3H), 1.67-1.59 (m, 2H), 1.46 (d, J=6.5 Hz, 3H), 1.12 (d, J=6.5 Hz, 3H), 1.06 (d, J=6.7 Hz, 3H), 0.90 (d, J=6.6 Hz, 3H).

LCMS: 1,229.7 (M+H$^+$) for $C_{52}H_{56}N_{14}O_8S_7$

[Example 15] Preparation of Compound 20

XI

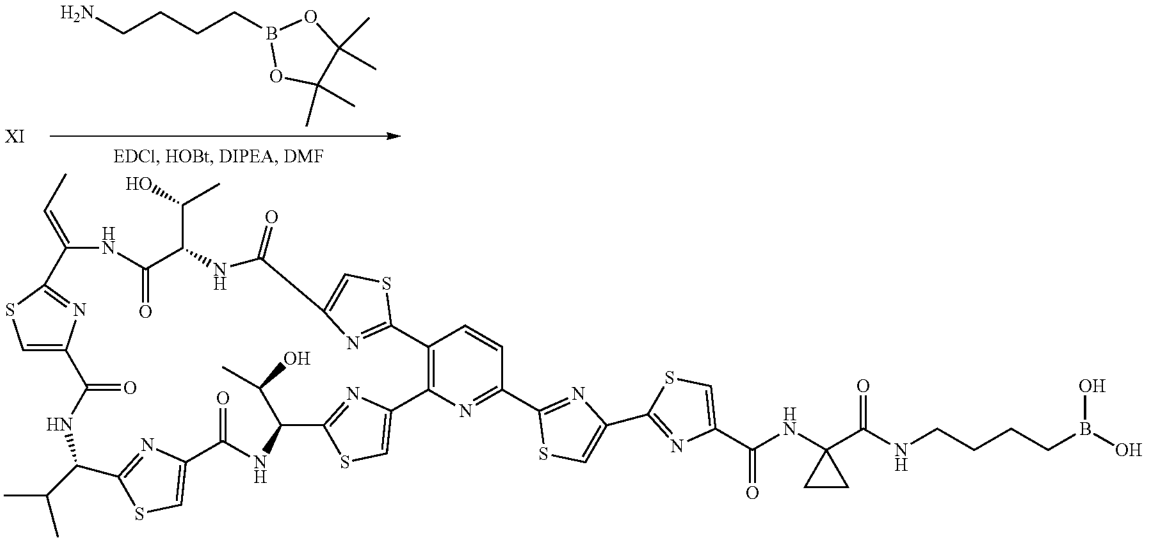

20

Compound 20 (3.1 mg, 26%) was obtained as a white solid from Compound XI in the same manner as that of Example 1.

$^1$H NMR (400 MHz, $CDCl_3$) δ 8.43 (d, J=9.6 Hz, 1H), 8.36-8.32 (m, 2H), 8.32-8.27 (m, 2H), 8.26 (s, 2H), 8.23-8.18 (m, 2H), 8.16-8.11 (m, 1H), 8.06-7.93 (m, 3H), 6.76-6.68 (m, 1H), 6.44 (q, J=7.0 Hz, 1H), 5.31-5.21 (m, 2H), 4.84 (d, J=8.2 Hz, 1H), 4.71-4.62 (m, 1H), 4.43-4.36 (m, 1H), 3.40-3.23 (m, 2H), 2.56-2.42 (m, 1H), 1.88 (d, J=7.0 Hz, 3H), 1.78-1.71 (m, 2H), 1.59-1.50 (m, 5H), 1.48-1.40 (m, 3H), 1.31-1.26 (m, 3H), 1.16 (d, J=6.7 Hz, 3H), 0.99 (d, J=6.6 Hz, 3H), 0.94-0.82 (m, 2H), 0.83-0.76 (m, 2H).

LCMS: 1,208.6 (M+Na$^+$) for $C_{49}H_{52}BN_{13}O_{10}S_6$

[Example 16] Preparation of Compound 21

XI

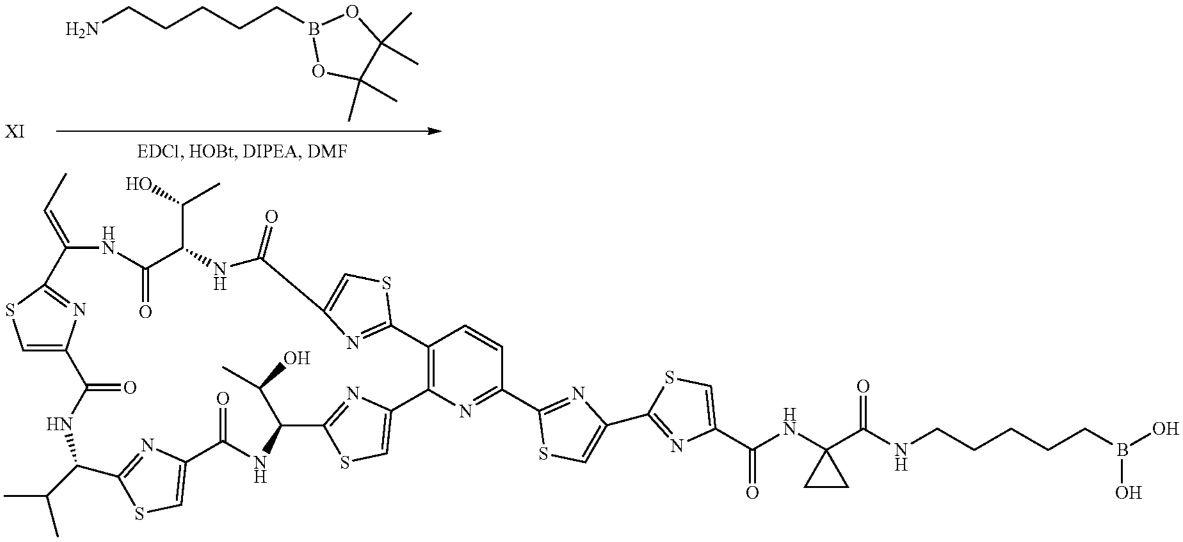

21

Compound 21 (3.3 mg, 28%) was obtained as a white solid from Compound XI in the same manner as that of Example 1.

$^1$H NMR (400 MHz, $CDCl_3$) δ 8.44 (d, J=9.6 Hz, 1H), 8.38-8.32 (m, 2H), 8.31-8.28 (m, 2H), 8.27 (s, 1H), 8.24-8.17 (m, 2H), 8.17-8.11 (m, 2H), 8.10-7.93 (m, 3H), 6.84-6.69 (m, 1H), 6.45 (q, J=7.0 Hz, 1H), 5.30-5.18 (m, 2H), 4.87-4.83 (m, 1H), 4.70-4.62 (m, 1H), 4.44-4.37 (m, 1H), 3.41-3.24 (m, 2H), 2.49 (td, J=15.4, 6.8 Hz, 1H), 1.86 (d, J=7.0 Hz, 3H), 1.76-1.70 (m, 2H), 1.57 (d, J=6.5 Hz, 3H), 1.56-1.48 (m, 2H), 1.48-1.38 (m, 3H), 1.34-1.27 (m, 2H), 1.16 (d, J=6.7 Hz, 3H), 0.99 (d, J=6.6 Hz, 3H), 0.89-0.81 (m, 2H), 0.81-0.69 (m, 2H)

LCMS: 1,199.5 (M+H$^+$) for $C_{50}H_{54}BN_{13}O_{10}S_6$

[Example 17] Preparation of Compound 22
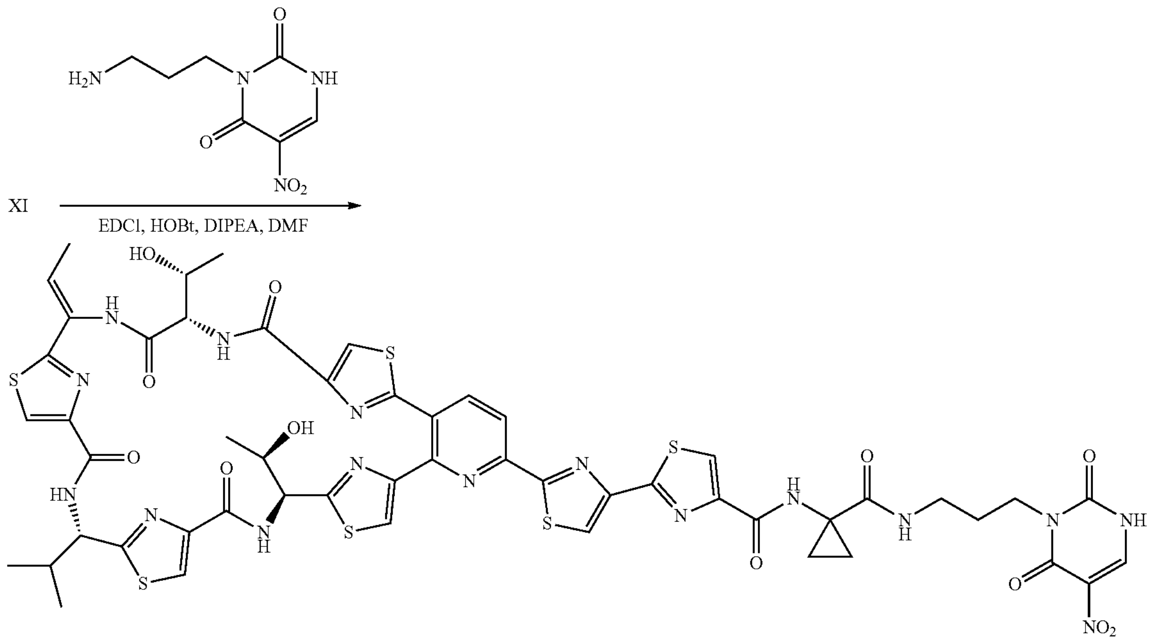
22
Compound 22 (3.3 mg, 26%) was obtained as a white solid from Compound XI in the same manner as that of Example 1.
$^1$H NMR (400 MHz, MeOD) δ 9.13 (s, 1H), 8.25 (s, 3H), 8.20 (s, 1H), 8.14 (s, 1H), 8.11 (s, 1H), 8.01 (s, 1H), 7.82 (s, 1H), 6.53-6.45 (m, 1H), 5.16-5.04 (m, 2H), 4.66 (d, J=3.1 Hz, 1H), 4.53-4.42 (m, 1H), 4.21-4.16 (m, 1H), 3.85 (t, J=6.9 Hz, 2H), 2.51 (td, J=13.6, 6.8 Hz, 1H), 1.97-1.79 (m, 4H), 1.74 (d, J=7.0 Hz, 3H), 1.54-1.47 (m, 2H), 1.43 (d, J=6.4 Hz, 3H), 1.04 (dd, J=20.7, 6.5 Hz, 6H), 0.87 (d, J=6.7 Hz, 3H).
LCMS: 1,283.8 (M+H$^+$) for $C_{52}H_{50}N_{16}O_{12}S_6$
[Example 18] Preparation of Compound 25
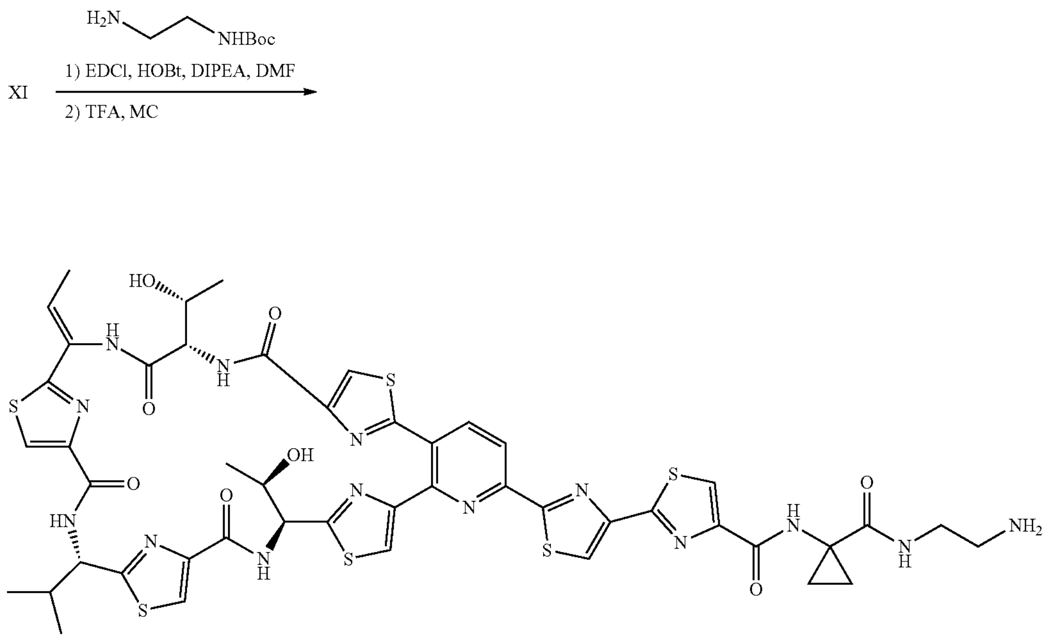
25

Compound XI (11 mg, 0.01 mmol) prepare in Preparation Example 1 was dissolved in DMF (0.1 mL), 1-ethyl-3-(3-dimethylaminopropyl)carbodiimide (3 mg, 0.015 mmol), hydroxybenzotriazole (2 mg, 0.015 mmol), N,N-diisopropylethylamine (3 uL, 0.015 mmol), and tert-butyl-(2-aminoethyl)carbamate (3.4 mg, 0.0015 mmol) were added, the mixture was stirred at room temperature for 12 hours, and then concentrated under reduced pressure, thereby obtaining an intermediate compound. The intermediate compound was added to dichloromethane (0.1 mL)/trifluoroacetic acid (0.1 mL), the mixture was stirred at room temperature for 30 minutes. The residue thus obtained was purified by high-performance liquid chromatography (GX-281 HPLC System, Gilson, USA; column tube 250 mm×21.2 mm on Kinetex 5 μM biphenyl, 100 Å) using (0 to 40% acetonitrile/100 to 60% water) as an eluent, thereby obtaining Compound 25 (1.5 mg, 13%).

$^1$H NMR (400 MHz, MeOD) δ 8.47-8.37 (m, 1H), 8.31-8.25 (m, 4H), 8.25-8.22 (m, 2H), 8.14 (s, 1H), 8.02 (s, 1H), 7.83 (s, 1H), 6.50 (q, J=6.9 Hz, 1H), 5.15-5.03 (m, 2H), 4.66 (d, J=3.1 Hz, 1H), 4.49-4.42 (m, 1H), 4.23-4.14 (m, 1H), 3.40 (t, J=5.5 Hz, 2H), 2.95 (t, J=5.5 Hz, 2H), 2.51 (td, J=21.9, 6.8 Hz, 1H), 2.08-1.90 (m, 2H), 1.74 (d, J=7.0 Hz, 3H), 1.57-1.51 (m, 2H), 1.43 (d, J=6.4 Hz, 3H), 1.05 (dd, J=21.7, 6.5 Hz, 6H), 0.87 (d, J=6.6 Hz, 3H).

LCMS: 1,129.8 (M+H$^+$) for $C_{47}H_{48}N_{14}O_8S_6$

[Example 19] Preparation of Compound 27

XI

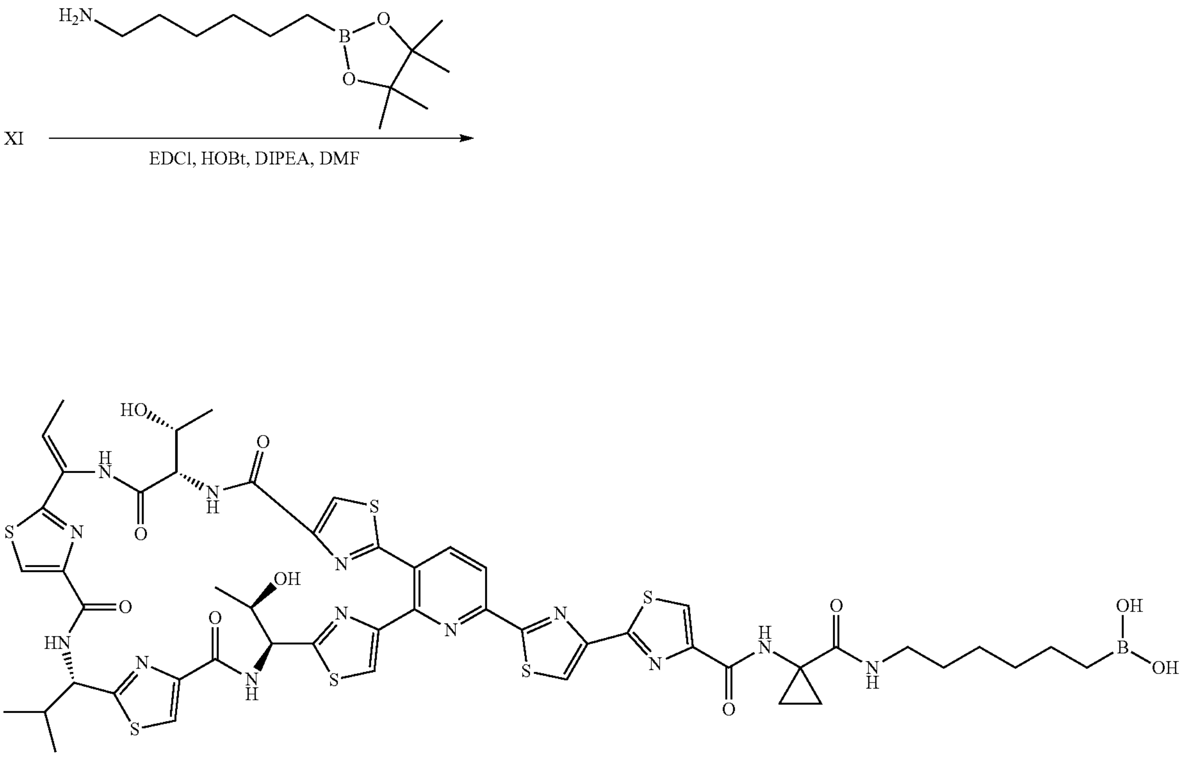

27

Compound 27 (1.1 mg, 9%) was obtained as a white solid from Compound XI in the same manner as that of Example 1.

$^1$H NMR (400 MHz, MeOD) δ 8.23 (s, 3H), 8.15 (d, J=5.0 Hz, 2H), 8.10 (s, 1H), 8.01 (s, 1H), 7.93-7.86 (broad peak, 1H), 7.83 (s, 1H), 6.53-6.42 (m, 1H), 5.16-5.07 (m, 2H), 4.66 (d, J=3.0 Hz, 1H), 4.55-4.32 (m, 1H), 4.28-4.08 (m, 1H), 3.14-3.04 (m, 2H), 2.57-2.43 (m, 1H), 2.00-1.87 (m, 4H), 1.79-1.59 (m, 5H), 1.43 (d, J=6.4 Hz, 3H), 1.04 (dd, J=19.7, 6.5 Hz, 6H), 0.87 (d, J=6.7 Hz, 3H), 0.85-0.71 (m, 4H), 0.64 (t, J=5.4 Hz, 2H).

[Example 20] Preparation of Compound 33

XI

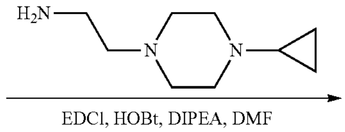

-continued

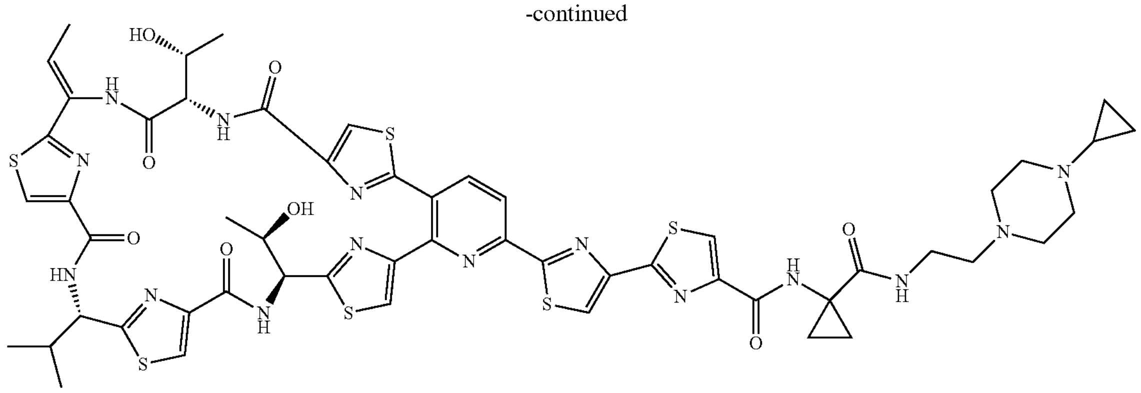

33

Compound 33 (1.1 mg, 9%) was obtained as a white solid from Compound XI in the same manner as that of Example 1.

$^1$H NMR (400 MHz, MeOD) δ 9.27 (s, 1H), 8.55 (dd, J=12.2, 9.7 Hz, 2H), 8.39 (dt, J=22.2, 6.8 Hz, 4H), 8.28 (d, J=10.0 Hz, 2H), 8.14 (s, 1H), 8.05-7.83 (m, 2H), 6.62 (q, J=6.9 Hz, 1H), 5.36-5.12 (m, 2H), 4.78 (dd, J=7.7, 3.0 Hz, 1H), 4.59 (dd, J=6.3, 3.0 Hz, 1H), 4.31 (dd, J=6.4, 2.9 Hz, 1H), 3.59-3.56 (m, 3H), 3.21-3.16 (m, 3H), 3.09-2.89 (m, 3H), 2.63 (td, J=15.5, 6.8 Hz, 1H), 2.02-1.95 (m, 1H), 1.86 (d, J=7.0 Hz, 3H), 1.68-1.65 (m, 2H), 1.55 (d, J=6.5 Hz, 3H), 1.36-1.25 (m, 2H), 1.20 (d, J=6.3 Hz, 3H), 1.14 (d, J=6.7 Hz, 3H), 0.99 (d, J=6.6 Hz, 3H), 0.71-0.59 (m, 2H), 0.55 (d, J=3.0 Hz, 2H).

LCMS: 1,238.8 (M+H$^+$) for $C_{54}H_{59}N_{15}O_8S_6$

[Example 21] Preparation of Compound 35

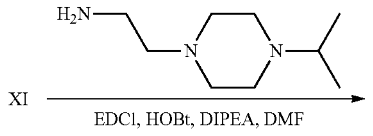

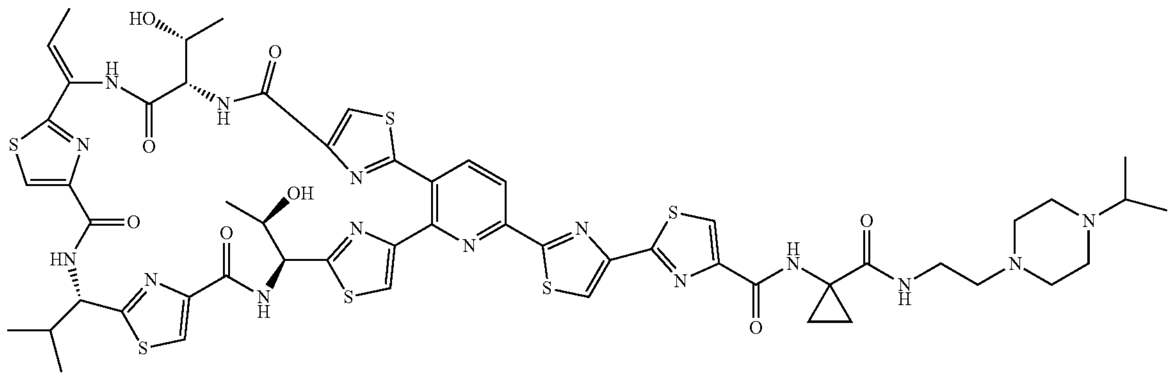

35

Compound 35 (2.2 mg, 18%) was obtained as a white solid from Compound XI in the same manner as that of Example 1.

$^1$H NMR (400 MHz, MeOD) δ 9.19 (s, 1H), 8.55 (dd, J=16.5, 9.6 Hz, 2H), 8.39 (d, J=6.8 Hz, 3H), 8.34 (s, 1H), 8.26 (d, J=2.8 Hz, 2H), 8.14 (s, 1H), 7.95 (t, J=3.8 Hz, 2H), 6.62 (q, J=6.9 Hz, 1H), 5.33-5.14 (m, 2H), 4.79 (dd, J=7.7, 3.0 Hz, 1H), 4.59 (dd, J=6.4, 3.1 Hz, 1H), 4.31 (dd, J=6.4, 2.8 Hz, 1H), 3.58-3.37 (m, 4H), 2.79 (t, J=6.1 Hz, 3H), 2.65-2.58 (m, 1H), 1.86 (d, J=7.0 Hz, 3H), 1.62 (dd, J=7.3, 3.8 Hz, 2H), 1.56 (d, J=6.4 Hz, 3H), 1.36-1.21 (m, 8H), 1.19 (d, J=6.3 Hz, 3H), 1.14 (d, J=6.7 Hz, 3H), 0.99 (d, J=6.6 Hz, 3H).

LCMS: 1,240.9 (M+H$^+$) for $C_{54}H_{61}N_{15}O_8S_6$

[Example 22] Preparation of Compound 36
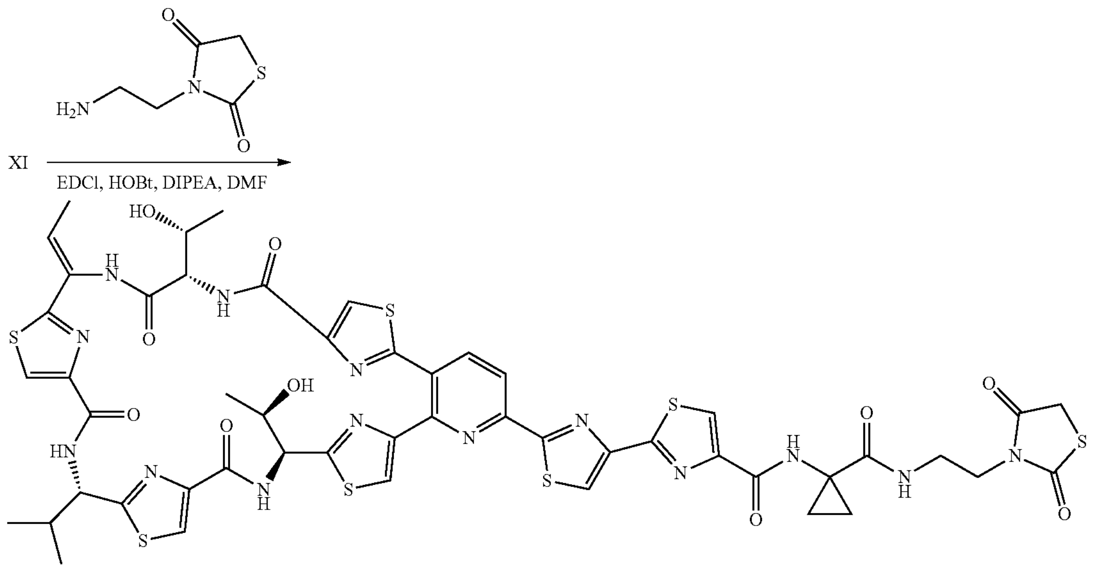
36
Compound 36 (2.6 mg, 21%) was obtained as a white solid from Compound XI in the same manner as that of Example 1.
$^1$H NMR (400 MHz, MeOD) δ 8.99 (s, 1H), 8.53 (dd, J=23.1, 9.6 Hz, 2H), 8.41-8.29 (m, 3H), 8.27 (d, J=2.3 Hz, 2H), 8.22 (s, 1H), 8.13 (s, 1H), 7.94 (s, 2H), 6.66-6.55 (m, 1H), 5.29-5.21 (m, 2H), 4.80 (dd, J=7.7, 2.8 Hz, 1H), 4.60 (dd, J=6.4, 3.0 Hz, 1H), 4.30 (dd, J=6.3, 2.8 Hz, 1H), 4.07 (s, 2H), 3.78-3.72 (m, 2H), 3.54-3.42 (m, 2H), 2.69-2.54 (m, 1H), 1.86 (d, J=6.9 Hz, 3H), 1.61-1.52 (m, 5H), 1.23-1.21 (m, 2H), 1.18 (d, J=6.3 Hz, 3H), 1.13 (d, J=6.7 Hz, 3H), 0.99 (d, J=6.7 Hz, 3H).
LCMS: 1,229.8 ($M+H^+$) for $C_{50}H_{48}N_{14}O_{10}S_7$
[Example 23] Preparation of Compound 37
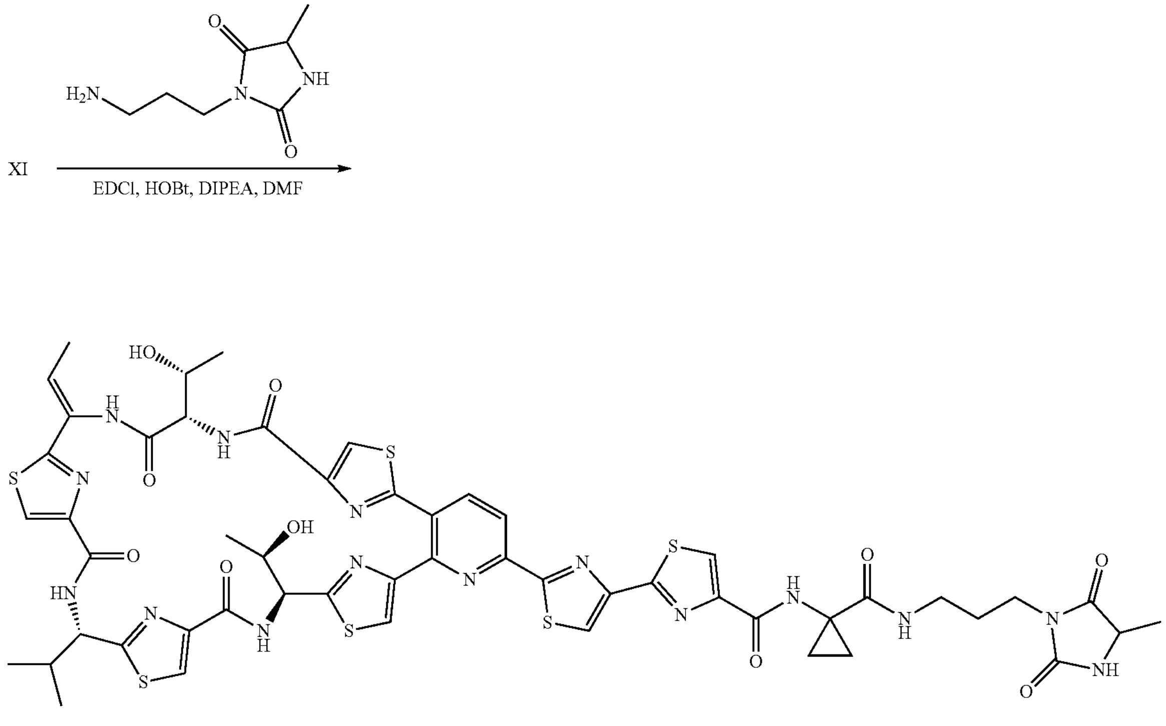
37

Compound 37 (2.8 mg, 23%) was obtained as a white solid from Compound XI in the same manner as that of Example 1.

$^1$H NMR (400 MHz, MeOD) δ 9.22 (s, 1H), 8.54 (dd, J=23.1, 9.7 Hz, 2H), 8.33 (d, J=7.3 Hz, 3H), 8.27 (d, J=1.9 Hz, 2H), 8.22 (s, 1H), 8.14 (s, 1H), 7.94 (d, J=8.1 Hz, 2H), 6.66-6.54 (m, 1H), 5.22 (t, J=9.5 Hz, 2H), 4.87 (dd, J=6.7, 4.2 Hz, 1H), 4.83-4.75 (m, 1H), 4.60 (dd, J=6.5, 2.9 Hz, 1H), 4.32-4.26 (m, 1H), 4.09 (td, J=13.6, 6.3 Hz, 2H), 3.58-3.45 (m, 2H), 2.65-2.61 (m, 1H), 1.94-1.82 (m, 3H), 1.81-1.72 (m, 2H), 1.58 (s, 3H), 1.51-1.41 (m, 2H), 1.37 (d, J=6.1 Hz, 3H), 1.34-1.28 (m, 2H), 1.16 (dd, J=15.0, 6.5 Hz, 6H), 0.99 (d, J=6.6 Hz, 3H)

LCMS: 1, 240.8 (M+H$^+$) for $C_{52}H_{53}N_{15}O_{10}S_6$

[Example 24] Preparation of Compound 28

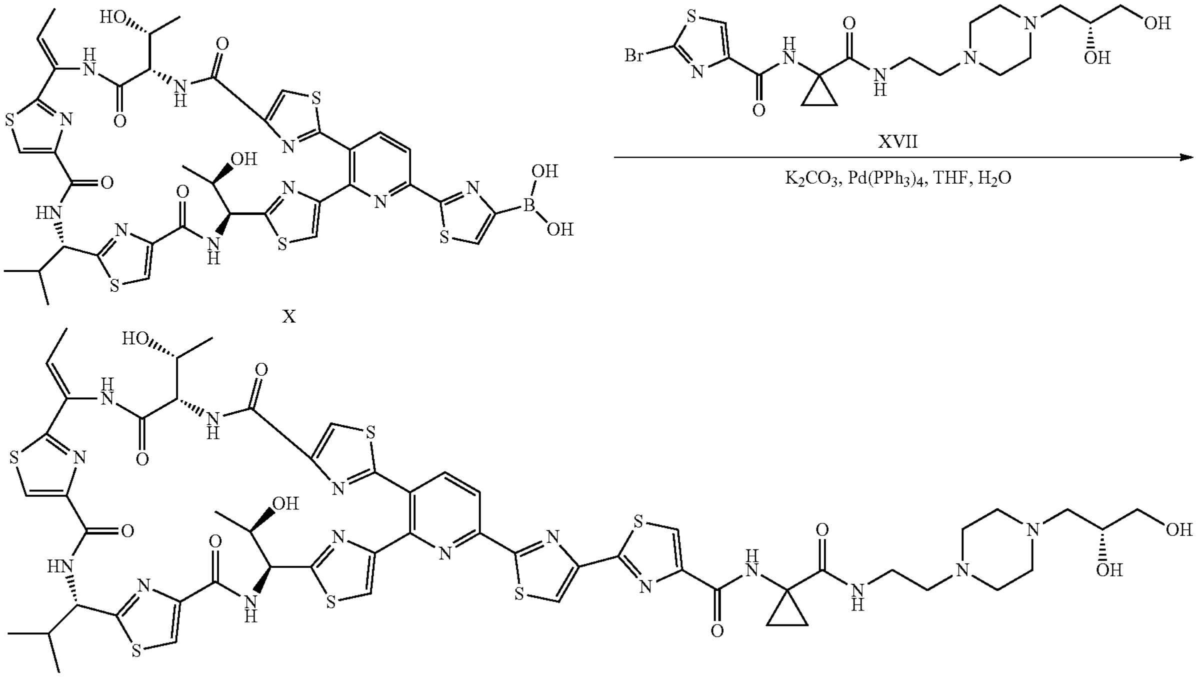

X

XVII

28

Compound X (41 mg, 0.044 mmol) prepared in Preparation Example 1 and Compound XVII (19 mg, 0.04 mmol) prepared in Preparation Example 2 were dissolved in a mixed solution of tetrahydrofuran/water (4:1, 1 mL), potassium carbonate (17 mg, 0.12 mmol) was added, argon gas was injected for 1 minute, tetrakis(triphenylphosphine)palladium(0) (4.6 mg, 10 mol %) was added, and then the reaction was allowed to proceed at 60° C. for 12 hours. The reactant was cooled to room temperature, diluted with chloroform/isopropyl alcohol (4:1, 10 mL), and washed with water. The residue thus obtained was purified by high-performance liquid chromatography (GX-281 HPLC System, Gilson, USA; column tube 250 mm×21.2 mm on Kinetex 5 μM biphenyl, 100 Å) using (0 to 45% acetonitrile/100 to 55% water) as an eluent, thereby obtaining Compound 28 (20 mg, 39%) as a white solid.

$^1$H NMR (400 MHz, MeOD) δ 9.17 (s, 1H), 8.53 (dd, J=20.4, 9.7 Hz, 2H), 8.36-8.31 (m, 4H), 8.27 (s, 1H), 8.20 (s, 1H), 8.14 (s, 1H), 7.98-7.90 (m, 2H), 6.60 (q, J=6.9 Hz, 1H), 5.25-5.20 (m, 2H), 4.80 (dd, J=7.7, 2.9 Hz, 1H), 4.60 (dd, J=6.4, 3.0 Hz, 1H), 4.29 (dd, J=6.3, 2.8 Hz, 1H), 4.02 (dd, J=9.4, 4.2 Hz, 1H), 3.65-3.50 (m, 4H), 3.47-3.43 (m, 4H), peaks hidden (5H) in $CD_3OD$, 3.24-3.10 (m, 2H), 3.09-3.04 (m, 2H), 2.61 (td, J=13.4, 6.6 Hz, 1H), 1.86 (d, J=7.0 Hz, 3H), 1.65-1.61 (m, 2H), 1.56 (d, J=6.4 Hz, 3H), 1.34-1.24 (m, 2H), 1.16 (dd, J=15.3, 6.5 Hz, 6H), 0.99 (d, J=6.6 Hz, 3H).

LCMS: 1,272.7 (M+H$^+$) for $C_{54}H_{61}N_{15}O_{10}S_6$

[Example 25] Preparation of Compound 1

X

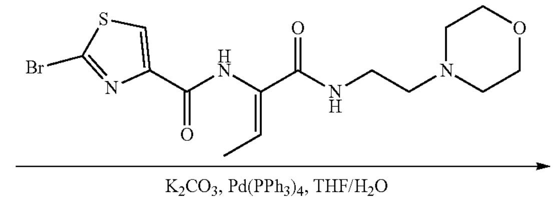

-continued

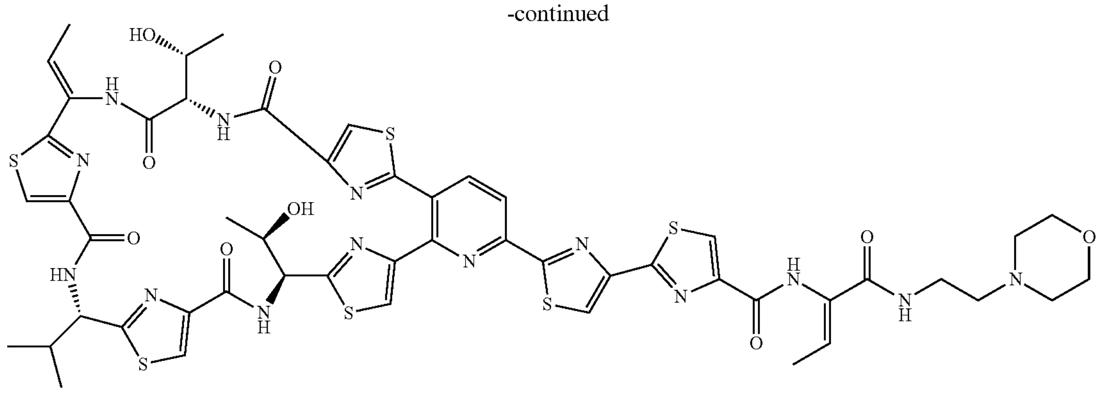

1

Compound 1 (19 mg, 40%) was obtained as a white solid from Compound X in the same manner as that of Example 24.

$^1$H NMR (400 MHz, $CDCl_3$) δ 9.23 (s, 1H), 8.42 (dd, J=16.4, 6.5 Hz, 2H), 8.34-8.17 (m, 3H), 8.17-8.05 (m, 3H), 7.98 (dd, J=24.0, 6.7 Hz, 3H), 6.92-6.76 (m, J=6.6 Hz, 1H), 6.43 (q, J=7.0 Hz, 1H), 5.32-5.18 (m, 2H), 4.85 (d, J=7.8 Hz, 1H), 4.64 (d, J=5.4 Hz, 1H), 4.40 (d, J=6.5 Hz, 1H), 4.31-4.17 (m, 4H), 4.09-3.97 (m, 4H), 3.96-3.78 (broad peak, 2H), 3.83-3.74 (m, 2H), 3.35 (bs, 2H), 2.95 (bs, 2H), 2.54-2.38 (m, 1H), 1.56 (d, J=6.4 Hz, 3H), 1.22 (d, J=6.4 Hz, 3H), 1.15 (d, J=6.7 Hz, 3H), 0.99 (d, J=6.6 Hz, 3H). Note: methyl peak hidden in water peak.

LCMS: 1,201.3 ($M+H^+$) for $C_{51}H_{54}N_{14}O_9S_6$

[Example 26] Preparation of Compound 3

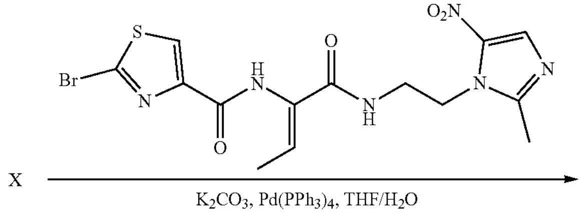

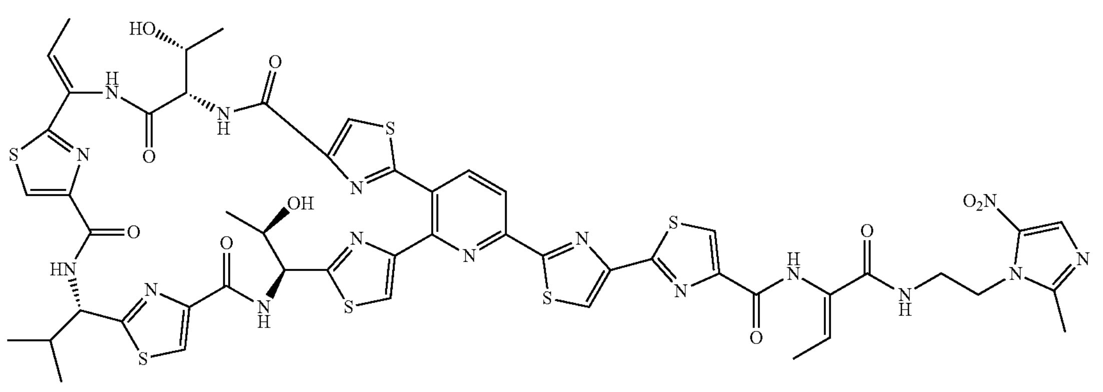

3

Compound 3 (21 mg, 42%) was obtained as a white solid from Compound X in the same manner as that of Example 24.

$^1$H NMR (400 MHz, $CDCl_3$) δ 8.62 (s, 1H), 8.55-8.44 (m, 1H), 8.32-8.16 (m, 4H), 8.17-7.97 (m, 7H), 7.87 (d, J=7.8 Hz, 1H), 6.81 (q, J=7.1 Hz, 1H), 6.44 (q, J=7.0 Hz, 1H), 5.29-5.22 (m, 2H), 4.78 (d, J=6.8 Hz, 1H), 4.71-4.58 (m, 2H), 4.54-4.45 (m, 1H), 4.42-4.33 (m, 1H), 3.81 (broad peak, 2H), 2.66 (s, 3H), 1.95-1.81 (m, 6H), 1.52 (d, J=6.3 Hz, 3H), 1.19 (dd, J=18.7, 6.5 Hz, 6H), 0.98 (d, J=6.6 Hz, 3H).

LCMS: 1,239.8 ($M+H^+$) for $C_{51}H_{50}N_{16}O_{10}S_6$

[Example 27] Preparation of Compound 8
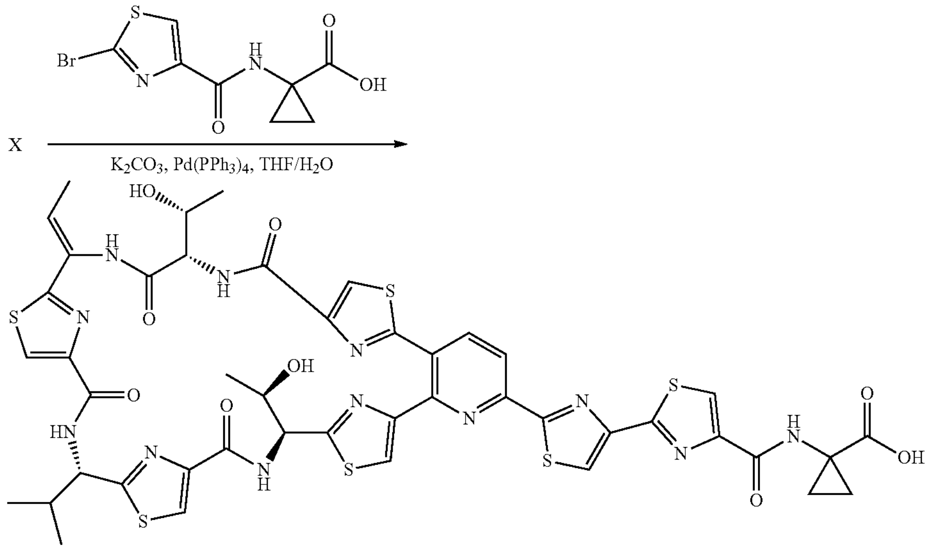
8
Compound 8 (24 mg, 55%) was obtained as a white solid from Compound X in the same manner as that of Example 24.
$^1$H NMR (400 MHz, MeOD) δ 8.49-8.38 (m, 5H), 8.34-8.22 (m, 5H), 8.14 (s, 1H), 7.95 (s, 1H), 6.65-6.62 (m, 1H), 5.31-5.12 (m, 2H), 4.81-4.75 (m, 1H), 4.62-4.56 (m, 1H), 4.38-4.25 (m, 1H), 2.72-2.61 (m, 1H), 1.86 (d, J=7.0 Hz, 3H), 1.68-1.59 (m, 2H) 1.53 (d, J=6.4 Hz, 3H), 1.25-1.02 (m, 8H), 1.00 (d, J=6.6 Hz, 3H)
LCMS: 1,088.8 (M+H$^+$) for $C_{45}H_{42}N_{12}O_9S_6$
[Example 28] Preparation of Compound 16
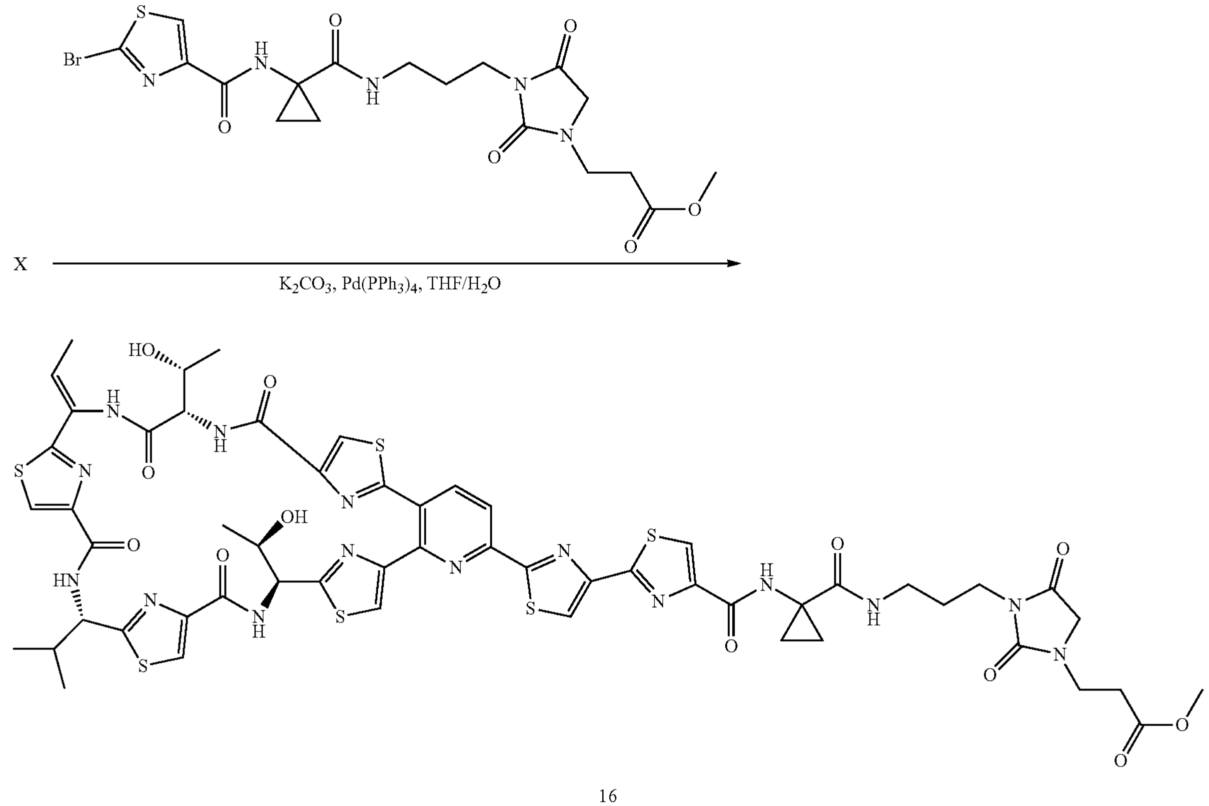
16

Compound 16 (12 mg, 23%) was obtained as a white solid from Compound X in the same manner as that of Example 24.

$^1$H NMR (400 MHz, MeOD) δ 8.60-8.39 (m, 1H), 8.37-8.22 (m, 4H), 8.19 (s, 1H), 8.12 (s, 1H), 7.95 (s, 1H), 6.66-6.54 (m, 1H), 5.29-5.18 (m, 2H), 4.84-4.78 (m, 1H), 4.64-4.58 (m, 1H), 4.32-4.24 (m, 1H), 3.96 (s, 2H), 3.63 (s, 3H), 3.59-3.52 (m, 4H), 3.29-3.23 (m, 2H), 2.68-2.49 (m, 3H), 1.85 (d, J=7.0 Hz, 3H), 1.81-1.73 (m, 2H), 1.64-1.58 (m, 2H), 1.56 (d, J=6.5 Hz, 3H), 1.28-1.23 (m, 2H), 1.16 (dd, J=13.3, 6.5 Hz, 6H), 0.99 (d, J=6.7 Hz, 3H).

LCMS: 1,312.8 (M+H$^+$) for $C_{55}H_{57}N_{15}O_{12}S_6$

[Example 29] Preparation of Compound 19

16 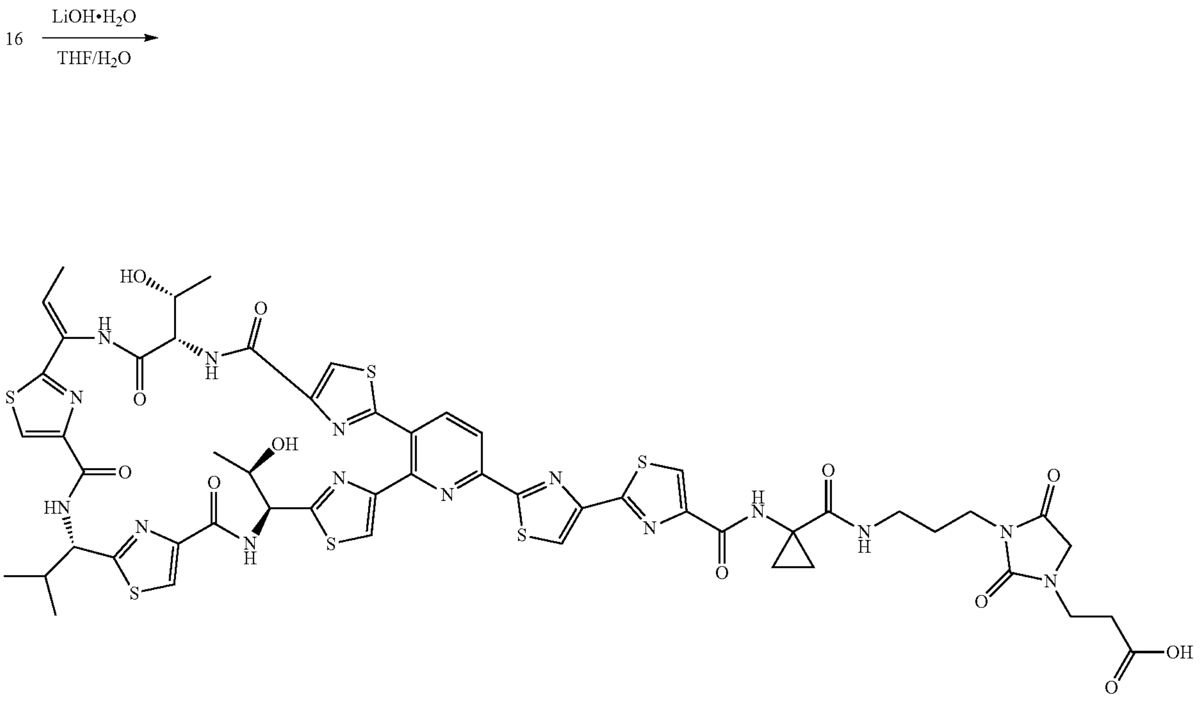

19

Compound 16 (12 mg, 0.01 mmol) prepared in Example 28 was added to tetrahydrofuran (1 mL)/water (1 mL), lithium hydroxide monohydrate (1 mg, 0.025 mmol) was added, and then the mixture was stirred at room temperature for 2 hours. The concentrate was diluted with chloroform/isopropyl alcohol (4:1, 10 mL) and washed with water. The residue thus obtained was purified by high-performance liquid chromatography (GX-281 HPLC System, Gilson, USA; column tube 250 mm×21.2 mm on Kinetex 5 μM biphenyl, 100 Å) using (0 to 45% acetonitrile/100 to 55% water) as an eluent, thereby obtaining Compound 19 (4 mg, 31%).

$^1$H NMR (400 MHz, MeOD) δ 8.42 (dd, J=13.0, 9.8 Hz, 1H), 8.29-8.19 (m, 3H), 8.21-8.08 (m, 3H), 8.01 (s, 1H), 7.83 (s, 1H), 6.49 (q, J=7.0 Hz, 1H), 5.16-5.08 (m, 2H), 4.67 (d, J=2.9 Hz, 1H), 4.52-4.42 (m, 1H), 4.22-4.13 (m, 1H), 3.86 (s, 2H), 3.51-3.34 (m, 4H), 3.19-3.08 (m, 2H), 2.56-2.46 (m, 1H), 2.42 (t, J=6.7 Hz, 2H), 1.99-1.87 (m, 2H), 1.74 (d, J=6.9 Hz, 3H), 1.70-1.60 (m, 2H), 1.43 (d, J=6.4 Hz, 3H), 1.04 (dd, J=18.6, 6.5 Hz, 6H), 0.87 (d, J=6.6 Hz, 3H).

LCMS: 1,298.7 (M+H$^+$) for $C_{54}H_{55}N_{15}O_{12}S_6$

[Example 30] Preparation of Compound 23

X 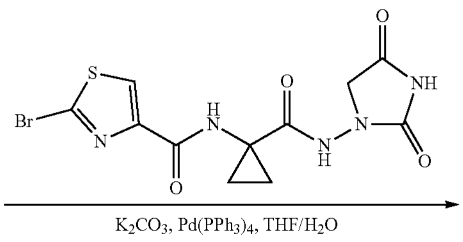

-continued

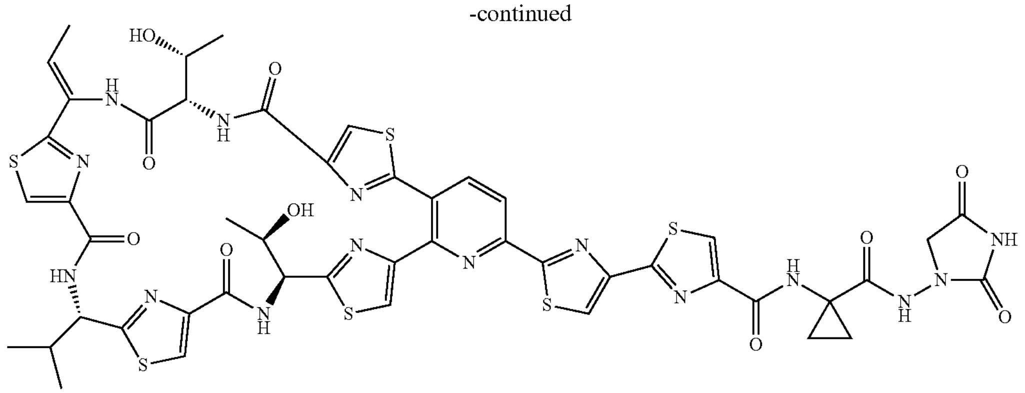

23

Compound 23 (16.6 mg, 35%) was obtained as a white solid from Compound X in the same manner as that of Example 24.

$^1$H NMR (400 MHz, MeOD) δ 8.48-8.30 (m, 1H), 8.26-8.14 (m, 5H), 8.09-7.90 (m, 2H), 7.81 (s, 1H), 6.49 (q, J=7.0 Hz, 1H), 5.16-5.03 (m, 2H), 4.68 (d, J=3.2 Hz, 1H), 4.49-4.39 (m, 1H), 4.19-4.12 (m, 1H), 4.02 (s, 2H), 2.49 (td, J=13.9, 6.7 Hz, 1H), 1.77 (d, J=6.9 Hz, 3H), 1.65-1.47 (m, 2H), 1.44 (d, J=6.4 Hz, 3H), 1.06 (d, J=6.3 Hz, 3H), 0.97 (d, J=6.5 Hz, 3H), 0.86 (d, J=6.7 Hz, 3H).

LCMS: 1,184.7 (M+H$^+$) for $C_{48}H_{45}N_{15}O_{10}S_6$

[Example 31] Preparation of Compound 24

Compound 24 (13.3 mg, 26%) was obtained as a white solid from Compound X in the same manner as that of Example 24.

$^1$H NMR (400 MHz, MeOD) δ 8.42 (dd, J=13.6, 9.6 Hz, 1H), 8.30-8.19 (m, 4H), 8.14 (d, J=7.6 Hz, 2H), 8.02 (s, 1H), 7.83 (s, 1H), 7.58-7.42 (m, 1H), 6.49 (q, J=6.9 Hz, 1H), 5.15-5.06 (m, 2H), 4.66 (d, J=3.1 Hz, 1H), 4.51-4.41 (m, 1H), 4.22-4.15 (m, 1H), 3.59 (s, 3H), 3.42 (t, J=5.7 Hz, 2H), 3.15-3.00 (broad peak, 4H), 2.98-2.80 (broad peak, J=6.8 Hz, 6H), 2.61-2.45 (m, 3H), 1.74 (d, J=7.0 Hz, 3H), 1.56-1.47 (m, 2H), 1.43 (d, J=6.4 Hz, 3H), 1.07 (d, J=6.3 Hz, 3H), 1.02 (d, J=6.7 Hz, 3H), 0.87 (d, J=6.7 Hz, 3H). Note: some of cyclopropane peaks are hidden under the grease.

LCMS: 1,284.9 (M+H$^+$) for $C_{55}H_{61}N_{15}O_{10}S_6$

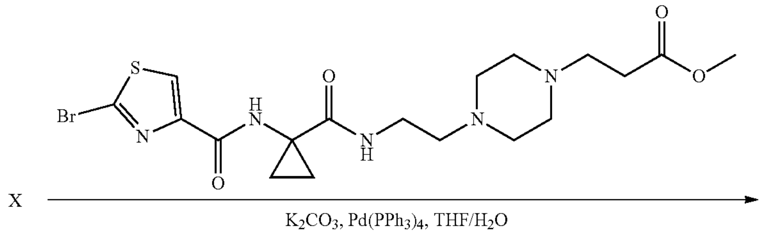

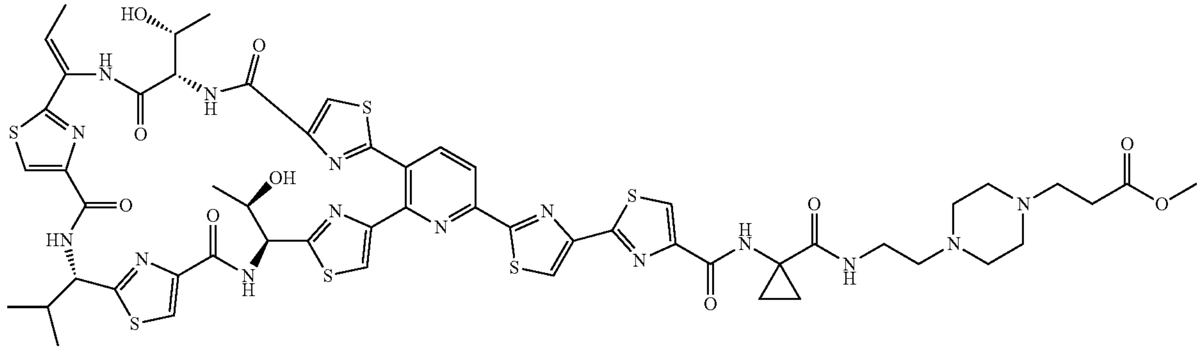

24

[Example 32] Preparation of Compound 26
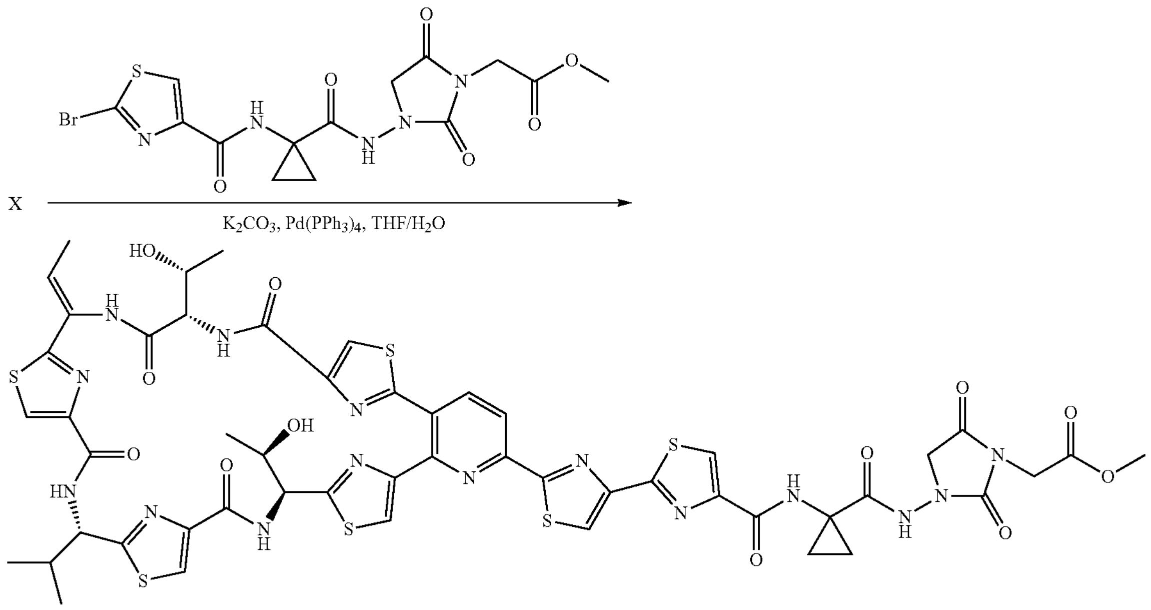
26
Compound 26 (6 mg, 12%) was obtained as a white solid from Compound X in the same manner as that of Example 24.
$^1$H NMR (400 MHz, $CDCl_3$) δ 10.54 (bs, 1H), 9.22 (s, 1H), 8.51 (s, 1H), 8.37 (d, J=9.7 Hz, 1H), 8.18 (s, 1H), 8.15-7.94 (m, 5H), 7.89 (d, J=8.7 Hz, 2H), 7.82 (d, J=7.7 Hz, 1H), 7.72 (bs, 1H), 6.48 (q, J=6.9 Hz, 1H), 5.30-5.21 (m, 2H), 5.09 (d, J=6.0 Hz, 1H), 4.49-4.45 (m, 2H), 4.42-4.26 (m, 4H), 3.77 (s, 3H), 2.44 (td, J=15.8, 6.7 Hz, 1H), 1.94 (d, J=6.9 Hz, 3H), 1.77-1.70 (m, 2H), 1.61 (d, J=6.3 Hz, 3H), 1.22-1.17 (m, 2H), 1.15 (dd, J=13.4, 6.5 Hz, 6H), 0.96 (d, J=6.6 Hz, 3H).
LCMS: 1,257.6 (M+H$^+$) for $C_{51}H_{49}N_{15}O_{12}S_6$
[Example 33] Preparation of Compound 29
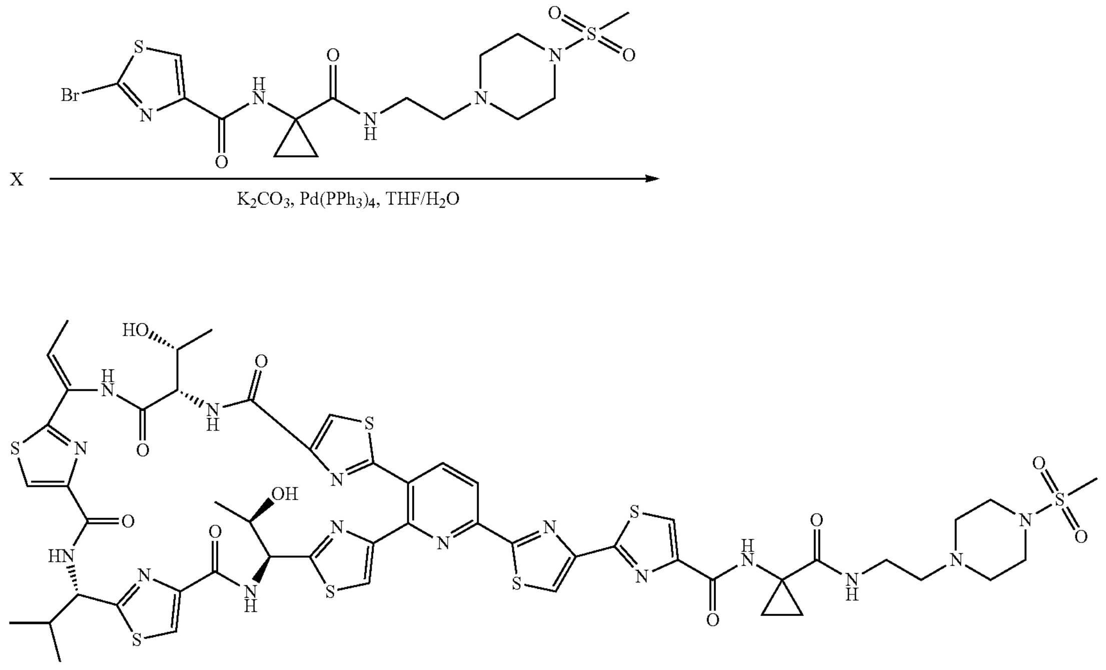
29

Compound 29 (12 mg, 23%) was obtained as a white solid from Compound X in the same manner as that of Example 24.

$^1$H NMR (400 MHz, MeOD) δ 9.16 (s, 1H), 8.59-8.43 (m, 2H), 8.32-8.22 (m, 5H), 8.13 (s, 2H), 7.98-7.88 (m, 2H), 6.57 (q, J=6.7 Hz, 1H), 5.25-5.20 (m, 2H), 4.82-4.75 (m, 1H), 4.62-4.60 (m, 1H), 4.29-4.27 (m, 1H), 3.66-3.38 (broad peak—piperazine peaks and methylene adjacent to the piperazine 10H), 3.36 (d, J=2.8 Hz, 2H), 2.99 (s, 3H), 2.71-2.49 (m, 1H), 1.86 (d, J=6.9 Hz, 3H), 1.65-1.60 (m, 2H), 1.57 (d, J=6.4 Hz, 3H), 1.27-1.20 (m, 2H), 1.16 (dd, J=9.8, 6.6 Hz, 6H), 0.99 (t, J=6.6 Hz, 3H)

LCMS: 1,276.7 (M+H$^+$) for $C_{52}H_{57}N_{15}O_{10}S_7$

[Example 34] Preparation of Compound 30

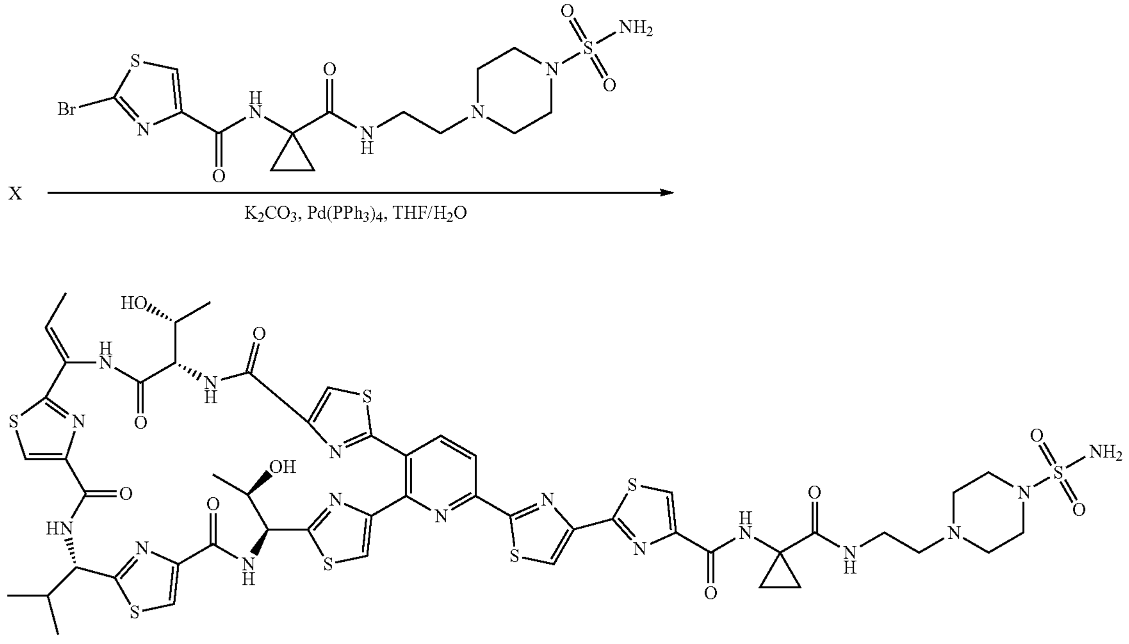

30

Compound 30 (16.8 mg, 33%) was obtained as a white solid from Compound X in the same manner as that of Example 24.

$^1$H NMR (400 MHz, MeOD) δ 9.19 (s, 1H), 8.58-8.48 (m, 2H), 8.38-8.24 (i, 5H), 8.13 (d, J=4.7 Hz, 2H), 7.99-7.89 (m, 2H), 7.62-7.42 (m, 2H), 6.58 (q, J=6.9 Hz, 1H), 5.25-5.20 (m, 2H), 4.81-4.78 (m, 1H), 4.62-4.59 (m, 1H), 4.30-4.27 (m, 1H), 4.14-3.90 (broad peak, 5H), 3.66 (bs, 2H), 3.54-3.42 (broad peak, 4H), 3.39-3.34 (m, 2H), 2.60 (td, J=15.2, 6.7 Hz, 1H), 1.86 (d, J=7.0 Hz, 3H), 1.70-1.63 (m, 2H), 1.57 (d, J=6.3 Hz, 3H), 1.37-1.22 (m, 2H), 1.16 (dd, J=11.3, 6.5 Hz, 6H), 0.98 (d, J=6.6 Hz, 3H).

[Example 35] Preparation of Compound 31

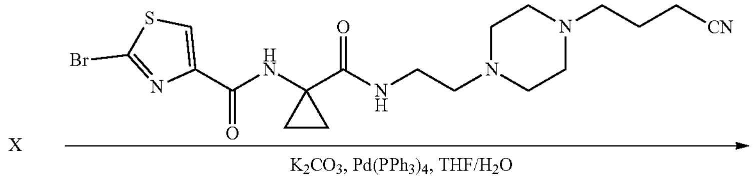

-continued

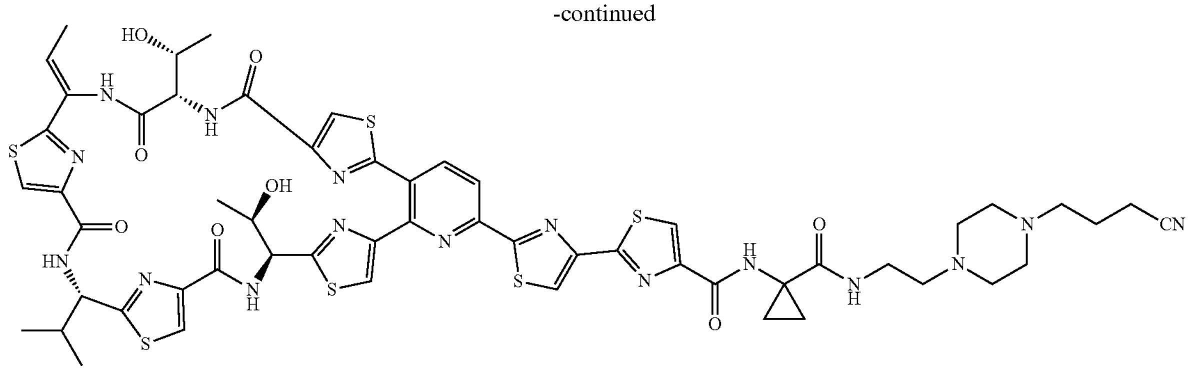

31

Compound 31 (11.6 mg, 23%) was obtained as a white solid from Compound X in the same manner as that of Example 24.

$^1$H NMR (400 MHz, MeOD) δ 9.10 (s, 1H), 8.42 (dd, J=14.4, 9.7 Hz, 1H), 8.29-8.21 (m, 3H), 8.15 (s, 1H), 8.11 (s, 1H), 8.02 (s, 1H), 7.84-7.81 (m, 1H), 7.62-7.50 (m, 3H), 7.50-7.41 (m, 2H), 6.49 (q, J=6.8 Hz, 1H), 5.18-5.08 (m, 2H), 4.73-4.65 (m, 1H), 4.52-4.44 (m, 1H), 4.22-4.18 (m, 1H), 3.49-3.42 (m, 2H), 3.08-3.01 (m, 2H), 2.94-2.71 (broad peak, 3H), 2.63 (t, J=7.0 Hz, 2H), 2.53-2.38 (m, 3H), 2.05-1.90 (m, 2H), 1.85-1.78 (m, 3H), 1.74 (d, J=7.0 Hz, 3H), 1.56-1.49 (m, 2H), 1.44 (d, J=6.4 Hz, 3H), 1.04 (dd, J=17.9, 6.5 Hz, 6H), 0.87 (d, J=6.7 Hz, 3H).

LCMS: 1,265.8 (M+H$^+$) for $C_{55}H_{60}N_{16}O_8S_6$

[Example 36] Preparation of Compound 32

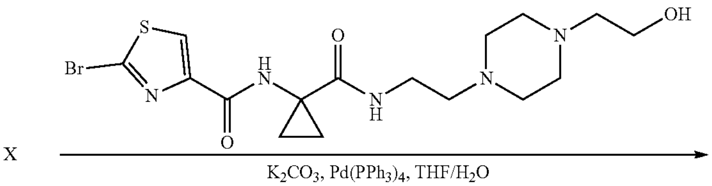

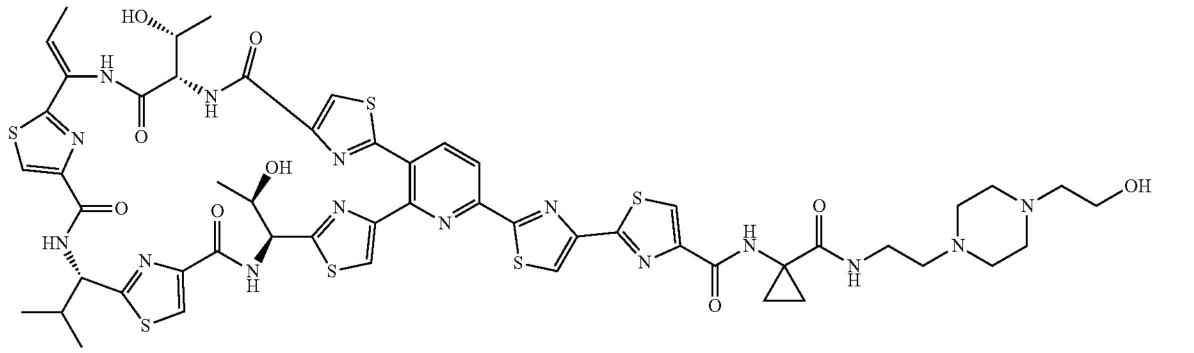

32

Compound 32 (12 mg, 24%) was obtained as a white solid from Compound X in the same manner as that of Example 24.

$^1$H NMR (400 MHz, MeOD) δ 9.16 (s, 1H), 8.53 (dd, J=21.9, 9.6 Hz, 2H), 8.38-8.29 (m, 4H), 8.27 (s, 1H), 8.19 (s, 1H), 8.14 (s, 1H), 7.99-7.89 (m, 2H), 6.60 (q, J=6.8 Hz, 1H), 5.25-5.21 (m, 2H), 4.84-4.78 (m, 1H), 4.61 (dd, J=6.4, 3.0 Hz, 1H), 4.29 (dd, J=6.3, 2.8 Hz, 1H), 3.93-3.83 (m, 2H), 3.59-3.41 (m, 7H), 3.29-3.20 (m, 3H), 3.09 (t, J=5.4 Hz, 2H), 2.61 (td, J=13.5, 6.7 Hz, 1H), 1.86 (d, J=6.9 Hz, 3H), 1.63 (d, J=3.1 Hz, 2H), 1.57 (d, J=6.4 Hz, 3H), 1.31-1.29 (m, 2H), 1.16 (dd, J=13.9, 6.5 Hz, 6H), 0.99 (d, J=6.6 Hz, 3H).

LCMS: 1,242.8 (M+H$^+$) for $C_{53}H_{59}N_{15}O_9S_6$

[Example 37] Preparation of Compound 34
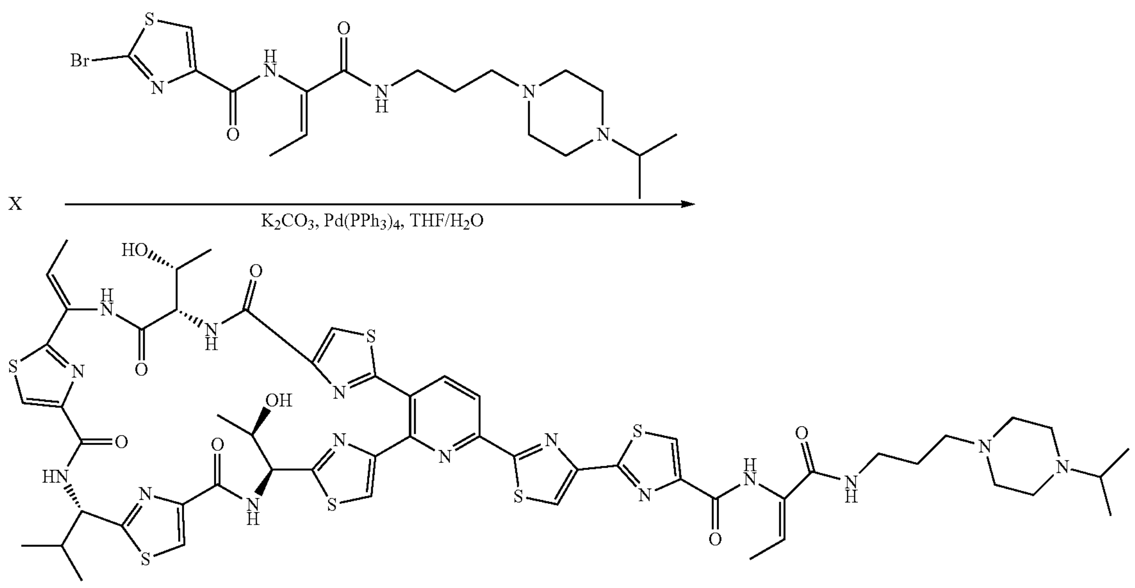
34
Compound 34 (6 mg, 12%) was obtained as a white solid from Compound X in the same manner as that of Example 24.
$^{1}$H NMR (400 MHz, MeOD) δ 8.55 (dd, J=13.5, 9.6 Hz, 2H), 8.48-8.31 (m, 5H), 8.27 (s, 2H), 8.14 (s, 1H), 7.98-7.96 (m, 2H), 6.73-6.52 (m, 2H), 5.35-5.17 (m, 2H), 4.79 (dd, J=7.8, 3.0 Hz, 1H), 4.59 (dd, J=6.5, 3.1 Hz, 1H), 4.31 (dd, J=6.3, 2.8 Hz, 1H), 3.56-3.34 (m, 6H), 3.08 (t, J=6.8 Hz, 2H), 2.63 (dd, J=15.4, 6.8 Hz, 1H), 2.10-1.92 (m, 2H), 1.87 (dd, J=11.2, 7.0 Hz, 6H), 1.55 (d, J=6.4 Hz, 3H), 1.39-1.28 (m, 6H), 1.17 (dd, J=20.0, 6.5 Hz, 6H), 0.99 (d, J=6.6 Hz, 3H).
LCMS: 1,254.9 (M+H$^+$) for $C_{55}H_{63}N_{15}O_8S_6$
[Example 38] Preparation of Compound 38
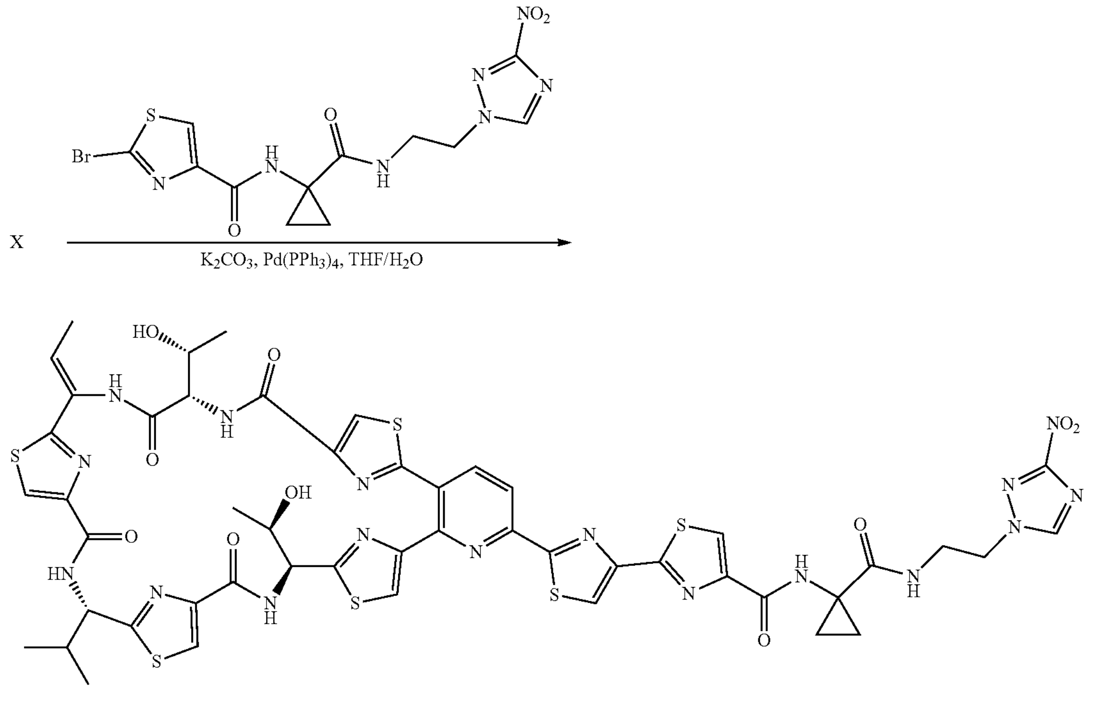
38

Compound 38 (21 mg, 17%) was obtained as a white solid from Compound X in the same manner as that of Example 24.

$^1$H NMR (400 MHz, $CDCl_3$) δ8.77 (s, 1H), 8.58 (s, 1H), 8.31 (d, J=9.8 Hz, 1H), 8.22-8.03 (m, 5H), 8.03-7.85 (m, 5H), 7.80 (s, 1H), 7.67 (d, J=8.1 Hz, 1H), 6.42 (q, J=7.0 Hz, 1H), 5.31-5.21 (m, 2H), 4.85 (d, J=8.3 Hz, 1H), 4.74-4.59 (m, 1H), 4.54-4.42 (m, 3H), 4.32-4.41 (m, 1H), 4.01-3.92 (m, 1H), 3.82-3.71 (m, 1H), 2.64-2.58 (m, 1H), 2.55-2.35 (m, 1H), 2.01-1.96 (m, 1H), 1.88 (d, J=44.2 Hz, 4H), 1.60-1.53 (m, 3H), 1.23-1.04 (m, 8H), 0.96 (d, J=6.5 Hz, 3H).

LCMS: 1,226.3 ($M+H^+$) for $C_{49}H_{47}N_{17}O_{10}S_6$

[Example 39] Preparation of Compound 39

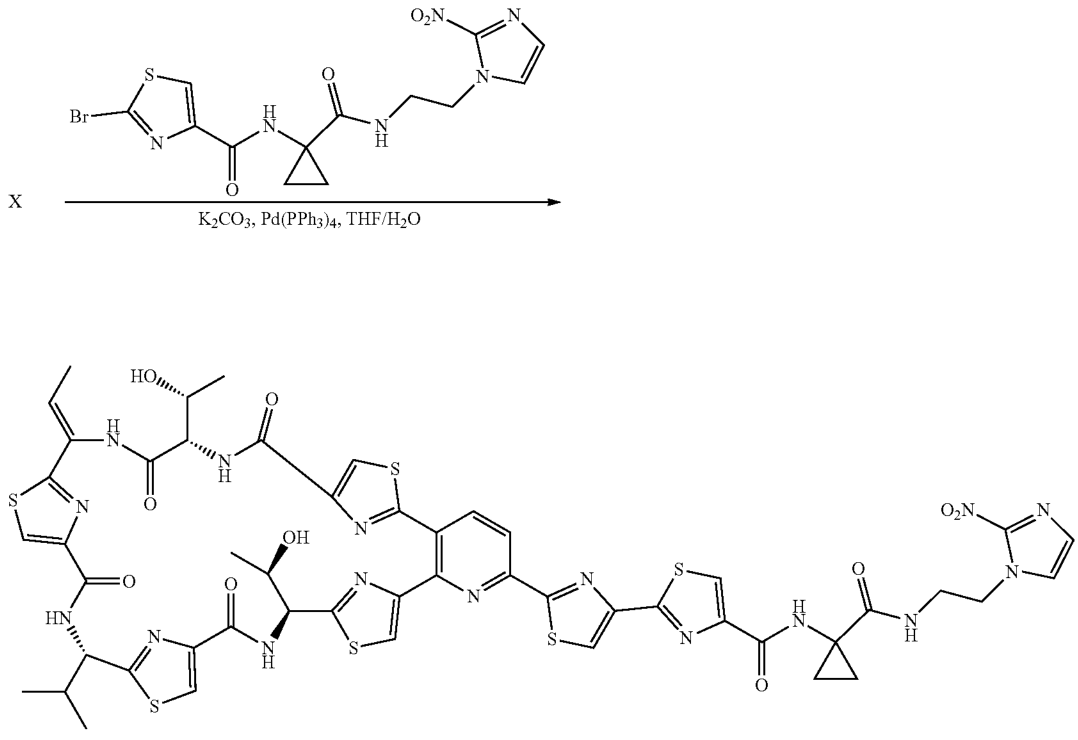

39

Compound 39 (25 mg, 20%) was obtained as a white solid from Compound X in the same manner as that of Example 24.

$^1$H NMR (400 MHz, $CDCl_3$) δ9.25 (s, 1H), 8.84 (s, 1H), 8.20-8.04 (m, 5H), 8.03-7.94 (m, 2H), 7.91 (d, J=8.1 Hz, 1H), 7.80-7.56 (m, 2H), 7.23 (s, 1H), 7.19 (s, 1H), 6.41 (q, J=7.0 Hz, 1H), 5.33-5.09 (m, 2H), 5.01-4.91 (m, 1H), 4.74-4.61 (m, 2H), 4.34-4.28 (m, 2H), 3.92-3.85 (m, 1H), 3.82-3.73 (m, 1H), 2.79-2.71 (m, 1H), 2.20-1.99 (m, 2H), 1.94 (d, J=7.0 Hz, 3H), 1.46-1.33 (m, 3H), 1.32-1.22 (m, 2H), 1.22-1.06 (m, 6H), 0.93 (d, J=6.6 Hz, 3H).

LCMS: 1,225.5 ($M+H^+$) for $C_{50}H_{48}N_{16}O_{10}S_6$

[Example 40] Preparation of Compound 40

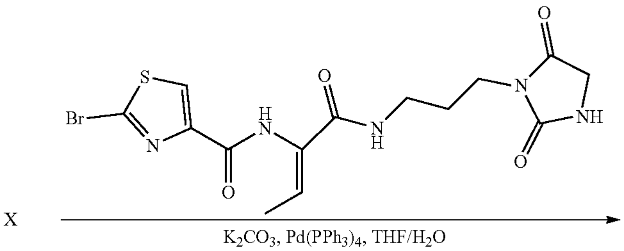

-continued

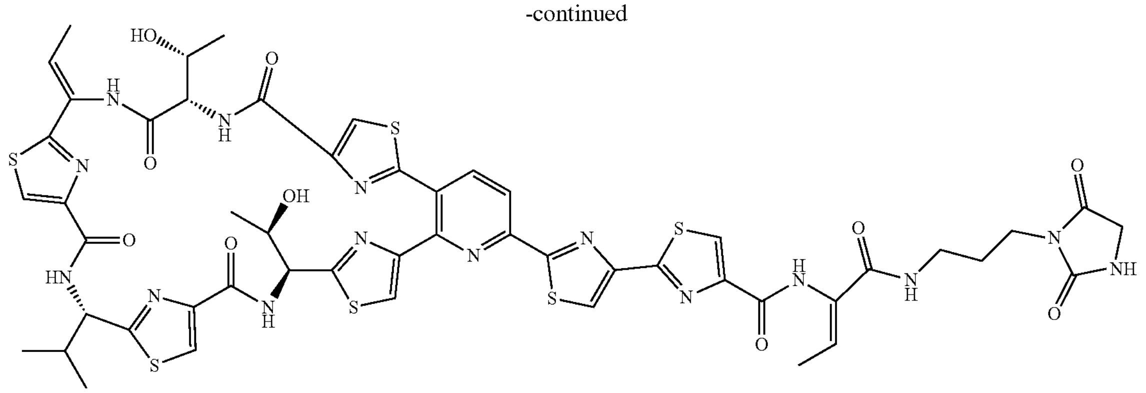

40

Compound 40 (26 mg, 46%) was obtained as a white solid from Compound X in the same manner as that of Example 24.

$^1$H NMR (400 MHz, $CDCl_3$) δ8.84 (s, 1H), 8.58 (s, 1H), 8.40 (d, J=9.7 Hz, 1H), 8.31 (d, J=8.1 Hz, 1H), 8.28-8.21 (m, 3H), 8.18 (s, 1H), 8.12 (d, J=7.7 Hz, 2H), 8.04-7.97 (m, 2H), 7.95 (d, J=7.8 Hz, 1H), 7.15 (t, J=6.2 Hz, 1H), 6.70 (q, J=7.1 Hz, 1H), 6.41 (q, J=7.0 Hz, 1H), 5.91 (s, 1H), 5.25 (t, J=9.3 Hz, 2H), 4.86 (dd, J=7.9, 2.1 Hz, 1H), 4.63 (d, J=6.6 Hz, 1H), 4.49 (d, J=6.2 Hz, 1H), 4.40 (d, J=6.3 Hz, 1H), 3.98 (s, 2H), 3.65 (t, J=6.2 Hz, 2H), 3.35 (dd, J=12.2, 6.2 Hz, 2H), 2.98 (d, J=2.4 Hz, 1H), 2.49 (td, J=13.5, 6.8 Hz, 1H), 1.92-1.79 (m, 6H), 1.56 (d, J=6.5 Hz, 3H), 1.20 (d, J=6.4 Hz, 3H), 1.15 (d, J=6.7 Hz, 3H), 0.97 (d, J=6.6 Hz, 3H).

LCMS: 1,226.6 ($M+H^+$) for $C_{51}H_{51}N_{15}O_{10}S_6$

[Example 41] Preparation of Compound 41

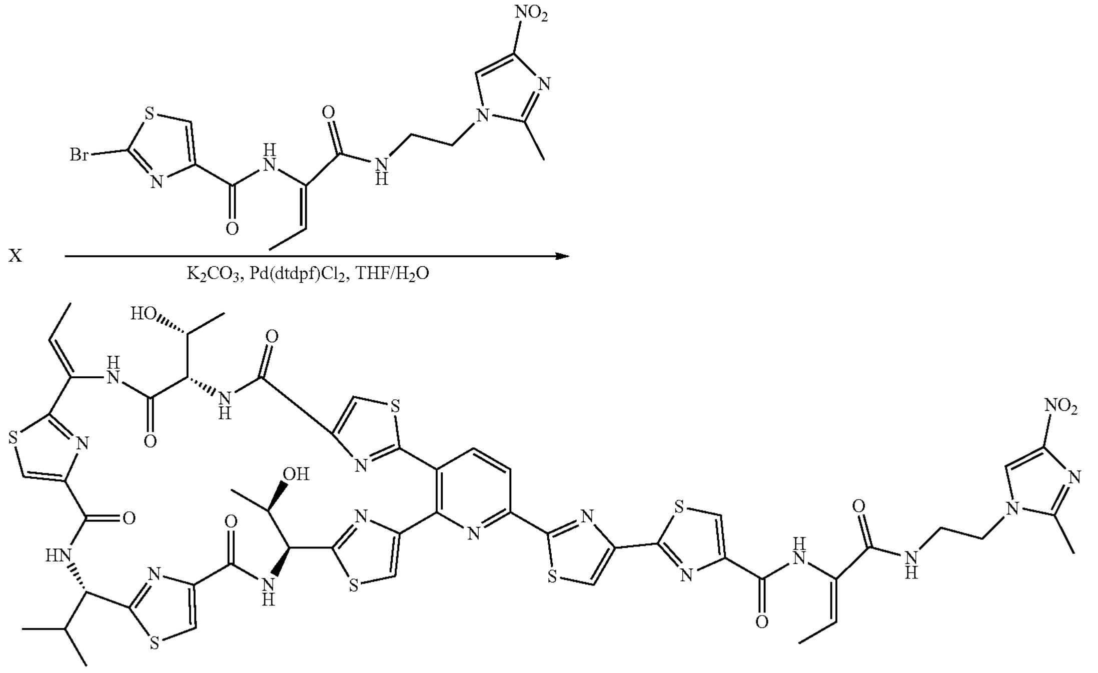

41

Compound 41 (16 mg, 43%) was obtained as a white solid from Compound X in the same manner as that of Example 24.

$^1$H NMR (400 MHz, $CDCl_3$) δ9.32 (s, 1H), 9.03 (d, J=8.7 Hz, 1H), 8.31 (s, 1H), 8.26-8.09 (m, 5H), 8.06 (s, 1H), 7.95 (dd, J=19.5, 8.1 Hz, 3H), 7.81 (s, 1H), 7.74 (dd, J=23.8, 15.1 Hz, 2H), 6.95 (q, J=6.9 Hz, 1H), 6.40 (q, J=7.0 Hz, 1H), 5.23 (d, J=10.8 Hz, 1H), 5.16 (t, J=9.5 Hz, 1H), 4.72-4.59 (m, 2H), 4.51-4.31 (m, 2H), 4.22-4.08 (m, 1H), 4.00-3.83 (m, 1H), 3.53 (dd, J=13.1, 8.5 Hz, 1H), 2.76-2.61 (m, 1H), 1.92 (d, J=7.0 Hz, 3H), 1.86 (d, J=7.2 Hz, 3H), 1.35 (d, J=6.4 Hz, 3H), 1.17 (d, J=6.6 Hz, 3H), 1.11 (d, J=6.4 Hz, 3H), 0.91 (d, J=6.6 Hz, 3H).

LCMS: 1,239.6 ($M+H^+$) for $C_{51}H_{50}N_{16}O_{10}S_6$

[Example 42] Preparation of Compound 42
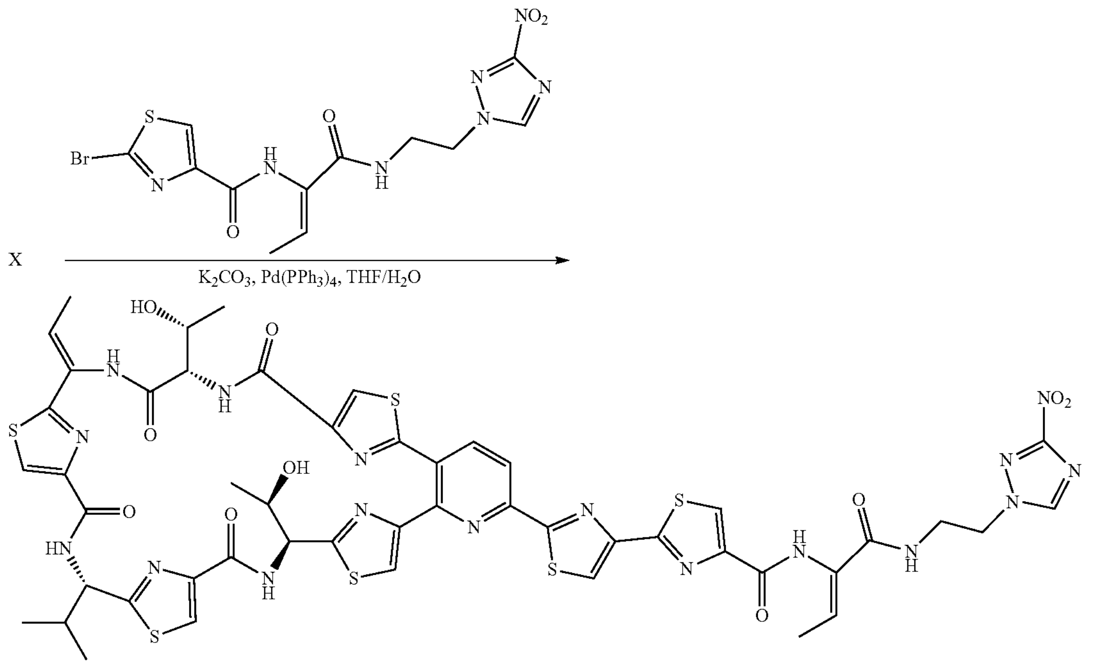
42
Compound 42 (22 mg, 18%) was obtained as a white solid from Compound X in the same manner as that of Example 24.
$^1$H NMR (400 MHz, $CDCl_3$) δ8.65 (d, J=14.2 Hz, 2H), 8.58 (s, 1H), 8.38 (d, J=9.8 Hz, 1H), 8.26-8.15 (m, 3H), 8.15-8.03 (m, 4H), 8.07-7.89 (m, 2H), 7.81 (d, J=8.1 Hz, 1H), 7.38 (s, 1H), 6.63 (q, J=7.0 Hz, 1H), 6.42 (q, J=7.0 Hz, 1H), 5.28-5.24 (m, 2H), 4.84-4.79 (m, 1H), 4.70-4.51 (m, 4H), 4.36-4.41 (m, 1H), 3.98-3.91 (m, 1H), 3.87-3.79 (m, 1H), 2.70 (s, 1H), 2.57-2.42 (m, 1H), 1.86 (dd, J=7.1, 2.4 Hz, 6H), 1.54 (d, J=6.1 Hz, 3H), 1.17 (dd, J=12.7, 6.6 Hz, 6H), 0.97 (d, J=6.6 Hz, 3H)
LCMS: 1,226.6 (M+H$^+$) for $C_{49}H_{47}N_{17}O_{10}S_6$
[Example 43] Preparation of Compound 43
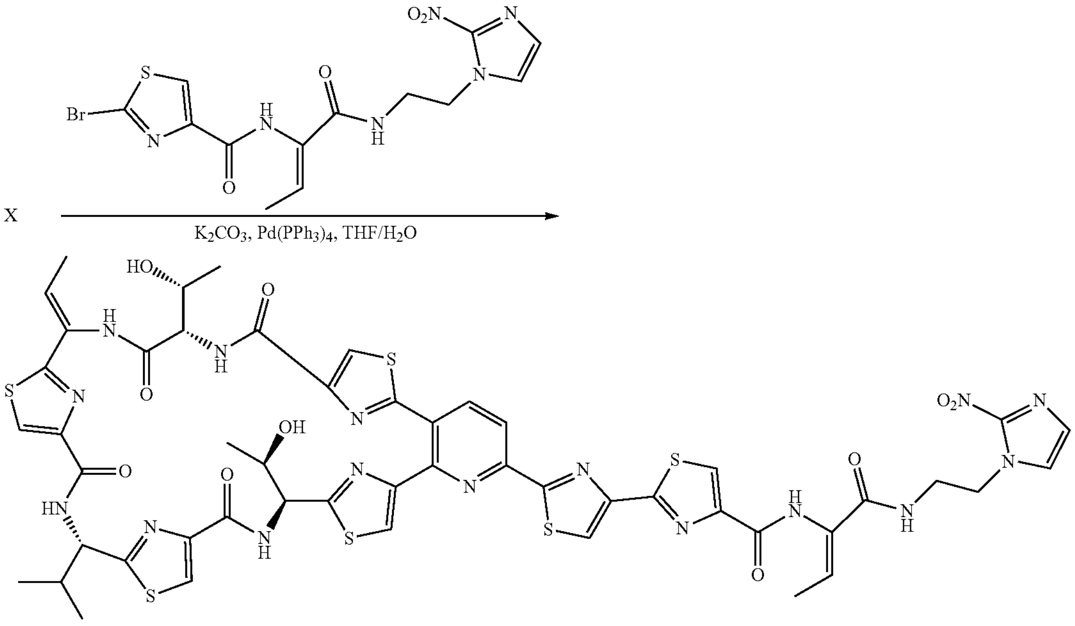
43

Compound 43 (23 mg, 19%) was obtained as a white solid from Compound X in the same manner as that of Example 24.

$^1$H NMR (400 MHz, $CDCl_3$) δ9.25 (s, 1H), 8.79 (d, J=9.3 Hz, 1H), 8.28 (s, 1H), 8.22-7.99 (m, 5H), 7.97 (d, J=6.4 Hz, 2H), 7.92 (d, J=8.1 Hz, 1H), 7.84 (s, 1H), 7.74 (s, 1H), 7.67 (d, J=8.5 Hz, 1H), 7.22 (d, J=10.7 Hz, 2H), 6.91 (q, J=7.1 Hz, 1H), 6.41 (q, J=7.0 Hz, 1H), 5.28-5.09 (m, 2H), 4.96 (t, J=8.9 Hz, 1H), 4.78-4.55 (m, 2H), 4.33-4.18 (m, 2H), 4.05-3.91 (m, 1H), 3.80 (d, J=4.8 Hz, 1H), 2.87-2.61 (m, 1H), 1.91 (d, J=7.0 Hz, 3H), 1.85 (d, J=7.1 Hz, 3H), 1.42 (d, J=6.4 Hz, 3H), 1.17 (dd, J=6.2, 5.0 Hz, 6H), 0.93 (d, J=6.6 Hz, 3H).

LCMS: 1,225.6 ($M+H^+$) for $C_{50}H_{48}N_{16}O_{10}S_6$

[Example 44] Preparation of Compound 44

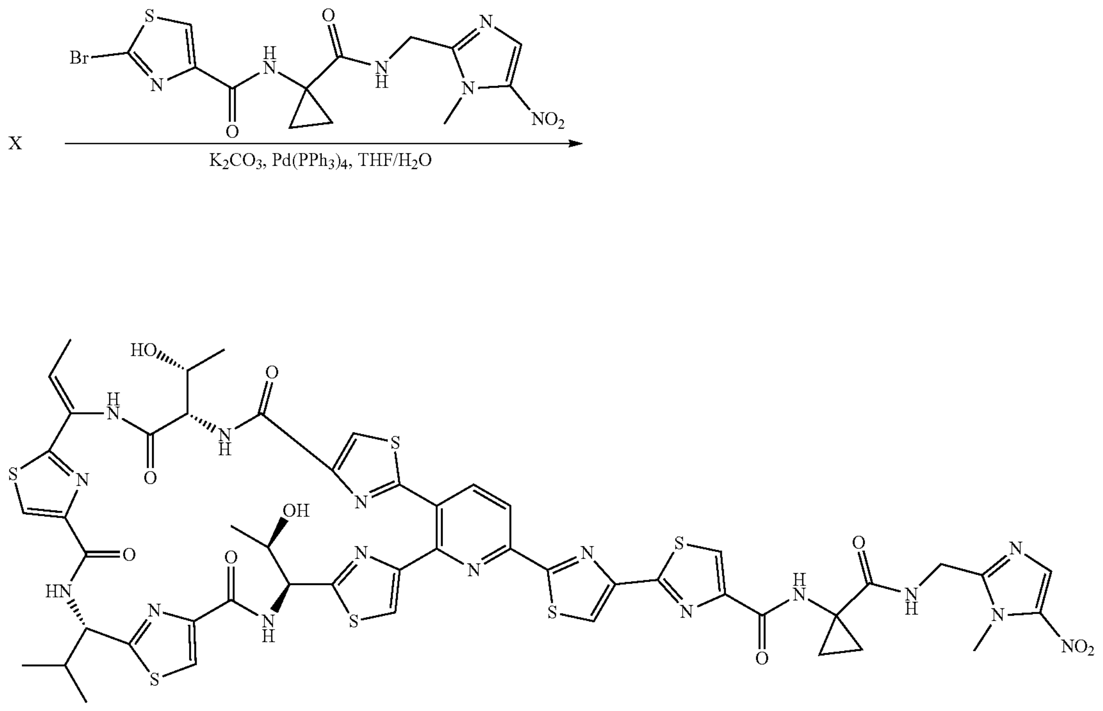

44

Compound 44 (6.3 mg, 13%) was obtained as a white solid from Compound X in the same manner as that of Example 24.

$^1$H NMR (400 MHz, MeOD) δ9.14 (s, 1H), 8.75 (s, 1H), 8.53 (dd, J=17.1, 9.7 Hz, 3H), 8.39-8.31 (m, 4H), 8.29-8.23 (m, 3H), 8.21 (s, 1H), 8.14 (s, 1H), 7.94 (d, J=5.3 Hz, 1H), 6.62 (d, J=6.9 Hz, 1H), 5.27-5.22 (m, 2H), 5.07-4.97 (m, 1H), 4.59-4.42 (m, 4H), 4.37-4.28 (m, 1H), 4.00 (s, 2H), 2.72-2.51 (m, 1H), 1.87 (d, J=7.0 Hz, 3H), 1.67-1.61 (m, 2H), 1.55 (d, J=6.5 Hz, 3H), 1.34-1.21 (m, 2H), 1.18 (d, J=6.3 Hz, 3H), 1.13 (d, J=6.6 Hz, 3H), 0.99 (d, J=6.7 Hz, 3H).

LCMS: 1,225.9 ($M+H^+$) for $C_{50}H_{48}N_{16}O_{10}S_6$

[Example 45] Preparation of Compound 45

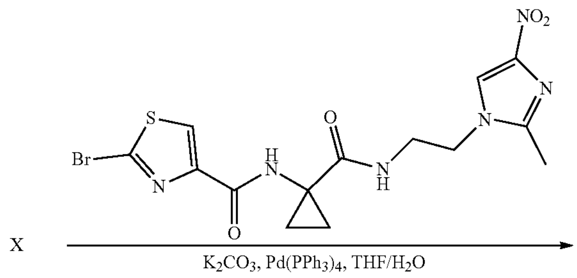

-continued

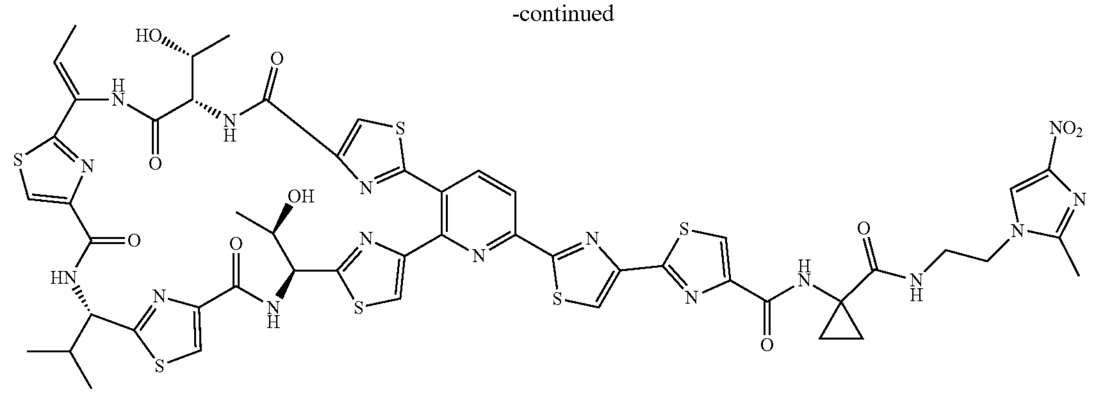

45

Compound 45 (10 mg, 16%) was obtained as a white solid from Compound X in the same manner as that of Example 24.

$^1$H NMR (400 MHz, DMSO) δ9.54 (s, 1H), 8.92 (s, 1H), 8.55 (s, 1H), 8.45 (d, J=8.2 Hz, 1H), 8.41-8.32 (m, 4H), 8.31 (d, J=4.3 Hz, 1H), 8.23 (d, J=13.1 Hz, 3H), 8.19-8.14 (m, 1H), 8.09 (s, 1H), 7.85 (d, J=7.9 Hz, 1H), 6.48 (q, J=6.8 Hz, 1H), 5.44 (d, J=6.1 Hz, 1H), 5.22-4.97 (m, 2H), 4.89-4.57 (m, 2H), 4.42-4.35 (m, 1H), 4.22-3.95 (m, 3H), 2.09 (s, 3H), 1.76 (d, J=6.9 Hz, 3H), 1.45-1.36 (m, 5H), 1.11-1.01 (m, 5H), 0.98 (d, J=6.5 Hz, 3H), 0.87 (d, J=6.6 Hz, 3H).

LCMS: 1,239.6 ($M+H^+$) for $C_{51}H_{50}N_{16}O_{10}S_6$

[Example 46] Preparation of Compound 46

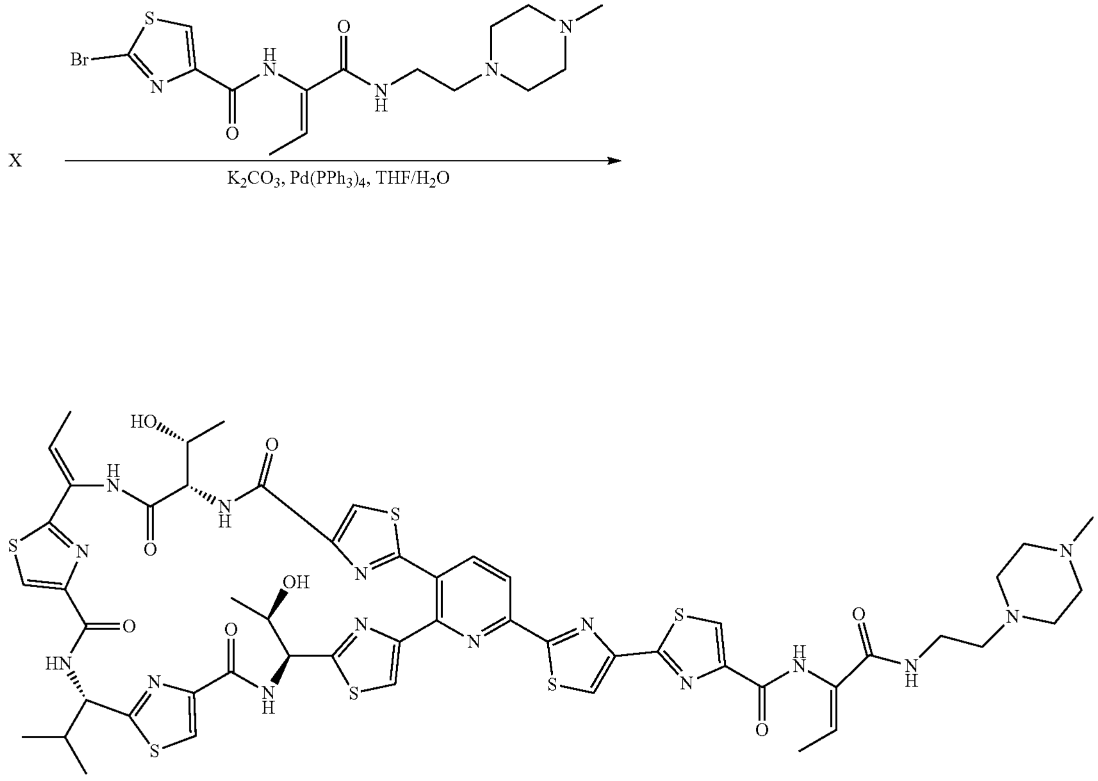

46

Compound 46 (12 mg, 10%) was obtained as a white solid from Compound X in the same manner as that of Example 24.

$^1$H NMR (400 MHz, MeOD) δ8.31-8.21 (m, 5H), 8.13 (s, 1H), 8.09 (s, 1H), 7.97 (s, 1H), 6.67 (q, J=6.9 Hz, 1H), 6.55 (d, J=6.2 Hz, 1H), 5.22 (d, J=8.3 Hz, 2H), 4.66-4.57 (m, 3H), 4.28 (dd, J=6.2, 2.5 Hz, 1H), 3.47-3.42 (m, 2H), 2.91-2.69 (broad peak, 7H), 2.67-2.59 (m, 3H), 2.56 (s, 3H), 1.92-1.72 (m, 6H), 1.57 (d, J=6.3 Hz, 3H), 1.16 (dd, J=10.7, 6.2 Hz, 6H), 0.98 (d, J=6.5 Hz, 3H)

LCMS: 1,212.6 ($M+H^+$) for $C_{52}H_{57}N_{15}O_8S_6$

[Example 47] Preparation of Compound 47
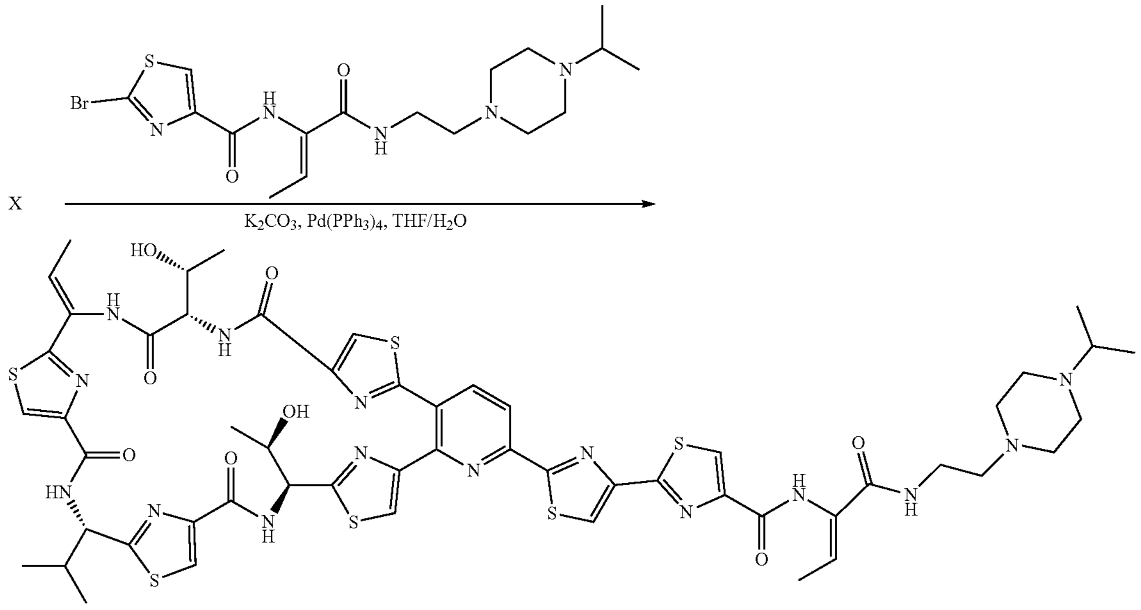
47
Compound 47 (15 mg, 11%) was obtained as a white solid from Compound X in the same manner as that of Example 24.
$^1$H NMR (400 MHz, MeOD) δ 8.17 (d, J=7.6 Hz, 4H), 8.11 (d, J=8.1 Hz, 1H), 8.01 (s, 1H), 7.96 (s, 1H), 7.85 (s, 1H), 6.57 (q, J=7.0 Hz, 1H), 6.42 (d, J=6.5 Hz, 1H), 5.19-4.98 (m, 2H), 4.16 (dd, J=6.3, 2.7 Hz, 1H), 3.36-3.28 (m, 2H), 2.94-2.82 (m, 1H), 2.77 (broad band, 3H), 2.59 (broad band, 2H), 2.55-2.36 (m, 4H), 1.71 (dd, J=10.3, 7.2 Hz, 6H), 1.45 (d, J=6.4 Hz, 3H), 1.11-0.95 (m, 12H), 0.86 (d, J=6.6 Hz, 3H).
LCMS: 1,240.8 (M+H$^+$) for $C_{54}H_{61}N_{15}O_8S_6$
[Example 48] Preparation of Compound 48
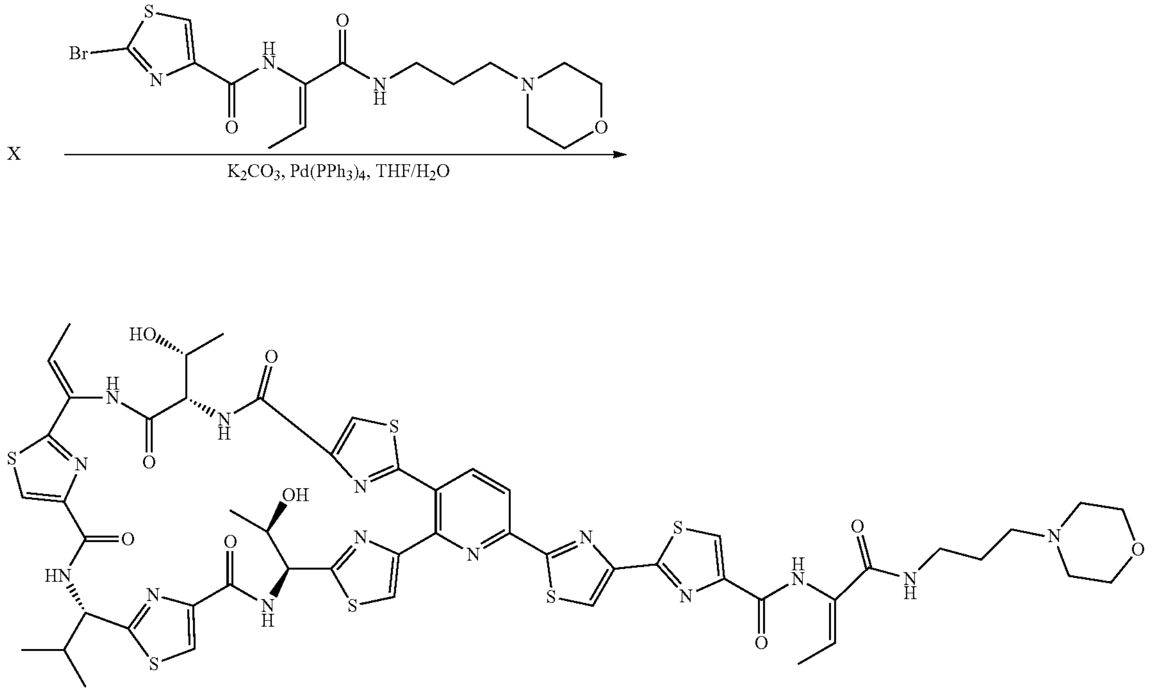
48

Compound 48 (12 mg, 10%) was obtained as a white solid from Compound X in the same manner as that of Example 24.

$^1$H NMR (600 MHz, $CDCl_3$) δ 8.81 (s, 1H), 8.60 (s, 1H), 8.39 (d, J=9.3 Hz, 1H), 8.33 (d, J=7.9 Hz, 1H), 8.27-8.16 (m, 4H), 8.12 (d, J=8.7 Hz, 2H), 8.06-7.85 (m, 3H), 7.49 (s, 1H), 6.60 (dd, J=13.9, 7.0 Hz, 1H), 6.43 (d, J=6.9 Hz, 1H), 5.26 (d, J=8.3 Hz, 2H), 4.87 (d, J=7.1 Hz, 1H), 4.76 (s, 1H), 4.65 (d, J=4.8 Hz, 1H), 4.52 (s, 1H), 4.40 (d, J=5.6 Hz, 1H), 3.69 (s, 4H), 3.48 (d, J=5.1 Hz, 2H), 2.99 (s, 1H), 2.52 (d, J=14.9 Hz, 6H), 1.97-1.67 (m, 6H), 1.36-1.24 (m, 3H), 1.21 (d, J=5.7 Hz, 3H), 1.16 (d, J=6.3 Hz, 3H), 0.98 (d, J=6.2 Hz, 3H).

LCMS: 1,213.3 ($M+H^+$) for $C_{52}H_{56}N_{14}O_9S_6$

[Experimental Example 1] Antibacterial Activity Experiment

The antibacterial activity was measured using the compounds prepared in Examples 1 to 48 of the present invention.

1) Experiment of Antibacterial Activity Against Aerobic Pathogens

The antibacterial activity of the compounds of Examples 1 to 48 of the present invention against aerobic pathogens were evaluated by measuring the minimum concentration of the antibiotic capable of inhibiting bacterial growth by 90% compared to the growth of the non-drug treated control group. MIC was measured by the broth microdilution method based on CLSI standards [Reference: Clinical and Laboratory Standards Institute Document. (2000) Methods for Dilution Antimicrobial Susceptibility Test for Bacteria that Grow Aerobically-Fifth Edition: M7-A5. CLSI, Villanova, PA].

Test Strains

All 13 strains such as methicillin susceptible *Staphylococcus aureus* (MSSA), methicillin resistant *Staphylococcus aureus* (MRSA), Vancomycin resistant *Staphylococcus aureus* (VRSA), *Staphylococcus epidermidis*, methicillin resistant *Staphylococcus epidermidis, Enterococcus faecalis*, Vancomycin resistant *Enterococcus faecalis, Enterococcus faecium*, Vancomycin resistant *Enterococcus faecium* were used. The results are shown in Tables 1 to 6.

2) Experiment of Antibacterial Activity Against *Clostridioides difficile*

The inhibitory activity against *C. difficile* was measured using strains distributed from Korean Collection for Type Cultures (KCTC) or strains distributed from American Type Culture Collection (ATCC). MIC was evaluated for the inhibitory activity by the agar dilution method according to the Clinical and Laboratory Standards Institute (CLSI) guidelines [Methods for Antimicrobial Susceptibility Testing of Anaerobic Bacteria; Approved Standard-Seventh Edition, CLSI document M11-A7, 2007]. BHIS medium was used for liquid culture of *C. difficile*, and a supplemented *brucella* agar was used as a nutrient agar. The agar medium was prepared so that the concentrations of all the tested compounds were 8 μg/ml to 0.06 μg/ml. One day before liquid culture of *C. difficile* strain, BHIS medium was placed in an anaerobic chamber and oxygen in the broth was removed for one day. One day before the experiment, the bacteria were cultured in 4 ml of BHIS medium. The bacteria cultured for one day were diluted using BHIS medium so as to be about 4 to $5\times10^7$ CFU/ml. 10 μl of the diluted bacterial solution was dropped into a medium containing the antibiotic, and culture was performed in an anaerobic chamber for 18 hours or longer. The observed results are shown in Tables 1 to 6.

3) Test of Antibacterial Activity Against *Mycobacterium*

In order to test the antibacterial activity, the medium of *Mycobacterium* cultured to late log phase was diluted so as to be $4.0\times10^5$ cells/well in Middlebrook 7H10 agar medium (Difco) supplemented with 10% oleic acid, albumin, dextrose, catalase (OADC, Becton Dickinson) and 0.05% Tween 80 (Sigma Aldrich) and was dispensed into a 96-well plate. The compounds were treated so that DMSO was 1%, and after 3 days, a 0.025% resazurin (REMA) solution was dispensed, and the growth of the bacteria was confirmed after culturing. The MIC value was measured for the antibacterial activity through resazurin (excitation 530 nm, emission 590 nm).

TABLE 1

| Test Strain/ | Control drug | | | Example compound No | | | | | |
|---|---|---|---|---|---|---|---|---|---|
| MIC (μg/ml) | Van | Lin | Cla | 1 | 2 | 3 | 4 | 5 | 6 |
| 1 *S. aureus*$^{MS}$ | 0.5 | 2 | — | 0.125 | 1 | 0.0625 | 0.5 | 0.25 | 0.5 |
| 2 *S. aureus*$^{MS}$ | 0.25 | 1 | — | 0.125 | 1 | <0.0625 | 0.5 | 0.25 | 0.25 |
| 3 *S. aureus*$^{MR}$ | 0.5 | 4 | — | — | — | 1 | 1 | 1 | — |
| 4 *S. aureus*$^{VR}$ | >128 | 8 | — | 1 | — | 0.25 | 1 | 1 | 1 |
| 5 *S. epidermis* | 1 | 1 | — | 0.125 | 0.25 | 0.25 | 0.25 | 0.5 | 0.5 |
| 6 *S. epidermis*$^{MR}$ | 0.5 | 1 | — | 0.125 | 0.5 | 0.125 | 0.5 | 0.5 | 1 |
| 7 *E. faecalis* | 1 | 2 | — | 0.25 | 0.5 | 0.0625 | 0.25 | 0.25 | 0.125 |
| 8 *E. faecalis*$^{VanA}$ | >128 | 2 | — | 0.125 | 0.5 | 0.125 | 0.5 | 0.5 | 1 |
| 9 *E. faecalis*$^{LinR}$ | 1 | 64 | — | 0.125 | 1 | 0.125 | 1 | 0.5 | 0.125 |
| 10 *E. faecium* | 0.5 | 4 | — | 0.5 | — | 0.125 | 0.5 | 1 | 0.25 |
| 11 *E. faecium*$^{VRE}$ | >128 | 2 | — | — | — | 0.25 | — | — | 1 |
| 12 *E. faecium*$^{LinR}$ | 0.5 | 32 | — | 1 | — | 0.25 | 1 | 0.5 | 0.5 |
| 13 *C. difficile* 9689 | 2 | — | — | — | — | — | — | 1 | 1 |
| 14 *C. difficile* 152 | 1 | — | — | — | — | 1 | — | 0.5 | 0.06 |
| 15 *C. difficile* 159 | 2 | — | — | — | — | 1 | — | 1 | — |
| 16 *C. difficile* 161 | 1 | — | — | 0.5 | — | 0.25 | — | — | — |
| 17 *C. difficile* 173 | 0.5 | — | — | 1 | — | 0.5 | — | 1 | 0.06 |
| 18 *C. difficile* 174 | 0.5 | — | — | 0.5 | — | 0.25 | — | 0.25 | 0.06 |
| 19 *C. difficile* 181 | 0.5 | — | — | | — | 0.5 | — | 0.125 | 0.06 |
| 20 *M. tuberculosis* | — | — | — | 0.076 | — | 0.1 | — | — | — |
| 21 *M. avium* | — | — | 0.205 | — | — | — | 0.115 | 0.043 | — |
| 22 *M. intracelluare* | — | — | 0.143 | — | — | — | 0.143 | 0.155 | — |
| 23 *M. abscessus* | — | — | 1.282 | — | — | — | 0.157 | 0.504 | — |

TABLE 2

| Test Strain/ MIC (μg/ml) | Example compound No 7 | 8 | 9 | 10 | 11 | 12 | 13 | 14 | 15 |
|---|---|---|---|---|---|---|---|---|---|
| 1 *S. aureus*$^{MS}$ | 0.25 | — | 0.25 | 0.125 | 0.5 | 1 | — | 0.125 | 1 |
| 2 *S. aureus*$^{MS}$ | 0.25 | — | 0.25 | 0.0625 | 0.5 | 1 | — | 0.0625 | 1 |
| 3 *S. aureus*$^{MR}$ | 0.5 | — | 1 | 0.5 | — | — | — | — | — |
| 4 *S. aureus*$^{VR}$ | 1 | — | 1 | 0.5 | — | — | — | — | — |
| 5 *S. epidermis* | 0.0625 | — | 0.125 | 0.0625 | 0.125 | 0.5 | — | 0.25 | 1 |
| 6 *S. epidermis*$^{MR}$ | 0.125 | — | 0.25 | 0.125 | 0.5 | 1 | — | 0.5 | 1 |
| 7 *E. faecalis* | 0.25 | — | 0.25 | 0.25 | 0.25 | 1 | — | 0.5 | 1 |
| 8 *E. faecalis*$^{VanA}$ | 0.25 | — | 0.5 | 0.25 | 1 | 1 | — | — | — |
| 9 *E. faecalis*$^{LinR}$ | 0.125 | — | 0.5 | 0.125 | 0.5 | 1 | — | 0.5 | 0.5 |
| 10 *E. faecium* | 0.25 | — | 0.5 | 0.25 | 1 | 1 | — | 0.5 | 1 |
| 11 *E. faecium*$^{VRE}$ | 1 | — | 1 | — | — | — | — | — | — |
| 12 *E. faecium*$^{LinR}$ | 0.5 | — | 0.5 | 0.5 | — | — | — | — | — |
| 13 *C. difficile* 9689 | 0.25 | — | 0.5 | 0.5 | 1 | 0.5 | 0.5 | 1 | — |
| 14 *C. difficile* 152 | 0.06 | 0.06 | 0.06 | 0.06 | 0.25 | 1 | 1 | — | — |
| 15 *C. difficile* 159 | 0.25 | — | 0.5 | 0.25 | 0.5 | — | — | — | — |
| 16 *C. difficile* 161 | 0.5 | — | 0.5 | 0.125 | 0.5 | 0.5 | 0.5 | 1 | — |
| 17 *C. difficile* 173 | 0.06 | 0.06 | 0.06 | 0.06 | 0.125 | 1 | 0.5 | — | — |
| 18 *C. difficile* 174 | 0.06 | 0.06 | 0.06 | 0.06 | 0.125 | 0.125 | 0.125 | 1 | — |
| 19 *C. difficile* 181 | 0.25 | 0.5 | 0.25 | 0.25 | 0.125 | 0.125 | 0.5 | 1 | — |
| 20 *M. tuberculosis* | — | — | — | — | — | — | — | — | — |
| 21 *M. avium* | 0.083 | — | | — | — | 0.135 | — | 0.130 | — |
| 22 *M. intracelluare* | 0.107 | — | — | — | — | — | — | 0.029 | — |
| 23 *M. abscessus* | 0.322 | — | 0.370 | — | — | — | — | — | — |

TABLE 3

| Test Strain/ MIC (μg/ml) | Example compound No 16 | 17 | 18 | 19 | 20 | 21 | 22 | 23 | 24 |
|---|---|---|---|---|---|---|---|---|---|
| 1 *S. aureus*$^{MS}$ | 1 | 1 | 0.25 | 0.5 | 0.25 | 0.25 | 0.25 | 0.5 | 0.5 |
| 2 *S. aureus*$^{MS}$ | 0.5 | 1 | 1 | — | 0.125 | 0.125 | 0.125 | 0.5 | 1 |
| 3 *S. aureus*$^{MR}$ | — | — | — | — | — | — | — | — | — |
| 4 *S. aureus*$^{VR}$ | — | — | — | — | — | — | — | — | — |
| 5 *S. epidermis* | — | — | 0.5 | — | 0.5 | — | — | 1 | 0.25 |
| 6 *S. epidermis*$^{MR}$ | — | — | 1 | — | 0.5 | — | — | 1 | 1 |
| 7 *E. faecalis* | — | — | 1 | — | 0.5 | — | — | — | 1 |
| 8 *E. faecalis*$^{VanA}$ | — | — | | — | — | — | — | — | — |
| 9 *E. faecalis*$^{LinR}$ | 0.25 | — | 0.5 | — | 0.25 | 0.5 | 0.5 | 1 | 1 |
| 10 *E. faecium* | — | — | 1 | — | 0.5 | — | — | — | — |
| 11 *E. faecium*$^{VRE}$ | — | — | | — | 1 | — | — | — | — |
| 12 *E. faecium*$^{LinR}$ | — | — | | — | 1 | — | — | — | — |
| 13 *C. difficile* 9689 | — | — | 0.5 | — | 0.25 | 0.25 | 0.125 | 0.25 | — |
| 14 *C. difficile* 152 | — | — | 0.25 | — | 0.25 | 0.25 | 0.125 | 0.25 | — |
| 15 *C. difficile* 159 | 0.5 | — | | — | 0.5 | — | — | 0.5 | — |
| 16 *C. difficile* 161 | — | — | 1 | — | 1 | — | — | — | — |
| 17 *C. difficile* 173 | — | — | 1 | — | 0.5 | 0.5 | 0.5 | 1 | — |
| 18 *C. difficile* 174 | — | — | 0.25 | — | 0.25 | 0.25 | 0.125 | 0.125 | — |
| 19 *C. difficile* 181 | — | — | — | — | 1 | 1 | — | — | — |
| 20 *M. tuberculosis* | — | — | — | — | — | — | — | — | — |
| 21 *M. avium* | — | — | 0.082 | — | — | — | — | — | — |
| 22 *M. intracelluare* | — | — | 0.127 | — | — | — | — | — | — |
| 23 *M. abscessus* | — | — | 0.173 | — | — | — | — | 0.226 | — |

TABLE 4

| Test Strain/ MIC (μg/ml) | Example compound No 25 | 26 | 27 | 28 | 29 | 30 | 31 | 32 | 33 |
|---|---|---|---|---|---|---|---|---|---|
| 1 *S. aureus*$^{MS}$ | 1 | 1 | 0.25 | 0.25 | 0.25 | 0.5 | 0.5 | 0.5 | 1 |
| 2 *S. aureus*$^{MS}$ | 1 | — | 0.5 | 0.5 | 0.25 | 1 | 1 | 0.5 | — |
| 3 *S. aureus*$^{MR}$ | — | — | — | — | — | — | — | — | — |
| 4 *S. aureus*$^{VR}$ | — | — | — | — | — | — | — | — | — |
| 5 *S. epidermis* | — | 0.5 | — | — | 0.5 | 0.25 | 0.25 | — | 1 |
| 6 *S. epidermis*$^{MR}$ | — | 1 | — | — | 0.5 | 1 | 0.5 | — | 0.5 |

TABLE 4-continued

| Test Strain/ MIC (μg/ml) | Example compound No 25 | 26 | 27 | 28 | 29 | 30 | 31 | 32 | 33 |
|---|---|---|---|---|---|---|---|---|---|
| 7 *E. faecalis* | — | 1 | — | — | 1 | 1 | 1 | — | — |
| 8 *E. faecalis*$^{VanA}$ | — | — | — | — | | | 1 | — | — |
| 9 *E. faecalis*$^{LinR}$ | | — | 0.5 | 0.5 | 0.25 | 0.5 | — | — | 0.5 |
| 10 *E. faecium* | — | — | — | — | — | — | — | — | — |
| 11 *E. faecium*$^{VRE}$ | — | — | — | — | — | — | — | — | — |
| 12 *E. faecium*$^{LinR}$ | — | — | — | — | — | — | — | — | — |
| 13 *C. difficile* 9689 | — | 1 | — | — | — | — | — | — | — |
| 14 *C. difficile* 152 | — | 0.5 | — | — | — | — | — | — | — |
| 15 *C. difficile* 159 | — | — | — | — | — | — | — | — | — |
| 16 *C. difficile* 161 | — | 0.5 | — | — | — | — | — | — | — |
| 17 *C. difficile* 173 | — | 0.5 | — | — | — | — | — | — | — |
| 18 *C. difficile* 174 | — | 0.5 | — | — | — | — | — | — | — |
| 19 *C. difficile* 181 | — | 1 | — | — | — | — | — | — | — |
| 20 *M. tuberculosis* | — | — | — | — | — | — | — | — | — |
| 21 *M. avium* | — | | — | 0.130 | 0.161 | 0.089 | — | 0.153 | — |
| 22 *M. intracelluare* | — | 0.043 | — | 0.115 | 0.130 | 0.024 | — | 0.116 | — |
| 23 *M. abscessus* | — | 0.726 | — | 0.490 | 0.430 | 0.559 | — | 0.153 | — |

TABLE 5

| Test Strain/ MIC (μg/ml) | Example compound No 34 | 35 | 36 | 37 | 38 | 39 | 40 | 41 | 42 |
|---|---|---|---|---|---|---|---|---|---|
| 1 *S. aureus*$^{MS}$ | 0.5 | 0.5 | 0.25 | 0.25 | 1 | — | 0.5 | — | 1 |
| 2 *S. aureus*$^{MS}$ | 1 | — | 0.5 | 0.25 | 1 | — | 0.5 | — | 1 |
| 3 *S. aureus*$^{MR}$ | — | — | — | — | — | — | 1 | — | 1 |
| 4 *S. aureus*$^{VR}$ | — | — | — | — | 1 | — | 0.5 | — | 1 |
| 5 *S. epidermis* | 0.25 | 0.25 | 0.5 | 0.25 | 1 | — | 0.5 | — | 0.5 |
| 6 *S. epidermis*$^{MR}$ | 0.5 | 0.5 | 0.5 | 0.25 | 1 | — | 0.25 | — | 0.5 |
| 7 *E. faecalis* | 1 | 0.5 | 0.5 | 0.5 | — | — | 0.25 | — | 0.5 |
| 8 *E. faecalis*$^{VanA}$ | 1 | — | — | — | 1 | — | 0.5 | — | 0.5 |
| 9 *E. faecalis*$^{LinR}$ | — | 1 | — | 1 | — | — | 0.5 | — | 0.5 |
| 10 *E. faecium* | — | — | — | 0.5 | 0.5 | — | 0.5 | — | 1 |
| 11 *E. faecium*$^{VRE}$ | — | — | — | 1 | 1 | — | 1 | — | 1 |
| 12 *E. faecium*$^{LinR}$ | — | 1 | 1 | — | 1 | — | 1 | — | 1 |
| 13 *C. difficile* 9689 | — | — | — | — | — | 0.25 | 1 | 0.5 | 0.5 |
| 14 *C. difficile* 152 | — | — | — | — | — | 0.25 | 0.5 | 0.25 | 0.5 |
| 15 *C. difficile* 159 | — | — | — | — | — | 1 | 1 | 0.5 | 0.5 |
| 16 *C. difficile* 161 | — | — | — | — | — | 0.25 | 0.5 | 0.25 | 1 |
| 17 *C. difficile* 173 | — | — | — | — | — | 0.5 | — | 0.5 | 0.5 |
| 18 *C. difficile* 174 | — | — | — | — | — | 1 | 0.5 | 0.25 | 0.5 |
| 19 *C. difficile* 181 | — | — | — | — | — | 0.5 | — | 1 | 0.5 |
| 20 *M. tuberculosis* | — | — | — | — | — | — | — | — | — |
| 21 *M. avium* | — | 0.109 | — | 0.082 | — | — | — | — | — |
| 22 *M. intracelluare* | — | 0.139 | — | | — | — | — | — | — |
| 23 *M. abscessus* | — | 0.123 | — | | — | — | — | — | — |

TABLE 6

| Test Strain/ MIC (μg/ml) | Example compound No 43 | 44 | 45 | 46 | 47 | 48 |
|---|---|---|---|---|---|---|
| 1 *S. aureus*$^{MS}$ | — | — | — | 0.5 | 0.5 | 0.5 |
| 2 *S. aureus*$^{MS}$ | — | — | — | 0.5 | 0.5 | 0.5 |
| 3 *S. aureus*$^{MR}$ | — | — | — | 1 | 1 | 1 |
| 4 *S. aureus*$^{VR}$ | — | — | — | 0.5 | 1 | 1 |
| 5 *S. epidermis* | — | — | — | 0.25 | 0.5 | 0.5 |
| 6 *S. epidermis*$^{MR}$ | — | — | — | 0.25 | 0.5 | 0.5 |
| 7 *E. faecalis* | — | — | — | 0.5 | 0.5 | 0.5 |
| 8 *E. faecalis*$^{VanA}$ | — | — | — | 0.5 | 0.5 | 0.5 |
| 9 *E. faecalis*$^{LinR}$ | — | — | — | 0.25 | 1 | 1 |
| 10 *E. faecium* | — | — | — | 0.25 | 0.5 | 0.5 |
| 11 *E. faecium*$^{VRE}$ | — | — | — | 0.5 | 1 | 1 |
| 12 *E. faecium*$^{LinR}$ | — | — | — | 0.5 | 1 | 1 |
| 13 *C. difficile* 9689 | 0.5 | 0.5 | 0.5 | | — | — |
| 14 *C. difficile* 152 | 0.5 | 0.25 | 0.5 | | — | — |
| 15 *C. difficile* 159 | 0.5 | — | 0.5 | | — | — |

TABLE 6-continued

| Test Strain/ MIC (μg/ml) | Example compound No 43 | 44 | 45 | 46 | 47 | 48 |
|---|---|---|---|---|---|---|
| 16 *C. difficile* 161 | 0.5 | 0.25 | 0.5 | — | — | — |
| 17 *C. difficile* 173 | 1 | 0.5 | 1 | — | — | — |
| 18 *C. difficile* 174 | 0.5 | 0.5 | 0.5 | — | — | — |
| 19 *C. difficile* 181 | 0.5 | 0.5 | 1 | — | — | — |
| 20 *M. tuberculosis* | — | — | — | — | — | — |
| 21 *M. avium* | — | — | — | — | — | — |
| 22 *M. intracelluare* | — | — | — | — | — | — |
| 23 *M. abscessus* | — | — | — | — | — | — |

Van: Vancomycin
Lin: Linezolid
Cla: Clarithromycin
1. *Staphylococcus aureus*
2. *Staphylococcus aureus*
3. Methicillin resistant *Staphylococcus aureus*

4. Vancomycin resistant *Staphylococcus aureus*
5. *Staphylococcus epidermidis*
6. Methicillin resistant *Staphylococcus epidermidis*
7. *Enterococcus faecalis*
8. Vancomycin resistant *Enterococcus faecalis*
9. Linezolid resistant *Enterococcus faecalis*
10. *Enterococcus faecium*
11. Vancomycin resistant *Enterococcus faecium*
12. Linezolid resistant *Enterococcus faecium*
13-19. *Clostridioides difficile*
20. *Mycobacterium tuberculosis*
21. *Mycobacterium avium*
22. *Mycobacterium intracellulare*
23. *Mycobacterium abscessus*

As shown in Tables 1 to 6, it can be appreciated that the compound of the present invention has excellent antibacterial activity against various bacteria.

In particular, the compound of the present invention is effective against Gram-positive bacteria, particularly, Gram-positive bacteria (MRSA, VRSA, VRE, and the like) resistant to conventional antibiotics at a much lower concentration than the control substance, vancomycin (VAN). It can be seen that the compound of the present invention shows significantly excellent antibacterial activity against *C. difficile*, and thus is likely to be effectively used for treatment of the corresponding strain. In addition, the compound of the present invention has significantly excellent antibacterial activity against Mycobacteria tuberculosis, nontuberculous mycobacteria (*Mycobacterium avium, Mycobacterium intracellulare*, and *Mycobacterium abscessus*) compared to clarithromycin (CLA), which is a control substance, which shows that the compound of the present invention may be effectively used for treatment of pathogens that may become a major problem in the future.

Hereinabove, although the present invention has been described by specific matters, limited embodiments, and drawings, they have been provided only for assisting in the entire understanding of the present invention. Therefore, the present invention is not limited to the embodiments. Various modifications and changes may be made by those skilled in the art to which the present invention pertains from this description.

Therefore, the spirit of the present invention should not be limited to the described embodiments, but the claims and all modifications equal or equivalent to the claims are intended to fall within the spirit of the present invention.

The invention claimed is:

1. A compound represented by the following Chemical Formula 1, or pharmaceutically acceptable salt thereof:

[Chemical Formula 1]

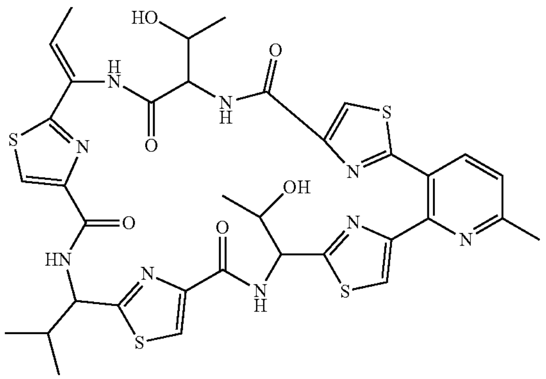

-continued

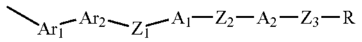

in Chemical Formula 1, $Ar_1$ and $Ar_2$ are each independently

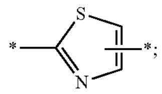;

$Z_1$ is —$CONR_1$—;

$Z_2$ is —$CONR_1$— or —COO—;

$Z_3$ is a single bond, or —$NR_6$—;

$R_1$ and R' are each independently hydrogen;

$A_1$ is

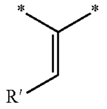

or

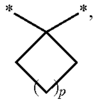,

R' is hydrogen, C1-C10 alkyl, C2-C10 alkenyl, or C1-C10 alkoxy C1-C10 alkyl, and p is an integer of 0 to 4;

$A_2$ is a single bond, C1-C10 alkylene, C3-C10 cycloalkylene, C3-C10 heterocycloalkylene, C6-C20 arylene, or C6-C20 heteroarylene; and R is hydrogen, —$B(OH)_2$, C3-C10 heterocycloalkyl, or C3-C20 heteroaryl the heterocycloalkyl, or heteroaryl of R may be further substituted with one or more selected from the group consisting of halogen, amino, nitro, hydroxy, a carboxylic acid group,—$B(OH)_2$, C1-C10 alkylcarbonyl, C1-C10 alkoxycarbonyl, C2-C10 alkenyl, C1-C10 alkyl, halo C1-C10 alkyl, C3-C10 heterocyclocarbonyl, allylamino, C1-C10 alkylsulfonyl, aminosulfonyl, amino C1-C10 alkyl, hydroxy C1-C10 alkyl, dihydroxy C1-C10 alkyl, cyano C1-C10 alkyl, C1-C10 alkylamino, di C1-C10 alkylamino, C6-C20 arylamino, di C6-C20 arylamino, C3-C20 heteroaryl, halo C6-C20 aryl, halo C1-C10 alkyl C6-C20 aryl, C6-C20 aryl, C3-C10 cycloalkyl, C3-C10 cycloalkylcarbonyl, C1-C10 alkoxycarbonyl C1-C10 alkyl, and carboxy C1-C10 alkyl.

2. The compound of claim 1, or pharmaceutically acceptable salt thereof, wherein Chemical Formula 1 is represented by the following Chemical Formula 2:

[Chemical Formula 2]

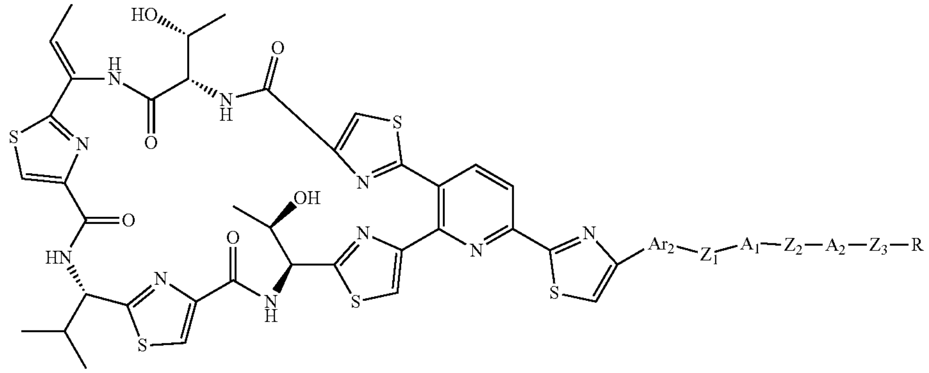

in Chemical Formula 2, $Ar_2$, $Z_1$ to $Z_3$, $A_1$, $A_2$ and R are the same as defined in Formula 1 of claim 1.

3. The compound of claim 2, or pharmaceutically acceptable salt thereof, wherein, in Chemical Formula 2, $A_1$ is

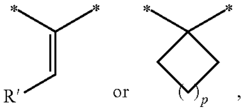

or ,

R' is hydrogen or C1-C10 alkyl, and p is an integer of 0 to 2; and $A_2$ is a single bond, C1-C10 alkylene, or C3-C10 heterocycloalkylene.

4. The compound of claim 1, or pharmaceutically acceptable salt thereof, wherein Chemical Formula 1 is represented by the following Chemical Formula 3:

[Chemical Formula 3]

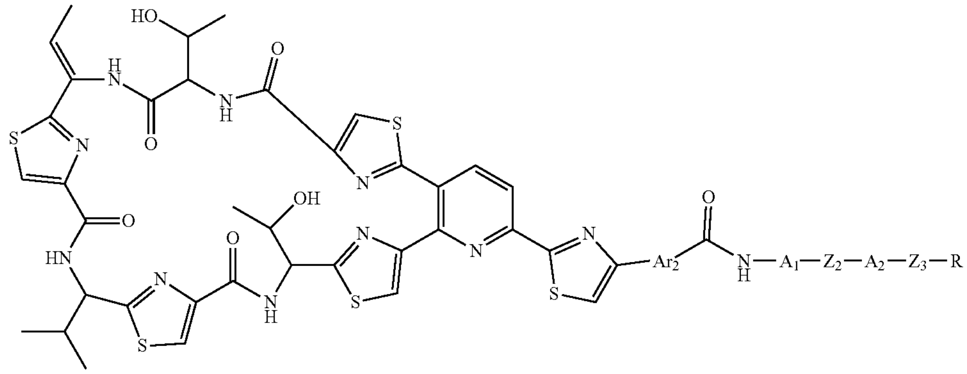

in Chemical Formula 3, $Ar_2$, $Z_2$, $Z_3$, and R are the same as defined in Formula 1 of claim 1;

$A_1$ is

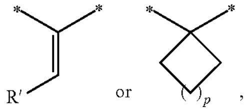

or ,

R' is hydrogen or C1-C10 alkyl, and p is an integer of 0 to 2; and $A_2$ is a single bond, C1-C10 alkylene, or C3-C10 heterocycloalkylene.

5. The compound of claim 4, or pharmaceutically acceptable salt thereof, wherein, in Chemical Formula 3, $A_1$ is

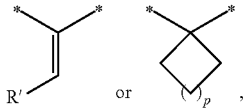

or ,

R' is C1-C10 alkyl, and p is an integer of 0 to 2; and $A_2$ is a single bond or C1-C10 alkylene.

6. The compound of claim 4, or pharmaceutically acceptable salt thereof, wherein Chemical Formula 3 is represented by the following Chemical Formula 4-1 or 4-2:

[Chemical Formula 4-1]

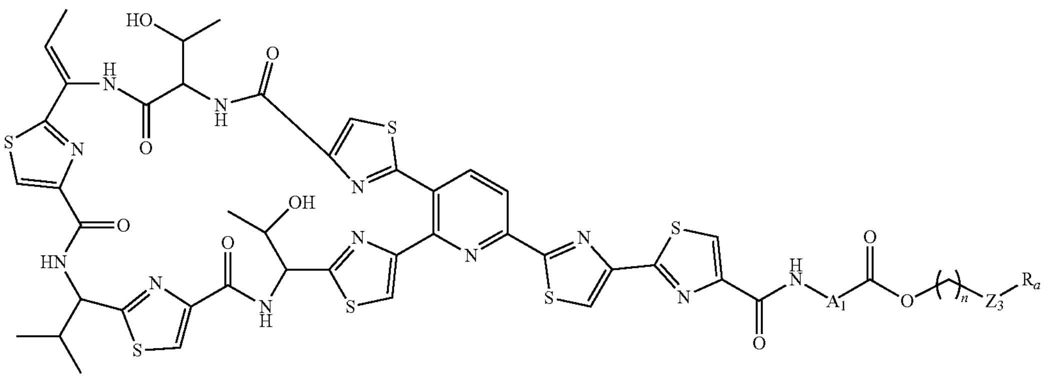

[Chemical Formula 4-2]

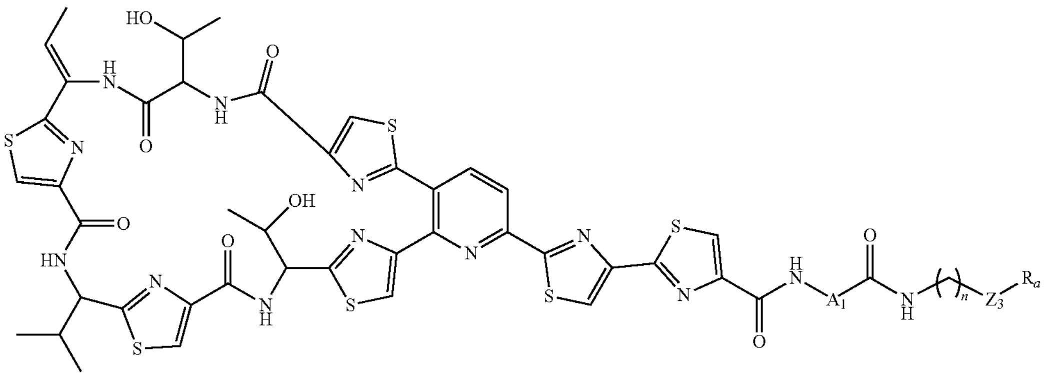

in Chemical Formulas 4-1 and 4-2, $A_1$ is

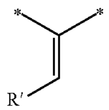

or

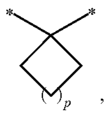

,

R' is C1-C10 alkyl, and p is an integer of 0 to 2;

n is an integer of 0 to 5;

$Z_3$ is a single bond or $—NR_6—$, and $R_6$ is hydrogen;

$R_a$ is hydrogen or $—B(OH)_2$, or is any one selected from the following structures;

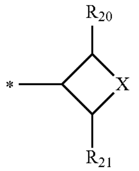

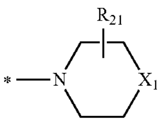

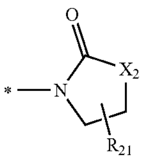

-continued

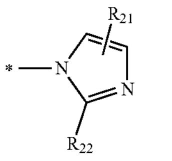

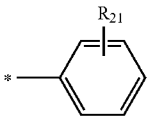

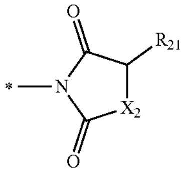

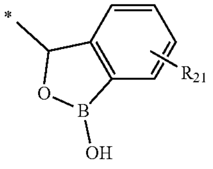

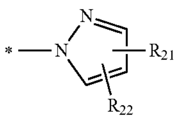

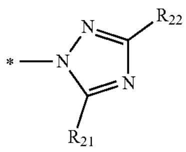

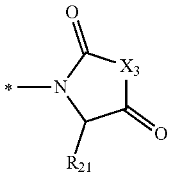

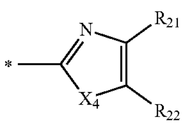

-continued

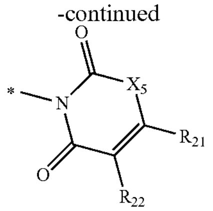

X is O or S;
$X_1$ is $NR_{31}$, O, S, or $SO_2$;
$X_2$ to $X_5$ are each independently $NR_{32}$, O, or S; and $R_{20}$ to $R_{22}$, $R_{31}$, and $R_{32}$ are each independently hydrogen, halogen, nitro, C1-C10 alkylcarbonyl, C1-C10 alkoxycarbonyl, C1-C10 alkyl, C1-C10 alkylsulfonyl, aminosulfonyl, hydroxy C1-C10 alkyl, dihydroxy C1-C10 alkyl, cyano C1-C10 alkyl, C3-C10 cycloalkyl, C1-C10 alkoxycarbonyl C1-C10 alkyl, or carboxy C1-C10 alkyl.

7. The compound of claim 1, or pharmaceutically acceptable salt thereof, wherein Chemical Formula 1 is represented by any one of the following Chemical Formulas 5 to 12:

[Chemical Formula 5]

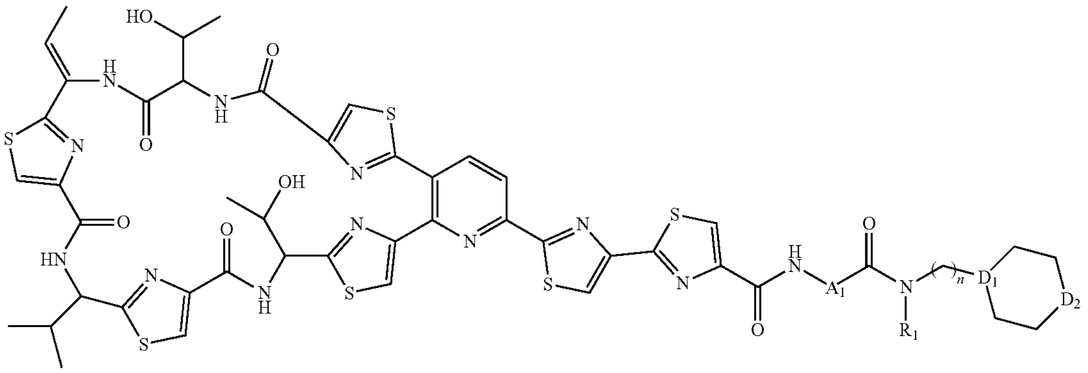

[Chemical Formula 6]

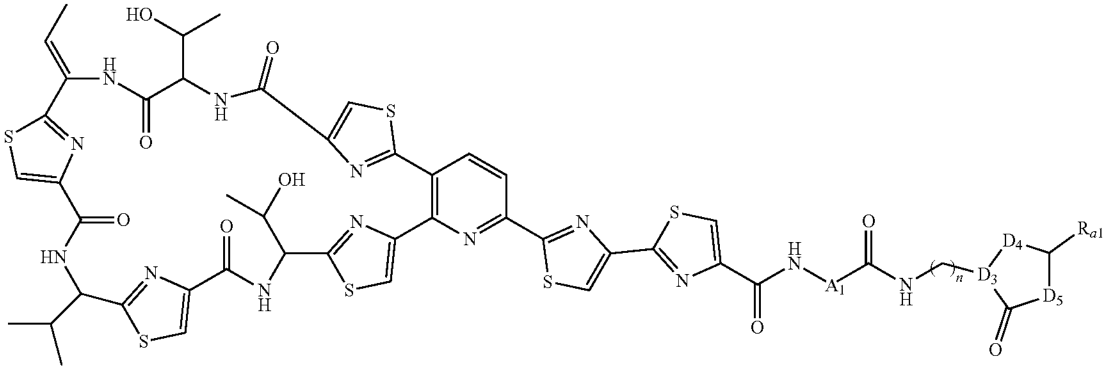

[Chemical Formula 7]

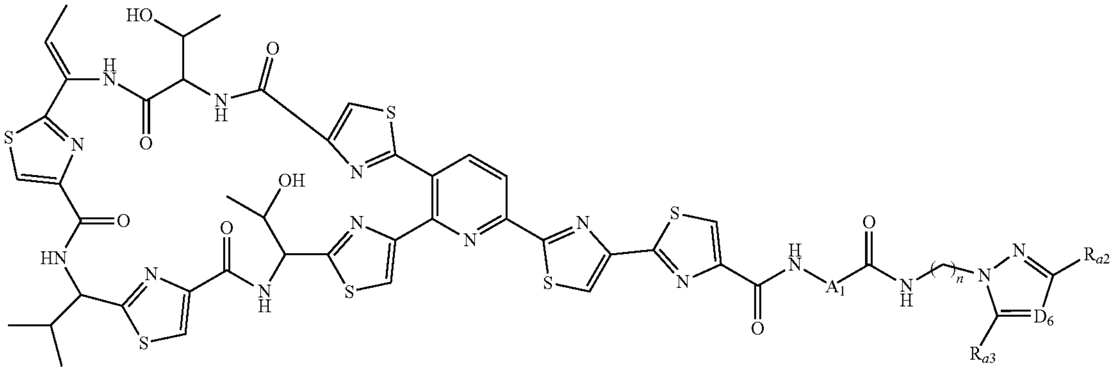

-continued
[Chemical Formula 8]
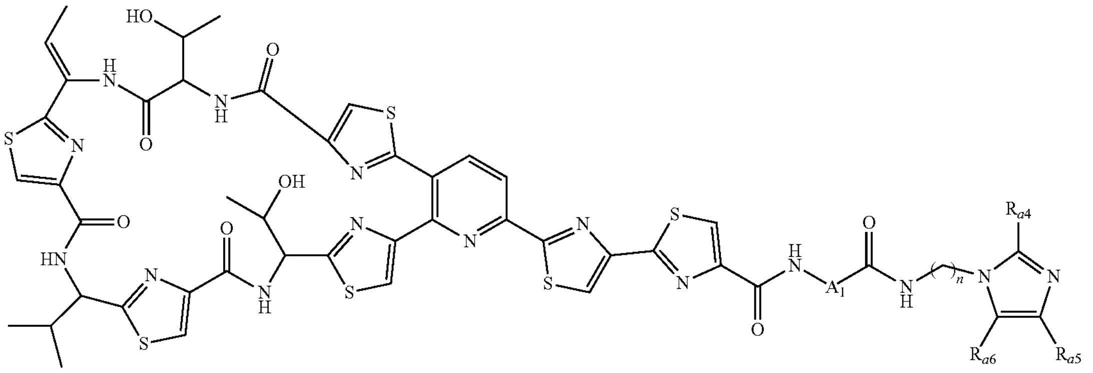
[Chemical Formula 9]
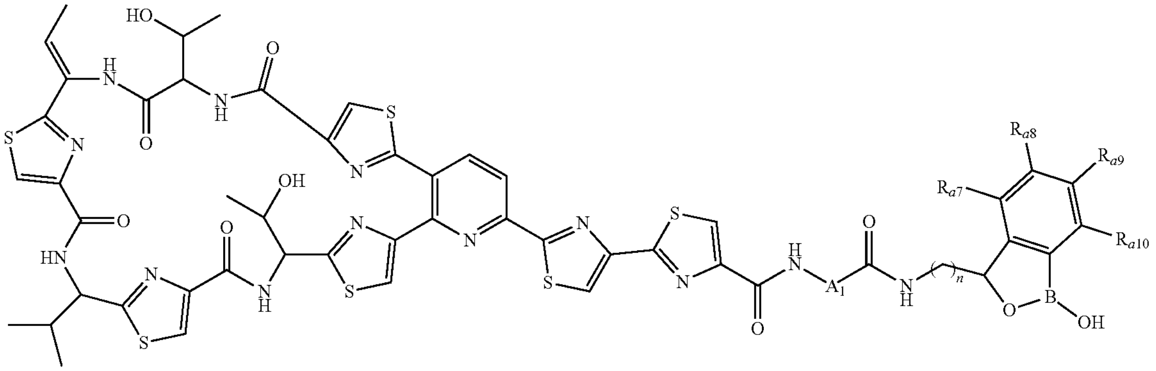
[Chemical Formula 10]
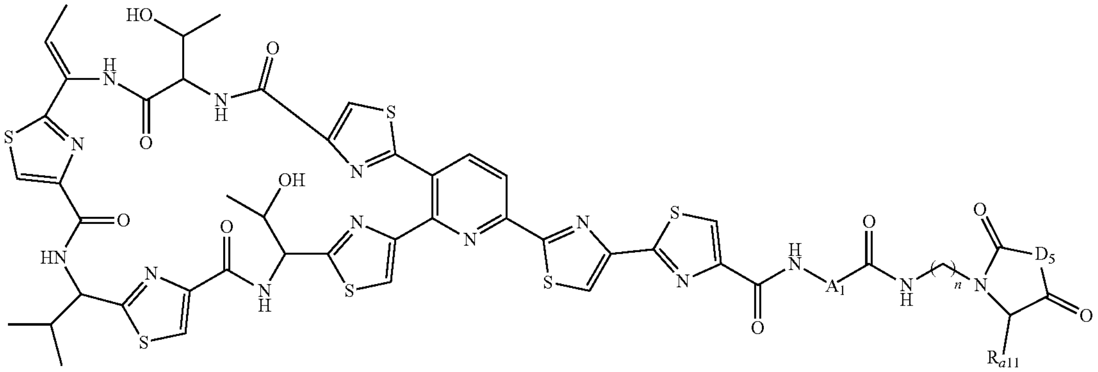
[Chemical Formula 11]
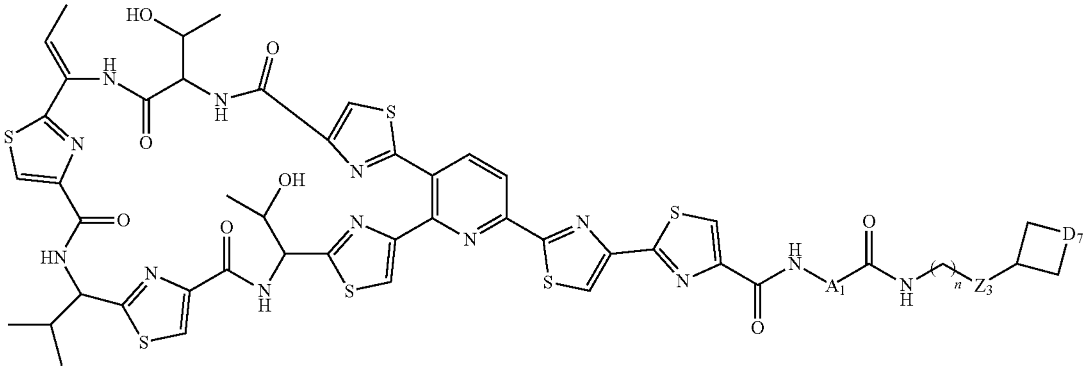

-continued

[Chemical Formula 12]

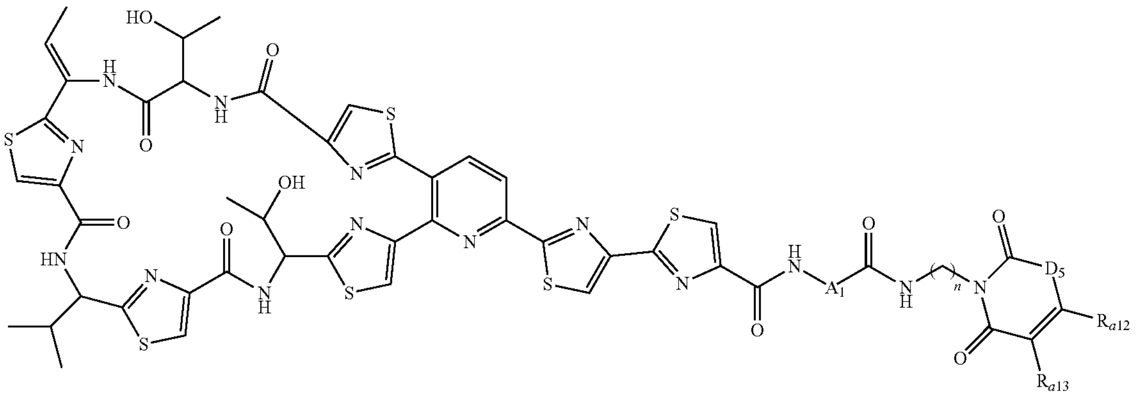

in Chemical Formulas 5 to 12, $A_1$ is

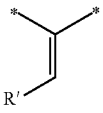 or 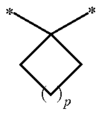 ,

R' is C1-C10 alkyl, and p is an integer of 0 to 2;

$D_1$ is CH or N;

$D_2$ is O, S, $SO_2$, $C(R_{b1})(R_{b2})$, or $NR_{c1}$;

$D_3$ is CH or N;

$D_4$ is CO, NH, or CH;

$D_5$ is O, S, or $NR_{c2}$;

$D_6$ is $CR_{b3}$ or N;

$D_7$ is O or S;

$R_1$ is hydrogen;

$Z_3$ is a single bond or —$NR_6$—, and $R_6$ is hydrogen;

$R_{a1}$ to $R_{a13}$, $R_{b1}$ to $R_{b3}$, $R_{c1}$, and $R_{c2}$ are each independently hydrogen, halogen, amino, nitro, hydroxy, a carboxylic acid group, —$B(OH)_2$, C1-C10 alkylcarbonyl, C1-C10 alkoxycarbonyl, C2-C10 alkenyl, C1-C10 alkyl, halo C1-C10 alkyl, C3-C10 heterocyclocarbonyl, allylamino, C1-C10 alkylsulfonyl, aminosulfonyl, amino C1-C10 alkyl, hydroxy C1-C10 alkyl, dihydroxy C1-C10 alkyl, cyano C1-C10 alkyl, C1-C10 alkylamino, di C1-C10 alkylamino, C6-C20 arylamino, di C6-C20 arylamino, C3-C20 heteroaryl, halo C6-C20 aryl, halo C1-C10 alkyl C6-C20 aryl, C6-C20 aryl, C3-C10 cycloalkyl, C3-C10 cycloalkylcarbonyl, C1-C10 alkoxycarbonyl C1-C10 alkyl, or carboxy C1-C10 alkyl; and n is an integer of 0 to 5.

8. The compound of claim 1, or pharmaceutically acceptable salt thereof, wherein Chemical Formula 1 is represented by the following Chemical Formula 13-1 or 13-2:

[Chemical Formula 13-1]

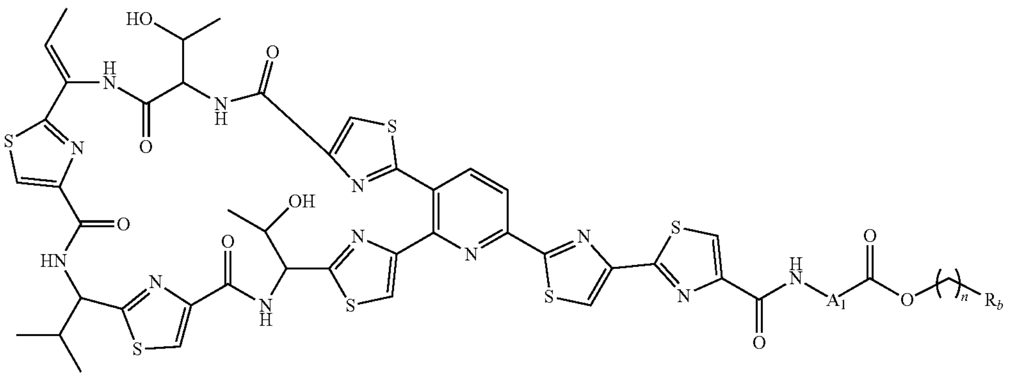

-continued
[Chemical Formula 13-2]
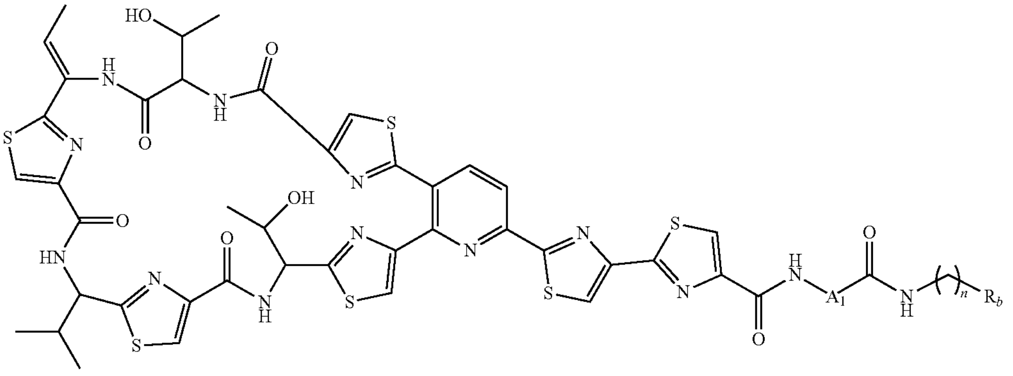
in Chemical Formulas 13-1 and 13-2,
$R_b$ is hydrogen or —$B(OH)_2$;
$A_1$ is
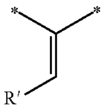 or 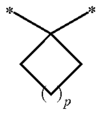 ,
R' is C1-C10 alkyl, and p is an integer of 0 to 2; and
n is an integer of 0 to 10.
9. The compound of claim 1, or pharmaceutically acceptable salt thereof, wherein the compound is selected from the following compounds:
1
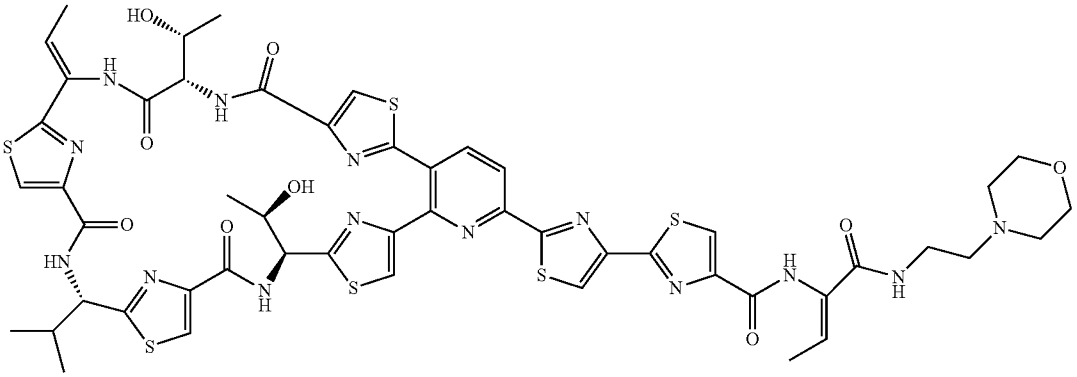
2
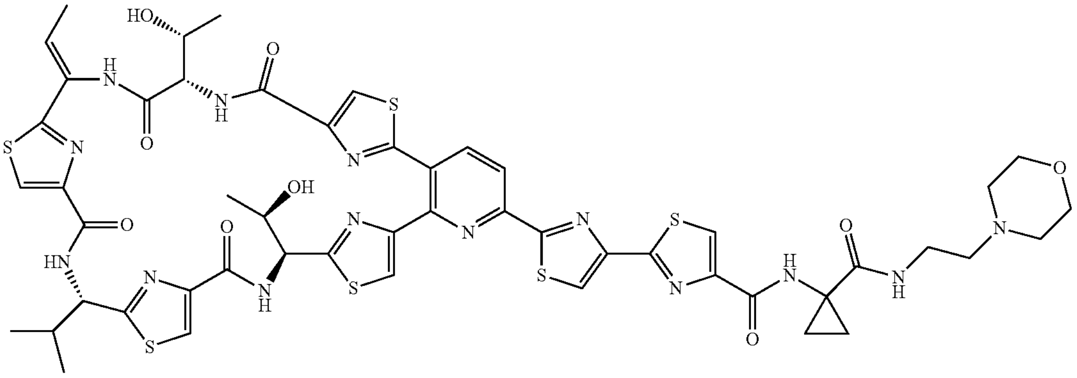

-continued
3
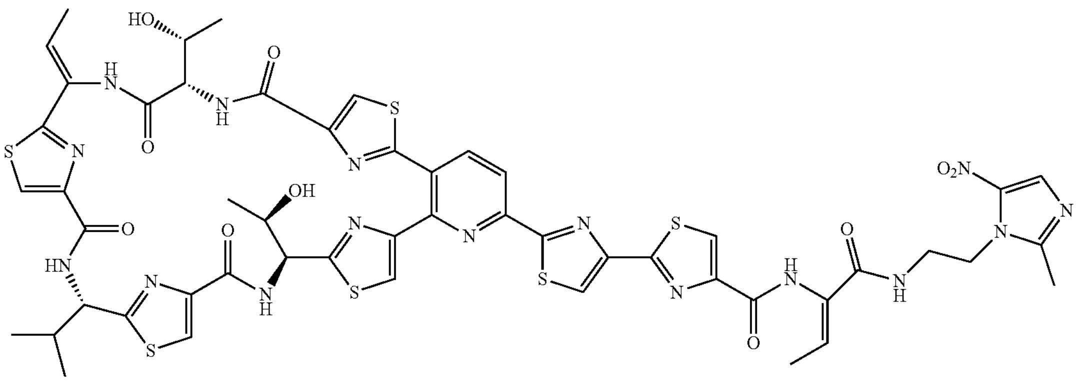
4
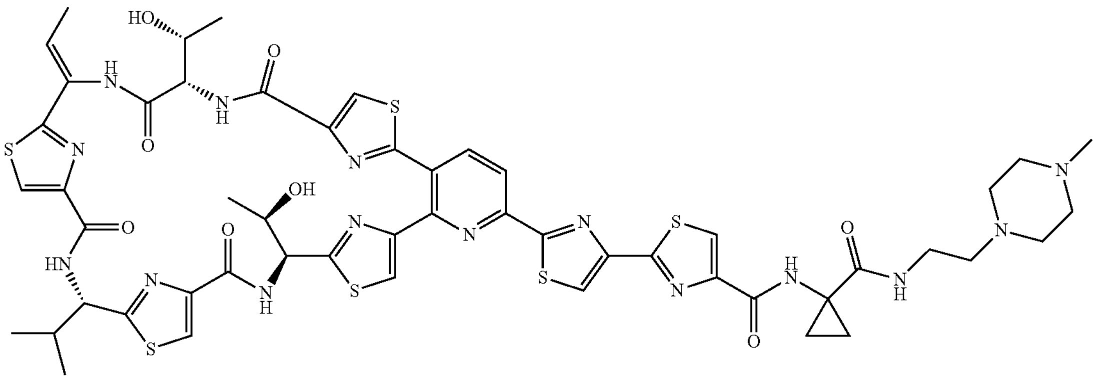
5
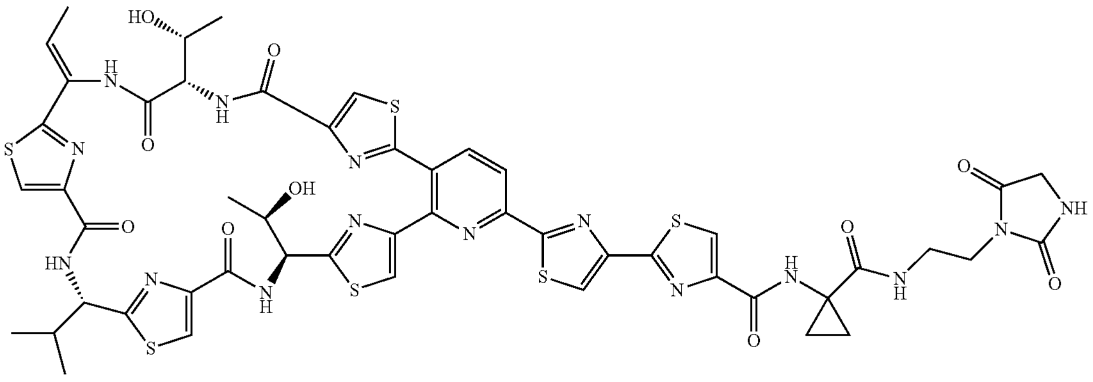
6
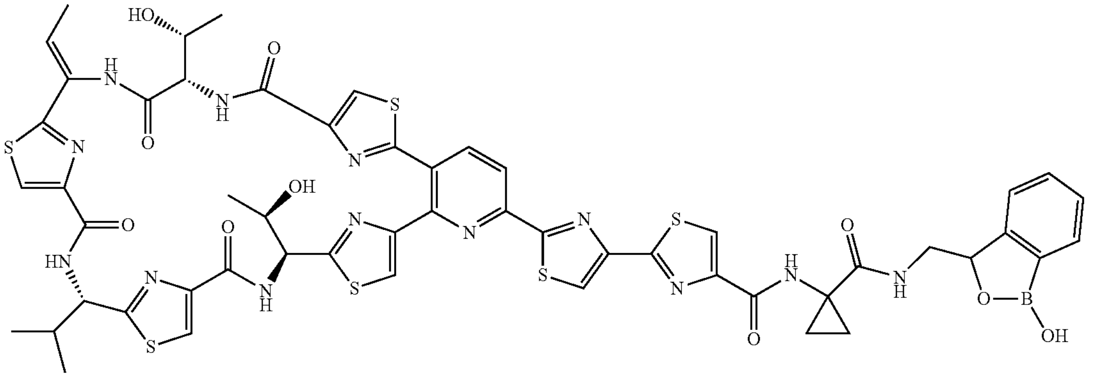

-continued
7
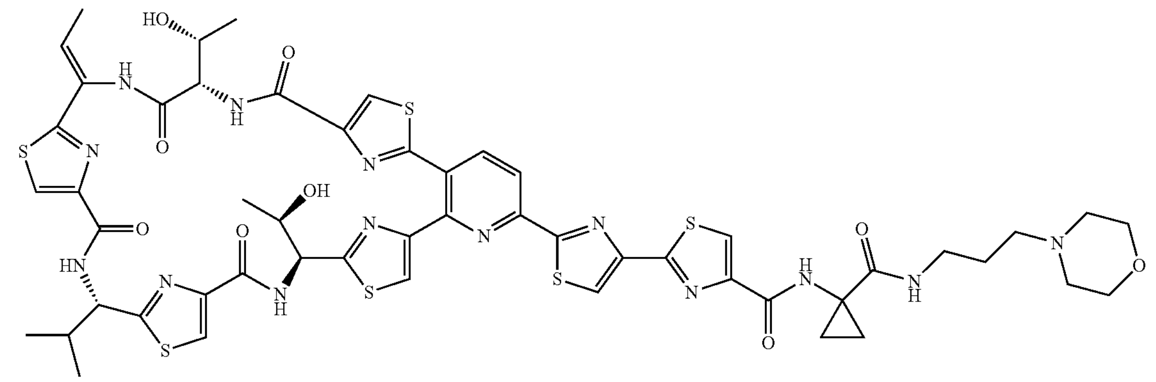
8
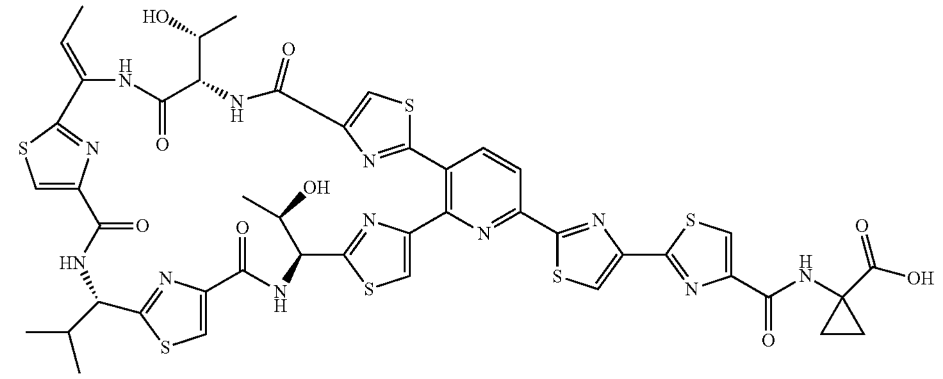
9
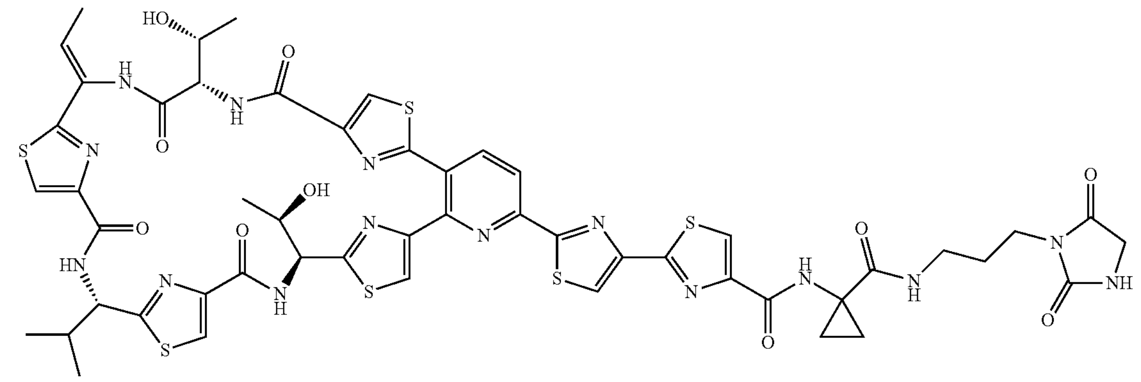
10
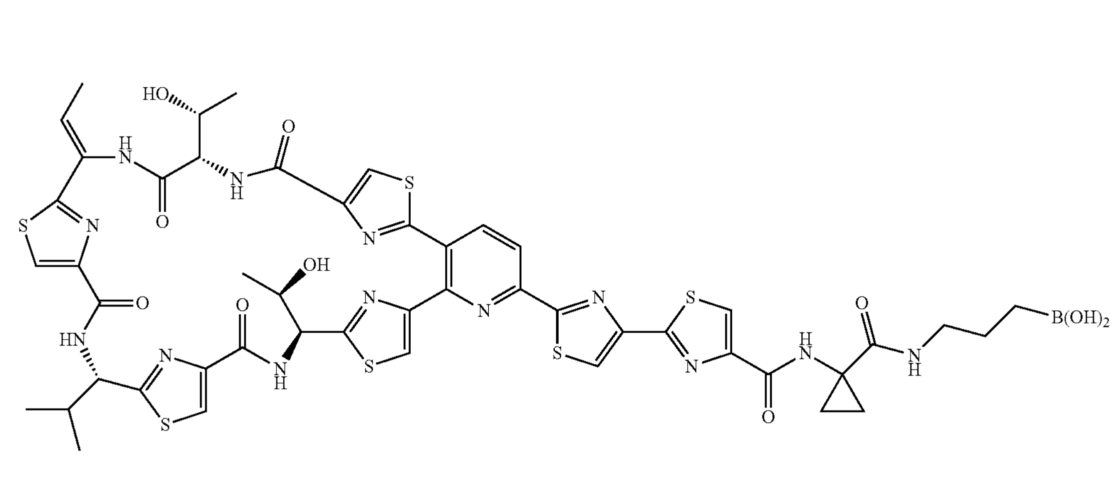

-continued
11
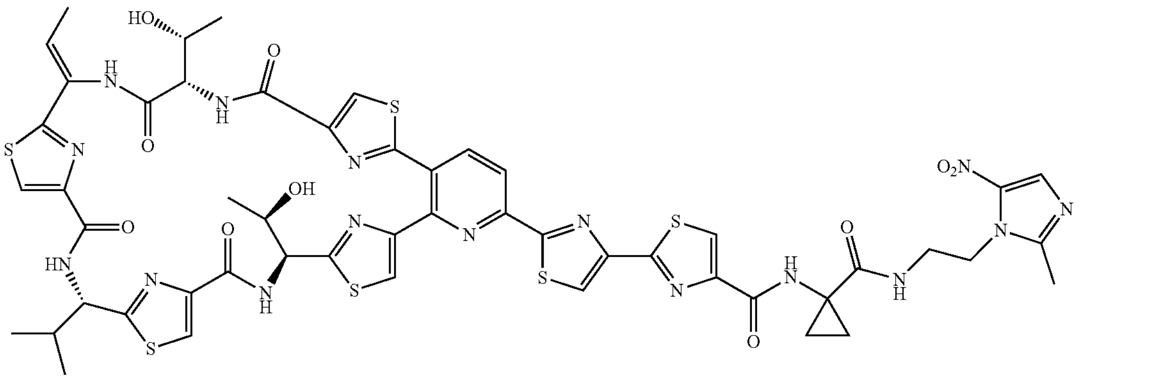
12
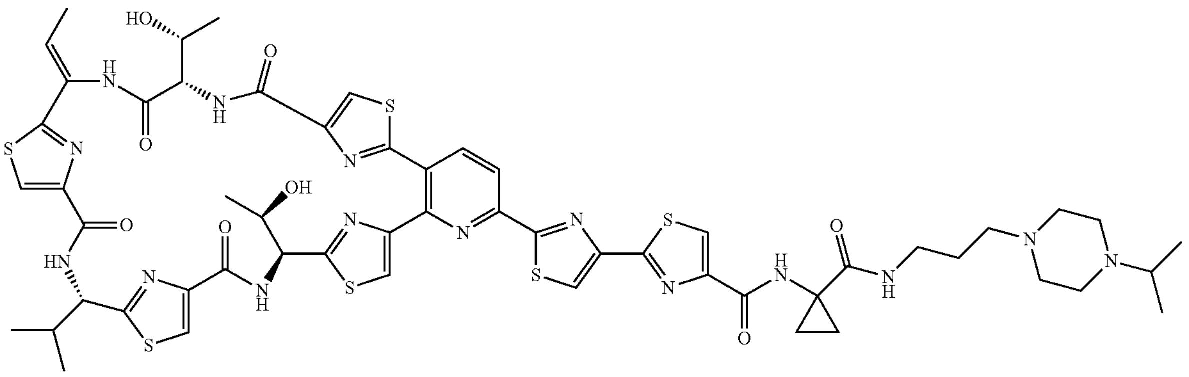
13
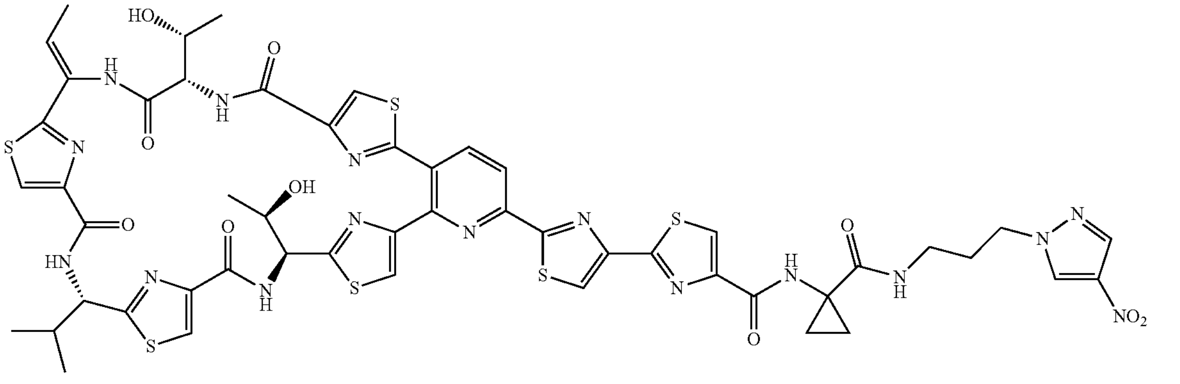
14
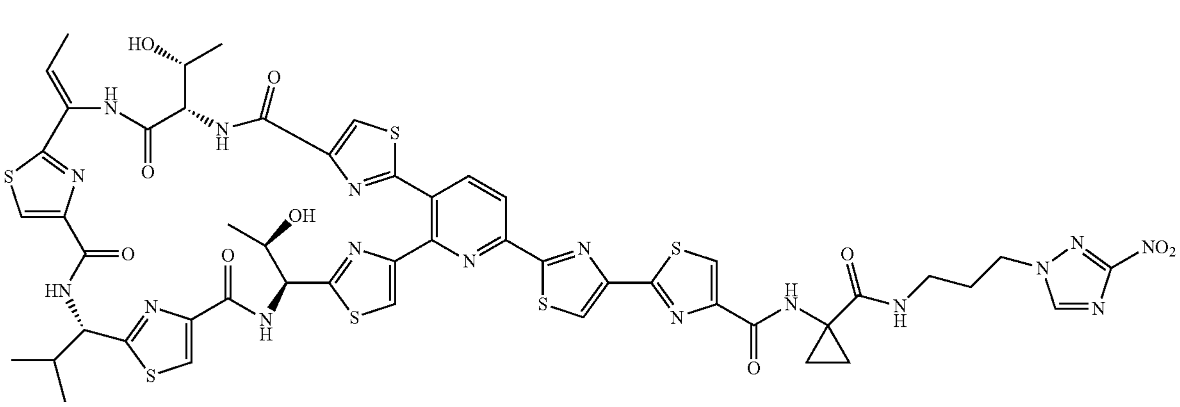

-continued
15
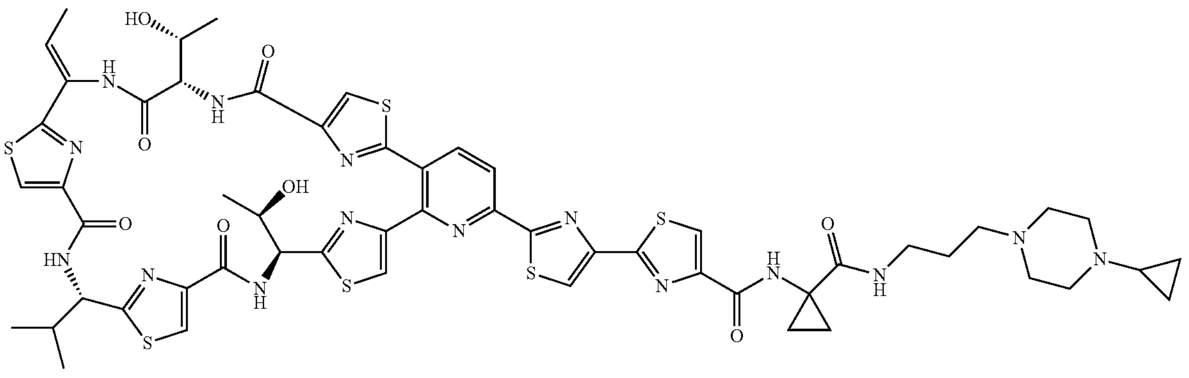
16
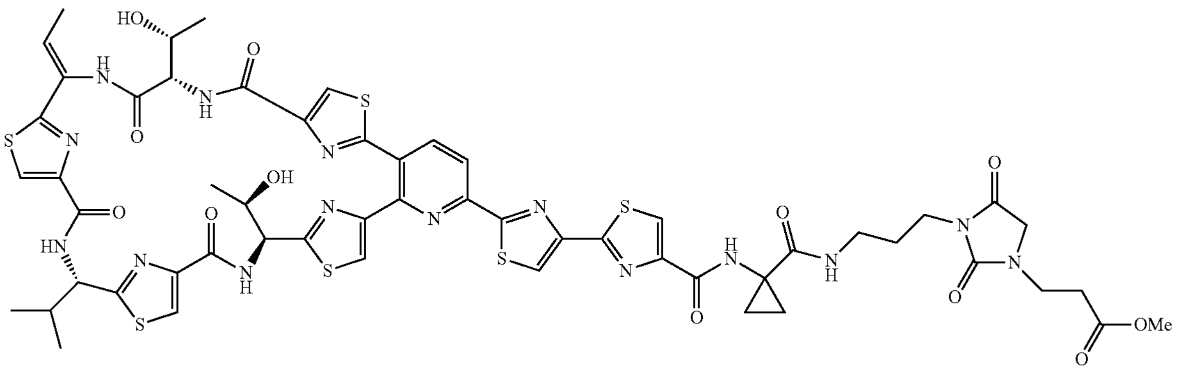
17
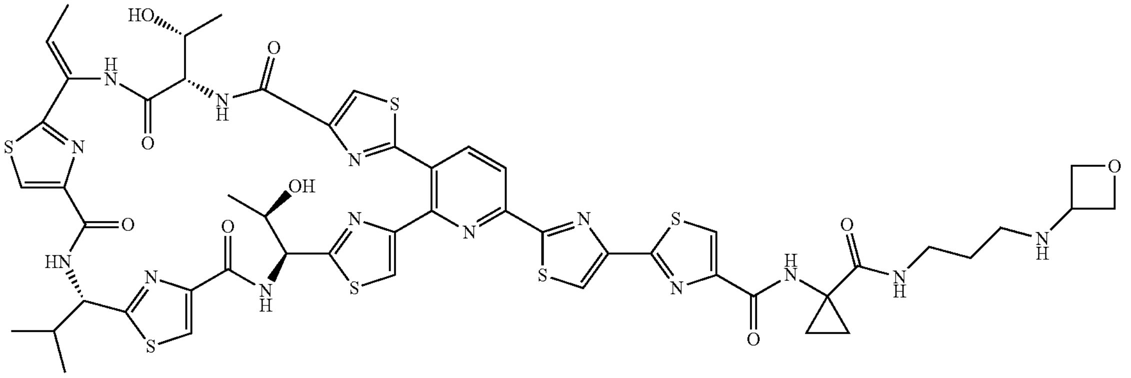
18
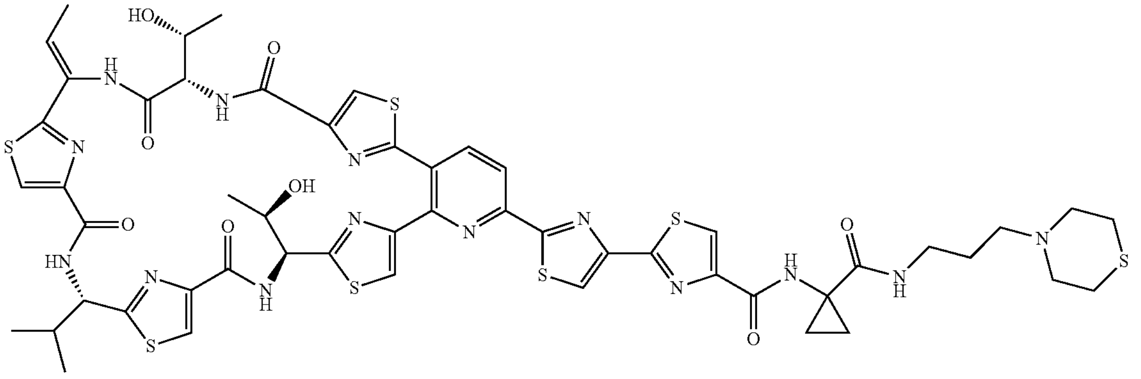

-continued
19
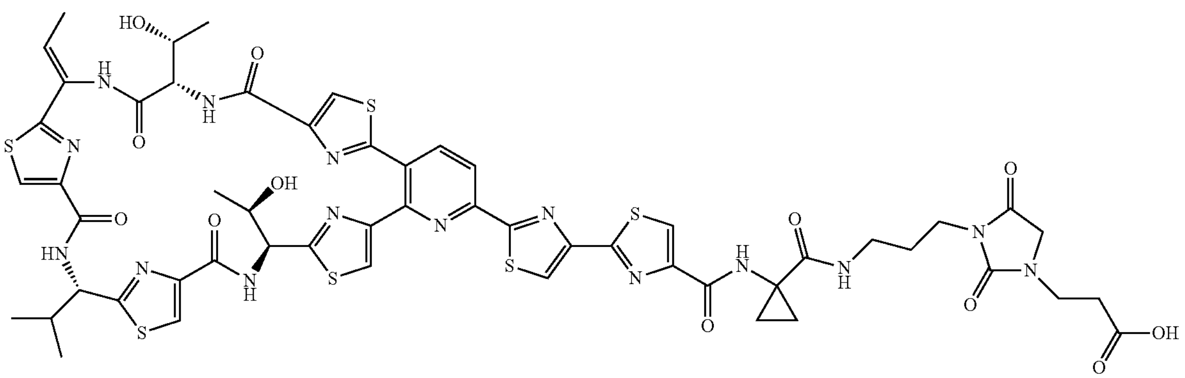
20
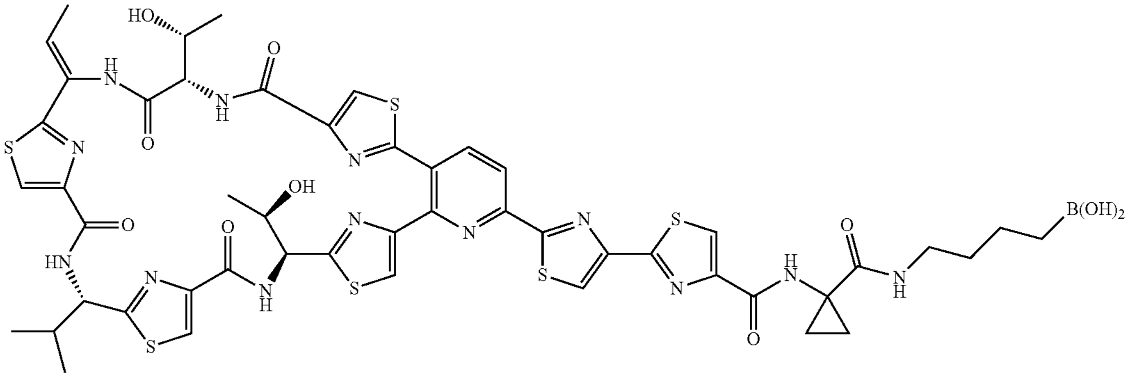
21
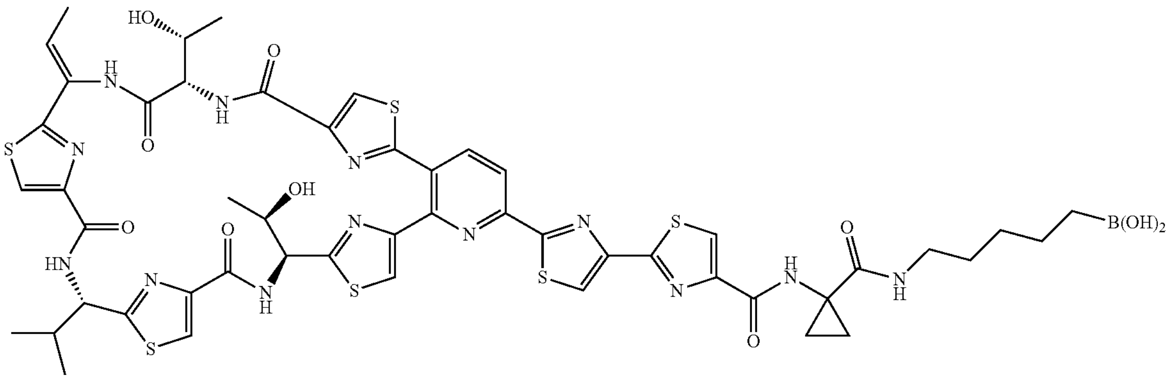
22
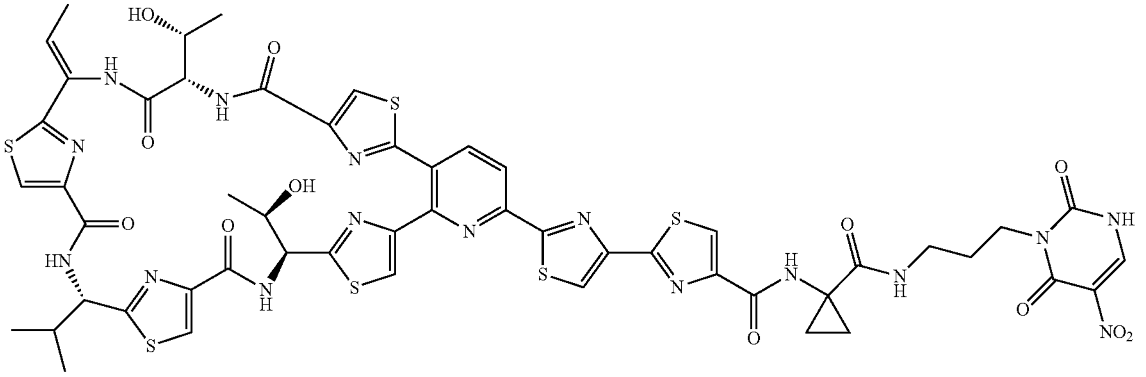

-continued
23
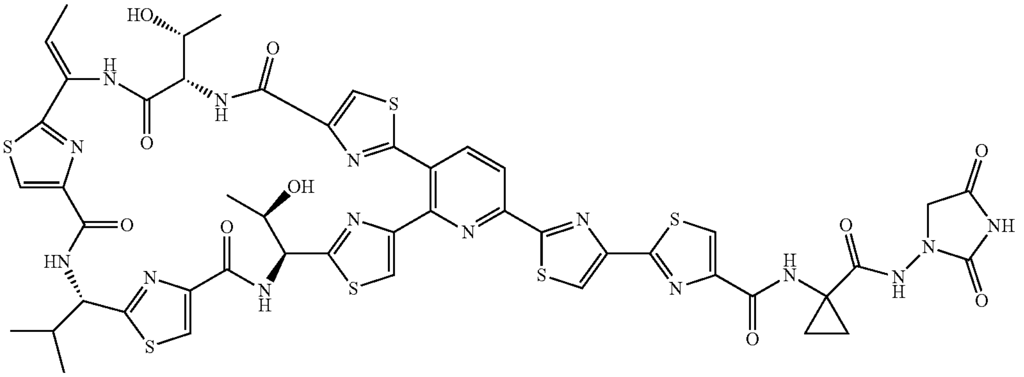
24
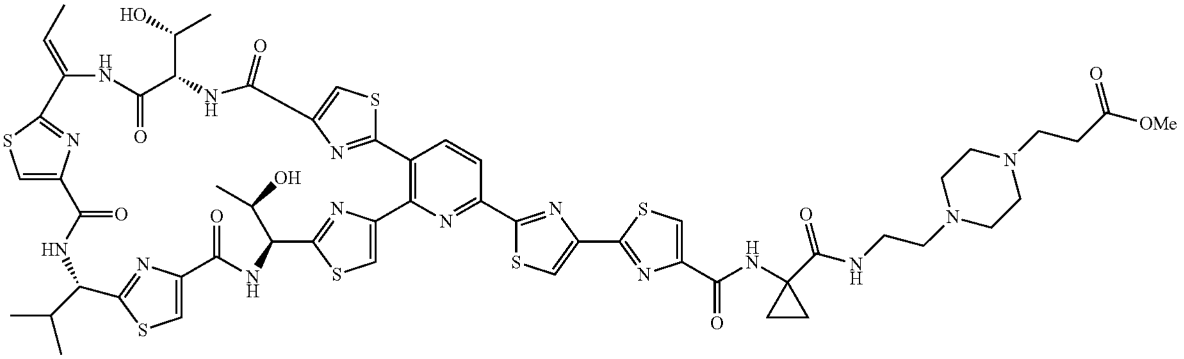
26
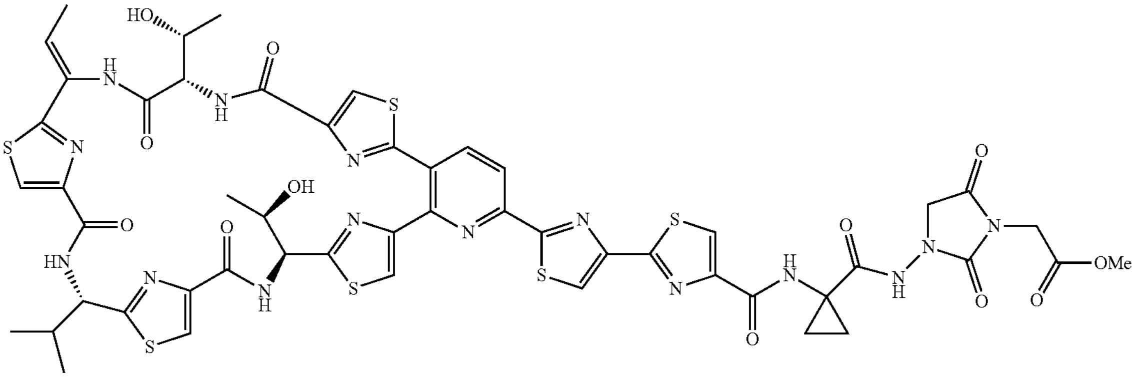
27
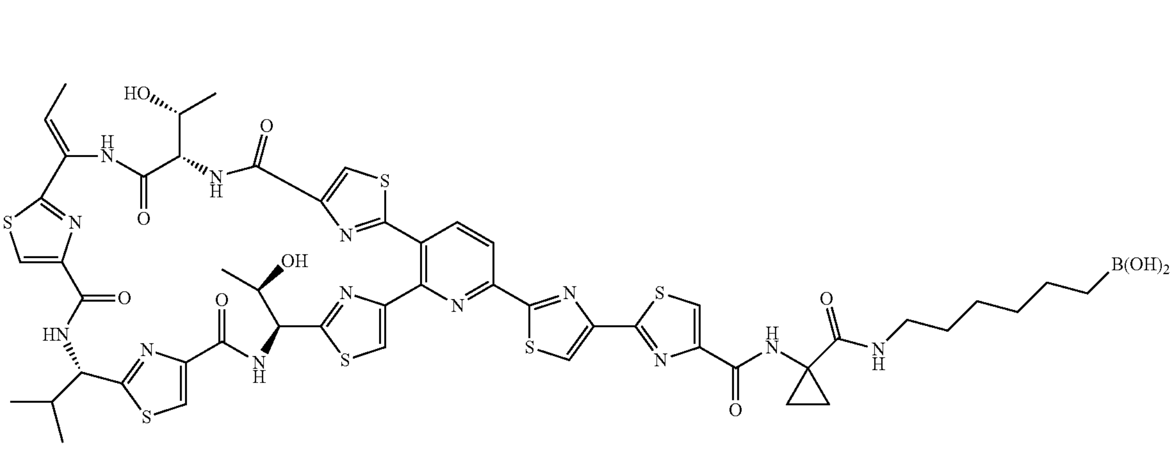

-continued
28
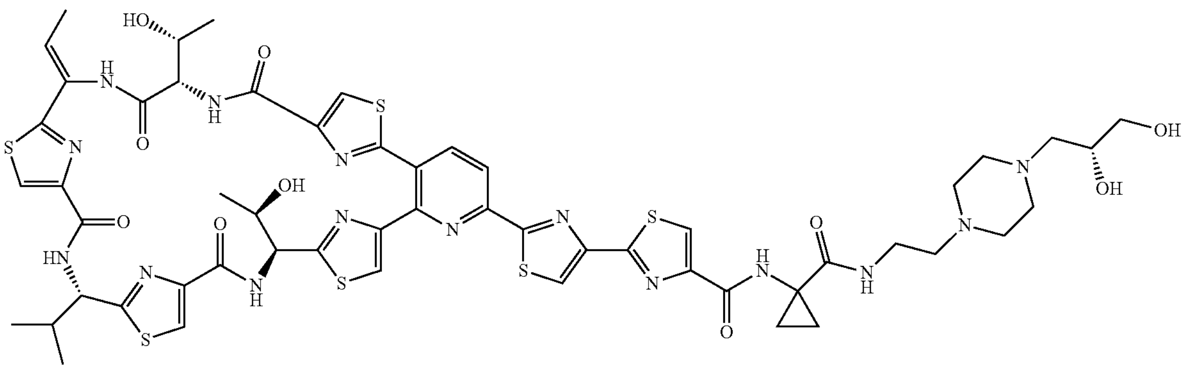
29
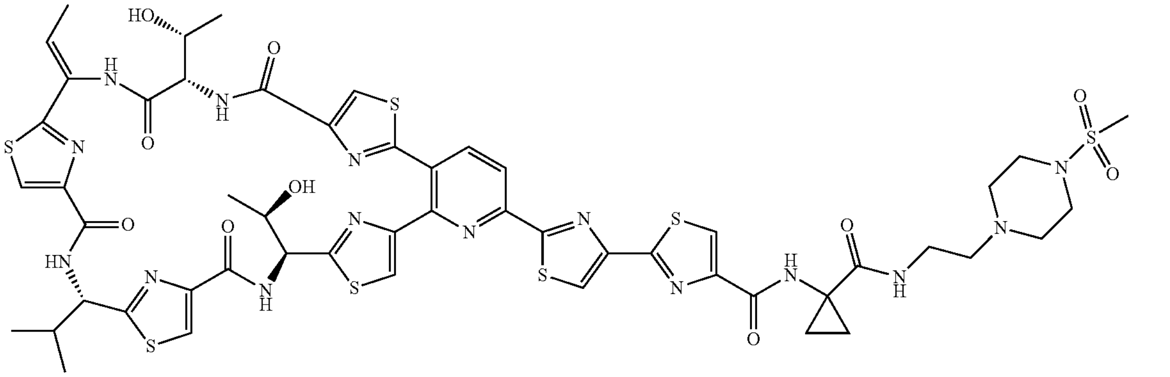
30
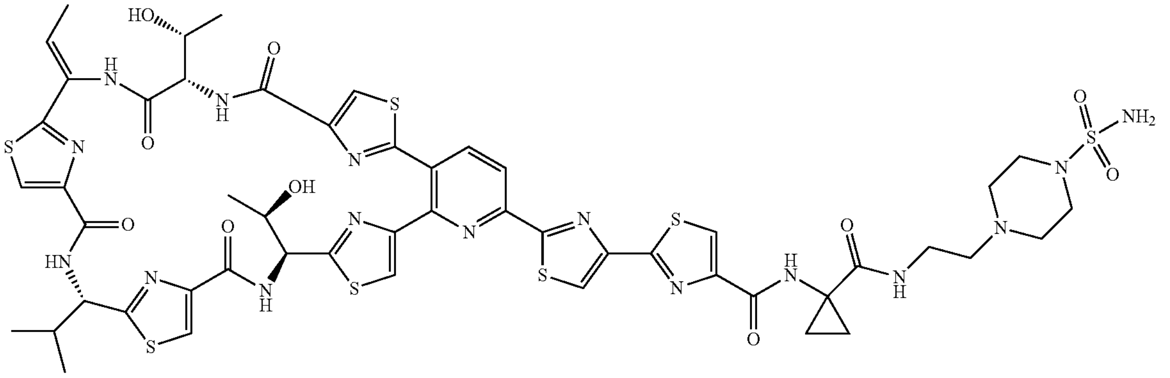
31
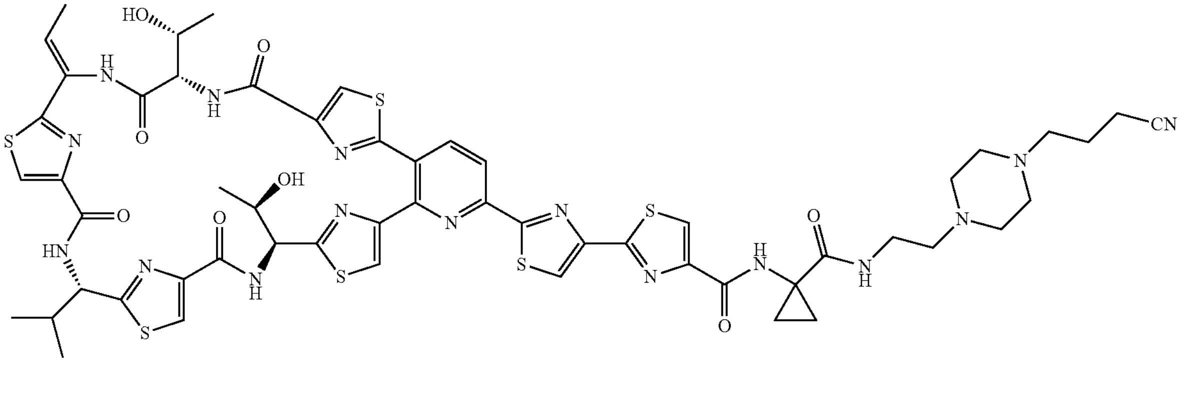

-continued
32
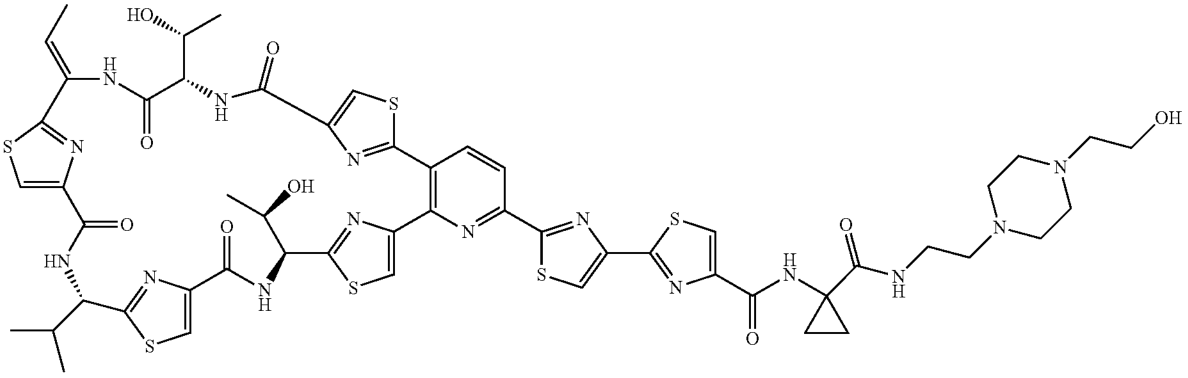
33
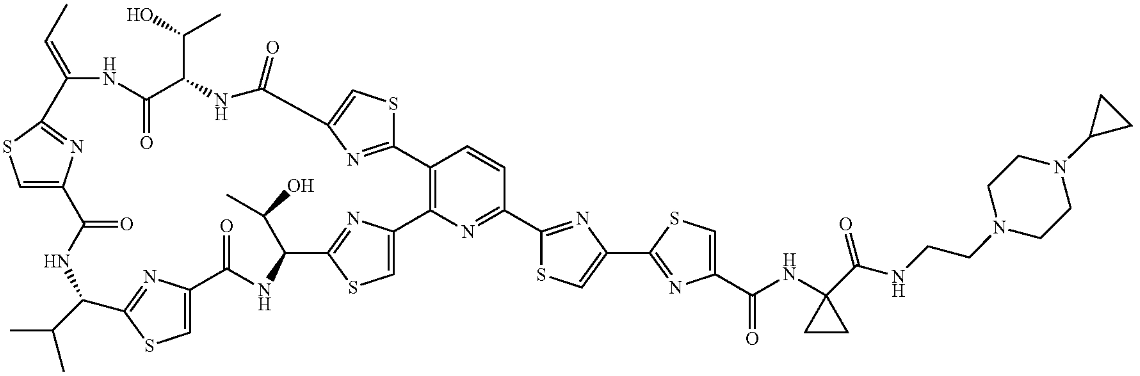
34
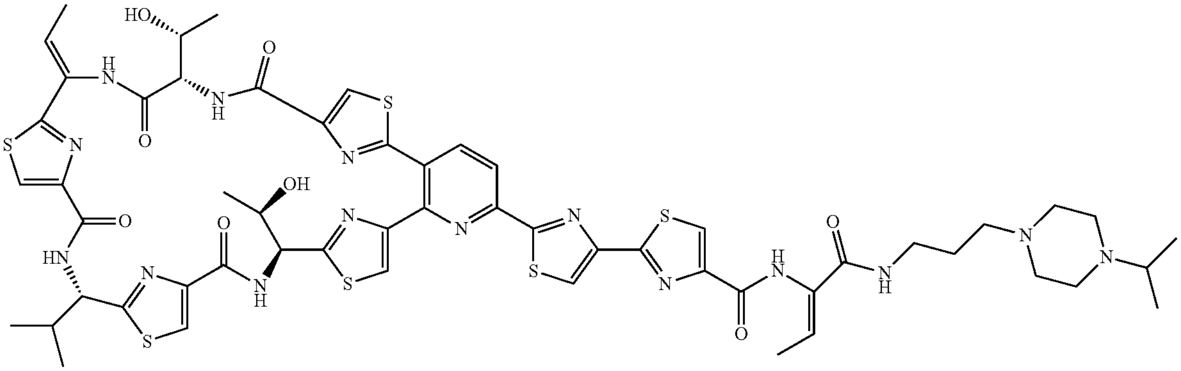
35
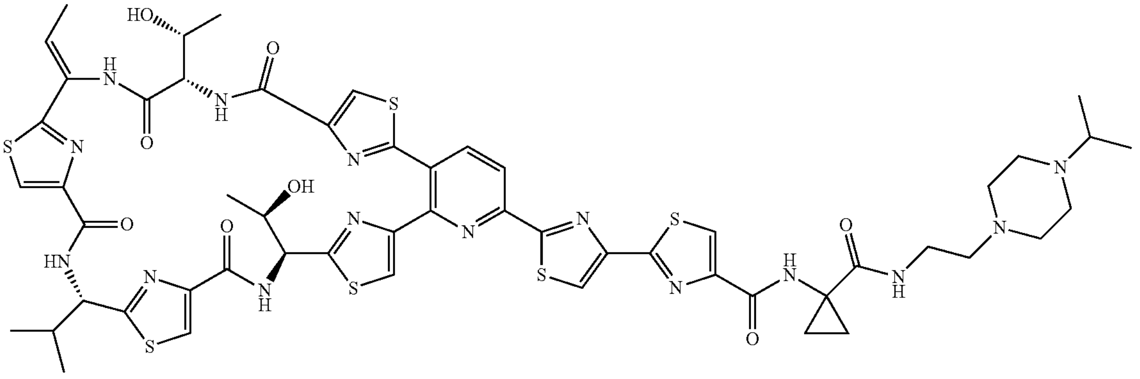

-continued
36
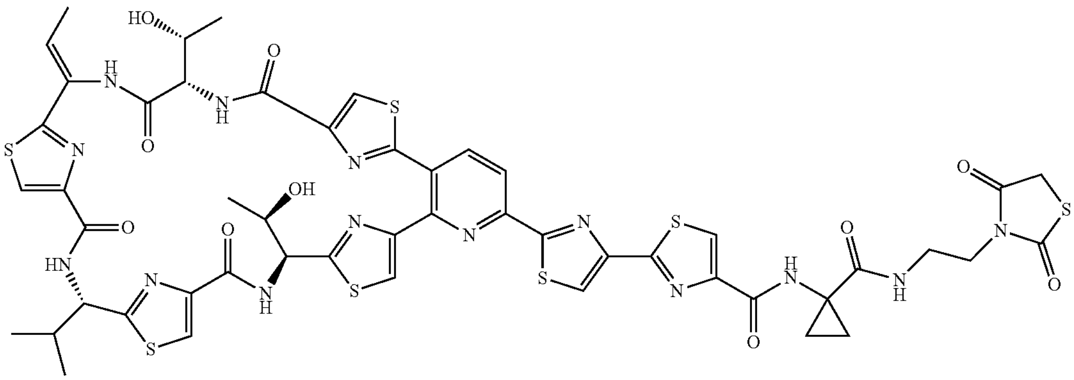
37
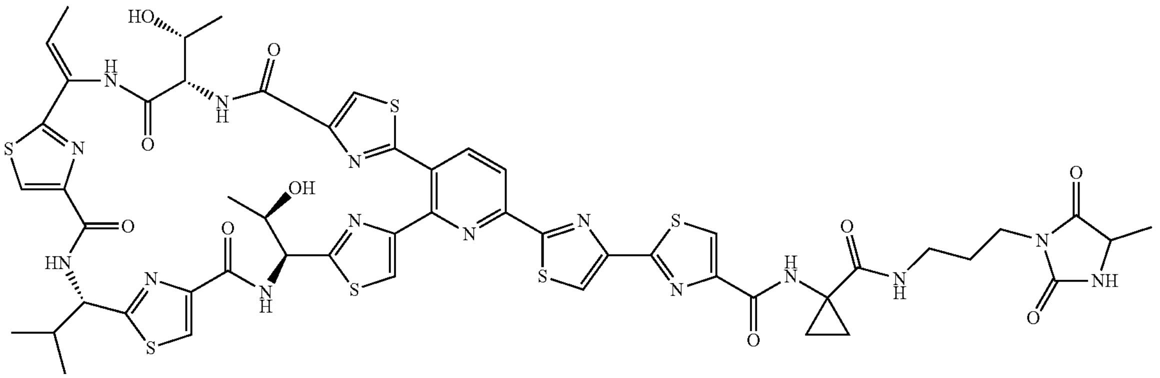
38
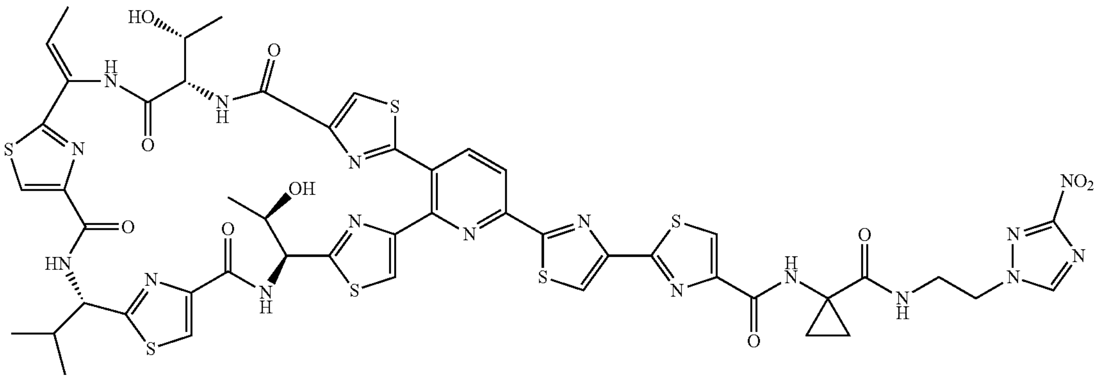
39
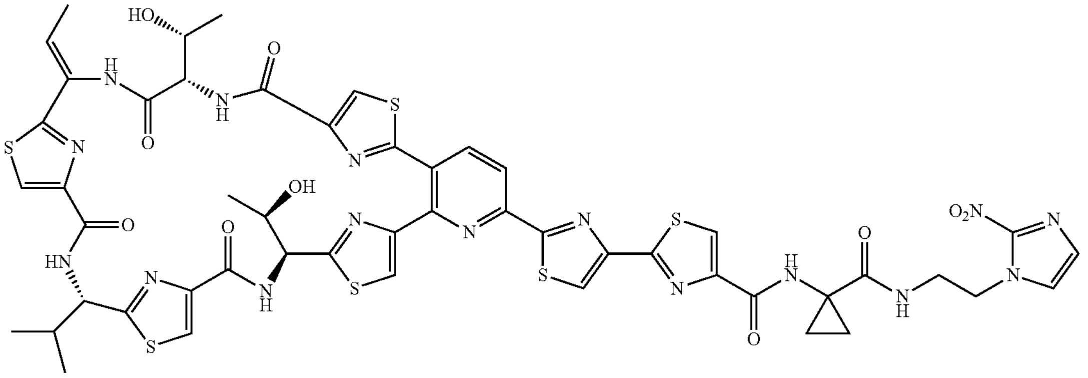

-continued
40
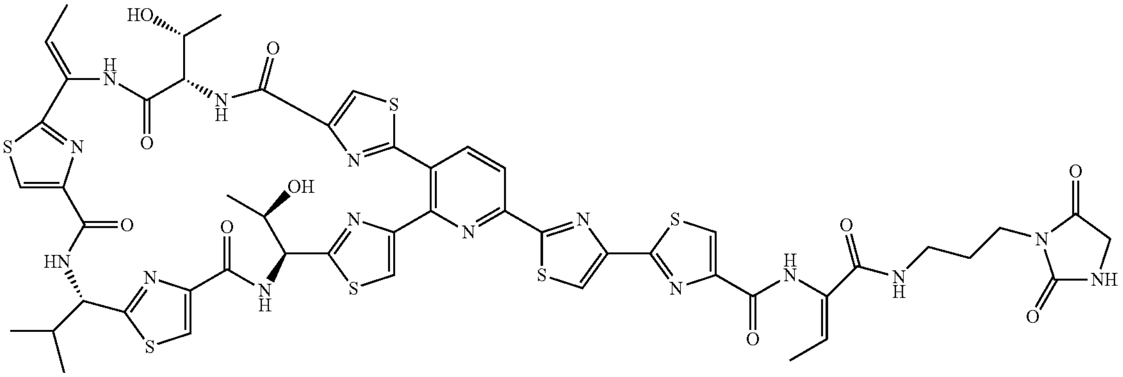
41
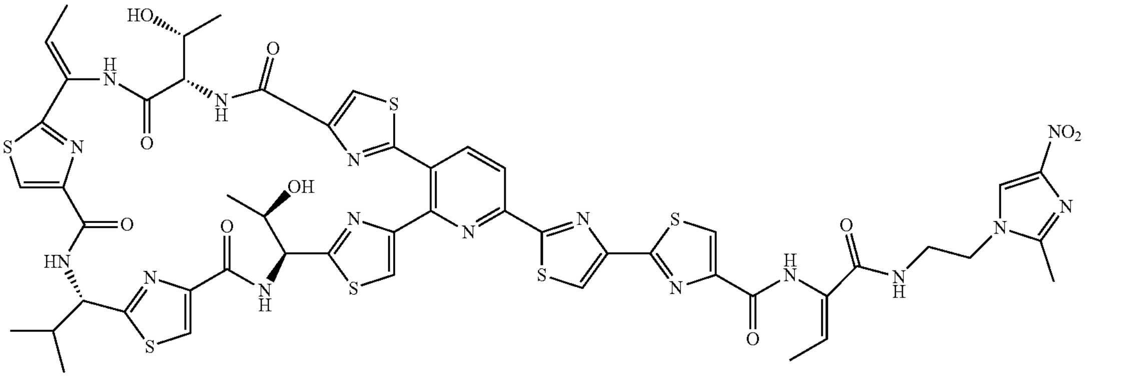
42
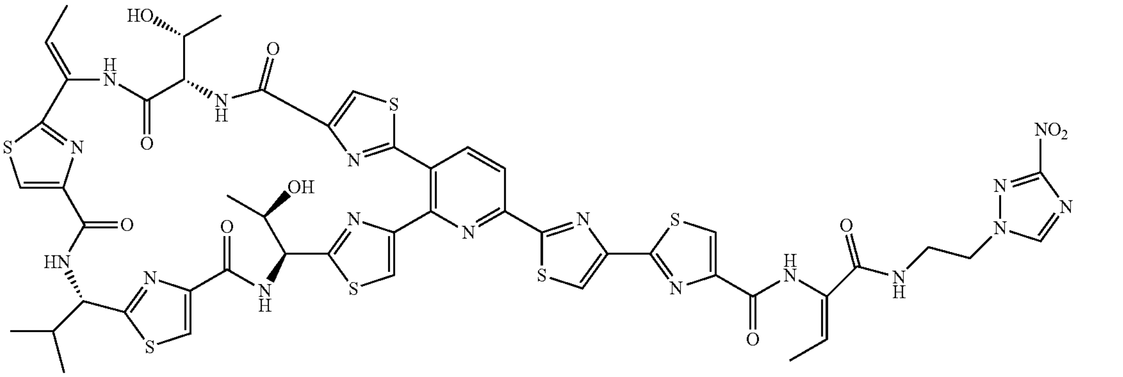
43
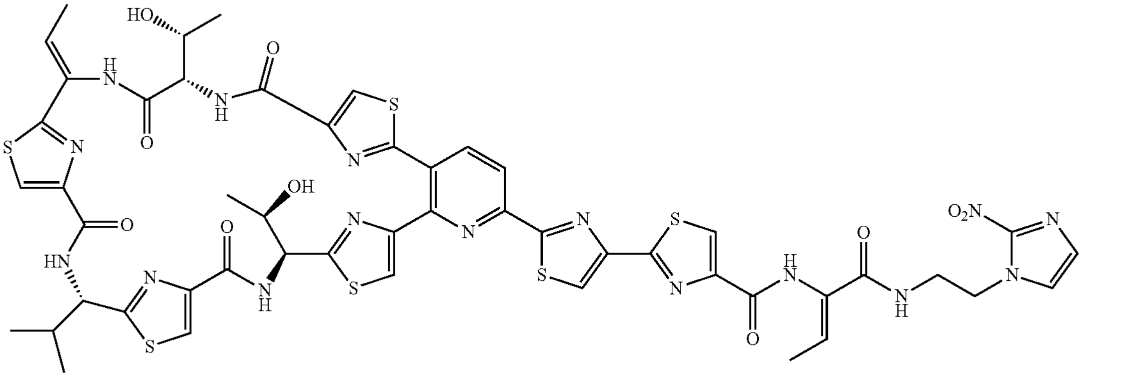

-continued
44
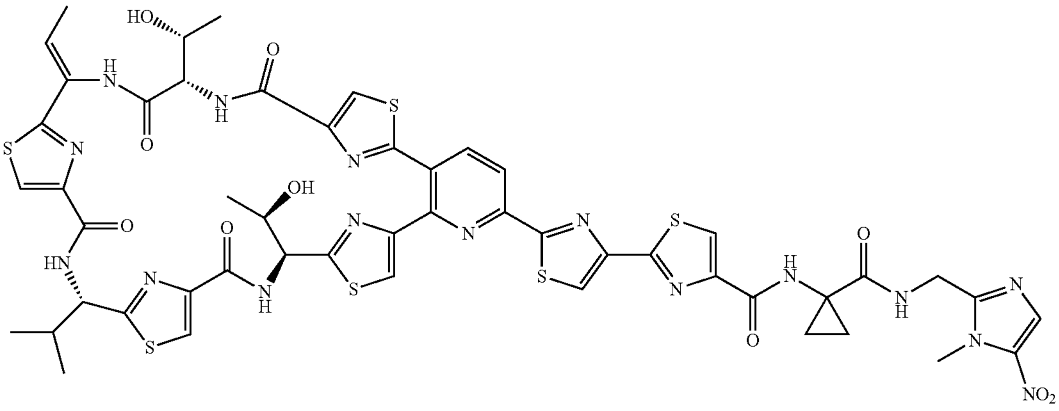
45
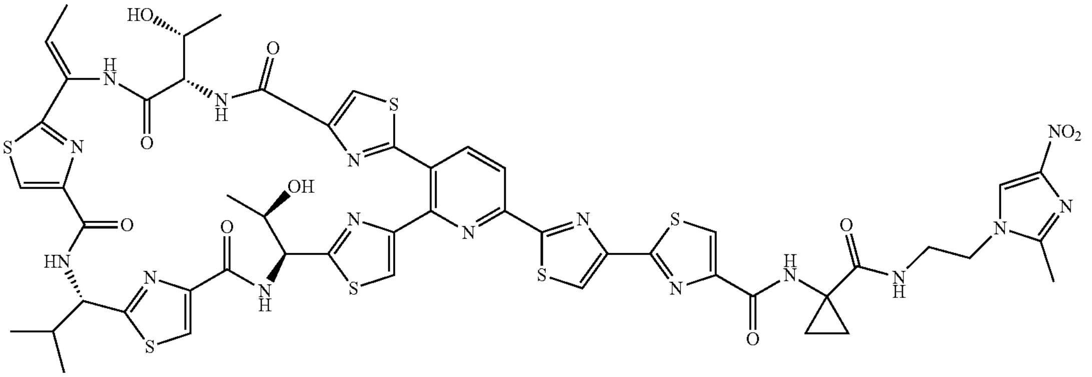
46
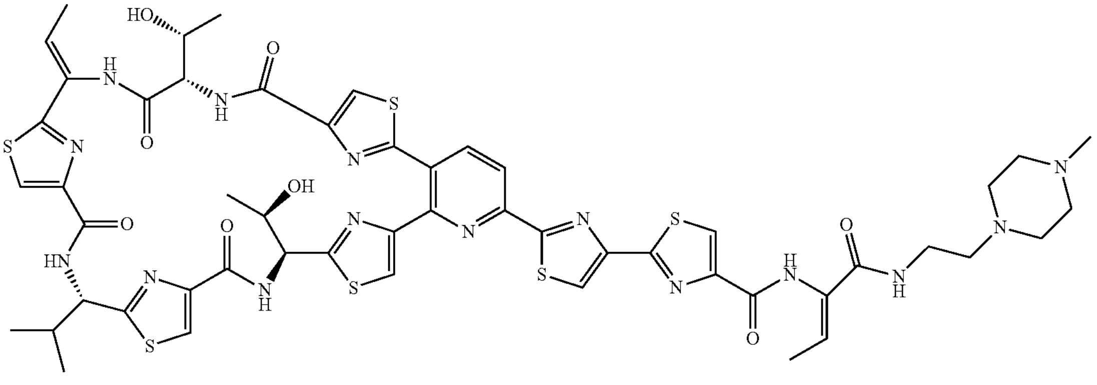
47
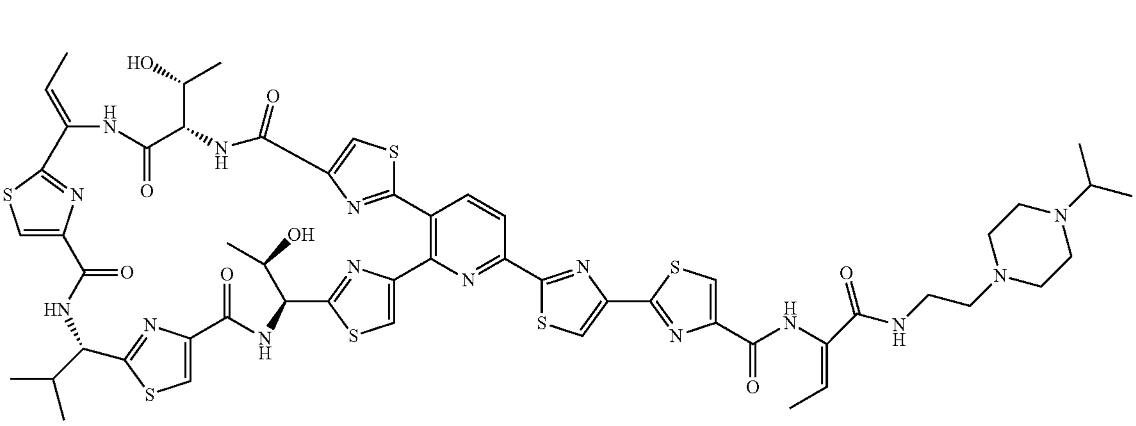

-continued

48

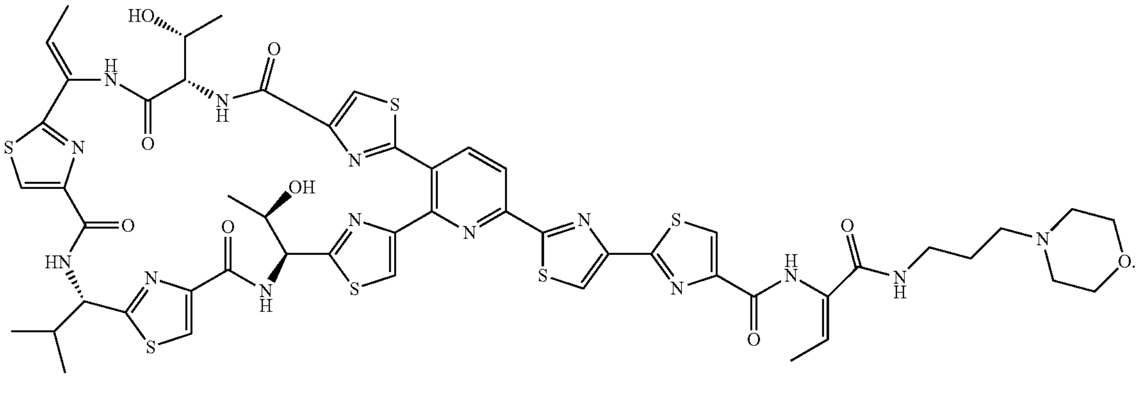

10. An antibiotic composition comprising, as an active ingredient, the compound of claim 1, or pharmaceutically acceptable salt thereof.

11. The antibiotic composition of claim 10, wherein the antibiotic composition is used for treatment or prevention of a bacterial infection.

12. The antibiotic composition of claim 11, wherein the bacterial infections are associated with *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella enterica, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis*, Kingella, *Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium-intracellulare* complex, *Mycobacterium avium, Mycobacterium intracellulare, Mycobacterium abscessus, Mycobacterium leprae, Mycobacterium bolletii, Mycobacterium kansasii, Mycobacterium xenopi, Mycobacterium malmoense, Mycobacterium scrofulaceum, Mycobacterium marinum, Mycobacterium fortuitum, Mycobacterium chelonae, Mycobacterium ulcerans, Mycobacterium haemophilusrynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus* saccharolyticus, or are associated with *Plasmodium falciparum, Plasmodium vivax, Plasmodium malariae, Plasmodium Ovale*, and *Plasmodium knowlesi.*

13. The antibiotic composition of claim 10, further comprising a pharmaceutically acceptable carrier.

14. The antibiotic composition of claim 10, wherein the compound, or pharmaceutically acceptable salt thereof is contained in an amount of 0.001 to 10 wt % with respect to the total weight of the antibiotic composition.

15. A method for preparing a compound represented by the following Chemical Formula 1, the method comprising:

preparing a compound of the following Chemical Formula 22 by reacting a compound of the following Chemical Formula 21 with a boronic acid precursor; and preparing a compound of the following Chemical Formula 1 by reacting the compound of Chemical Formula 22 with a compound of the following Chemical Formula 23:

[Chemical Formula 1]

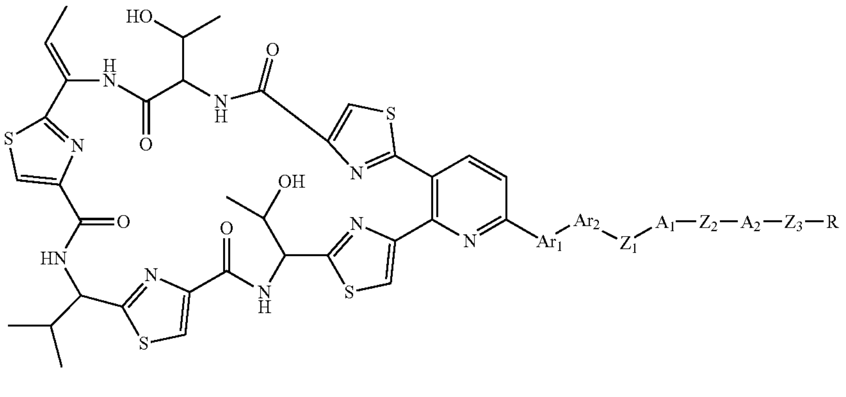

-continued

[Chemical Formula 21]

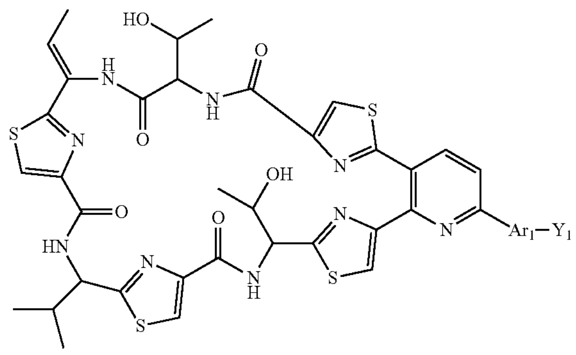

[Chemical Formula 22]

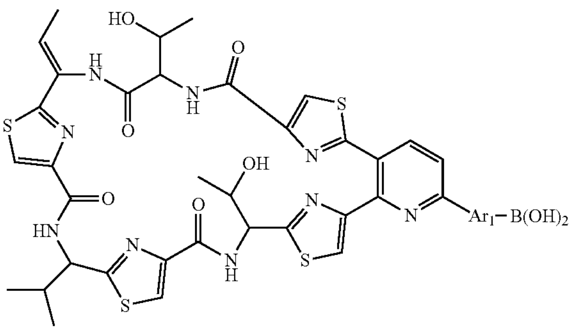

[Chemical Formula 23]

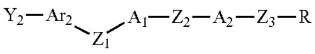

in Chemical Formula 1 and Chemical Formulas 21 to 23, $Ar_1$ and $Ar_2$ are each independently

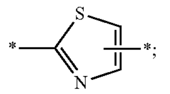

$Z_1$ to $Z_3$ are each independently a single bond, —$CONR_1$—, —COO—, or —$NR_6$—;

$R_1$ and $R_6$ are each independently hydrogen;

$A_1$ is

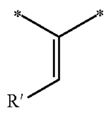 or 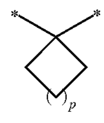 ,

R' is hydrogen, C1-C10 alkyl, C2-C10 alkenyl, or C1-C10 alkoxy C1-C10 alkyl, and p is an integer of 0 to 4;

$A_2$ is a single bond, C1-C10 alkylene, C3-C10 cycloalkylene, C3-C10 heterocycloalkylene, C6-C20 arylene, or C6-C20 heteroarylene;

R is hydrogen, amino, —$B(OH)_2$, C3-C10 heterocycloalkyl, or C3-C20 heteroaryl, the heterocycloalkyl, or heteroaryl of R may be further substituted with one or more selected from the group consisting of halogen, amino, nitro, hydroxy, a carboxylic acid group, —$B(OH)_2$, C1-C10 alkylcarbonyl, C1-C10 alkoxycarbonyl, C2-C10 alkenyl, C1-C10 alkyl, halo C1-C10 alkyl, C3-C10 heterocyclocarbonyl, allylamino, C1-C10 alkylsulfonyl, aminosulfonyl, amino C1-C10 alkyl, hydroxy C1-C10 alkyl, dihydroxy C1-C10 alkyl, cyano C1-C10 alkyl, C1-C10 alkylamino, di C1-C10 alkylamino, C6-C20 arylamino, di C6-C20 arylamino, C3-C20 heteroaryl, halo C6-C20 aryl, halo C1-C10 alkyl C6-C20 aryl, C6-C20 aryl, C3-C10 cycloalkyl, C3-C10 cycloalkylcarbonyl, C1-C10 alkoxycarbonyl C1-C10 alkyl, and carboxy C1-C10 alkyl; and $Y_1$ and $Y_2$ are each independently halogen.

16. The method of claim 15, wherein the compound of Chemical Formula 21 is prepared by:

preparing a compound of the following Chemical Formula 26 by reacting a compound of the following Chemical Formula 24 with a compound of the following Chemical Formula 25; and preparing the compound of Chemical Formula 21 by deprotecting the compound of Chemical Formula 26:

[Chemical Formula 24]

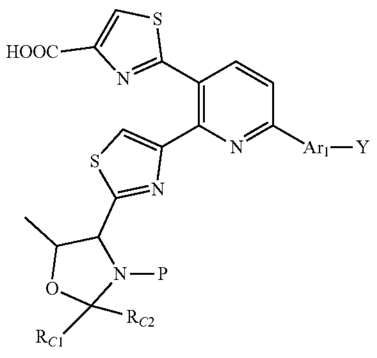

[Chemical Formula 25]

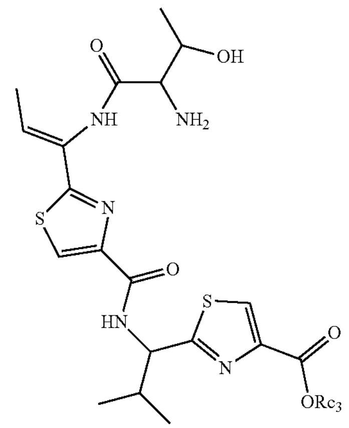

-continued
[Chemical Formula 26]
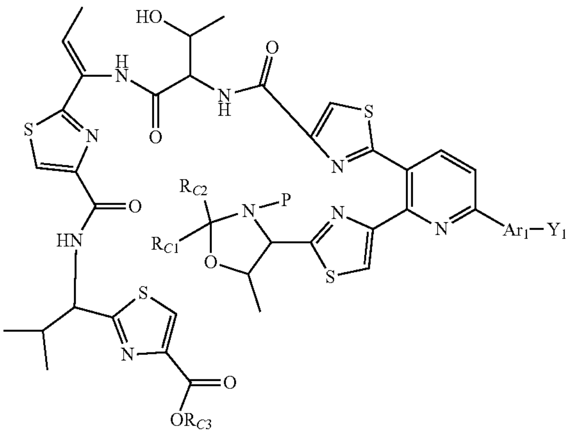
in Chemical Formulas 24 to 26, $Ar_1$ and $Y_1$ are the same as the definitions in claim 13;
$R_{c1}$ to $R_{c3}$ are each independently C1-C10 alkyl; and
P is a protecting group.
* * * * *